(12) United States Patent
Smrcka et al.

(10) Patent No.: US 8,975,259 B2
(45) Date of Patent: Mar. 10, 2015

(54) COMPOSITIONS AND METHODS FOR INHIBITING G PROTEIN SIGNALING

(75) Inventors: Alan V Smrcka, Rochester, NY (US); Burns C. Blaxall, Pittsford, NY (US); Jean M. Bidlack, Pittsford, NY (US)

(73) Assignee: University of Rochester, Rochester, NY (US)

( * ) Notice: Subject to any disclaimer, the term of this patent is extended or adjusted under 35 U.S.C. 154(b) by 925 days.

(21) Appl. No.: 12/597,509

(22) PCT Filed: Apr. 28, 2008

(86) PCT No.: PCT/US2008/061757
§ 371 (c)(1),
(2), (4) Date: Jan. 28, 2010

(87) PCT Pub. No.: WO2009/020677
PCT Pub. Date: Feb. 12, 2009

(65) Prior Publication Data
US 2010/0130505 A1 May 27, 2010

Related U.S. Application Data

(60) Provisional application No. 60/914,659, filed on Apr. 27, 2007.

(51) Int. Cl.
| | |
|---|---|
| *A61K 31/50* | (2006.01) |
| *A61K 31/495* | (2006.01) |
| *G01N 33/74* | (2006.01) |
| *G01N 33/564* | (2006.01) |
| *G01N 33/68* | (2006.01) |
| *G01N 33/94* | (2006.01) |
| *A61K 31/122* | (2006.01) |
| *A61K 31/4709* | (2006.01) |
| *A61K 31/498* | (2006.01) |

(52) U.S. Cl.
CPC .............. *G01N 33/74* (2013.01); *G01N 33/564* (2013.01); *G01N 33/6893* (2013.01); *G01N 33/9486* (2013.01); *A61K 31/122* (2013.01); *A61K 31/4709* (2013.01); *A61K 31/498* (2013.01); *G01N 2333/726* (2013.01); *G01N 2500/04* (2013.01); *G01N 2800/32* (2013.01); *G01N 2800/325* (2013.01)
USPC .......................................................... 514/250

(58) Field of Classification Search
None
See application file for complete search history.

(56) References Cited

U.S. PATENT DOCUMENTS

| | | | |
|---|---|---|---|
| 7,097,993 B2 | 8/2006 | Anderson et al. | |
| 2007/0042435 A1 | 2/2007 | Zuker et al. | |

FOREIGN PATENT DOCUMENTS

WO     2006/096690     9/2006

OTHER PUBLICATIONS

Li et al (Gene Therapy 10:1354-1361, 2003).*
Bonacci et al (Science 312:443-446, Apr. 21, 2006).*
Bonacci et al., "Differential Targeting of Gβγ-Submit Signaling with Small Molecules," 2006, Science 312:443-446.
Davis et al., "Structural and Molecular Characterization of a Preferred Protein Interaction Surface on G Protein βγ Subunits," 2005, Biochemistry 44:10593-10604.
Ford et al. "Molecular basis for interactions of G protein beta gamma subunits with effectors," 1998, Science 280:1271-1274.
Gao et al., "G protein beta subunit [Homo sapiens]," 1987, Proc. Natl. Acad. Sci. U.S.A., 84(17):6122-6125.
Gaudet et al., "Crystal structure at 2.4 angstroms resolution of the complex of transducin beta gamma and its regulator, phosducin," 1996, Cell 87:577-588.
Ghosh et al., "Receptor- and nucleotide Exchange-independent Mechanisms for Promoting G Protein Subunit Dissociation," 2003, J Biol Chem.278(37):34747-50.
Goubaeva et al., "Stimulation of Cellular Signaling and G Protein Subunit Dissociation by G Protein beta gamma Subunit-binding Peptides," 2003, J Biol Chem 278(22):13634-19641.
Lambright et al., "The 2.0 angstroms crystal structure of a heterotrimeric G protein," 1996, Nature 379:311-319.
Li et al., "Sites for Galpha Binding on the G Protein Beta Subunit Overlap with Sites for Regulation of Phospholipase Cbeta and Adenylyl Cyclase," 1998, J Biol Chem 273(26):16265-16272.
Lodowski et al., "Keeping G Proteins at Bay: A Complex Between G Protein-Coupled Receptor Kinase 2 and G beta gamma," 2003, Science 300:1256-1262.
Loew et al., "Phosducin induces a structural change in transducing beta gamma," 1998, Structure 6(8):1007-1019.
Ray et al., "G-protein beta-subunit [Rattus norvegicus]," 1994, Gene 149(2):337-340.
Sarvazyan et al., "Determinants of gi1alpha and beta gamma binding. Measuring high affinity interactions in a lipid environment using flow cytometry," 1998, J Biol Chem 273(14):7934-7940.
Scott et al., "Evidence that a protein-protein interaction 'hot spot' on heterotrimeric G protein beta gamma subunits is used for recognition of a subclass of effectors," 2001, EMBO J. 20(4):767-776.
Snow et al., "Fidelity of G protein beta-subunit association by the G protein gamma-subunit-like domains of RGS6, RGS7 and RGS11," 1999, Proc Natl Aced Sci USA 96:6489-6494.
Sondek et al., "Crystal structure of a G-protein beta gamma dimer at 2.1A resolution," 1996, Nature 379:369-374.
Wall et al., "The structure of the G protein heterotrimer Gi alpha 1 beta 1 gamma 2," 1995, Cell 83:1047-1058.
Yao, et al. "Addicting drugs utilize a synergistic molecular mechanism in common requiring adenosine and Gi-beta gamma dimers," 2003, PNAS 100(24):14379-14384.
Zhou, et al., "Selective regulation of N-type Ca channels by different combinations of G-protein beta/gamma subunits and RGS proteins,": 2000, J Neurosci 20(19):7143-7148.
European Search Opinion for EP Application No. 08827151.5, based on PCT/US08/61757, dated Aug. 6, 2010.
Annex to Communication from EPO Examining Division, for EP Application No. 08827151.5, based on PCT/US08/61757, dated Jun. 4, 2011.

* cited by examiner

Primary Examiner — Craig Ricci
(74) Attorney, Agent, or Firm — Riverside Law LLP

(57) ABSTRACT

Disclosed are compositions and methods for treating diseases associated with G protein βγ subunit activity.

4 Claims, 26 Drawing Sheets

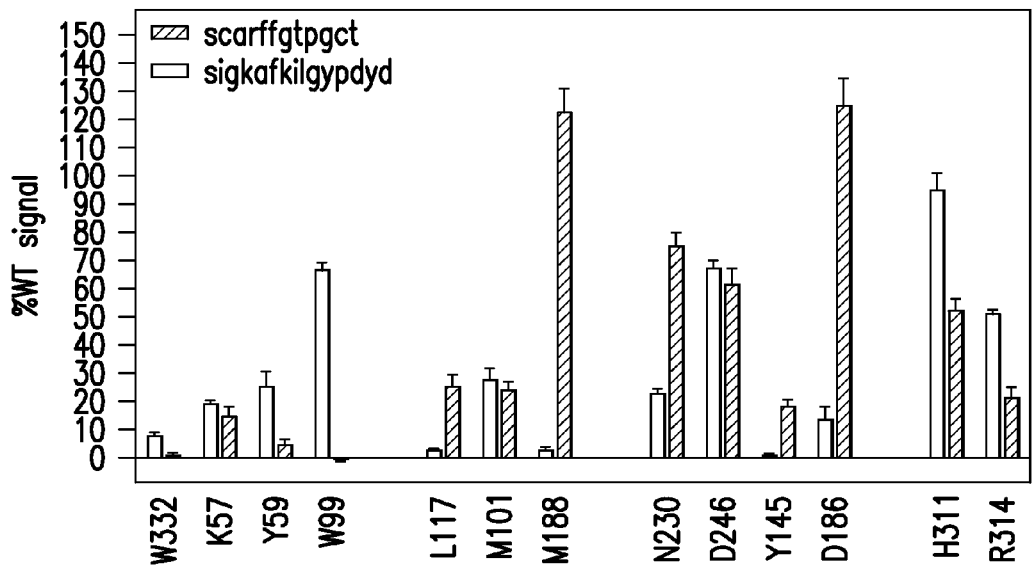
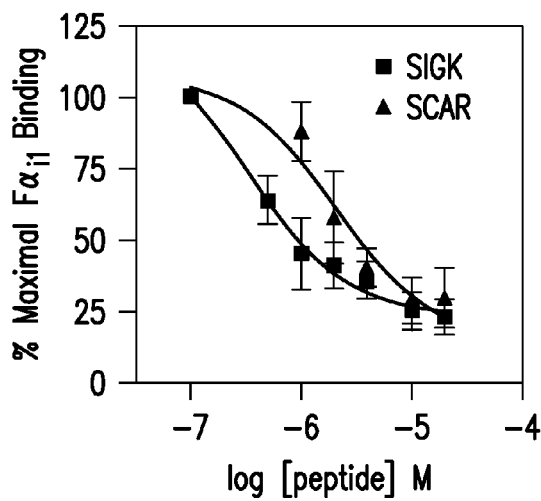
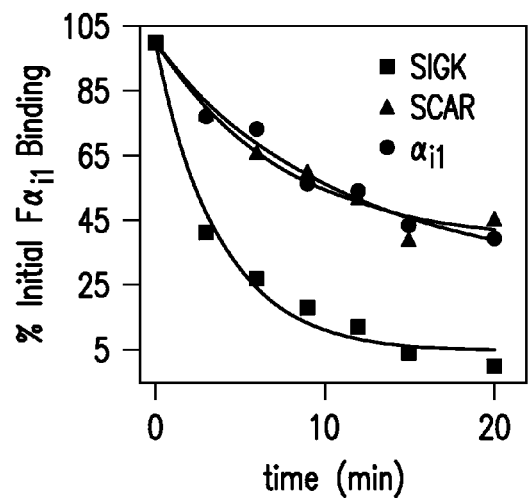
FIG.1A
FIG.1B
FIG.1C

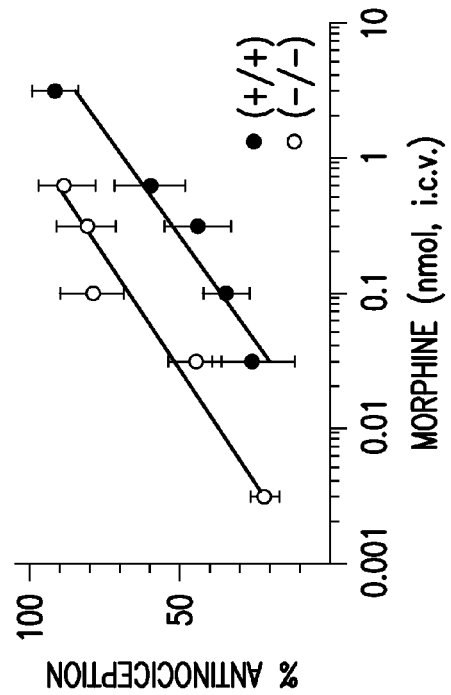
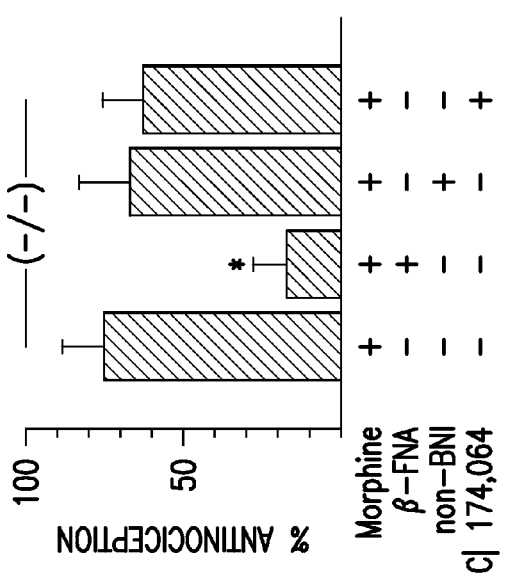
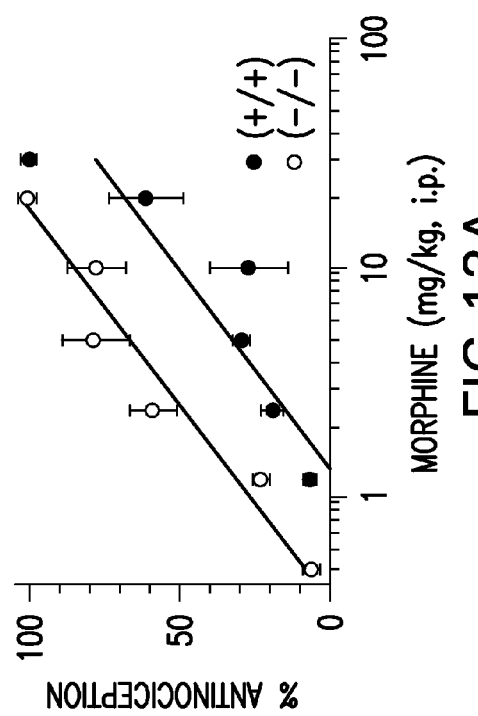
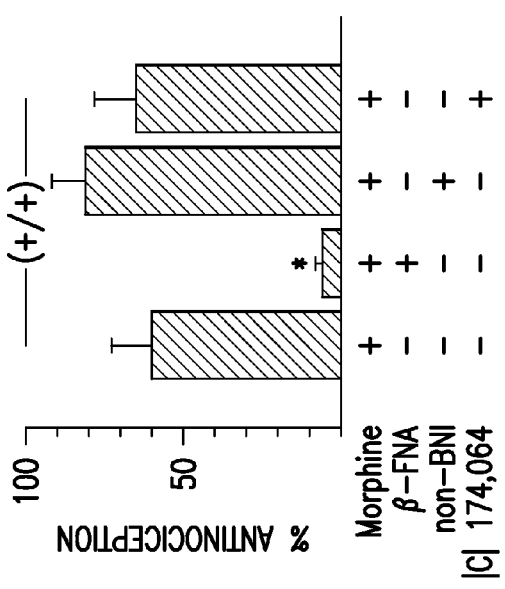

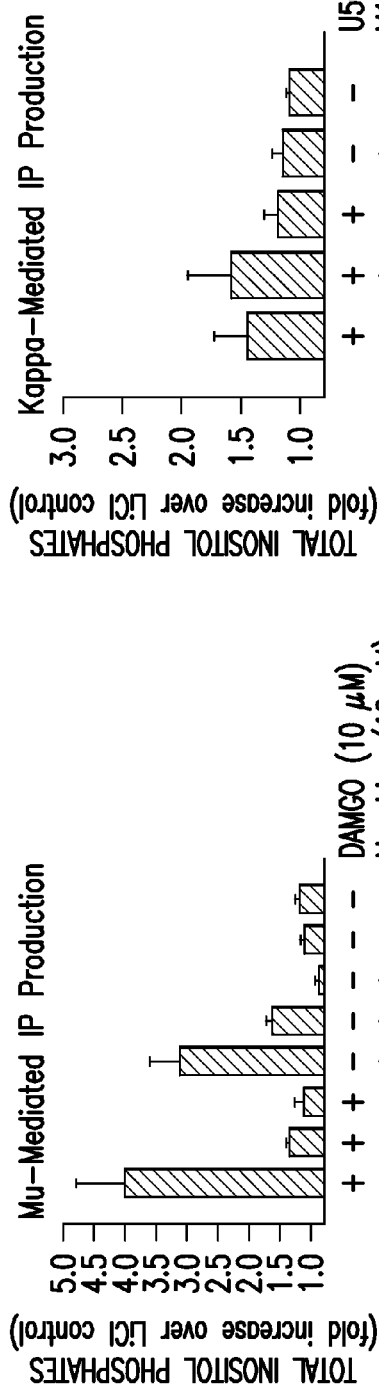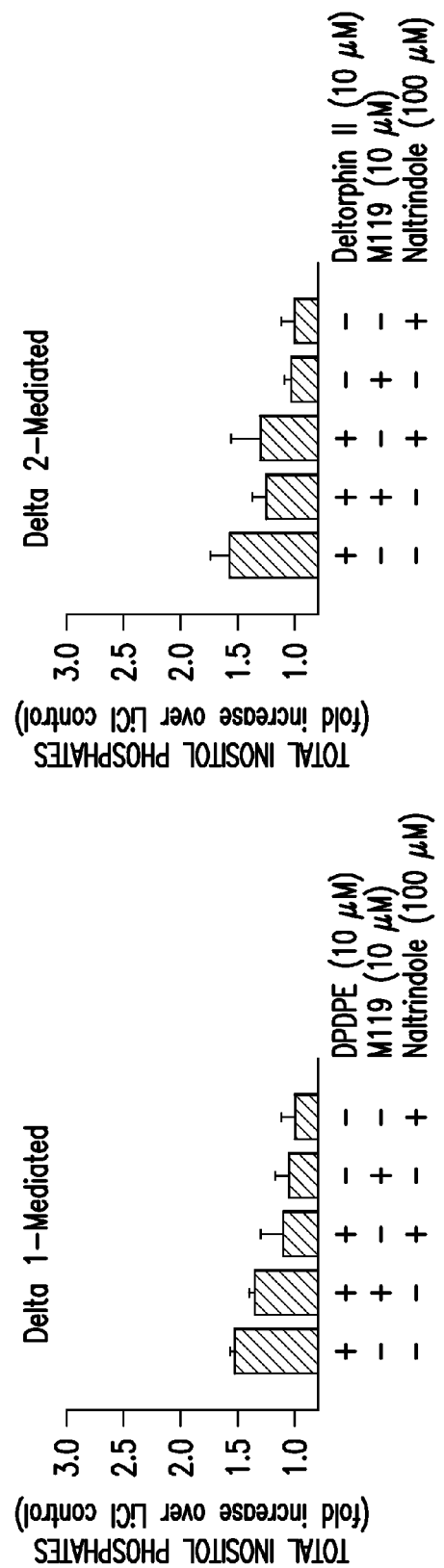

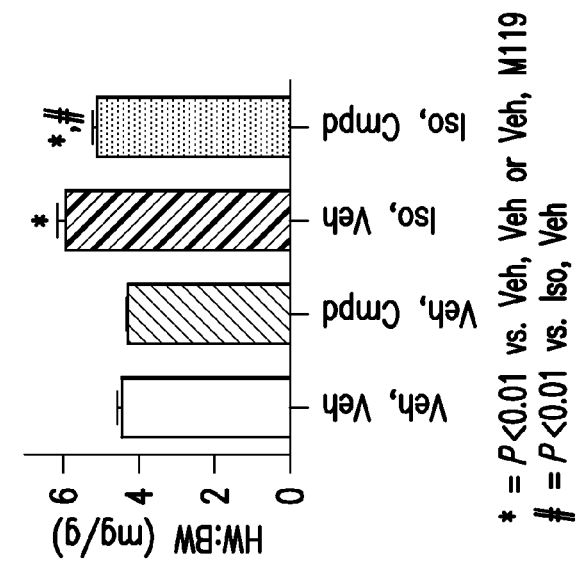
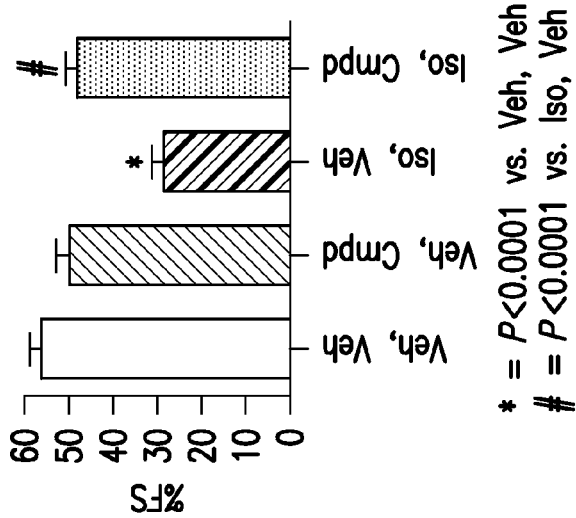
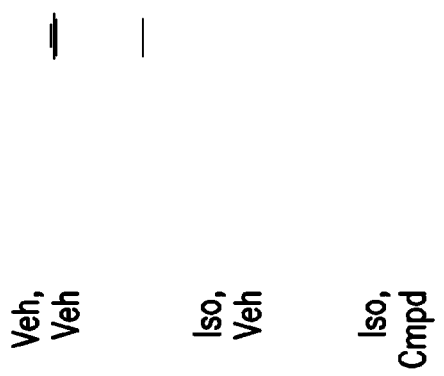
FIG. 17A
FIG. 17B
FIG. 17C

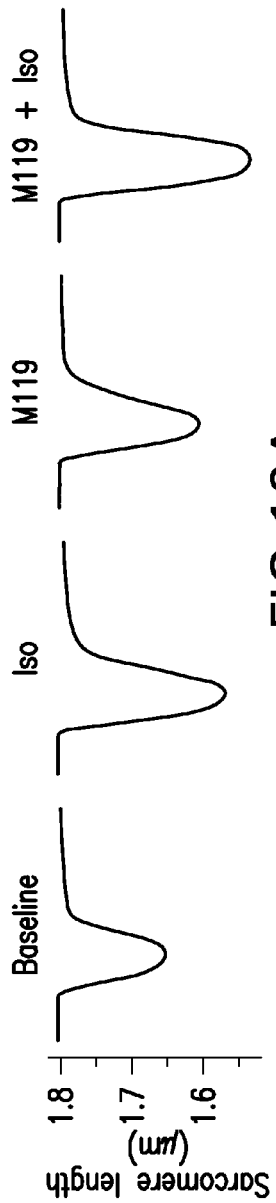
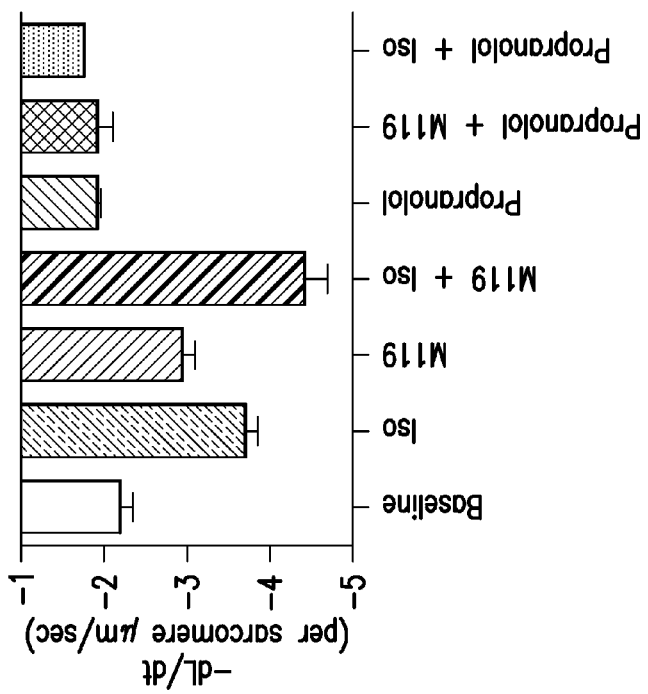
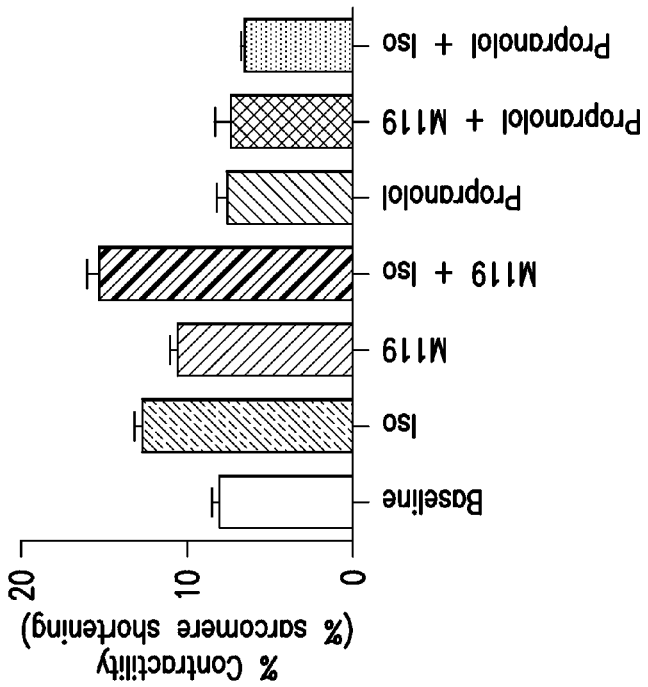
FIG. 19A
FIG. 19B
FIG. 19C

ID NO:1). The SIRK peptide inhibited PLC β2 activation by# COMPOSITIONS AND METHODS FOR INHIBITING G PROTEIN SIGNALING

CROSS-REFERENCE TO RELATED APPLICATION

The present application is a 35 U.S.C. §371 national phase application from, and claiming priority to, International Application No. PCT/US2008/061757, filed Apr. 28, 2008, and published under PCT Article 21(2) in English, which claims priority to U.S. Provisional Patent Application No. 60/914,659, filed Apr. 27, 2007, which applications are incorporated by reference herein in their entireties.

STATEMENT REGARDING FEDERALLY SPONSORED RESEARCH OR DEVELOPMENT

This invention was made in the course of research sponsored by the National Institutes of Health Grant Nos. GM60286, DK46371, and K05-DA00360. The U.S. government has certain rights in this invention.

I. BACKGROUND

Five mammalian isoforms of the G protein β subunit (37 kDa) and twelve isoforms of G protein Y (7.8 kDa) have been identified (Offermanns (2003) Prog. Biophys. Mol. Biol 83:101-30). Obligate heterodimers composed of G protein β and Y subunits (Gβγ) function as regulatory molecules in various pathways in eukaryotic cells (Neves, et al. (2002) Science 296:1636-9; Clapham and Neer (1997) Annu. Rev. Pharmacol. Toxicol. 37:167-203). First characterized as a guanine nucleotide dissociation inhibitor (GDI), Gβγ associates tightly with GDP-bound G protein α subunits (Ga) and thereby constitutes the basal form of the G protein heterotrimer in which neither Ga nor GβY are active in signaling. Agonist-stimulated G protein coupled receptors (GPCRs) catalyze the exchange of GDP for GTP upon Ga and release of Gβγ from the heterotrimer complex, liberating two active signaling species: Gaα>>GTP and Gβγ. Targets of Gβγ signaling include the G protein-regulated inward-rectifying potassium channel (GIRK) (Krapivinsky, et al. (1993) J. Biol. Chem. 273:16946-52); type I, type II, and type IV isoforms of adenylyl cyclase (Tang and Gilman(1991) Science 254:1500-3; Sunahara, et al. (1996) Annu. Rev. Pharmacol. Toxicol. 36:461-80); mitogen-activated protein kinase (MAPK) (Schwindinger and Robishaw (2001) Oncogene 20:1653-60); phosphotidylinositol-3-kinase (PI3K) (Schwindinger and Robishaw (2001) supra); phosducin (Schulz (2001) Pharmacol Res 43:1-10); at least two members of the G protein receptor kinase (GRK) family (Koch, et al. (1993) J. Biol. Chem. 268:8256-60; Inglese, et al. (1994) Proc. Natl. Acad. Sci. USA 91:3637-41); and other plextrin-homology (PH) domain-containing proteins including the dynamins (Lin, et al. (1998) Proc. Natl. Acad. Sci. USA 95:5057-60; Scaife and Margolis (1997) Cell Signal 9:395-401) and the β1, β2, and β3 isoforms of phospholipase C β (PLC β) (Sternweis and Smrcka (1992) Trends Biochem. Sci. 17:502-6; Li, et al. (1998) J. Biol. Chem. 273:16265-72) and many others.

Gβ is a cone-shaped toroidal structure composed of seven four-stranded β-sheets arranged radially about a central axis (Wall, et al. (1995) Cell 83:1047-58; Lambright, et al. (1996) Nature 379:311-9). Each β-sheet is formed from elements of two consecutive WD-40 repeats, named for a conserved C-terminal Trp-Asp sequence in each repeat (Gettemans, et al. (2003) Sci STKE 2003:PE27). The GY subunit, an extended helical molecule, is nested in a hydrophobic channel that runs across the base of the cone. The slightly narrower, "top" surface of the Gβ cone is the main binding site of Ga (through its switch II region) (Wall, et al. (1995) supra; Lambright, et al. (1996) supra), phosducin (Loew, et al. (1998) Structure 6:1007-19; Gaudet, et al. (1996) Cell 87:577-88), and GRK2 (Lodowski, et al. (2003) Science 300:1256-62), as shown by the crystal structures of these complexes. Mutational analysis indicates that many interaction partners of Gβy, including PLC β2 and adenylyl cyclase, bind to the same surface (Li, et al. (1998) supra; Ford, et al. (1998) Science 280:1271-4). Sites located along the sides of the Gβ torus serve as auxiliary binding surfaces that are specifically recognized by certain Gβy targets, exemplified in the crystal structures of Ga and phosducin bound to Gβy (Wall, et al. (1995) supra; Loew, et al. (1998) supra; Gaudet, et al. (1996) supra; Wall, et al. (1998) Structure 6:1169-83).

Phage display of randomized peptide libraries has been used to identify sequence requirements for binding and screen for peptide that bind to Gβ1γ$_2$ dimers (Scott, et al. (2001) EMBO J. 20:767-76). Although billions of individual clones were screened, most of the peptides that bound Gβχγ$_2$ could be classified into four, unrelated groups based on amino acid sequence. One of these groups included a linear peptide (the ^^SIRK" peptide) with the sequence Ser-Ile-Arg-Lys-Ala-Leu-Asn-Ile-Leu-Gly-Tyr-Pro-Asp-Tyr-Asp (SEQ ID NO:1). The SIRK peptide inhibited PLC β2 activation by Gβ1γ$_2$ subunits with an IC$_{50}$ of 5 µM and blocked activation of PI3K. In contrast, the SIRK peptide had little or no effect on Gβ$_1$γ$_2$ regulation of type I adenylyl cyclase or voltage-gated N-type Ca$^{++}$ channel activity (Scott, et al. (2001) supra). This demonstrated that selective inhibition of Gβy binding partners could be achieved. Peptides belonging to all four groups competed with each other with a range of affinities for binding to Gβ$_1$γ$_2$, suggesting that all of the clones isolated from the phage display screen shared a common binding site on Gβ1γ$_2$ (Scott, et al. (2001) supra).

Subsequent experiments have shown that not only does the SIRK peptide block heterotrimer formation, but it also displaces Gaα from a Gβ1γ$_2$>>Gaii complex in the absence of Gaii activation and activates G protein-dependent ERK1 and ERK2 pathways in intact cells (Ghosh, et al. (2003) J. Biol. Chem. 278:34747-50; Goubaeva, et al. (2003) J. Biol. Chem. 278:19634-41). In vitro experiments revealed that SIRK facilitated nucleotide exchange-independent-A-heterotrimer dissociation (Goubaeva, et al. (2003) supra; Ghosh, et al. (2003) supra) potentially explaining the activation of ERK in intact cells. Other Gβy binding peptides such as QEHA, derived from adenylyl cyclase II (Weng, et al. (1996) J. Biol. Chem. 271:26445-26448; Chen, et al. (1997) Proc. Natl. Acad. Sci. USA 94:2711-2714) and amino acids 643-670 from the C-terminal region of βARK(GRK2) (Koch, et al. (1993) supra) could not promote dissociation of the heterotrimer, despite competing for Ga subunit binding (Ghosh, et al. (2003) supra). This indicates that competition for Ga-Gβy subunit binding is not sufficient for these peptides to accelerate subunit dissociation.

Using a doping mutagenesis and rescreening strategy, a peptide similar to the SIRK peptide was derived that had higher affinity for Gβ$_1$γ$_2$. The sequence of this peptide is Ser-Ile-Gly-Lys-Ala-Phe-Lys-Ile-Leu-Gly-Tyr-Pro-Asp-Tyr-Asp (SEQ ID NO:2) (SIGK). In vitro studies with the SIGK peptide indicate that it too can displace Gaα from a heterotrimeric complex and also effectively prevents heterotrimer formation (Ghosh, et al. (2003) supra). The mechanism by which SIRK/SIGK mediates the dissociation of Gαii*·GDP from Gβ1γ2 is not fully understood (Ghosh, et al. (2003) supra).

II. SUMMARY

The present invention relates to a method for identifying an agent that modulates at least one activity of a G protein. This method involves contacting a G protein β subunit with a test agent and determining whether the agent interacts with at least one amino acid residue of the protein interaction site of the β subunit thereby identifying an agent that modulates at least one activity of the G protein.

The present invention also relates to a method for identifying an agent that binds at least one amino acid residue of the protein interaction site of the β subunit. The method involves the steps of contacting a G protein β subunit with a test agent in the presence of a peptide that binds at least one amino acid residue of the protein interaction site of β subunit, and determining whether the agent inhibits the binding of the peptide to the at least one amino acid residue of the protein interaction site of the β subunit thereby identifying an agent that binds at least one amino acid residue of the protein interaction site of the β subunit.

The present invention further relates to a method for modulating at least one activity of a G protein. This method involves contacting a G protein with an effective amount of an agent that interacts with at least one amino acid residue of the protein interaction site of the G protein β subunit so that at least one activity of the G protein is modulated.

The present invention is also a method for preventing or treating a disease or condition involving at least one G protein βγ subunit activity. The method involves administering to a patient having or at risk of having a disease or condition involving at least one G protein βγ subunit activity an effective amount of an agent that interacts with at least one amino acid residue of the protein interaction site of the G protein β subunit so that the at least one activity of the G protein is modulated thereby preventing or treating the disease or condition involving the at least one G protein βγ subunit activity. Diseases or conditions which involve G protein βγ subunit activities include heart failure, addiction, inflammation, and opioid tolerance.

A kit for identifying an agent that binds at least one amino acid residue of the protein interaction site of the β subunit is also provided. The kit of the invention contains a SIGK peptide or SIGK peptide derivative. Or other of the family of phage display derived peptides from the original peptide screen described in Scott et al. 2001.

Agents identified in accordance with the screening methods of the present invention are further provided, wherein said agents have a structure of Formula I, II, or III.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows selective binding and modulation of the βγ "hot spot" by peptides. FIG. 1A shows single alanine substituted mutants of G β1 were purified as β1γ2 and tested for SIGK and SCAR binding in the phage ELISA. FIG. 1B shows the equilibrium measurements of SIGK and SCAR peptide dependent competition for a subunit binding. Peptides, Fα$_{i1}$GDP, and β1γ2 subunits were mixed for 1 h and Fα$_{i1}$ subunit binding was measured. FIG. 1C shows dissociation rate measurements of α subunit dissociation from a preformed Fα$_{i1}$GDPβ1γ2 heterotrimer. Peptides were added at time 0.

FIG. 2 shows that small molecules predicted to bind to the Gβ protein interaction site can interfere with peptide interactions at the protein interaction site. 1, control (DMSO); 2, NSC30820; 3, NSC12155; 4, NSC13984; 5, NSC117079; 6, NSC610930; 7, NSC293161; 8, NSC23128; 9, NSC402959; 10, NSC109268; 11, NSC125910; 12, SIGK in DMSO. 20 μM of SIGK or 200 μM of each small molecule were used in the assay.

FIG. 3 shows the identification of small molecule ligands that bind to the Gβγ "hot spot" A) depiction of the "hot spot" binding surface on Gβ1γ2 that was targeted in the computational screen. FIG. 3B shows competition ELISA data for three of the compounds identified in the virtual screen. Compounds were tested for their ability to inhibit binding of a phage displaying the peptide SIGKAFKILGYPDYD (Davis et al., 2005; Scott et al., 2001). M119 (■); M109 (▼); M117 (●). Data for the binding compounds are summarized in Table 1. FIG. 3C shows structures of representative βγ-binding compounds. FIG. 3D shows the competition of M119 for interactions between Gα$_{i1}$ and Gβ1γ2. F-α$_{i1}$ and M119 were simultaneously added to Gβ1γ2 immobilized on streptavidin beads. The amount of bead based fluorescence was assessed by flow cytometry as described (Ghosh et al., 2003; Sarvazyan et al., 1998)

FIG. 4 shows the differential effects of M119 and M201 on βγ-dependent regulation of downstream targets. FIG. 4A shows the effects of M119 and M201 (NSC201400) on Gβγ-activation of PLCβ2. Purified PLCβ2 (0.25 ng) was assayed in the presence (▲) or absence (■) of 100 nM purified Gβ1γ2. FIG. 4B shows the effects of M119 and M201 effects on purified PLCβ3 (0.5 ng) activity in the presence (▲) or absence (■) of 100 nM purified Gβ1γ2. FIG. 4C shows the effects of M119 and M201 on activation of PI3Kγ by Gβ1γ2. Assays contained 10 ng of purified p101/p110 PI3Kγ heterodimer with or without 100 nM purified Gβ1γ2. Left panel: (▲) 100 nM Gβ1γ2 or (■) no βγ. FIG. 4D shows the effects of M119 and M201 on Gβγ-GRK2 interactions. M119 or M201 and 25 nM purified GRK2 were added simultaneously to 250 nM biotinylated Gβ1γ2 (bGβ1γ2) immobilized on streptavidin agarose. GRK2 was detected with antibody to GRK2. Data are representative (mean ±SEM, except D) repeated at least three times each. FIG. 4E shows that M119 (10 μM) but not M201 (1 μM) blocks PLCβ binding to biotinylated-Gβ1γ2 (bGβ1γ2). 30 nM bGβ1γ2 was incubated with either 30 nM PLCβ2 or PLCβ3 in the presence or absence of M119 or M201 for 16 h at 4° C. before precipitation with avidin agarose and detection with PLCβ2,or Gβ antibodies. FIG. 4F shows that M201 enhances binding of PLCβ3 to bGβ1γ2. Same as 4E with PLCβ3.

FIG. 5 shows the effects of M119 and related compounds on Gβγ signaling in DMSO differentiated HL60 cells. FIG. 5A shows that M119 and related compounds block fMLP-dependent Ca$^{2+}$ release in cells loaded with 1 μM Fura2-AM. Cells were pretreated with DMSO or 10 μM compounds for 5 min prior to stimulation with 250 nM fMLP. FIG. 5B shows that there was no effect of M119 (10 μM) on carbachol-dependent Ca$^{2+}$ release from HEK-293 cells stably expressing M3 muscarinic receptors. Normalized peak Ca$^{2+}$ responses were pooled from three independent experiments each (mean±SEM). Cells were pretreated with DMSO (■) or compounds (▲) for 5 min prior to stimulation. FIG. 5C is the same as A except 10 μM M201 was tested. FIG. 5D shows pooled data for FIG. 5C. FIG. 5E shows the M119 and M201 inhibition of GRK2 translocation. Differentiated HL60 cells were treated with 10 μM compound prior to stimulation with 250 nM fMLP. Translocation of endogenous GRK2 was determined by Western blotting with a GRK2 antibody and quantitative chemiluminescence. Data are mean±SEM from 5 experiments, * P<0.05, P<0.01 ANOVA. FIG. 5F shows M119 and M158C inhibition of GFP-PHAkt translocation. Differentiated HL60 cells stably over-expressing GFP-PHAkt were treated with 10 μM compound prior to stimulation with 100 nM fMLP. Translocation of GFP-PHAkt to the membrane was determined by Western blotting with an anti-GFP antibody and quantitative chemiluminescence. Data are mean±SEM from 4 experiments. * P<0.001 ANOVA. FIG. 5G shows the lack of effect of M119, 158C and M201 on fMLP-induced ERK1 and ERK2 activation. Differentiated HL60 cells were pretreated with 10 μM of compound prior to stimulation with 1 μM fMLP for 5 min. Levels of phosphorylated and total ERK were determined by Western blotting.

Figure 8A:
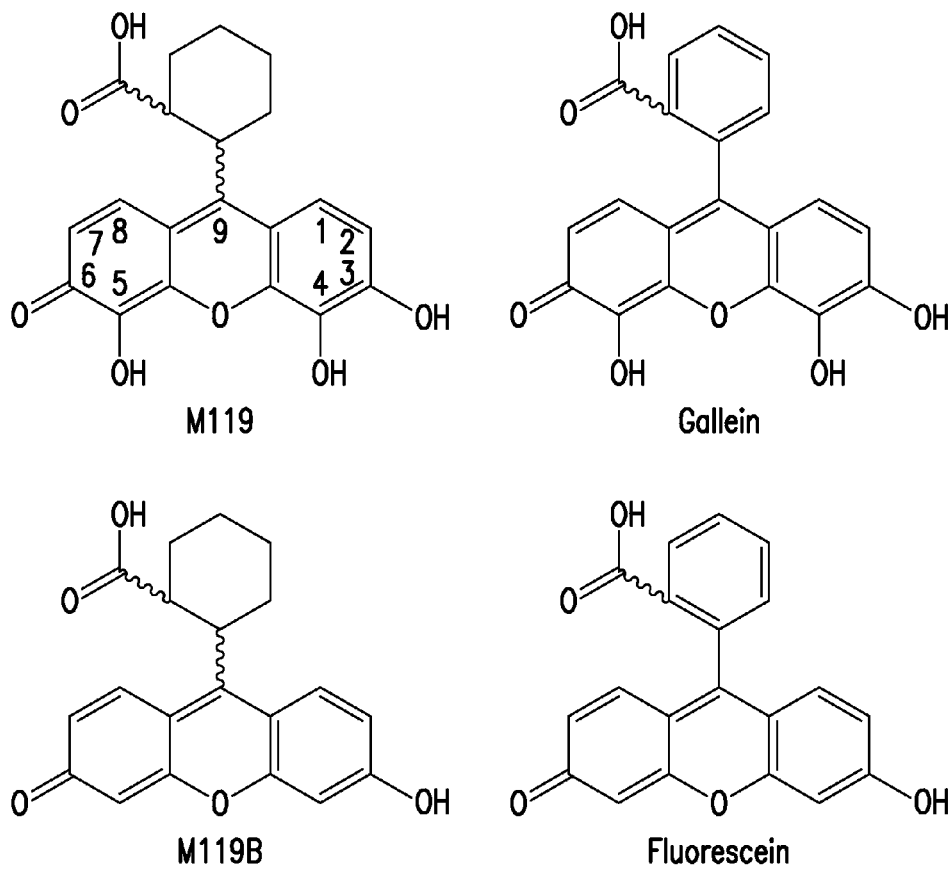
Figure 8B:
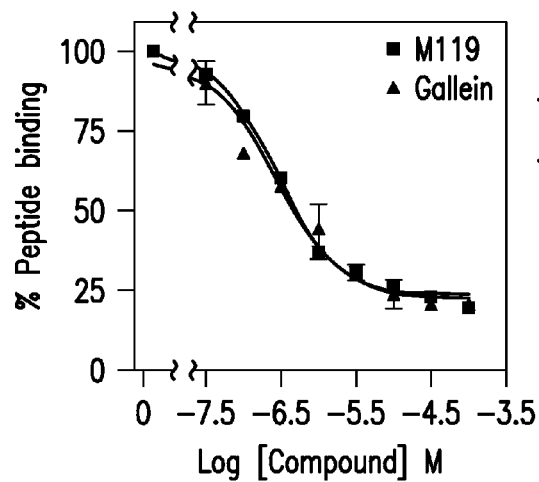
Figure 8C:
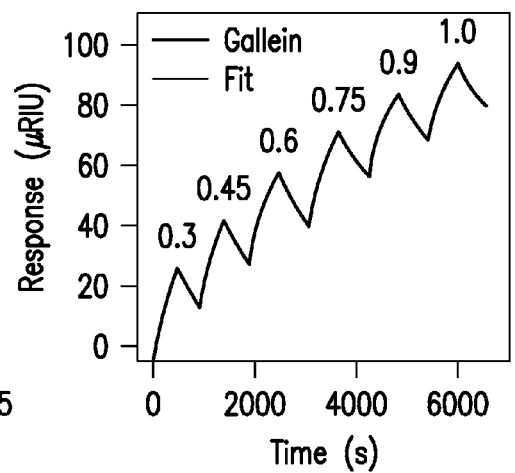

FIG. 8 shows small molecule binding profiles. FIG. 8A shows the structures of M119, M119B, gallein, and fluorescein are shown. FIG. 8B shows that M119 and gallein bind with comparable affinities in the competition phage ELISA. M119 and gallein were tested for their ability to inhibit binding of a phage displaying the peptide SIGK to the Gβγ "hot spot" as described previously (Bonacci et al., 2006). Data shown is representative of three independent experiments, each in duplicate, ±S.D. FIG. 8C shows direct binding analysis of gallein bind to Gβγ by SPR. A representative experiment for gallein binding to $bG\beta_1\gamma_2$. Gallein binding was tested at sequentially higher micromolar concentrations indicated at the peak of each association followed by a dissociation phase with the compound removed between each addition. All data were fit with a kinetic titration model (Karlsson et al., 2006) to give $k_a$ and $k_d$ values. In the experiment shown, the fits resulted in $k_a=1130\pm17$ $M^{-1}$ $s^{-1}$ and $k_d=4.3\pm0.04\times 10^{-4}$ $s^{-1}$. Pooled data from three separate experiments are given in Table 21.

FIG. 9 shows that "Hot spot" binding small molecules modulate key leukocyte functions. FIG. 9A shows that M119 and gallein inhibit GFP-PH-Akt translocation. Differentiated HL60 cells stably expressing GFP-PH-Akt were challenged with 250 nM fMLP in the presence and absence of 10 μM concentrations of the indicated compounds. Translocation of GFP-PH-Akt to the plasma membrane was evaluated by Western blot. Quantification shown below. ***, P<0.001 analysis of variance (ANOVA) is statistically different from control (PBS+vehicle). Western blot shown is representative of three independent experiments and quantitation contains data pooled from three independent experiments±S.E.M. FIG. 9B shows that M119 and gallein block activation of Rac1. Differentiated HL60 cells were challenged with 1 μM fMLP in the presence and absence of 10 μM concentrations of the indicated compounds. Rac1 activation was assessed by Western blots of affinity-precipitated GTP-Rac1 from HL60 cell lysates. Western blot shown is representative of three independent experiments and quantitation contains data pooled from three independent experiments±S.E.M. *P<0.05 ANOVA is statistically different from control (DMSO only). n=3. FIGS. 9C and 9D shows that M119 and gallein inhibit superoxide production in fMLP-challenged HL60 cells. Differentiated HL60 cells were challenged with 250 nM fMLP or 250 nM PMA in the presence and absence of 10 μM compounds or 100 nM Wortmannin (Wtmn). NADPH oxidase activity was determined after reaction with NBT by absorbance at 540 nm. Data shown is contains data pooled from three independent experiments (each in duplicate)±S.E.M. *, P<0.05 ANOVA is statistically different from control (DMSO only).

FIG. 10 shows Gβγ "hot spot" binding small molecules inhibit neutrophil recruitment and acute phase inflammation in vivo. FIG. 10A shows gallein inhibition of carrageenan-induced paw edema. Male mice (35-40 g) were injected i.p. with 100 mg/kg gallein or 2.5 mg/kg indomethacin in PBS 1 h before subplantar injection of 50 μl of 2% carrageenan (Cg) into the test paw. The contralateral paw was injected with saline as control. Each paw was measured 3 times every 2 h. Change in paw thickness was quantified by subtracting the average thickness of the contralateral paw from the average thickness of the test paw. Each point represents the average paw thickness of four mice, each measurement done in duplicate. Data shown is representative of more than three independent experiments. Data are mean±S.E.M. FIG. 10B shows that gallein inhibits carrageenan-induced paw edema in a dose-dependent manner. Mice (four mice per plotted point) were treated and quantified as described above. Data are mean±S.E.M. FIG. 10C shows that neutrophil recruitment is attenuated by gallein. Mice (four mice per plotted point) were treated as described above. Two hours after carrageenan injection, paws were severed and the number of neutrophils contained within edematous fluid was determined. Data are mean±S.E.M. *, P<0.001 and , P<0.01 ANOVA are statistically different from control. FIG. 10D shows that paw swelling is reduced by gallein. Mice (four mice per plotted point) were treated as described above. Two hours after carrageenan injection, paws were severed, and the volume of edematous fluid was determined. ***P<0.001 ANOVA is statistically different from control. FIG. 10E shows the differentiated HL60 cells (200 k) were pre-treated with 10 μM M119 and then placed in the upper chamber with 250 nM fMLP in the lower chamber for one hour. Chemokinesis (CK) was tested using fMLP in both the upper and lower compartments of the Boyden chamber. n=2, each in duplicate. FIG. 10F shows the effects of M119, DL382, and wortmannin on fMLP-induced chemotaxis in primary human neutrophils (expressed as % of uninhibited fMLP-dependent migration). Same as A with purified human neutrophils.

FIG. 11 shows that "Hot spot" binding small molecules inhibit GPCR-coupled chemoattract-dependent chemotaxis. FIG. 11A shows that M119 and gallein inhibit fMLP-induced chemotaxis in differentiated HL60 cells. Differentiated HL60 cells (200 k) were pretreated with 10 μM concentrations of the indicated compound, challenged with 250 nM fMLP, and assayed for chemotaxis in a Boyden chamber for 1 h at 37° C. Chemotaxis was quantified by counting Diffquik-stained cells in three random microscope fields, subtracting out background cells (0-10 cells) in the absence of chemoattractant to obtain total transmigrated cells (~125 cells fMLP+vehicle), and represented as the percentage of fMLP-treated control cells. *, P<0.001 ANOVA is statistically different from control. Data shown pooled from three independent experiments, each in duplicate, ±S.E.M. FIG. 11B shows that neither M119 nor gallein blocks 1 μM GM-CSF-induced chemotaxis in a Boyden chamber. Chemotaxis was quantified as above by subtracting out background cells (0-10 cells) in the absence of chemoattractant to obtain total transmigrated cells (~100 cells GM-CSF+vehicle) and represented as the percentage of GM-CSF-treated control cells. No statistically significant difference from control was seen by ANOVA. Data shown are pooled from two independent experiments, each performed in duplicate, ±S.E.M. FIG. 11C shows that M119 and gallein inhibit fMLP- and IL-8-induced chemotaxis in human neutrophils in a Boyden chamber. Primary human neutrophils were isolated from whole blood to ≥80% purity. Neutrophils (2×10$^5$) were pretreated with gallein (10 µM), M119 (10 µM), M119B (10 µM), or wortmannin (wtmn.) (1 µM) and then challenged with 250 nM fMLP or 10 nM IL-8 to evaluate chemotaxis in a Boyden chamber for 1 h at 37° C. Chemotaxis was quantified as above by subtracting out background cells (0-10 cells) to obtain total transmigrated cells (fMLP ~100 cells and IL-8 ~175 cells) and represented as the percentage of chemoattractant-treated control cells. *, $P<0.001$ ANOVA is statistically different from control. NS, not statistically different from control. Data are mean±S.E.M. Data shown are pooled from three independent experiments, each in duplicate, ±S.E.M. FIG. 11D shows that gallein dose-dependently inhibits human neutrophil chemotaxis in a Boyden chamber. Primary human neutrophils were isolated and treated (250 nM fMLP±gallein) as described above. Chemotaxis was quantified as above by subtracting out background cells to obtain total transmigrated cells and represented as the percentage of fMLP-treated control cells. Data shown are pooled from two independent experiments, each in duplicate, ±S.E.M.

Figure 12:
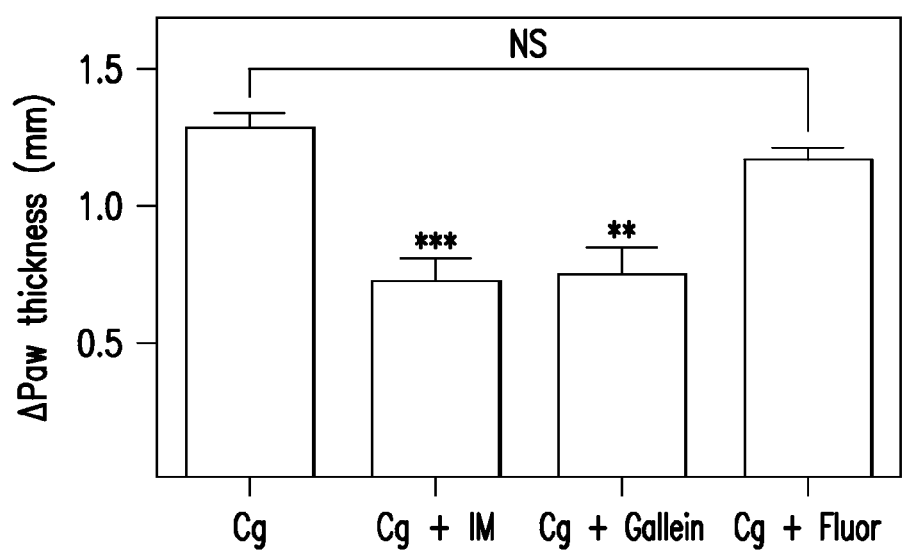

FIG. 12 shows that Gallein is effective with oral administration. Male mice (35-40 g) were dosed by oral gavage with 30 mg/kg gallein 1 h before challenge with 2% carrageenan. Methods are as described in FIG. 4. Each bar represents the average paw thickness of four mice at 3 h after carrageenan injection, each measurement done in duplicate. Data are mean±S.E.M. *, $P<0.001$ and , $P<0.01$ ANOVA are statistically different from vehicle. NS, not statistically different from control. Data shown are representative of two independent experiments.

FIG. 13 shows the antinociceptive effect of morphine (A and B). Wild-type (●, +/+) or mutant (○, −/−) mice were administered different doses of morphine i.p. (A) or i.c.v. (B). Receptor selectivity of antinociceptive effect (C and D). Morphine was administered i.c.v. to wild-type (C) or transgenic (D) mice with or without pretreatment with i.c.v. β-FNA (20 nmol, −24 hr) or co-administered either the κ-selective antagonist, nor-BNI (3 nmol), or the δ-selective antagonist, ICI 174,864 (4 nmol). Antinociception was measured in the mouse tail flick assay 20 min after the administration of morphine. Data are presented as the mean percentage antinociception±SEM. Six to 10 mice were used to obtain each point. *, Significantly different from morphine, $P<0.01$. Data are from Xie et al. (1999).

FIG. 14 shows shows the effects of M119 on morphine-induced anti-nociception in A) WT and B) PLCβ3−/− mice. Morphine was administered i.c.v. to mice (■) with or without (▲) 100 nmol M119. Anti-nociception was measured 20 min. after injection using the 55° C. tail flick test. Mean±SEM, 7-10 animals at each point.

FIG. 15 shows that the µ agonists, DAMGO (10 µM) and morphine (10 µM) both significantly increased the total inositol phosphates measured in hMOR-CHO cells, ** $p<0.01$ compared to control (A). Both M119 (10 µM) and β-FNA (10 µM) attenuated this response, *$p<0.05$ compared to the agonist alone. The κ-selective agonist, U50,488 (10 µM) had no significant effect on IP generation with or without M119 (10 µM) or nor-BNI (10 µM), in the hKOR-CHO cells (B). In the hDOR-CHO cells neither δ-selective agonist, DPDPE (10 µM) (C) or Deltorphin II (10 µM) (D) significantly increased IP generation over control treated cells. The δ-selective antagonist, naltrindole (100 µM), had no effect.

Figure 16A:
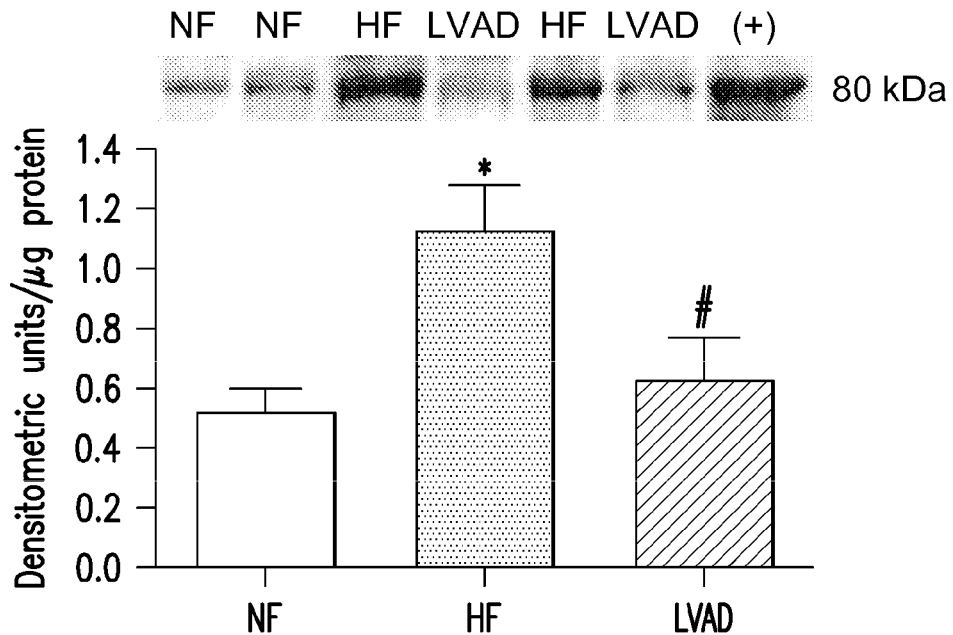
Figure 16B:
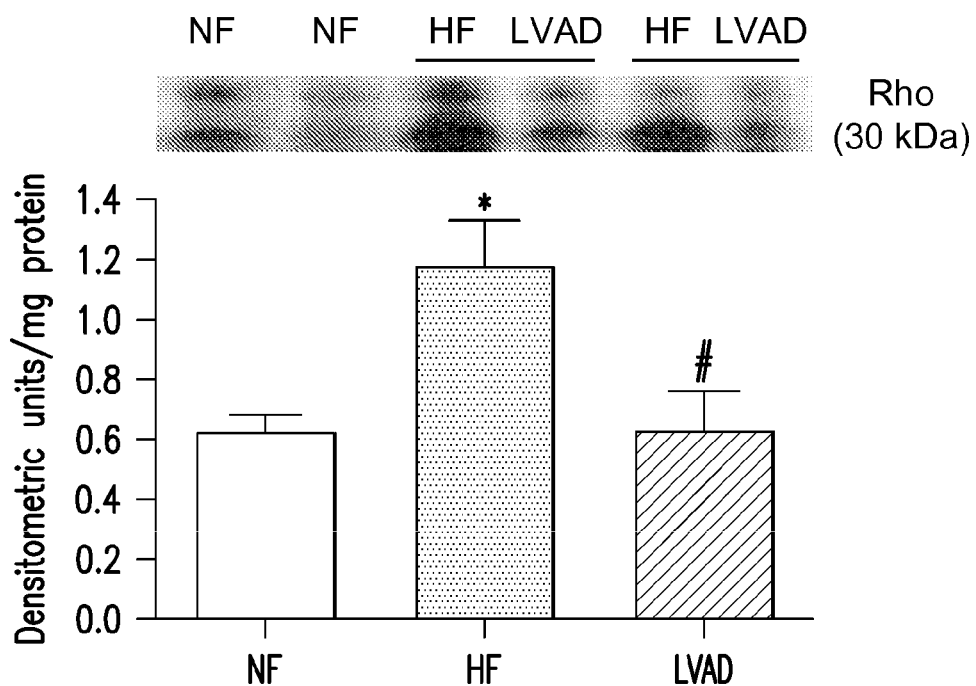

FIG. 16 shows GRK2 expression and activity in non-failing (NF, n=6) and paired LV samples (n=12) obtained upon LVAD implantation (HF) and subsequent cardiac transplantation (LVAD). (A) GRK2 protein immunoblotting, mean±SEM. Samples from non-failing hearts (NF) were also analyzed (n=6). (+) control is purified GRK2. (B) Soluble cardiac lysates were incubated with [32P-ATP] and purified rod outer segment membranes enriched with the GPCR rhodopsin (Rho). incorporation into Rho after gel electrophoresis. *, $p<0.05$ HF vs NF; #, $p<0.0005$ LVAD vs HF.

FIG. 17 shows that Gβγ blockade with M119 normalizes cardiac function and reduces pathologic cardiac hypertrophy. FIG. 17A shows M-mode echocardiographic images of conscious adult C57/B16 male mice following 1 week of either vehicle or Iso (30 mg/kg/day) delivered by miniosmotic pumps (Veh, . . . or Iso, . . . , respectively) and concurrent daily vehicle or M119 (100 mg/kg) injections ( . . . , Veh, or . . . , Cmpd, respectively). FIG. 17B shows that animals were treated the same as in (A). Conscious echocardiography was performed on animals prior to sacrifice. % FS is a measure of cardiac contractility derived from end-diastolic and end-systolic diameters. FIG. 17C shows gross morphological assessment of HW:BW in animals from (A) and (B). Heart weight to body weight ratio (HW:BW) was assessed upon sacrifice of the animal. (n=7-8 per condition)

Figure 18:
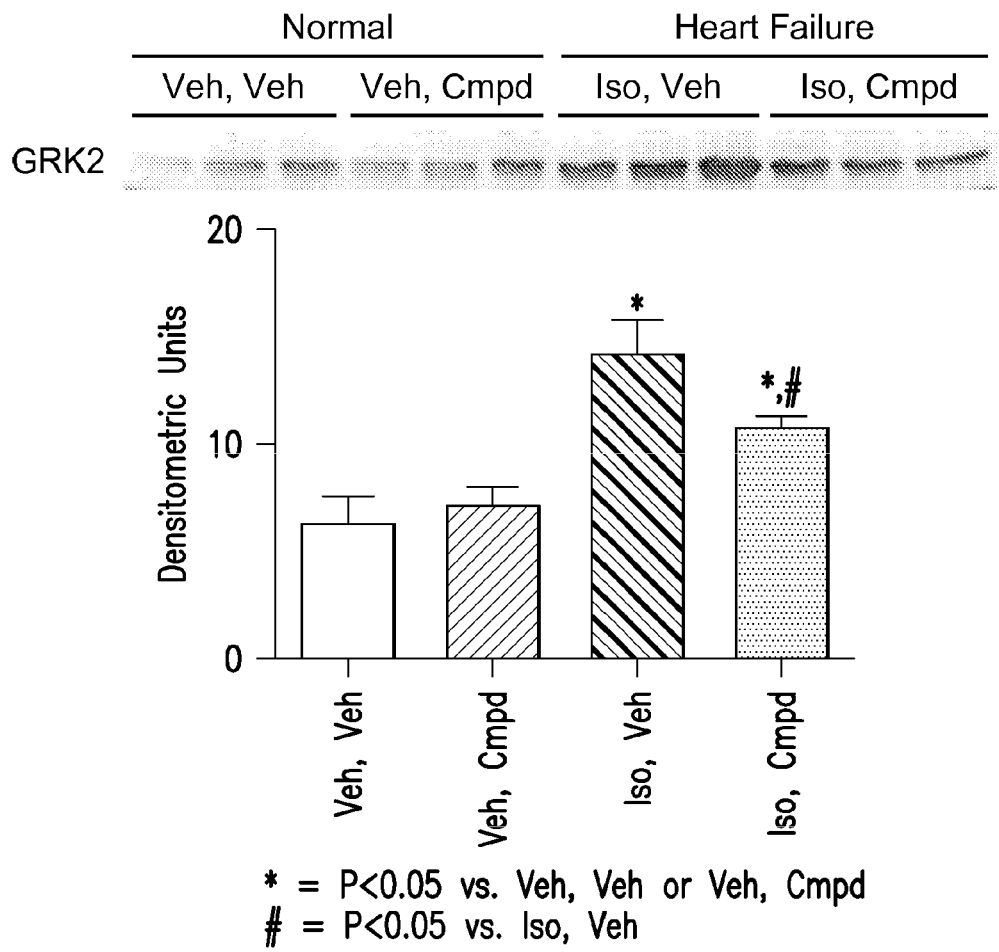

FIG. 18 shows that Gβγ blockade with M119 normalizes GRK2 expression in HF. Immunoblot for GRK2 of equal amounts of total protein isolated from hearts of adult C57/B16 male mice following 1 week of either vehicle or Iso (30 mg/kg/day) delivered by miniosmotic pumps (Veh, . . . or Iso, . . . , respectively) and concurrent daily vehicle or M119 (100 mg/kg) daily injections ( . . . , Veh, or . . . , Cmpd, respectively).

FIG. 19 shows that M119 enhances cardiomyocyte contractility in vitro. FIG. 19A shows representative tracings of untreated isolated adult cardiomyocytes and cells treated with M119, Iso, or M119 and Iso. FIG. 19B shows the averaging of 4-7 independent experiments (1 experiment=average of≥7 cardiomyocytes per condition) showing that M119 treatment significantly increased percent contractility over baseline and enhanced Iso-stimulated contractility. Pretreatment with the general β-AR antagonist, propranolol, abolishes the effects of M119 and Iso on cardiomyocyte contractility. FIG. 19C shows that DL382 also increases the rate of shortening both in the presence and absence of Iso. *$P<.05$, $P<.01$, *$P<.001$

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Treatment," "treat," or "treating" mean a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression. For example, a disclosed method for reducing the effects of inflammation, treating seizures, treating heart malfunction, or any other method disclosed herein is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition.

A "decrease" can refer to any change that results in a smaller amount of a composition or compound, such as AR. Thus, a "decrease" can refer to a reduction in an activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed.

An "increase" can refer to any change that results in a larger amount of a composition or compound, such as AR relative to a control. Thus, for example, an increase in the amount in AR can include but is not limited to a 10%, 20%, 30%, 40%, 50%, 60%, 70%, 80%, 90%, or 100% increase.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The protein interaction site for G proteins has now been appreciated. The structure of Gβγ bound to SIGK was elucidated and indicates that SIGK binds to Gβγ as an α helix across the Gα interaction surface, in a position occupied by an α helical region of the switch II domain of Gα in the heterotrimer. The conformations of Gβγ in the presence and absence of SIGK are very similar. Thus, the crystal structure reveals how the peptide blocks Gα-Gβγ interactions. The structure further indicates that Gβ has evolved a highly reactive and specialized surface for interaction with diverse protein partners. This specialized surface is referred to herein as the "protein interaction site" or "protein interaction site of Gβ." Analysis of various characteristics of the protein interaction site led to the understanding that the basis for this surface as a preferred interaction surface is not an inherent conformational flexibility or unusually high surface accessibility of the site, but rather the prevalence of multiple types of potential interaction chemistries in this single binding surface. The specific amino acid combinations at this surface required for amino acid sequence recognition at the protein interaction site have also been determined. Moreover, the specific molecular interactions necessary for either acceleration of heterotrimer dissociation or inhibition of protein complex formation have been demonstrated.

Accordingly, the present invention relates to a method for identifying an agent that modulates (i.e., blocks or inhibits, or activates or potentiates) at least one activity of a G protein by contacting a G protein β subunit with a test agent (e.g., in a high-throughput screen) and determining whether the test agent interacts with at least one amino acid residue of the protein interaction site of the G protein β subunit. A G protein β subunit is intended to include any one of the five known mammalian G protein β subunit isoforms (Offermanns (2003) supra). An activity of a G protein is intended to mean the transduction of signals through the G protein to one or more downstream proteins including, but not limited to, G protein-regulated inward-rectifying potassium channel (GIRK); type I, type II, and type IV isoforms of adenylyl cyclase; mitogen-activated protein kinase (MAPK); phosphotidylinositol-3-kinase (PI3K); G protein receptor kinase (GRK) family members; and other plextrinhomology (PH) domain-containing proteins including the dynamins and the β1, β2, and β3 isoforms of phospholipase C β (PLC β). Modulation of G protein activity occurs via binding of the agent to at least one amino acid residue of the protein interaction site thereby blocking interactions between the Gβγ subunits and Gα subunit or the Gβγ subunits and the downstream proteins described herein.

The crystal structure of Gβγi bound to SIGK revealed that the SIGK peptide interacts with residues of Gβ1 subunit that are utilized by several Gβγ binding proteins {e.g., downstream proteins). For example, Lys57, Tyr59, Trp99, Met101, Leu117, Tyr145, Met188, Asp246, and Trp332 of Gβ1 are involved in contacts with the GRK2 PH domain in the crystal structure of the Gβ1γ$_2$>>GRK2 complex, and all of these residues of Gβ1 are involved in SIGK contacts as well (Table 1). This is in spite of the fact that the secondary-structures of the PH domain that contact Gβ1 (the RH-PH loop, the αCT region, and β4 strand) are completely dissimilar to the purely helical SIGK peptide (Lodowski, et al. (2003) supra). This theme is recapitulated in the complex of Gβ1 with phosducin (Ford, et al. (1998) supra) where a common subset of Gβ1 residues contacts a binding partner with different secondary structure from GRK2. Notably, the switch II region of Gαii forms an α-helix that is bound in almost the same orientation as the SIGK peptide. However, switch II of Gαn has no sequence similarity to the SIGK peptide, although it contains a lysine (Lys210) which is oriented in almost the same position as Lys4 of SIGK (Goubaeva, et al. (2003) supra).

TABLE 1

| Gα$_{i1}$ | Phosducin | GRK2 | SIGK | PLCβ | AC | GIRK | Ca$^{++}$ |
|---|---|---|---|---|---|---|---|
|  | 42 |  |  |  |  |  |  |
|  | 44 |  |  |  |  |  |  |
|  | 46 |  |  |  |  |  |  |
|  | 47 |  |  |  |  |  |  |
| 52 |  |  |  |  |  |  |  |
| 53 |  |  |  |  |  |  |  |
| 55 |  | 55 |  |  | 55 | 55 | 55 |
| <u>57</u> | <u>57</u> | <u>57</u> | Lys57 |  | <u>57</u> |  | <u>57</u> |
| <u>59</u> | <u>59</u> | <u>59</u> | Tyr59 |  |  | <u>59</u> |  |
| 75 | 75 | 75 |  |  |  |  |  |
|  |  | 76 |  |  |  |  |  |
| 78 |  | 78 |  |  | 78 | 78 | 78 |
| 80 |  |  | 80 |  |  | 80 |  |
| 88 |  |  |  |  |  |  |  |
| 89 |  |  | 89 |  | 89 | 89 |  |

TABLE 1-continued

| Gα$_{i1}$ | Phosducin | GRK2 | SIGK | PLCβ | AC | GIRK | Ca$^{++}$ |
|---|---|---|---|---|---|---|---|
| 90 |  |  |  |  |  |  |  |
| 91 |  |  |  |  |  |  |  |
| 92 |  |  |  |  |  |  |  |
|  |  |  | 95 |  |  |  |  |
|  |  |  | 96 |  |  |  |  |
|  | 98 | 98 |  |  |  |  |  |
| <u>99</u> | <u>99</u> | <u>99</u> | Trp99 | <u>99</u> | <u>99</u> | <u>99</u> |  |
|  |  |  | Val100 |  |  |  |  |
| <u>101</u> | <u>101</u> | <u>101</u> | Met101 | <u>101</u> | <u>101</u> |  | <u>101</u> |
| <u>117</u> | <u>117</u> | <u>117</u> | Leu117 | <u>117</u> | <u>117</u> |  | <u>117</u> |
| 119 |  |  |  | 119 | 119 |  | 119 |
| 132 |  |  |  |  |  |  |  |
| 143 |  |  |  |  | 143 |  | 143 |
| 144 |  |  |  |  |  |  |  |
| <u>145</u> | <u>145</u> | <u>145</u> | Tyr145 |  |  |  |  |
|  | 162 |  |  |  |  |  |  |
| 182 |  |  |  |  |  |  |  |
| <u>186</u> | <u>186</u> |  | Asp186 | <u>186</u> | <u>186</u> |  | <u>186</u> |
| <u>188</u> | <u>188</u> | <u>188</u> | Met188 |  |  |  |  |
| 204 | 204 | 204 |  |  |  |  |  |
| <u>228</u> | <u>223</u> |  | Asp228 | <u>228</u> | <u>228</u> | <u>228</u> | <u>228</u> |
| <u>230</u> | <u>230</u> |  | Asn230 |  |  |  |  |
| <u>246</u> | <u>246</u> | <u>246</u> | Asp246 | <u>246</u> | <u>246</u> |  |  |
|  | 274 |  |  |  |  |  |  |
|  | 290 | 290 |  |  |  |  |  |
|  | 292 |  |  |  |  |  |  |
|  | 304 |  |  |  |  |  |  |
|  | 310 |  |  |  |  |  |  |
|  | 311 |  |  |  |  |  |  |
|  | 314 | 314 |  |  |  |  |  |
| <u>332</u> | <u>332</u> | <u>332</u> | Trp332 | <u>332</u> | <u>332</u> |  | 332 |
| 41% | 44% | 44% | — | 54% | 67% | 43% | 60% |

Key to column headings: Gαn, the crystal structure of the Gαii>>Gβ1γ$_2$ heterotrimer (Wall, et al. (1995) supra; Wall, et al. (1998) supra); phosducin, the phosducin>>Gβ1γ$_2$ complex (Gaudet, et al. (1996) supra); GRK2, the GRK2>>Gβ1γ$_2$ complex (Lodowski, et al. (2003) supra); SIGK, the SIGK>>Gβ1γ$_2$ complex; PLC β, mutational analysis of the PLC β2/3#Gβ1Y2 complexes (Li, et al. (1998) supra; Ford, et al. (1998) supra); AC, mutational analysis of the adenylyl cyclase type I/II>>Gβ1γ$_2$ complex (Ford, et al. (1998) supra); GIRK, mutational analysis of Gβχγ$_2$ interaction with the GIRK1/4 channels (Ford, et al; i998) supra); Ca$^{++}$, mutational analysis of Gβ1γ$_2$ interaction with N or P/Q type calcium channels (Ford, et al. (1998) supra; Agler, et al. (2003) J. Gen. Physiol. 121: 495-510). Underlined residues indicate residues important for the SIGK>>Gβ1γ$_2$ interaction. The last row indicates the percentage of residues that are shared between the target and the SIGK interfaces.

When mutational data for Gβγ targets PLC β2, adenylyl cyclase, and GIRK and CCα1B calcium channels are included in this analysis, the footprint of SIGK upon Gβ is similar to the footprints of these former targets (Li, et al. (1998) supra; Ford, et al. (1998) supra). Of the thirteen residues from Gβ that encompass the protein interaction site, nine (Lys57, Tyr59, Trp99, Met101, Leu117, Tyr145, Met188, Asp246, and Trp332) are also found as contacting residues in the Gα, GRK2, and phosducin complexes (Table 1). These residues reflect a consensus set of residues utilized by many Gβ binding partners. An additional three of the thirteen residues (Asp186, Asp228, and Asn230) are shared amongst SIGK and two of the other protein complex structures. One of the thirteen, Val100, contacts SIGK through its main chain oxygen and is not involved in binding interactions in the other complexes. The SIGK binding residues that are most sensitive to mutational perturbation are also the most frequently involved in interactions with other Gβ binding partners. SIGK was identified from a random peptide phage display where multiple peptides, unrelated by sequence, appeared to bind to a common protein interaction site on Gβa.

Because of the extensive overlap between the residues of Gβ1 that are accessed by SIGK and those involved in the binding of protein Gβγ targets, SIGK is a competitive inhibitor of multiple Gβγ binding reactions. The closely related SIRK peptide has effects on several Gβγ-dependent pathways; it blocks Gβγ-mediated activation of PLC β2, PLC β3 and PI3K in enzyme assays, and induces ERK I/II activation in a cell-based assay (Scott, et al. (2001) supra; Goubaeva, et al. (2003) supra). These effects are sensitive to mutations of residues in SIGK that interact with the surface of Gβ, as Lys4, Ala5, Phe6, Ile8, Leu9, and Gly10 of SIGK have all been shown by alanine scanning to be important for inhibition of PLC β2 activation by Gβ1γ$_2$ (Scott, et al. (2001) supra). In addition, Leu9 of SIGK is important for the ability of SIGK to activate MAPK pathways in cell culture (Goubaeva, et al. (2003) supra). However, SIRK does not block inhibition of adenylyl cyclase type I or N-type Ca$^{2+}$ channel regulation, even though their footprints are quite similar to those of Gα and PLC β2 (Scott, et al. (2001) supra). Conversely, mutations in Gβ that abrogate SIGK binding do not equally affect interaction with other Gβγ binding partners. For example, mutation of Leu117 to alanine decreases the ability of Gβ1γ$_2$ to activate adenylyl cyclase type II and PLC β3 and to bind GRK2 and SIGK, but has no effect on GIRK1/GIRK4 potassium channel activation, CCα1B calcium channel activation, or PLC β2 activation (Table 1) (Li, et al. (1998) supra; Ford, et al. (1998) supra). Similarly, mutation of Trp332 of Gβ1γ$_2$ to alanine reduces affinity of Gβ1γ$_2$ for SIGK and impairs stimulatory activity towards adenylyl cyclase type II, CCα1B and both PLC β2 and PLC β3, but does not affect interaction with GRK2, activation of GIRK1/GIRK4, or inhibition of adenylyl cyclase type I (Li, et al. (1998) supra; Ford, et al. (1998) supra). Both Leu117 and Trp332 of Gβχγ$_2$ form part of the Gα$_t$ and Gαn binding sites of Gβ1 (Wall, et al. (1995) supra; Lambright, et al. (1996) supra; Wall, et al. (1998) supra) and mutation of Leu117 also affects Gαi$_1$ association with Gβ1γ$_2$ (Li, et al. (1998) supra; Ford, et al. (1998) supra). Unlike other peptides that block heterotrimer formation (Ghosh, et al. (2003) supra), SIGK promotes nucleotide exchange-independent dissociation of Gβ1γ$_2$ from Gαii (Ghosh, et al. (2003) supra; Goubaeva, et al. (2003) supra). For example, a peptide derived from the C-terminus of GRK2 blocks heterotrimer formation (Ghosh, et al. (2003) supra) but does not promote Gαii*Gβ1γ$_2$ subunit dissociation, even though the structure of the GRK2<<Gβ1γ$_2$ complex indicates that this peptide should utilize much the same surface of Gβ1 as SIGK (Lodowski, et al. (2003) supra). Not to be bound by theory, SIGK could promote heterotrimer dissociation by either of two mechanisms. SIGK may induce conformational changes on Gβ1 that propagate beyond the SIGK binding site and disrupt other interactions between Gβ1 and Gαii. However, the Gβ1γ$_2$>>SIGK structure shows that SIGK does not induce substantial conformational change in Gβ1 outside of the SIGK binding site itself. The second mechanism relies on the assumption that Gαn can dynamically detach from and rebind to either of two surfaces on Gβ: the switch II interaction site on the top face of Gβ1, where SIGK binds in a similar orientation, and the N-terminal interaction surface on blade one of Gβ1. Transient release from Gαn at the switch II interface would allow SIGK access to Gβ1. Complete release of Gαn from Gβ could then occur if the off-rate for SIGK is slower than that for dissociation of the N-terminus of Gαn. Thus the GRK2 peptide, which binds the top surface of Gβ, may dissociate too quickly to promote dissociation of Ga. This dynamic model of Gβγ interactions is biologically relevant, since many Gβγ binding targets exhibit binding outside of the top surface of Gβ and may also transiently sample alternate surfaces on Gβ.

The ability of the protein interaction site of Gβ1γ$_2$ to recognize a range of protein ligands with diverse secondary structures indicates that it may be an example of a preferential protein binding site (see, e.g., Delano, et al. (2000) Science 287:1279-1283). Preferential binding surfaces are characterized as having high solvent accessibility, low polarity, and a large degree of conformational flexibility (Scott, et al. (2001) supra; Ma, et al. (2001) Curr. Opin. Struct. Biol. 11:364-9; Bogan and Thorn (1998) J. Mol. Biol. 280:1-9; Clackson and Wells (1995) Science 267:383-6; DeLano (2002) Curr. Opin. Struct. Biol. 12:14-20). Moreover, preferential binding sites are likely to contain an unusually high concentration of so-called "hot spots", i.e., residues that, if mutated to alanine, reduce binding energy at least ten-fold (DeLano (2002) supra). Hot spots have been described for both protein-protein and protein-small molecule interfaces; often point mutations to any hot spot on a surface completely abrogate complex formation, even when the binding interfaces bury several hundred A2 of total surface area (Bogan and Thorn (1998) supra; Clackson and Wells (1995) supra; Thanos, et al. (2003) J. Am. Chem. Soc. 125:15280-1; Zhang, et al. (2003) J. Biol. Chem. 278:33097-104). These criteria have been used herein to evaluate the protein interaction site of Gβ1 as a protein surface that is predisposed by its chemical composition and surface properties to serve as a protein binding site. Of the twelve residues in the protein interaction site of Gβ, eight (Lys57, Tyr59, Leu117, Tyr145, Asp186, Met188, Asn230, and Trp332) met the energetic criterion for a hot spot residue. Replacement of any of these residues by alanine resulted in a 10-fold reduction in the affinity of Gβ1Y2 for SIGK. It is clear that all of these residues act as energetically important nodes that contribute favorably to SIGK binding. The SIGK binding surface of Gβ1 contains several residues that have been shown to be enriched in hot spots (Bogan and Thorn (1998) supra). These include tyrosine, tryptophan and arginine; bulky residues that are capable of forming both polar and non-polar interactions. The protein interaction site of Gβ is significantly more populated with aromatic residues than the rest of the Gβ surface. 38% of the SIGK binding surface versus 8.5% of the total non-glycine surface accessible Gβ residues is composed of Phe, Tyr, His, or Trp. Therefore, the protein interaction site of Gβ is more nonpolar; in total, 62% of the protein interaction site of Gβ is nonpolar compared to 29% of Gβ surface accessible residues. Further, asparagine and aspartic acid, which have a moderately favorable distribution among hot spot surfaces, account for four of the thirteen residues in the protein interaction site of Gβ. This combination of aromatic and charged residues allows for accommodation of binding partners with diverse chemical properties at the Gβ protein interaction site. Preferential binding surfaces are expected to have high surface accessibility (DeLano, et al. (2000) supra). To analyze this property of the protein interaction site of Gβ, the total surface accessible area was calculated for the Gβ molecule on a residue, main chain, and side chain basis. Most amino acids in the protein interaction site of Gβ were not significantly more accessible than others of their type in Gβ. However, five residues showed significant deviation from the mean: Tyr59, Trp99, Met101, Leu117, and Trp332. In the case of Trp99, side chain surface accessibility was significantly greater than the type average; the main chain of Tyr59, Trp99, and Met101 were more accessible than the mean. Leu117 had significantly higher main chain and side chain accessibility than the mean.

Conformational flexibility or adaptability has been cited as an important determinant of a preferential binding surface, since such surfaces are better able to bind to structurally unrelated protein targets (DeLano, et al. (2000) supra). Residue flexibility can be quantified in terms of relative positional variation in the context of several protein complexes. Histogram analysis of the RMSD relative to uncomplexed Gβ1Yi of all Gβ residues in four crystal structures (Gp$_1$Y$_2$ 'SIGK; Gβ1γ$_2$#Gαii; Gβ1γ$_2$>>GRK2; Gβ1Yi#phosducin) shows that the protein interaction site residues of Gβ exhibit only slightly greater than average side chain positional dispersity (1.42 A compared to 1.35 A), with the side chains of Trp99, Asp228, and Trp332 having the largest positive deviation from the average (each greater than 2 A). In particular, Arg314 and Trp332 in blade seven move more than 10 A towards the outside of the Gβ1 torus to interact with phosducin. Atomic B factors also provide a measure of conformational flexibility. In the structure of uncomplexed Gβ1Yi the B factors for Trp99, Val100, and Met101 exceed the mean value by least one standard deviation (Trp99 is greater than two standard deviations from the mean). In complexes with Gαn, GRK2, phosducin, and SIGK complexes, these binding site residues become more well-ordered with B values close to the mean and in some cases up to one standard deviation below the mean. Thus, the capacity of Gβ to recognize structurally diverse binding partners does not require a high degree of conformational flexibility for most residues in the protein interaction site of Gβ. Small structural adaptations in Gβ1 are sufficient to accommodate a range of co-evolving binding partners. Structural and mutagenic analysis demonstrates that the protein interaction site on Gβ can be regarded as a hot surface, co-evolved to promote tight binding with multiple protein targets. However, the mechanism by which Gβy acts as a hot surface is complex. Trp332 is the only residue which meets all four of the criteria for a hot spot, although Tyr59 and Trp99 have three of the four characteristics of hot spot residues that were tested. There are other residues in the top face of Gβ that are sensitive to mutational perturbation and are utilized in many binding partner interactions but do not exhibit the characteristics of conformational flexibility, solvent accessibility, or nonpolarity expected of hot spots. Especially notable among this group are Lys57 and Met188; both of these residues are energetically significant binding determinants in Gβ as shown by mutational analysis and comparison to known Gβy complex structures, and yet do not meet any of the additional statistical criteria for hot spot residues.

Accordingly, an amino acid residue of the protein interaction site of a Gβ is intended to include Lys57, Tyr59, Trp99, Val100, Met101, Leu117, Tyr145, Asp186, Met188, Asp228, Asn230, Asp246, and Trp332. By way of illustration, the location of these residues is provided in the rat Gβ amino acid sequence of:

```
MGEMEQLKQE AEQLKKQIAD ARKACADITL AELVSGLEVV

GRVQMRTRRT LRGHLAKIYA MHWATDSKLL VSASQDGKLI

VWDTYTTNKV HAIPLRSSWV MTCAYAPSGN FVACGGLDNM

CSIYSLKSRE GNVKVSRELS AHTGYLSCCR FLDDNNIVTS

SGDTTCALWD IETGQQKTVF VGHTGDCMSL AVSPDYKLFI

SGACDASAKL WDVREGTCRQ TFTGHESDIN AICFFPNGEA

ICTGSDDASC RLFDLRADQE LTAYSHESII CGITSVAFSL

SGRLLFAGYD DFNCNVWDSL
```

KCERVGVLSG HDNRVSCLGV TADGMAVATG SWDSFLKIWN (GENBANK Accession No. AAA62620; SEQ ID NO: 3), wherein the protein interaction site residues are underlined.

Likewise, these residues are located in the same position in a human Gβ having the amino acid sequence of:
MSELEQLRQE AEQLRNQIRD ARKACGDSTL TQITAGLDPV GRIQMRTRRT LRGHLAKIYA MHWGTDSRLL VSASQDGKLI IWDSYTTNKV HAIPL- RSSWV MTCAYAXSGN FVACGGLDNI CSIYSLKTRE GNVRVSRELP GHTGYLSCCR FLDDNQIITS SGDT- TCALWD IETGQQTVGF AGHSGDVMSL SLAPN- GRTFV SGACDASIKL WDVRDSMCRQ TFIGHESDIN AVAFFPNGYA FTTGSDDATC RLFDLRADQE LLMY- SHDNH CGITSVAFSR SGRLLLAGYD DFNCNIWDAM KGDRAGVLAG HDNRVSCLGV TDDGMAVATG SWDSFLKIWN (GENBANK Accession No. AAA35922; SEQ ID N0:4), wherein the protein interaction site residues are underlined.

An agent which interacts with at least one of these amino acid residues of the protein interaction site of Gβ can bind via various heterogeneous non-bonded interactions including, but not limited to van der Waals contacts {e.g., with methionine or leucine), polar contacts {e.g., with aspartate or asparagine), or both {e.g., with lysine, tryptophan, or tyrosine) to contribute to the energy of binding. In general, it is desirable that the agent interacts with 2, 3, 4, 5, 6, 7, 8, 9, 10, 11, 12 or 13 of the amino acid residues of the protein interaction site of G/3 to enhance the specificity of the agent for one or more G protein interacting proteins and therefore one or more G protein-mediated signaling pathways.

Determining whether the agent interacts with at least one amino acid residue of the protein interaction site of the β subunit can be accomplished using various in vitro or in vivo assays based on detecting protein-protein interactions between the Gβy subunits and other peptides or proteins known to interact with Gβy subunits {e.g., SIGK peptide, Ga subunit, or downstream proteins). An exemplary in vitro assay has been disclosed herein. This assay consists of obtaining an isolated Gβy complex; contacting the Gβy complex with a test agent in the presence of a peptide that binds at least one amino acid residue of the protein interaction site of β subunit, {e.g., a SIGK peptide or SIGK peptide derivative of SEQ ID NO:1, SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13); and detecting the ability of the agent to inhibit the binding of the peptide to the protein interaction site of the β subunit using, for example, an ELISA assay. Other phage displayed peptides identified in the original screen (Scott, et al. (2001) supra) could also be used.

Alternatively, an in vivo assay can be used to determine whether a test agent interacts with at least one amino acid residue of the protein interaction site of the β subunit. By way of illustration, a two-hybrid assay is contemplated where the test agent is contacted with a cell expressing Gβy subunits and a peptide such as SIGK, wherein the β subunit is fused to, e.g., a DNA-binding domain and the SIGK peptide is fused to an activation domain. When the SIGK peptide is bound to the protein interaction site of GβY, reporter protein expression is induced. If the test agent disrupts the binding of the SIGK peptide to the protein interaction site of Gβy, reporter protein expression is blocked.

Additional screens such as well-established computational screens or screens that detect the activity of G protein-dependent downstream proteins {e.g., PLC β enzymatic activity) are also contemplated for use in conjunction with the assays disclosed herein.

Test agents, also referred to herein as compounds, which can be screened in accordance with the methods of the present invention are generally derived from libraries of agents or compounds. Such libraries can contain either collections of pure agents or collections of agent mixtures. Examples of pure agents include, but are not limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, the methods of this invention are not only used to identify those crude mixtures that possess the desired activity, but also provide the means to monitor purification of the active agent from the mixture for characterization and development as a therapeutic drug. In particular, the mixture so identified can be sequentially fractionated by methods commonly known to those skilled in the art which can include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained. Library screening can be performed as exemplified herein or can be performed in any format that allows rapid preparation and processing of multiple reactions. Stock solutions of the test agents as well as assay components are prepared manually and all subsequent pipeting, diluting, mixing, washing, incubating, sample readout and data collecting is done using commercially available robotic pipeting equipment, automated work stations, and analytical instruments for detecting the signal generated by the assay. Examples of such detectors include, but are not limited to, luminometers, spectrophotometers, and fluorimeters, and devices that measure the decay of radioisotopes.

To further evaluate the efficacy of a compound identified using a screening method of the invention, one of skill will appreciate that a model system of any particular disease or disorder involving G protein signaling can be utilized to evaluate the adsorption, distribution, metabolism and excretion of a compound as well as its potential toxicity in acute, sub-chronic and chronic studies. For example, overexpression of $\beta\gamma$ inhibitors in NG108-15/D2 cells and rat primary hippocampal neurons has been shown to block $\delta$-opioid and cannabinoid receptor-induced PKA Ca translocation and gene expression by preventing $\beta\gamma$ activation of adenylyl cyclase (Yao, et al. (2003) Proc. Natl. Acad. Sci. USA 100: 14379-84). Accordingly, to analyze the efficacy of a compound of the instant invention for treating addiction, NG108-15/D2 cells and/or rat primary hippocampal neurons are contacted with said compound and the effect on PKA Ca translocation is determined. Compounds which block $\delta$-opioid and cannabinoid receptor-induced PKA Ca translocation will be useful in treating addiction. Efficacy of compounds of the instant invention for preventing or treating heart failure can be analyzed in a genetic model of murine-dilated cardiomyopathy which involves the ablation of a muscle-restricted gene that encodes the muscle LIM protein (MLP$^{-/-}$) (Arber, et al. 1997) Cell 88:393-403). Using this model, it has been demonstrated that a beta-adrenergic receptor kinase 1 inhibitor, BARK-ct, which binds to $\beta\gamma$ and blocks $\beta\gamma$-dependent activation of beta-adrenergic receptor kinase 1 activity, can enhance cardiac contractility in vivo with or without isoproterenol (Koch, et al. (1995) Science 268:1350-3) and restore left ventricular size and function (Rockman, eta 1. (1998) Proc. Natl. Acad. Sci. 95:7000-7005). Similarly, compounds of the instant invention which block $\beta\gamma$-dependent activation of beta-adrenergic receptor kinase 1 activity will be useful in preventing or treating heart failure.

The effectiveness of compounds of the instant to prevent opioid tolerance can be analyzed in acute (Jiang, et al. (1995) J. Pharmacol. Exp. Ther. 273:680-8) and chronic (Wells, et al. (2001) J. Pharmacol. Exp. Ther. 297:597-605) dependence model systems, wherein mice are injected intracerebroventricularly with a compound of the instant invention and tolerance to a select opioid (e.g., morphine) is determined. Compounds which decrease the amount of opioid necessary to achieve an analgesic effect will be useful in preventing opioid tolerance.

PLC-$\beta2$ and -$\beta3$ and PI3K$\gamma$ have been shown to be involved in the chemoattractant-mediated signal transduction pathway. Mice deficient in P13K$\gamma$ lack neutrophil production of PtdIns (3, 4, 5) P$_3$, neutrophil migration, and production of antibodies containing the $\lambda$ chain when immunized with T cell-independent antigen hydroxylnitrophenyl-FICOLL™ (Li, et al. (2000) Science 287:1046-1049). Mice lacking PLC-$\beta2$ and -$\beta3$ are deficient in Ca$^{2+}$ release, superoxide production, and MAC-I up-regulation in neutrophils (Li, et al. (2000) supra). Further, PLC-$\beta2$ deficient mice exhibit enhanced chemotaxis of different leukocyte populations and are sensitized to bacteria, viruses, and immune complexes (Jiang, et al. (1997) Proc. Natl. Acad. Sci. USA 94 (15): 7971-5).

Accordingly, to analyze the efficacy of a compound of the instant invention for modulating an inflammatory response, mice can be administered said compound and the effect on neutrophil production of PtdIns (3, 4, 5) P$_3$, neutrophil migration, Ca$^{2+}$ efflux, superoxide production, production of antibodies containing the $\lambda$ chain when immunized with T cell-independent antigen hydroxylnitrophenyl-FICOLL™ is determined. Compounds which selectively potentiate PLC-$\beta2$ and -$\beta3$ and/or block PI3K$\gamma$ activation thereby inhibiting production of PtdIns (3, 4, 5) P$_3$, neutrophil migration, and production of TI-IG$\lambda_L$, will be useful in treating inflammatory conditions such as arthritis, allergies, Chrohn's Disease and the like. Compounds which selectively block, e.g., PLC-$\beta2$ activation thereby facilitating neutrophil migration will be useful in facilitating immune responses to bacterial and viral infections.

Using the screening method of the present invention, various compounds have now been identified which bind to the protein interaction site of a G$\beta$ subunit to interfere with or potentiate physiologically relevant protein interactions {e.g., Ga subunit and PLC $\beta$ interactions) thereby modulating the activity of G protein signaling pathways.

1. Compounds and Small Molecules

The following chemical hierarchy is used throughout the specification to describe and enable the scope of the present invention and to particularly point out and distinctly claim the units which comprise the compounds of the present invention, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units may comprise only carbon atoms in the ring (carbocyclic and aryl rings) or may comprise one or more heteroatoms in the ring (heterocyclic and heteroaryl). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a C$_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and Unsubstituted Acyclic Hydrocarbyl:
For the purposes of the present invention the term "substituted and unsubstituted acyclic hydrocarbyl" encompasses 3 categories of units:
1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.
2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.
3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and Unsubstituted Cyclic Hydrocarbyl:
For the purposes of the present invention the term "substituted and unsubstituted cyclic hydrocarbyl" encompasses 5 categories of units:
1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:
i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), decalinyl ($C_{10}$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).
ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).
iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.
2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:
i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl (CO, 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).
ii) $C_6$ or $C_{10}$ aryl rings fused with 1 or 2 saturated rings non-limiting examples of which include, bicyclo[4.2.0]octa-1,3,5-trienyl ($C_8$), and indanyl ($C_9$).
3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which comprises the heteroatom is also not an aromatic ring." The following are non-limiting examples of "substituted and unsubstituted heterocyclic rings" which encompass the following categories of units:
i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$).
ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).
4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:
i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$)
ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

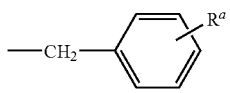

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

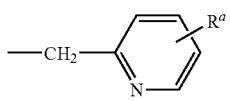

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purposes of the present invention carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present invention, and to provide consistency in defining the present invention, fused ring units, as well as spirocyclic rings, bicyclic rings and the like, which comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

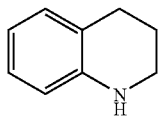

is, for the purposes of the present invention, considered a heterocyclic unit. 6,7-Dihydro-5H-cyclopentapyrimidine having the formula:

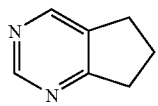

is, for the purposes of the present invention, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the invention. For example, 1,2,3,4-tetrahydro-[1,8]naphthyridine having the formula:

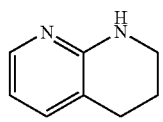

is, for the purposes of the present invention, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:

i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);

ii) $C_6$ and $C_{10}$ substituted or unsubstituted aryl; for example, 4-aminophenyl, 2-sulfamoylphenyl, 3-fluorophenyl, and 2-sulfamoyl-4-aminophenyl;

iii) —$OR^{100}$; for example, —OH, —$OCH_3$, —$OCH_2CH_3$, —$OCH_2CH_2CH_3$;

iv) —$C(O)R^{100}$; for example, —$COCH_3$, —$COCH_2CH_3$, —$COCH_2CH_2CH_3$;

v) —$C(O)OR^{100}$; for example, —$CO_2CH_3$, —$CO_2CH_2CH_3$, —$CO_2CH_2CH_2CH_3$;

vi) —$C(O)N(R^{100})_2$; for example, —$CONH_2$, —$CONHCH_3$, —$CON(CH_3)_2$;

vii) —$N(R^{100})_2$; for example, —$NH_2$, —$NHCH_3$, —$N(CH_3)_2$, —$NH(CH_2CH_3)$;

viii) halogen: —F, —Cl, —Br, and —I;

ix) —$CH_{m'}X_{n'}$; wherein X is halogen, m' is from 0 to 2, m'+n'=3; for example, —$CH_2F$, —$CHF_2$, —$CF_3$, —$CCl_3$, or —$CBr_3$; and x) —SO$_2$R$^{100}$; for example, —SO$_2$H; —SO$_2$CH$_3$; —SO$_2$C$_6$H$_5$; —SO$_2$NH$_2$;

wherein each R$^{100}$ is independently hydrogen, substituted or unsubstituted C$_1$-C$_4$ linear, branched, or cyclic alkyl, amino, alkylamino; or two R$^{100}$ units can be taken together to form a ring comprising 3-7 atoms. Substituents suitable for replacement of a hydrogen atom are further defined herein below in the iterations and examples. Substituents suitable for replacement of a hydrogen atom are further defined herein below.

The present disclosure relates to compounds capable of interacting with at least one amino acid residue of the protein interaction site of the β subunit of a G protein, and in the broadest sense, the compounds of the present disclosure comprise:

i) 2 or 3 fused rings, the rings comprising from 6 to 16 carbon atoms and from 0 to 10 heteroatoms chosen from oxygen, nitrogen, and sulfur; or ii) a first ring system containing 2 or 3 fused rings linked by a linking group comprising from 1 to 30 atoms to a second ring system containing 2 or 3 fused rings, the first ring system and the second ring system each independently containing from 6 to 16 carbon atoms and from 0 to 10 heteroatoms chosen from oxygen, nitrogen, and sulfur;

wherein any ring can optionally have one or more hydrogen atoms substituted by alkyl, alkoxy, alkenyl, alkynyl, aryl, arylalkylene, amino, substituted amino, halogen, cyano, nitro, and suflo; or any hydrogen on a ring can be substituted by a heterocyclic, heteroaryl, cycloalkyl, or aryl ring, the rings that substitute for hydrogen can be further substituted by alkyl, alkoxy, alkenyl, alkynyl, aryl, arylalkylene, amino, substituted amino, halogen, cyano, nitro, and suflo;

wherein further two substitutes on a carbon atom can be taken together to form a spirocyclic ring having from 3 to 10 carbon atoms and from 0 to 3 heteroatoms the spirocyclic ring having one or more hydrogen atoms substituted by alkyl, alkoxy, alkenyl, alkynyl, aryl, arylalkylene, amino, substituted amino, halogen, cyano, nitro, and suflo;

two substituents on a carbon atom can be taken together to form an exocyclic double bond to a unit having from 3 to 10 carbon atoms and from 0 to 3 heteroatoms, the unit can also be substituted by alkoxy, alkenyl, alkynyl, aryl, arylalkylene, amino, substituted amino, halogen, cyano, nitro, and suflo.

One aspect of the compounds disclosed herein is represented by the formula:

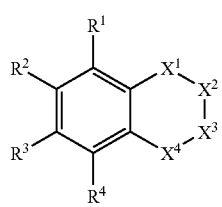

wherein X$^1$, X$^2$, X$^3$ and X$^4$ are ring units each of which may be present or absent and, therefore, depending upon the selection of units X$^1$, X$^2$, X$^3$ and X$^4$ and/or their presence or absence in the ring systems, the compounds of the present disclosure can be any one of the following non-limiting examples of ring systems:

Systems having 2 core rings:

i) fused rings wherein one of the rings is non-aryl, non-heterocyclic or non-heteroaryl, for example,

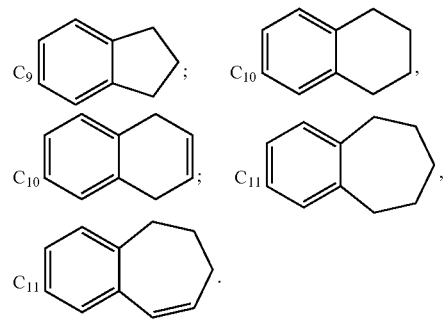

ii) C$_{10}$ aryl (naphthylene ring system);

iii) fused heterocyclic or heteroaryl rings wherein one ring contains at least one heteroatom, for example,

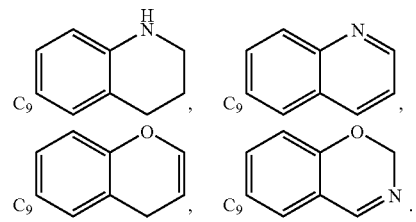

iv) fused rings wherein one ring may comprise a carbonyl or exocyclic double bond; for example,

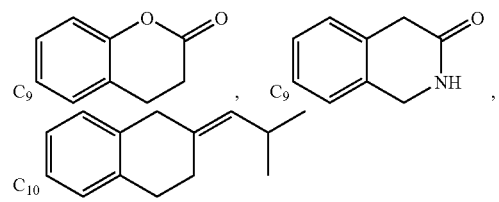

Systems having 3 core rings:

i) fused ring systems wherein at least two of the rings are non-aryl, non-heterocyclic or non-heteroaryl, for example,

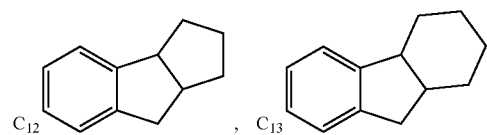

ii) C$_{14}$ aryl; anthracene, phenanthrene, and 3a$^1$H-phenalene.

iii) fused ring systems wherein two of the rings are aryl and the third ring is cycloalkyl, heterocyclic or heteroaryl, for example,

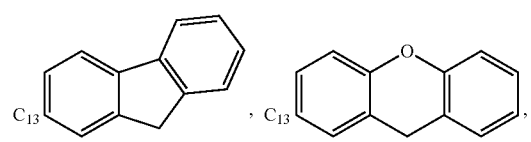

-continued

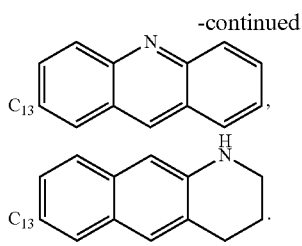

iv) fused rings wherein one ring may comprise a carbonyl or exocyclic double bond; for example,

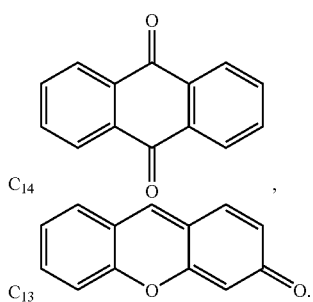

The following is a description of the compounds that comprise the present disclosure.
The formula:

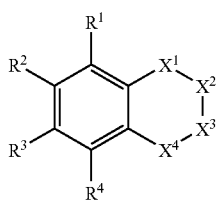

can be used to describe the compounds disclosed herein.
$X^1$ and $X^4$ are each independently:
i) —[C($R^{5a}$)($R^{5b}$)]—; for example, —[CH$_2$]—, —[CH(CH$_3$)]—, —[CH(substituted aryl)]—;
ii) —[C$R^{5c}$]═; for example, —[CH]═, —[C(substituted aryl)]═;
iii) —[C(Y)]—; for example, —[C(O)]—, —[C(S)]—, —[C(═NH)]—;
iv) —[N($R^6$)]—; for example, —[N(H)]—, —[N(substituted aryl)]—;
v) —[N]═;
vi) —[O]—;
vii) —[S]—;
$R^{5a}$, $R^{5b}$, and $R^{5c}$ are each independently chosen from:
i) —H;
ii) $C_1$-$C_{12}$ substituted or unsubstituted linear, branched, or cyclic alkyl; for example, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methyl-butyl ($C_5$), 3-methylbutyl ($C_5$), 1,2 dimethylpropyl ($C_5$), 1,1-dimethylpropyl ($C_5$), 2,2-dimethylpropyl ($C_5$), n-hexyl ($C_6$), 1-methylpentyl ($C_6$), 2-methylpentyl ($C_6$), 3-methylpentyl ($C_6$), 4-methylpentyl ($C_6$), 1,1-methylbutyl ($C_6$), 2,2-methylbutyl ($C_6$), 3,3-methylbutyl ($C_6$), 1,2-methylbutyl ($C_6$), 1,3-methylbutyl ($C_6$), 1,1,2-trimethypropyl ($C_6$), and 1,2,2-trimethypropyl ($C_6$);

iii) $C_2$-$C_{12}$ substituted or unsubstituted linear, branched, or cyclic alkenyl; for example, ethenyl ($C_2$), n-propenyl ($C_3$), iso-propenyl ($C_3$), n-butenyl ($C_4$), 1-methylpropen-1-yl ($C_4$), and 1-methylpropen-2-yl;
iv) $C_2$-$C_{12}$ substituted or unsubstituted linear or branched alkynyl; prop-1-yn-1-yl ($C_3$), prop-2-yn-1-yl (propargyl) ($C_3$);
v) $C_6$ or $C_{10}$ substituted or unsubstituted aryl, for example, 2-fluorophenyl, 3-fluorophenyl, 4-fluorophenyl, 4-methoxyphenyl, 2,3-dimethoxyphenyl, 2,4-dimethoxyphenyl, 3-aminophenyl, 4-aminophenyl, and the like;
vi) $C_7$-$C_{15}$ substituted or unsubstituted arylalkylene; for example, benzyl, 2-naphthylmethyl (naphthylen-2-ylmethyl);
vii) $C_1$-$C_9$ substituted or unsubstituted heterocyclic;
viii) $C_1$-$C_{11}$ substituted or unsubstituted heteroaryl;
ix) halogen; fluoro, chloro, bromo, and iodo;
x) —O$R^7$;
$R^7$ is chosen from:
a) —H; thereby forming a hydroxy unit;
b) $C_1$-$C_{12}$ substituted or unsubstituted linear, branched, or cyclic alkyl; forming alkoxy units, non-limiting examples include methoxy ($C_1$), ethoxy ($C_2$), n-propoxy ($C_3$), iso-propoxy ($C_3$), n-butoxy ($C_4$), sec-butoxy ($C_4$), iso-butoxy ($C_4$), and tert-butoxy ($C_4$);
c) $C_6$ or $C_{10}$ substituted or unsubstituted aryl;
d) $C_7$-$C_{15}$ substituted or unsubstituted arylalkylene;
e) $C_1$-$C_9$ substituted or unsubstituted heterocyclic;
f) $C_1$-$C_{11}$ substituted or unsubstituted heteroaryl;
xi) —N($R^{8a}$)($R^{8b}$);
$R^{8a}$ and $R^{8b}$ are each independently chosen from:
a) —H; when $R^{8a}$ and $R^{8b}$ equal hydrogen, —NH$_2$;
b) —O$R^9$;
$R^9$ is hydrogen or $C_1$-$C_4$ linear alkyl; for example, —NH(OCH$_3$);
c) $C_1$-$C_{12}$ substituted or unsubstituted linear, branched, or cyclic alkyl; for example, —NHCH$_3$, —N(CH$_3$)$_2$, —NH(CH$_2$CH$_3$);
d) $C_6$ or $C_{10}$ substituted or unsubstituted aryl; for example, —NH(4-Cl-phenyl), —N(3,5-dihydroxyphenyl)$_2$;
e) $C_7$-$C_{12}$ substituted or unsubstituted arylalkylene; for example, benzylamino;
f) $C_1$-$C_9$ substituted or unsubstituted heterocyclic;
g) $C_1$-$C_{11}$ substituted or unsubstituted heteroaryl; or
h) $R^{8a}$ and $R^{8b}$ can be taken together to form a substituted or unsubstituted ring having from 3 to 10 carbon atoms and from 0 to 3 heteroatoms chosen from oxygen, nitrogen, and sulfur; for example, aziridin-1-yl pyrrolidin-1-yl, piperidin-1-yl, piperazin-1-yl, and morpholin-4-yl;
xii) —CN;
xiii) —NO$_2$;
xiv) —SO$_2R^{10}$;
$R^{10}$ is hydrogen, hydroxyl, substituted or unsubstituted $C_1$-$C_4$ linear or branched alkyl; substituted or unsubstituted $C_6$, $C_{10}$, or $C_{14}$ aryl; $C_7$-$C_{15}$ arylalkylene; $C_1$-$C_9$ substituted or unsubstituted heterocyclic; or $C_1$-$C_{11}$ substituted or unsubstituted heteroaryl;
xv) a $R^{5a}$ and $R^{5b}$ on the same carbon atom can be taken together to form a substituted or unsubstituted spirocyclic ring having from 3 to 10 carbon atoms and from 0 to 3 heteroatoms chosen from oxygen, nitrogen, and sulfur; for example a compound having the formula:

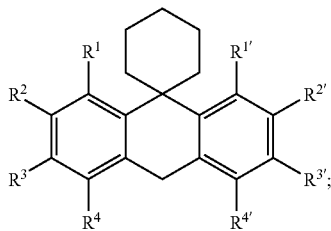

or xvi) $R^{5a}$ and $R^{5b}$ on the same carbon atom can be taken together to form an exocyclic double bond having the formula $=C(R^{5a'})(R^{5b'})$, for example,

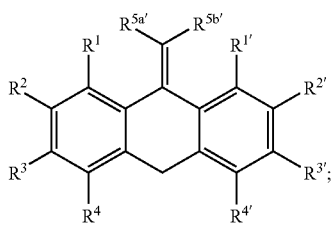

wherein $R^{5a'}$ and $R^{5b'}$ are each independently:
a) —H;
b) $C_1$-$C_{12}$ substituted or unsubstituted linear, branched, or cyclic alkyl;
d) $C_6$ or $C_{10}$ substituted or unsubstituted aryl;
e) $C_7$-$C_{15}$ substituted or unsubstituted arylalkylene;
r) $C_1$-$C_9$ substituted or unsubstituted heterocyclic;
g) $C_1$-$C_{11}$ substituted or unsubstituted heteroaryl; or
h) $R^{5a'}$ and $R^{5b'}$ can be taken together to form a substituted or unsubstituted ring having from 3 to 10 carbon atoms and from 0 to 3 heteroatoms chosen from oxygen, nitrogen, and sulfur.

Each $R^6$ is independently chosen from
i) —H;
ii) $C_1$-$C_{12}$ substituted or unsubstituted linear, branched, or cyclic alkyl;
iii) $C_6$ or $C_{10}$ substituted or unsubstituted aryl;
iv) $C_7$-$C_{15}$ substituted or unsubstituted arylalkylene;
v) $C_1$-$C_9$ substituted or unsubstituted heterocyclic;
vi) $C_1$-$C_{11}$ substituted or unsubstituted heteroaryl;
vii) halogen;
viii) —N($R^{11a}$)($R^{11b}$);
  $R^{11a}$ and $R^{11b}$ are each independently chosen from:
  a) —H; or
  b) $C_1$-$C_4$ linear or branched alkyl.

Each Y is independently chosen from:
i) =O;
ii) =S;
iii) =N$R^{12}$;
  $R^{12}$ is chosen from hydrogen, hydroxyl, or $C_1$-$C_{12}$ substituted or unsubstituted linear or branched alkyl;
iv) =C($R^{13a}$)($R^{13b}$);
  $R^{13a}$ and $R^{13b}$ are each independently chosen from
  a) —H;
  b) $C_1$-$C_{12}$ substituted or unsubstituted linear, branched, or cyclic alkyl;
  c) $C_6$ or $C_{10}$ substituted or unsubstituted aryl;
  d) $R^{13a}$ and $R^{13b}$ can be taken together to form a substituted or unsubstituted cycloalkyl, aryl, heterocyclic, or heteroaryl ring having from 3 to 10 carbon atoms and from 0 to 3 heteroatoms chosen from oxygen, nitrogen, and sulfur.

$X^2$ and $X^3$ are each independently:
i) —[C($R^{14a}$)($R^{14b}$)]—;
ii) —[C$R^{14c}$]=;
iii) —[C(Y)]—;
iv) —[N($R^{15}$)]—;
v) —[N]=;
vi) —[O]—;
vii) —[S]—;
$R^{14a}$, $R^{14b}$, and $R^{14c}$ are each independently chosen from:
i) —H;
ii) $C_1$-$C_{12}$ substituted or unsubstituted linear, branched, or cyclic alkyl;
iii) $C_2$-$C_{12}$ substituted or unsubstituted linear, branched, or cyclic alkenyl;
iv) $C_2$-$C_{12}$ substituted or unsubstituted linear or branched alkynyl;
v) halogen;
vi) —O$R^{16}$;
  $R^{16}$ is chosen from:
  a) —H;
  b) $C_1$-$C_{12}$ substituted or unsubstituted linear, branched, or cyclic alkyl;
  c) $C_6$ or $C_{10}$ substituted or unsubstituted aryl;
  d) $C_7$-$C_{12}$ substituted or unsubstituted arylalkylene;
  e) $C_1$-$C_9$ substituted or unsubstituted heterocyclic;
  f) $C_1$-$C_{11}$ substituted or unsubstituted heteroaryl;
vii) —N($R^{17a}$)($R^{17b}$);
  $R^{17a}$ and $R^{17b}$ are each independently chosen from:
  a) —H;
  b) —O$R^{21}$;
    $R^{18}$ is hydrogen or $C_1$-C4 linear alkyl;
  c) $C_1$-$C_{12}$ substituted or unsubstituted linear, branched, or cyclic alkyl;
  d) $C_6$ or $C_{10}$ substituted or unsubstituted aryl;
  e) $C_7$-$C_{15}$ substituted or unsubstituted arylalkylene;
  f) $C_1$-$C_9$ substituted or unsubstituted heterocyclic;
  g) $C_1$-$C_{11}$ substituted or unsubstituted heteroaryl; or
  h) $R^{17a}$ and $R^{17b}$ can be taken together to form a substituted or unsubstituted cycloalkyl, aryl, heterocyclic, or heteroaryl ring having from 3 to 10 carbon atoms and from 0 to 3 heteroatoms chosen from oxygen, nitrogen, and sulfur;
viii) —CN;
ix) —NO$_2$;
x) —SO$_2$$R^{19}$;
  $R^{19}$ is hydrogen, hydroxyl, substituted or unsubstituted $C_1$-$C_4$ linear or branched alkyl; substituted or unsubstituted $C_6$, $C_{10}$, or $C_{14}$ aryl; $C_7$-$C_{15}$ arylalkylene; $C_1$-$C_9$ substituted or unsubstituted heterocyclic; or $C_1$-$C_{11}$ substituted or unsubstituted heteroaryl;
xi) $R^{14a}$ and $R^{14b}$ can be taken together to form a spirocyclic ring can be taken together to form a substituted or unsubstituted ring having from 3 to 10 carbon atoms and from 0 to 3 heteroatoms chosen from oxygen, nitrogen, and sulfur;

each $R^{15}$ is chosen from
i) —H;
ii) $C_1$-$C_{12}$ substituted or unsubstituted linear, branched, or cyclic alkyl;
iii) $C_6$ or $C_{10}$ substituted or unsubstituted aryl;
iv) $C_7$-$C_{15}$ substituted or unsubstituted arylalkylene;
v) $C_1$-$C_9$ substituted or unsubstituted heterocyclic;
vi) $C_1$-$C_{11}$ substituted or unsubstituted heteroaryl;
vii) halogen;
viii) —N($R^{20a}$)($R^{20b}$);

$R^{20a}$ and $R^{20b}$ are each independently chosen from:
a) —H; or
b) $C_1$-$C_4$ linear or branched alkyl;
each Y is chosen from:
i) =O;
ii) =S;
iii) =$NR^{21}$;
  $R^{21}$ is chosen from hydrogen, hydroxyl, or $C_1$-$C_{12}$ substituted or unsubstituted linear or branched alkyl;
iv) =$C(R^{22a})(R^{22b})$;
  $R^{22a}$ and $R^{22b}$ are each independently chosen from
  a) —H;
  b) $C_1$-$C_{12}$ substituted or unsubstituted linear, branched, or cyclic alkyl;
  c) $C_6$ or $C_{10}$ substituted or unsubstituted aryl;
  d) $R^{22a}$ and $R^{22b}$ can be taken together to form a substituted or unsubstituted cycloalkyl, aryl, heterocyclic, or heteroaryl ring having from 3 to 10 carbon atoms and from 0 to 3 heteroatoms chosen from oxygen, nitrogen, and sulfur;)
when $X^2$ an $X^3$ are each —[C($R^{14a}$)($R^{14b}$)]— or are each —[$CR^{14c}$]=, and $R^{14a}$ or an $R^{14c}$ unit from $X^2$ and $X^3$ can be taken together to form a substituted or unsubstituted cycloalkyl, aryl, heterocyclic or heteroaryl ring containing from 4 to 10 carbon atoms any of which carbon atoms can be a carbonyl carbon, and from 0 to 3 heteroatoms chosen from oxygen, nitrogen, and sulfur; wherein the rings formed from an $R^{14a}$ or $R^{14b}$ on $X^2$ and an $R^{14a}$ or $R^{14b}$ on $X^3$ cam be substituted by one or more units $R^{1'}$, $R^{2'}$, $R^{3'}$, or $R^{4'}$, wherein each $R^{1'}$, $R^{2'}$, $R^{3'}$, or $R^{4'}$, can be the same as defined herein below for $R^1$, $R^2$, $R^3$, and $R^4$. Non-limiting examples of rings comprising $R^1$, $R^2$, $R^3$, $R^4$, $R^{1'}$, $R^{2'}$, $R^{3'}$, or $R^{4'}$, units include, for example, rings having the formulae:

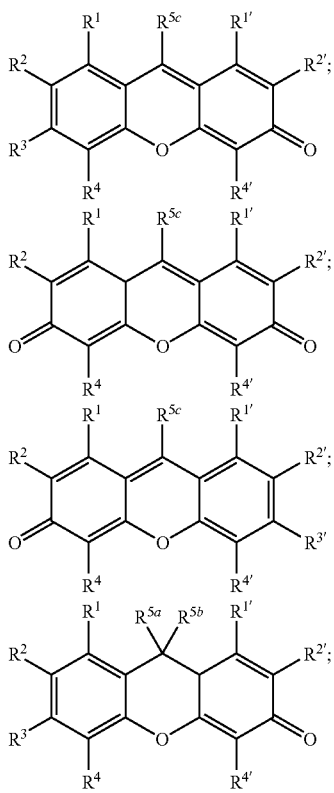

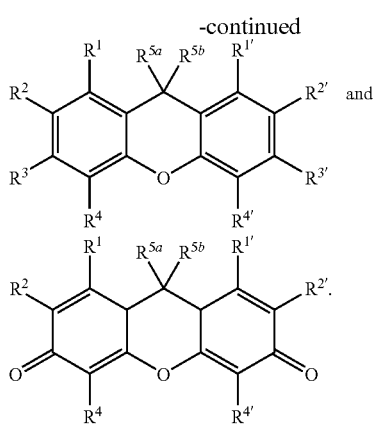

$R^1$, $R^2$, $R^3$, and $R^4$ are each independently chosen from:
i) —H;
ii) $C_1$-$C_{12}$ substituted or unsubstituted linear, branched, or cyclic alkyl;
iii) $C_2$-$C_{12}$ substituted or unsubstituted linear, branched, or cyclic alkenyl;
iv) $C_2$-$C_{12}$ substituted or unsubstituted linear or branched alkynyl;
v) $C_6$ or $C_{10}$ substituted or unsubstituted aryl;
vi) $C_7$-$C_{15}$ substituted or unsubstituted arylalkylene;
vii) $C_1$-$C_9$ substituted or unsubstituted heterocyclic;
viii) $C_1$-$C_{11}$ substituted or unsubstituted heteroaryl;
ix) —$OR^{27}$;
  $R^{27}$ is chosen from:
  a) —H;
  b) $C_1$-$C_{12}$ substituted or unsubstituted linear, branched, or cyclic alkyl;
  c) $C_6$ or $C_{10}$ substituted or unsubstituted aryl;
  d) $C_1$-$C_9$ substituted or unsubstituted heterocyclic;
  e) $C_1$-$C_{11}$ substituted or unsubstituted heteroaryl;
x) —$N(R^{28a})(R^{28b})$;
  $R^{28a}$ and $R^{28b}$ are each independently chosen from:
  a) —H;
  b) —$OR^{29}$;
    $R^{29}$ is hydrogen or $C_1$-C4 linear alkyl;
  c) $C_1$-$C_{12}$ substituted or unsubstituted linear, branched, or cyclic alkyl;
  d) $C_6$ or $C_{10}$ substituted or unsubstituted aryl;
  e) $C_7$-$C_{15}$ substituted or unsubstituted arylalkylene;
  f) $C_1$-$C_9$ substituted or unsubstituted heterocyclic;
  g) $C_1$-$C_{11}$ substituted or unsubstituted heteroaryl; or
  h) $R^{28a}$ and $R^{28b}$ can be taken together to form a substituted or unsubstituted cycloalkyl, aryl, heterocyclic, or heteroaryl ring having from 3 to 10 carbon atoms and from 0 to 3 heteroatoms chosen from oxygen, nitrogen, and sulfur;
xi) halogen;
xii) —CN;
xiii) —$NO_2$;
xiv) —$SO_2R^{30}$;
  $R^{30}$ is hydrogen, hydroxyl, substituted or unsubstituted $C_1$-$C_4$ linear or branched alkyl; substituted or unsubstituted $C_6$, $C_{10}$, or $C_{14}$ aryl; $C_7$-$C_{15}$ arylalkylene; $C_1$-$C_9$ substituted or unsubstituted heterocyclic; or $C_1$-$C_{11}$ substituted or unsubstituted heteroaryl;
a $R^{5a}$ unit from $X^1$ and a $R^{14a}$ unit from $X^2$ or a $R^{5a}$ unit from $X^4$ and a $R^{14a}$ unit from $X^3$ can be taken together to form a substituted or unsubstituted cycloalkyl, aryl, heterocyclic, or heteroaryl ring having from 3 to 10 carbon atoms and from 0 to 3 heteroatoms chosen from oxygen, nitrogen, and sulfur.

In addition to units comprising one 2 or 3 fused ring system, $R^1$, $R^2$, $R^3$, $R^4$, $X^1$, $X^2$, $X^3$, and $X^4$ are each independently a unit containing a linking group L capable of linking a first ring system with a second ring system through any of the $R^1$, $R^2$, $R^3$, $R^4$, $X^1$, $X^2$, $X^3$, or $X^4$ units of each ring, the linked rings having the formula:

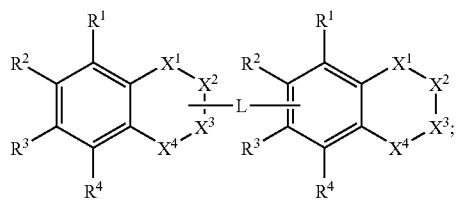

L is a linking unit having the formula:

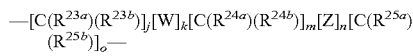

$R^{23a}$, $R^{23b}$, $R^{24a}$, $R^{24b}$, $R^{25a}$, and $R^{25b}$ are each independently chosen from;

i) —H; or ii) $C_1$-$C_4$ substituted or unsubstituted linear or branched alkyl;

iii) $C_6$ substituted or unsubstituted aryl; or iv) $C_7$-$C_{12}$ substituted or unsubstituted arylalkylene;

W and Z are each independently chosen from:

i) -M-;

ii) —C(=M)-;

iii) —C(=M)M-;

iv) -MC(=M)-;

v) -MC(=M)M-;

vi) -MC(=M)C(=M)M-;

vii) -MC(=M)MC(=M)M-;

each M is independently chosen from O, S, and $NR^{26}$; $R^{26}$ is hydrogen, hydroxyl, or $C_1$-$C_4$ linear or branched alkyl;

the indices k and n are 0 or 1; the indices j, m, and o are from 0 to 12.

As described herein above, the compounds presently disclosed can comprise substituted or unsubstituted heterocyclic and heteroaryl rings.

The following are non-limiting examples of substituted or unsubstituted $C_2$, $C_3$, $C_4$ 5-member heterocyclic rings, wherein $R^a$ represents one or more substitutions for hydrogen when the substitution is present.

i) a substituted pyrrolidinyl ring having the formula:

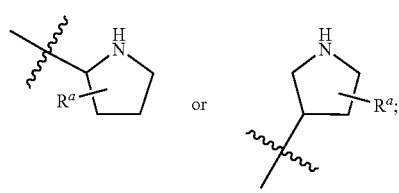

ii) a substituted pyrrolyl ring having the formula:

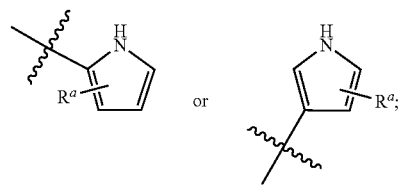

iii) a substituted 4,5-dihydroimidazolyl ring having the formula:

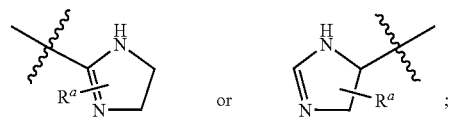

iv) a substituted pyrazolyl ring having the formula:

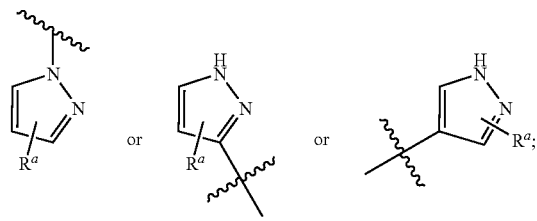

v) an substituted imidazolyl ring having the formula:

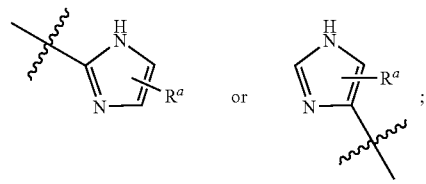

vi) a substituted [1,2,3]triazolyl ring having the formula:

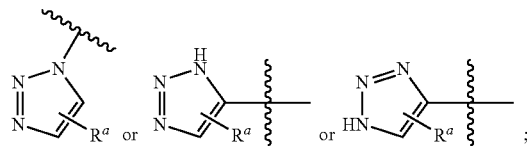

vii) a substituted [1,2,4] triazolyl ring having the formula:

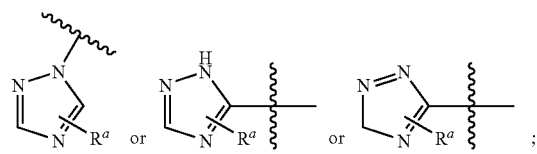

viii) a substituted tetrazolyl ring having the formula:

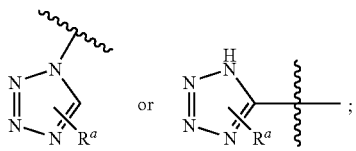

ix) a substituted [1,3,4] or [1,2,4]oxadiazolyl ring having the formula:

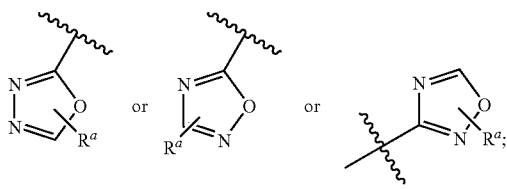

x) a substituted pyrrolidinonyl ring having the formula:

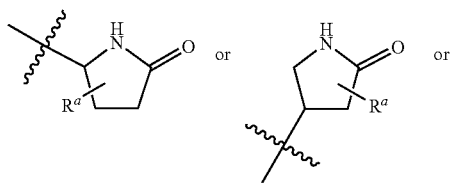

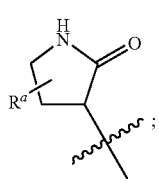

xi) a substituted imidazolidinonyl ring having the formula:

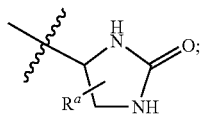

xii) a substituted imidazol-2-only ring having the formula:

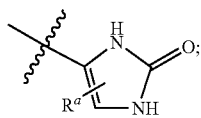

xiii) a substituted oxazolyl ring having the formula:

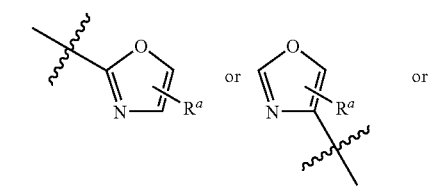

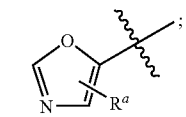

xiv) a substituted isoxazolyl ring having the formula:

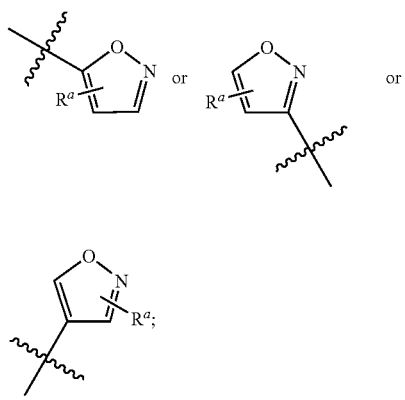

xv) a substituted thiazolyl ring having the formula:

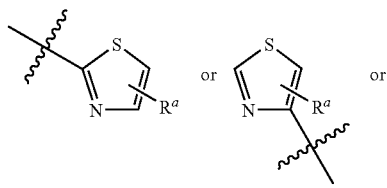

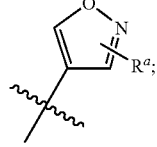

xvi) a substituted furanly ring having the formula:

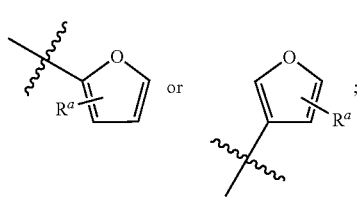

xvii) a substituted thiophenyl having the formula:

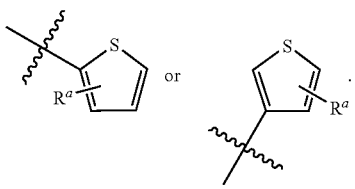

The following are non-limiting examples of substituted or unsubstituted $C_3$, $C_4$, $C_5$ 6-member heterocyclic rings, wherein $R^a$ represents one or more substitutions for hydrogen when the substitution is present.

i) a substituted morpholinyl ring having the formula:

ii) a substituted piperidinyl ring having the formula:

iii) a substituted pyridinyl ring having the formula:

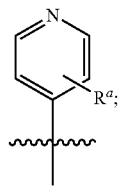

iv) a substituted pyrimidinyl ring having the formula:

v) a substituted piperazinyl ring having the formula:

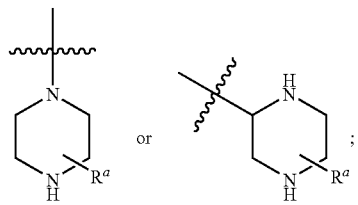

and vi) a substituted triazinyl ring having the formula:

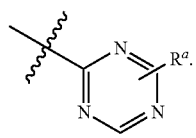

The $R^a$ substitutions for hydrogen in the above heterocyclic and heteroaryl units include the following non-limiting examples, each independently chosen from:
  i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);
  ii) $C_6$ and $C_{10}$ substituted or unsubstituted aryl; for example, 4-aminophenyl, 2-sulfamoylphenyl, 3-fluorophenyl, and 2-sulfamoyl-4-aminophenyl;
  iii) —$OR^a$; for example, —OH, —$OCH_3$, —$OCH_2CH_3$, —$OCH_2CH_2CH_3$;
  iv) —$C(O)R^a$; for example, —$COCH_3$, —$COCH_2CH_3$, —$COCH_2CH_2CH_3$;
  v) —$C(O)OR^a$; for example, —$CO_2CH_3$, —$CO_2CH_2CH_3$, —$CO_2CH_2CH_2CH_3$;
  vi) —$C(O)N(R^a)_2$; for example, —$CONH_2$, —$CONHCH_3$, —$CON(CH_3)_2$;

vii) —N($R^a$)$_2$; for example, —NH$_2$, —NHCH$_3$, —N(CH$_3$)$_2$, —NH(CH$_2$CH$_3$);

viii) halogen: —F, —Cl, —Br, and —I;

ix) —CH$_m$X$_{n'}$; wherein X is halogen, m' is from 0 to 2, m'+n'=3; for example, —CH$_2$F, —CHF$_2$, —CF$_3$, —CCl$_3$, or —CBr$_3$; and x) —SO$_2$R$^{a0}$; for example, —SO$_2$H; —SO$_2$CH$_3$; —SO$_2$C$_6$H$_5$; —SO$_2$NH$_2$;

wherein each $R^a$ is independently hydrogen, substituted or unsubstituted C$_1$-C$_4$ linear, branched, or cyclic alkyl, amino, alkylamino; or two $R^a$ units can be taken together to form a ring comprising 3-7 atoms. Substituents suitable for replacement of a hydrogen atom are further defined herein below in the iterations and examples.

A first category of compounds capable of interacting with at least one amino acid residue of the protein interaction site of the β subunit of a G protein according to the present disclosure relates to compounds having the formula:

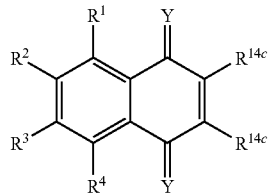

wherein $X^1$ and $X^4$ are each —[C(Y)]—, $X^2$ and $X^3$ are each —[CR$^{14c}$]=; and the $R^{14c}$ units from $X^2$ and $X^3$ are taken together to form a cycloalkyl or aryl ring having from 4 to 10 carbon atoms and $R^1$, $R^2$, $R^3$, and $R^4$ are further defined.

A first embodiment of this category of the present disclosure relates to compounds wherein Y equals (=O) and the $R^{14c}$ units are taken together to form an aryl ring, the compounds having the formula:

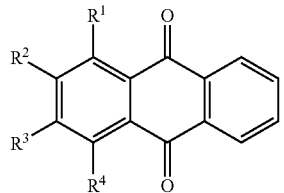

wherein $R^1$, $R^2$, $R^3$, and $R^4$ are each independently chosen from:

i) —H;

ii) C$_6$ or C$_{10}$ substituted or unsubstituted aryl;

iii) —OR$^{27}$;

R$^{27}$ is chosen from:
a) —H;
b) C$_1$-C$_{12}$ substituted or unsubstituted linear, branched, or cyclic alkyl;

iv) —N(R$^{28a}$)(R$^{28b}$);

R$^{28a}$ and R$^{28b}$ are each independently chosen from:
a) —H;
d) C$_6$ or C$_{10}$ substituted or unsubstituted aryl;

v) halogen;

vi) —SO$_2$R$^{30}$;

R$^{30}$ is hydrogen, substituted or unsubstituted C$_1$-C$_4$ linear or branched alkyl.

The substitutions for hydrogen in the above units are each independently chosen from:

i) C$_1$-C$_4$ linear or branched alkyl; for example, methyl (C$_1$), ethyl (C$_2$), n-propyl (C$_3$), iso-propyl (C$_3$), n-butyl (C$_4$), iso-butyl (C$_4$), sec-butyl (C$_4$), and tert-butyl (C$_4$);

ii) C$_6$ and C$_{10}$ substituted or unsubstituted aryl; for example, 4-aminophenyl, 2-sulfamoylphenyl, 3-fluorophenyl, and 2-sulfamoyl-4-aminophenyl;

iii) —OR$^{100}$; for example, —OH, —OCH$_3$, —OCH$_2$CH$_3$, —OCH$_2$CH$_2$CH$_3$;

iv) —C(O)R$^{100}$; for example, —COCH$_3$, —COCH$_2$CH$_3$, —COCH$_2$CH$_2$CH$_3$;

v) —C(O)OR$^{100}$; for example, —CO$_2$CH$_3$, —CO$_2$CH$_2$CH$_3$, —CO$_2$CH$_2$CH$_2$CH$_3$;

vi) —C(O)N(R$^{100}$)$_2$; for example, —CONH$_2$, —CONHCH$_3$, —CON(CH$_3$)$_2$;

vii) —N(R$^{100}$)$_2$; for example, —NH$_2$, —NHCH$_3$, —N(CH$_3$)$_2$, —NH(CH$_2$CH$_3$);

viii) halogen: —F, —Cl, —Br, and —I;

ix) —CH$_m$X$_{n'}$; wherein X is halogen, m' is from 0 to 2, m'+n'=3; for example, —CH$_2$F, —CHF$_2$, —CF$_3$, —CCl$_3$, or —CBr$_3$; and x) —SO$_2$R$^{100}$; for example, —SO$_2$H; —SO$_2$CH$_3$; —SO$_2$C$_6$H$_5$; —SO$_2$NH$_2$;

wherein each R$^{100}$ is independently hydrogen, substituted or unsubstituted C$_1$-C$_4$ linear, branched, or cyclic alkyl, amino, alkylamino; or two R$^{100}$ units can be taken together to form a ring comprising 3-7 atoms. Substituents suitable for replacement of a hydrogen atom are further defined herein below in the iterations and examples.

One iteration of this embodiment relates to compounds having the formula:)

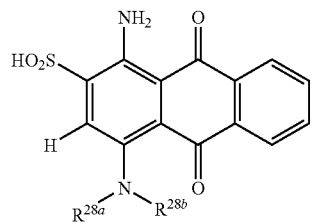

wherein R$^1$ is —N(R$^{28a}$)(R$^{28b}$), for which R$^{28a}$ and R$^{28b}$ are each hydrogen; R$^2$ is —SO$_2$R$^{30}$, R$^{30}$ is hydrogen; R$^3$ is hydrogen; and R$^4$ is —N(R$^{28a}$)(R$^{28b}$); R$^{28a}$ and R$^{28b}$ are further defined herein for this embodiment.

One example of this iteration includes R$^4$ units wherein both R$^{28a}$ and R$^{28b}$ are hydrogen, thereby providing 1,3-diamino-9,10-dioxo-9,10-dihydroanthracene-2-sulphonic acid having the formula:

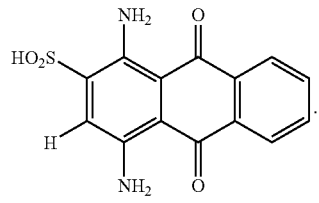

Another example of this iteration includes compounds wherein R$^{28b}$ is hydrogen and R$^{28a}$ is phenyl or substituted phenyl thereby providing 1-amino-9,10-dioxo-4-(substituted or unsubstituted phenylamino)-9,10-dihydroanthracene-2-sulphonic acids having the formula:

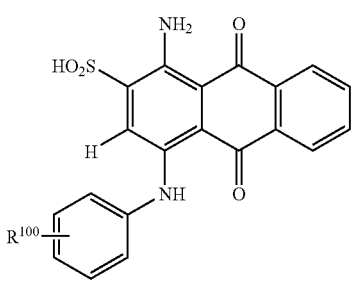

wherein $R^{100}$ represents one or more substitutions for hydrogen.

Non-limiting examples of the $R^{28a}$ units comprising $R^4$ include phenyl, 2-sulfophenyl, 3-sulfophenyl, 4-sulfophenyl, 2-aminophenyl, 3-aminophenyl, 4-aminophenyl, 2-sulfamoylphenyl, 3-sulfamoylphenyl, 4-sulfamoylphenyl, 2-methylaminophenyl, 3-methylaminophenyl, 4-methylaminophenyl, 2-(dimethylamino)phenyl, 3-(dimethyl-amino)phenyl, 4-(dimethylamino)phenyl, 2-methylphenyl, 3-methylphenyl, 4-methyl-phenyl, 2-(hydroxymethyl)phenyl, 3-(hydroxymethyl)phenyl, 4-(hydroxymethyl)phenyl, 2-sulfo-4-aminophenyl, 3-sulfo-4-aminophenyl, 2-amino-4-sulfophenyl, 3-amino-4-sulfophenyl, and 3-amino-5-sulfophenyl.

Another iteration of this embodiment includes compounds having the formula:

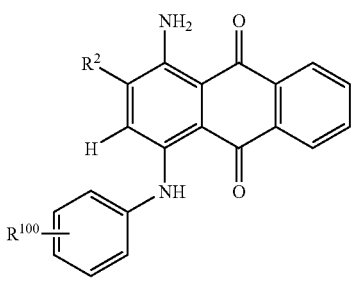

wherein $R^2$ is halogen and the $R^{28a}$ and $R^{28b}$ units for $R^4$ are the same as defined herein above, thereby providing 1-amino-2-halogen-4-(substituted or unsubstituted phenylamino)anthracene-9,10-diones.

This iteration includes the following examples of athracene-9,10-diones:

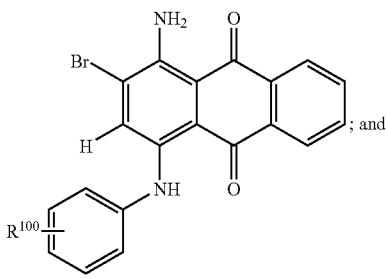

; and

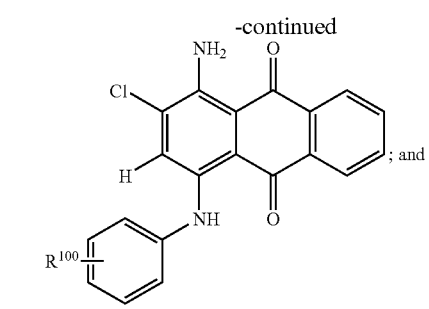

; and

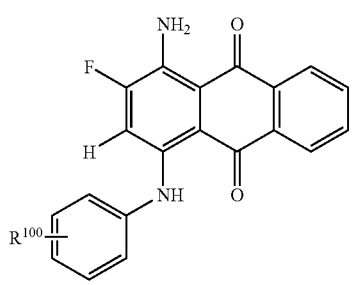

wherein $R^{100}$ is the same as described herein above thereby providing non-limiting examples of $R^{28a}$ that include phenyl, 2-sulfophenyl, 3-sulfophenyl, 4-sulfophenyl, 2-aminophenyl, 3-aminophenyl, 4-aminophenyl, 2-sulfamoylphenyl, 3-sulfamoyl-phenyl, 4-sulfamoylphenyl, 2-methylaminophenyl, 3-methylaminophenyl, 4-methylaminophenyl, 2-(dimethylamino)phenyl, 3-(dimethyl-amino)phenyl, 4-(dimethylamino)phenyl, 2-methylphenyl, 3-methylphenyl, 4-methyl-phenyl, 2-(hydroxymethyl)phenyl, 3-(hydroxymethyl)phenyl, 4-(hydroxymethyl)phenyl, 2-sulfo-4-aminophenyl, 3-sulfo-4-aminophenyl, 2-amino-4-sulfophenyl, 3-amino-4-sulfophenyl, and 3-amino-5-sulfophenyl.

A further iteration of this embodiment includes compounds having the formula:

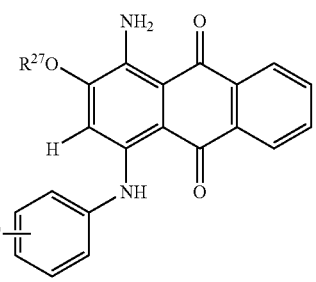

wherein $R^{27}$ is chosen from hydrogen or $C_1$-$C_{12}$ substituted or unsubstituted linear, branched, or cyclic alkyl and $R^{28a}$ and $R^{28b}$ are the same as defined herein above, thereby providing 1-amino-2-alkoxy-4-(substituted or unsubstituted phenylamino)anthracene-9,10-diones. Non-limiting examples of $R^{27}$ include methyl ($C_1$), ethyl ($C_2$), n-propyl ($C_3$), iso-propyl ($C_3$), n-butyl ($C_4$), sec-butyl ($C_4$), iso-butyl ($C_4$), and tent-butyl ($C_4$).

This iteration includes the following examples of athracene-9,10-diones having the formula:

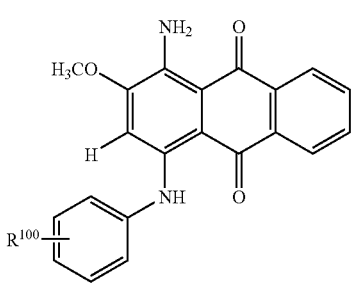

wherein $R^{100}$ is the same as described herein above thereby providing non-limiting examples of $R^{28a}$ that include phenyl, 2-sulfophenyl, 3-sulfophenyl, 4-sulfophenyl, 2-aminophenyl, 3-aminophenyl, 4-aminophenyl, sulfamoylphenyl, 3-sulfamoyl-phenyl, 4-sulfamoylphenyl, 2-methylaminophenyl, 3-methylaminophenyl, 4-methylaminophenyl, 2-(dimethylamino)phenyl, 3-(dimethyl-amino)phenyl, 4-(dimethylamino)phenyl, 2-methylphenyl, 3-methylphenyl, 4-methylphenyl, 2-(hydroxymethyl)phenyl, 3-(hydroxymethyl)phenyl, 4-(hydroxymethyl)phenyl, 2-sulfo-4-aminophenyl, 3-sulfo-4-aminophenyl, 2-amino-4-sulfophenyl, 3-amino-4-sulfophenyl, and 3-amino-5-sulfophenyl.

The following Tables I-IV provide binding data ($IC_{50}$) for compounds representative compounds of this embodiment at receptors $PLC\beta_2$, $PLC\beta_3$, and $PI_3K\gamma$.

TABLE 2

| Compound | Elisa $IC_{50}$ |
|---|---|
| 1-amino-9,10-dioxo-4-(3-sulfamoylphenylamino)-9,10-dihydroanthracene-2-sulfonic acid | 56 μM |
| 1-amino-9,10-dioxo-4-(4-aminophenylamino)-9,10-dihydroanthracene-2-sulfonic acid | 12 μM |

TABLE 2-continued

| Compound | Elisa $IC_{50}$ |
|---|---|
| 1-amino-9,10-dioxo-4-(3-aminophenylamino)-9,10-dihydroanthracene-2-sulfonic acid | 19 μM |
| 1-amino-9,10-dioxo-4-[4-(methylamino)phenylamino]-9,10-dihydroanthracene-2-sulfonic acid | 59 μM |
| 1-amino-4-(4'-amino-2'-sulfobiphenyl-4-ylamino)-9,10-dioxo-9,10-dihydroanthracene-2-sulfonic acid | 18 μM |

TABLE 3

| Compound | PLCβ$_2$ IC$_{50}$ |
|---|---|
| 1-amino-9,10-dioxo-4-(4-aminophenylamino)-9,10-dihydroanthracene-2-sulfonic acid | 75 μM |
| 1-amino-9,10-dioxo-4-(3-aminophenylamino)-9,10-dihydroanthracene-2-sulfonic acid | 14 μM |
| 1-amino-4-(4'-amino-2'-sulfobiphenyl-4-ylamino)-9,10-dioxo-9,10-dihydroanthracene-2-sulfonic acid | >30 μM |

TABLE 4

| Compound | PLC β$_3$ IC$_{50}$ |
|---|---|
| 1-amino-9,10-dioxo-4-(3-sulfamoylphenylamino)-9,10-dihydroanthracene-2-sulfonic acid | 58 μM |
| 1-amino-9,10-dioxo-4-(4-aminophenylamino)-9,10-dihydroanthracene-2-sulfonic acid | 12 μM |
| 1-amino-9,10-dioxo-4-(3-aminophenylamino)-9,10-dihydroanthracene-2-sulfonic acid | 15 μM |
| 1-amino-4-(4'-amino-2'-sulfobiphenyl-4-ylamino)-9,10-dioxo-9,10-dihydroanthracene-2-sulfonic acid | 62 μM |

TABLE 5

| Compound | PI₃Kγ IC$_{50}$ |
|---|---|
| 1-amino-9,10-dioxo-4-(3-sulfamoylphenylamino)-9,10-dihydroanthracene-2-sulfonic acid | 10 μM |
| 1-amino-9,10-dioxo-4-(4-aminophenylamino)-9,10-dihydroanthracene-2-sulfonic acid (M360) | 2.5 μM |
| 1-amino-9,10-dioxo-4-(3-aminophenylamino)-9,10-dihydroanthracene-2-sulfonic acid (M372) | 6 μM |
| 1-amino-4-(4′-amino-2′-sulfobiphenyl-4-ylamino)-9,10-dioxo-9,10-dihydroanthracene-2-sulfonic acid | 16 μM |

PI₃Kγ = phosphoinsotide 3 kinase γ.

Another category of compounds capable of interacting with at least one amino acid residue of the protein interaction site of the β subunit of a G protein according to the present disclosure relates to compounds having the formula:

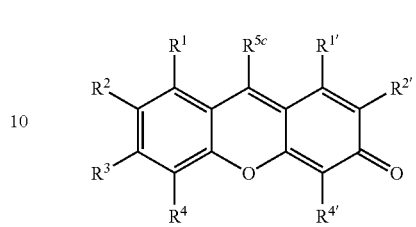

wherein $X^1$ is —[$CR^{5c}$]=, $X^4$ is —[O]—; $X^2$ and $X^3$ are each —[$CR^{14c}$]=; and the $R^{14c}$ unit from $X^2$ and $X^3$ are taken together to form an unsaturated cycloalkyl ring having 6 carbon atoms.

$R^1$, $R^2$, $R^3$, and $R^4$ are each independently chosen from:
  i) —H;
  ii) $C_6$ or $C_{10}$ substituted or unsubstituted aryl; or
  iii) —$OR^{27}$;
    $R^{27}$ is chosen from:
    a) —H; or
    b) $C_1$-$C_{12}$ substituted or unsubstituted linear, branched, or cyclic alkyl.

$R^{1'}$, $R^{2'}$, and $R^{4'}$ are each independently chosen from:
  i) —H;
  ii) $C_6$ or $C_{10}$ substituted or unsubstituted aryl; or
  iii) —$OR^{27}$;
    $R^{27}$ is chosen from:
    a) —H; or
    b) $C_1$-$C_{12}$ substituted or unsubstituted linear, branched, or cyclic alkyl.

$R^{5c}$ is chosen from:
  i) —H;
  ii) $C_1$-$C_{12}$ substituted or unsubstituted linear, branched, or cyclic alkyl;
  iii) $C_2$-$C_{12}$ substituted or unsubstituted linear, branched, or cyclic alkenyl; or
  iv) $C_6$ or $C_{10}$ substituted or unsubstituted aryl.

The substitutions for hydrogen in the above units are each independently chosen from:
  i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);
  ii) $C_6$ and $C_{10}$ substituted or unsubstituted aryl; for example, 4-aminophenyl, 2-sulfamoylphenyl, 3-fluorophenyl, and 2-sulfamoyl-4-aminophenyl;
  iii) —$OR^{100}$; for example, —OH, —$OCH_3$, —$OCH_2CH_3$, —$OCH_2CH_2CH_3$;
  iv) —$C(O)R^{100}$; for example, —$COCH_3$, —$COCH_2CH_3$, —$COCH_2CH_2CH_3$;
  v) —$C(O)OR^{100}$; for example, —$CO_2CH_3$, —$CO_2CH_2CH_3$, —$CO_2CH_2CH_2CH_3$;
  vi) —$C(O)N(R^{100})_2$; for example, —$CONH_2$, —$CONHCH_3$, —$CON(CH_3)_2$;
  vii) —$N(R^{100})_2$; for example, —$NH_2$, —$NHCH_3$, —$N(CH_3)_2$, —$NH(CH_2CH_3)$;
  viii) halogen: —F, —Cl, —Br, and —I;
  ix) —$CH_mX_n$; wherein X is halogen, m' is from 0 to 2, m'+n'=3; for example, —$CH_2F$, —$CHF_2$, —$CF_3$, —$CCl_3$, or —$CBr_3$; and
  x) —$SO_2R^{100}$; for example, —$SO_2H$; —$SO_2CH_3$; —$SO_2C_6H_5$; —$SO_2NH_2$;

wherein each $R^{100}$ is independently hydrogen, substituted or unsubstituted $C_1$-$C_4$ linear, branched, or cyclic alkyl, amino, alkylamino; or two $R^{100}$ units can be taken together to form a ring comprising 3-7 atoms. Substituents suitable for replacement of a hydrogen atom are further defined herein below in the iterations and examples.

One category of compounds disclosed herein are the 4,5,6-trihydroxy-9-substituted-3H-xanten-3-ones having the formula:

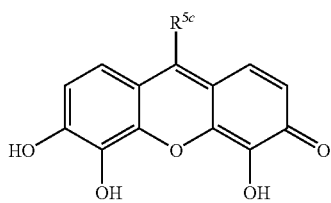

wherein $R^{5c}$ is chosen from:
i) $C_3$-$C_{12}$ substituted or unsubstituted cyclic alkyl;
ii) $C_3$-$C_{12}$ substituted or unsubstituted cyclic alkenyl;
iii) $C_6$ or $C_{10}$ substituted or unsubstituted aryl; and
iv) $C_7$-$C_{15}$ substituted or unsubstituted arylalkylene.

Suitable substitutions for the above $R^{5c}$ are
i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);
ii) $C_6$ and $C_{10}$ substituted or unsubstituted aryl; for example, 4-aminophenyl, 2-sulfamoylphenyl, 3-fluorophenyl, and 2-sulfamoyl-4-aminophenyl;
iii) —$OR^{100}$; for example, —OH, —$OCH_3$, —$OCH_2CH_3$, —$OCH_2CH_2CH_3$;
iv) —$C(O)R^{100}$; for example, —$COCH_3$, —$COCH_2CH_3$, —$COCH_2CH_2CH_3$;
v) —$C(O)OR^{100}$; for example, —$CO_2CH_3$, —$CO_2CH_2CH_3$, —$CO_2CH_2CH_2CH_3$;
vi) —$C(O)N(R^{100})_2$; for example, —$CONH_2$, —$CONHCH_3$, —$CON(CH_3)_2$;
vii) —$N(R^{100})_2$; for example, —$NH_2$, —$NHCH_3$, —$N(CH_3)_2$, —$NH(CH_2CH_3)$;
viii) halogen: —F, —Cl, —Br, and —I;
ix) —$CH_mX_{n'}$; wherein X is halogen, m' is from 0 to 2, m'+n'=3; for example, —$CH_2F$, —$CHF_2$, —$CF_3$, —$CCl_3$, or —$CBr$; and
x) —$SO_2R^{100}$; for example, —$SO_2H$; —$SO_2CH_3$; —$SO_2C_6H_5$; —$SO_2NH_2$.

However, it has been discovered that there is a need for understanding the relationship between the core 3H-xanten-3-one ring, the moieties that comprise $R^{5a}$ and binding. For example, 6-hydroxy-9-methyl-3H-xanten-3-one having the formula:

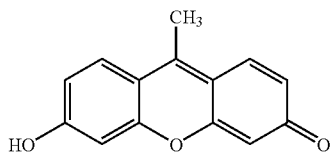 [SMILES: Cc1c2ccc(=O)cc-2oc2cc(O)ccc12]

was found not to bind to the G protein β subunit. Further addition of hydroxyl units to the core ring, for example, 2,6,7-trihydroxy-9-methyl-3H-xanten-3-one, having the formula:

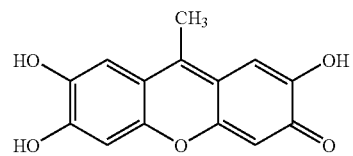 [SMILES: Cc1c2cc(O)c(=O)cc-2oc2cc(O)c(O)cc12]

did not provide a compound that exhibited binding. Extending the length of $R^{5a}$ and allowing for both free rotation of the $R^{5a}$ substituent (alkyl unit) and restricted rotation of the $R^{5a}$ unit (alkenyl unit), as well as providing a unit capable of increased hydrogen bonding (—$C(O)OR^{100}$ unit wherein $R^{100}$ is hydrogen) provided two compounds, 3-(6-hydroxy-3-oxo-3H-xanthen-9-yl)propionic acid and (E)-3-(6-hydroxy-3-oxo-3H-xanthe-9-yl)acrylic acid having the formulae respectively:

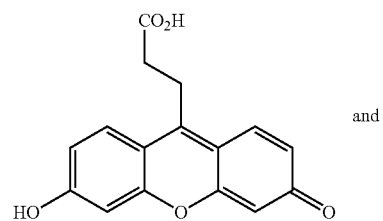

and

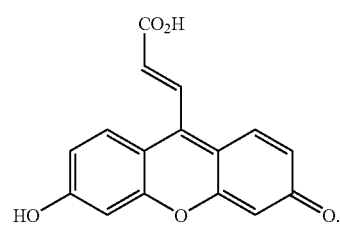

Neither of these compounds showed any binding to the G protein β subunit.

However, when these two $R^{5c}$ substituents were attached to the presently disclosed 4,5,6-trihydroxy-9-substituted-3H-xanten-3-one ring system, thereby forming the compounds 3-(4,5,6-trihydroxy-3-oxo-3H-xanthen-9-ylpropanoic acid and (E)-3-(4,5,6-trihydroxy-3-oxo-3H-xanthen-9-yl)acrylic acid having the formulae:

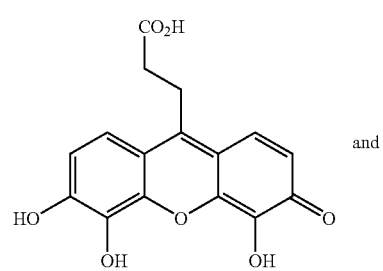

and

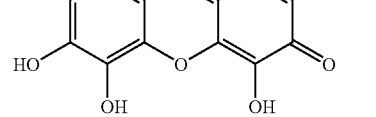

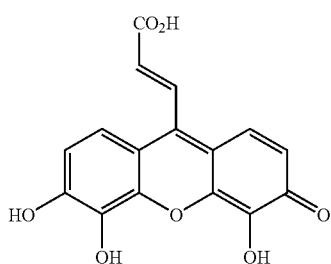

both of these compounds elicited significant binding; 2.5 µM and 200 nm respectively.

One embodiment of this category relates to compounds having the formula:

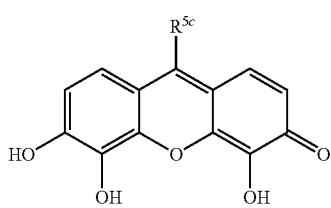

wherein $R^{5c}$ is a substituted or unsubstituted cycloalkyl unit. Non-limiting examples of unsubstituted cycloalkyl units include:

i) mono-cyclic alkyl; for example, cyclopropyl ($C_3$), cyclobutyl ($C_4$), cyclopentyl ($C_5$), cyclohexyl ($C_6$), cycloheptyl ($C_7$), and the like;

ii) mono-cyclic alkenyl; for example, cyclopent-1-en-1-yl ($C_5$), cyclohex-2-en-1-yl, and the like;

iii) bicycloalkyl; for example, bicyclo[3.1.0]hexanyl ($C_6$), bicyclo[4.1.0]-heptanyl ($C_7$), bicyclo[3.1.1]heptanyl ($C_7$); bicyclo[4.1.1]octanyl ($C_8$), and the like;

iv) unsaturated bicycloalkyl; for example, bicyclo[3.1.0]hex-2-enyl ($C_6$), bicyclo[4.1.0]-hept-3-enyl ($C_7$), bicyclo[3.1.1]hept-2-enyl ($C_7$); bicyclo[4.1.1]oct-3-enyl ($C_8$), and the like;

v) bridged fused ring alkyl; for example, the following unit, tricyclo[4.4.1] decalin-2-yl, ($C_{11}$) numbered as indicated;

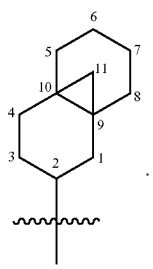

One iteration of this embodiment relatest compounds wherein $R^{5c}$ is a substituted or unsubstituted cycloalkyl ring, for example,

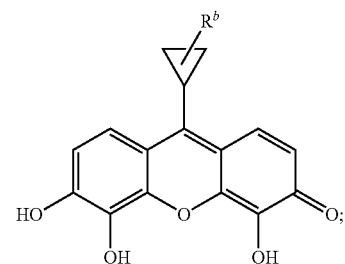

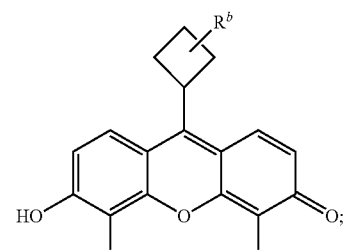

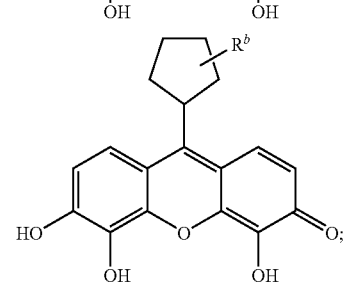

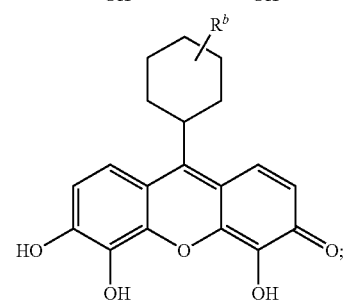

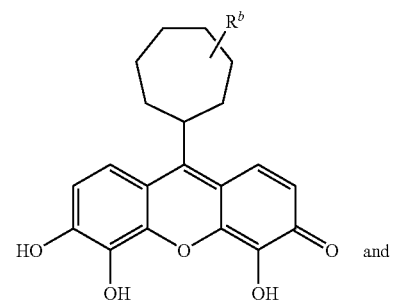

and

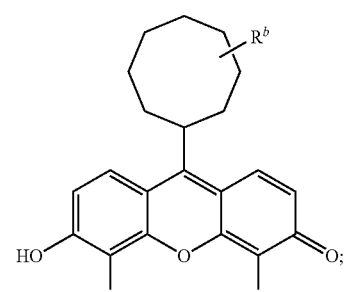

wherein $R^b$ represents one or more optionally present substitutions for hydrodgen. Non-limiting examples of $R^b$ units include units independently chosen from:

i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);

ii) $C_6$ and $C_{10}$ substituted or unsubstituted aryl; for example, 4-aminophenyl, 2-sulfamoylphenyl, 3-fluorophenyl, and 2-sulfamoyl-4-aminophenyl;

iii) —$OR^{200}$; for example, —OH, —$OCH_3$, —$OCH_2CH_3$, —$OCH_2CH_2CH_3$;

iv) —$C(O)R^{200}$; for example, —$COCH_3$, —$COCH_2CH_3$, —$COCH_2CH_2CH_3$;

v) —$C(O)OR^{200}$; for example, —$CO_2CH_3$, —$CO_2CH_2CH_3$, —$CO_2CH_2CH_2CH_3$;

vi) —$C(O)N(R^{200})_2$; for example, —$CONH_2$, —$CONHCH_3$, —$CON(CH_3)_2$;

vii) —$N(R^{200})_2$; for example, —$NH_2$, —$NHCH_3$, —$N(CH_3)_2$, —$NH(CH_2CH_3)$;

viii) halogen: —F, —Cl, —Br, and —I;

ix) —$CH_{m'}X_{n'}$; wherein X is halogen, m' is from 0 to 2, m'+n'=3; for example, —$CH_2F$, —$CHF_2$, —$CF_3$, —$CCl_3$, or —$CBr_3$; and x) —$SO_2R^{200}$; for example, —$SO_2H$; —$SO_2CH_3$; —$SO_2C_6H_5$; —$SO_2NH_2$;

wherein each $R^{200}$ is independently hydrogen, substituted or unsubstituted $C_1$-$C_4$ linear, branched, or cyclic alkyl, amino, alkylamino; or two $R^{200}$ units can be taken together to form a ring comprising 3-7 atoms.

Non-limiting examples of compounds according to this embodiment include 2-(4,5,6-trihydroxy-3-oxo-3H-xanthen-9-yl)cyclohexanecarboxylic acid having the formula:

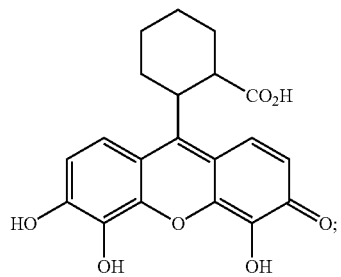 [SMILES: O=C(O)C1CCCCC1c1c2ccc(=O)c(O)c-2oc2c(O)c(O)ccc12]

2-(4,5,6-trihydroxy-3-oxo-3H-xanthen-9-yl)cyclohexanecarboxyamide having the formula:

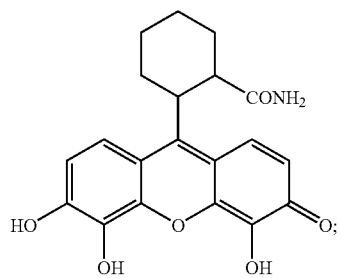 [SMILES: NC(=O)C1CCCCC1c1c2ccc(=O)c(O)c-2oc2c(O)c(O)ccc12]

9-(2-aminocyclohexyl)-4,5,6-trihydroxy-3H-xathnen-3-one having the formula:

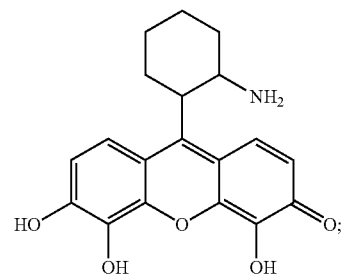 [SMILES: NC1CCCCC1c1c2ccc(=O)c(O)c-2oc2c(O)c(O)ccc12]

3-(4,5,6-trihydroxy-3-oxo-3H-xanthen-9-yl)cyclohexanecarboxylic acid having the formula:

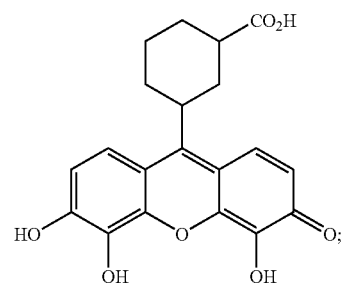 [SMILES: O=C(O)C1CCCC(c2c3ccc(=O)c(O)c-3oc3c(O)c(O)ccc23)C1]

4-(4,5,6-trihydroxy-3-oxo-3H-xanthen-9-yl)cyclohexanecarboxylic acid having the formula:

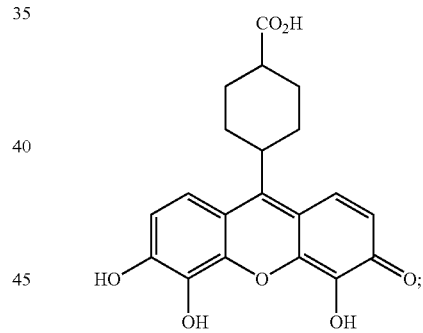

5-(4,5,6-trihydroxy-3-oxo-3H-xanthen-9-yl)cyclohexane-1,3-dicarboxylic acid having the formula:

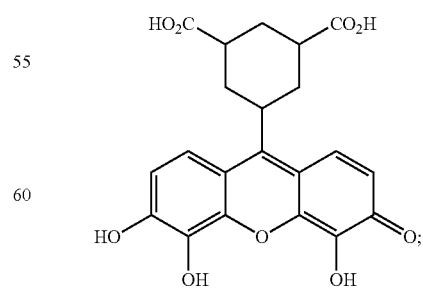

7-methyl-3-(4,5,6-trihydroxy-3-oxo-3H-xanthen-9-yl)bicyclo[2.2.1]hept-5-ene-2-carboxylic acid having the formula:

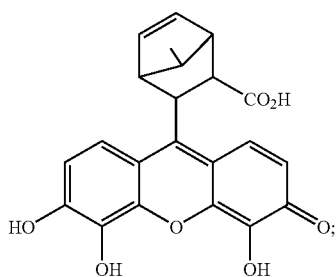 [SMILES: CC1C2C=CC1C(c1c3ccc(=O)c(O)c-3oc3c(O)c(O)ccc13)C2C(=O)O]

1,4,5,6,7,7-hexachloro-3-(4,5,6-trihydroxy-3-oxo-3H-xanthen-9-yl)bicyclo[2.2.1]hept-5-ene-2-carboxylic acid having the formula:

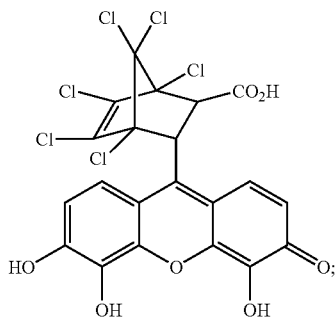 [SMILES: O=C(O)C1C(c2c3ccc(=O)c(O)c-3oc3c(O)c(O)ccc23)C2(Cl)C(Cl)=C(Cl)C1(Cl)C2(Cl)Cl]

and 7,8,9,10,11,11-hexachloro-3-(4,5,6-trihydroxy-3-oxo-3H-xanthen-9-yl)tricyclo[4.4.1]-decaline-2-carboxylic acid having the formula:

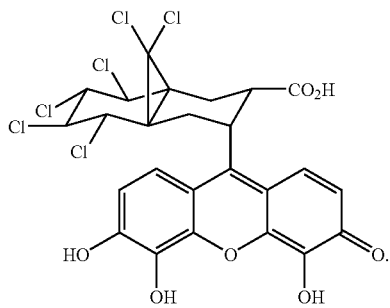 [SMILES: O=C(O)C1CC23C(Cl)C(Cl)C(Cl)C(Cl)C2(CC1c1c2ccc(=O)c(O)c-2oc2c(O)c(O)ccc12)C3(Cl)Cl]

Another category relates to compounds having the formula:

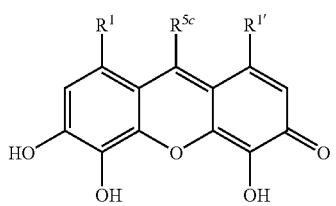

wherein $R^{5c}$ is the same as defined herein above, and $R^1$ and $R^{1'}$ can be hydrogen or a substitution independently chosen from:

i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);

ii) $C_6$ and $C_{10}$ substituted or unsubstituted aryl; for example, 4-aminophenyl, 2-sulfamoylphenyl, 3-fluorophenyl, and 2-sulfamoyl-4-aminophenyl;

iii) —$OR^{201}$; for example, —OH, —$OCH_3$, —$OCH_2CH_3$, —$OCH_2CH_2CH_3$;

iv) —$C(O)R^{201}$; for example, —$COCH_3$, —$COCH_2CH_3$, —$COCH_2CH_2CH_3$;

v) —$C(O)OR^{201}$; for example, —$CO_2CH_3$, —$CO_2CH_2CH_3$, —$CO_2CH_2CH_2CH_3$;

vi) —$C(O)N(R^{201})_2$; for example, —$CONH_2$, —$CONHCH_3$, —$CON(CH_3)_2$;

vii) —$N(R^{201})_2$; for example, —$NH_2$, —$NHCH_3$, —$N(CH_3)_2$, —$NH(CH_2CH_3)$;

viii) halogen: —F, —Cl, —Br, and —I;

ix) —$CH_{m'}X_{n'}$; wherein X is halogen, m' is from 0 to 2, m'+n'=3; for example, —$CH_2F$, —$CHF_2$, —$CF_3$, —$CCl_3$, or —$CBr_3$; and x) —$SO_2R^{201}$; for example, —$SO_2H$; —$SO_2CH_3$; —$SO_2C_6H_5$; —$SO_2NH_2$;

wherein each $R^{201}$ is independently hydrogen, substituted or unsubstituted $C_1$-$C_4$ linear, branched, or cyclic alkyl, amino, alkylamino; or two $R^{201}$ units can be taken together to form a ring comprising 3-7 atoms. Examples of this iteration include compound having the formulae:

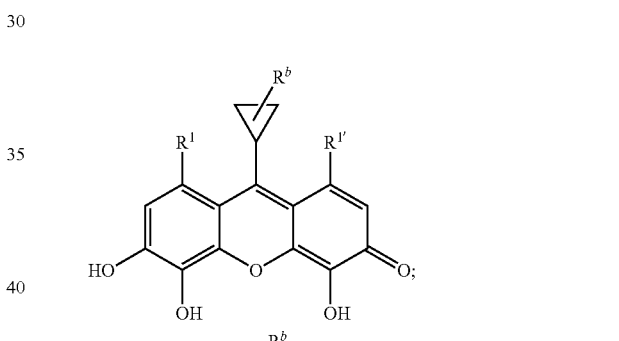

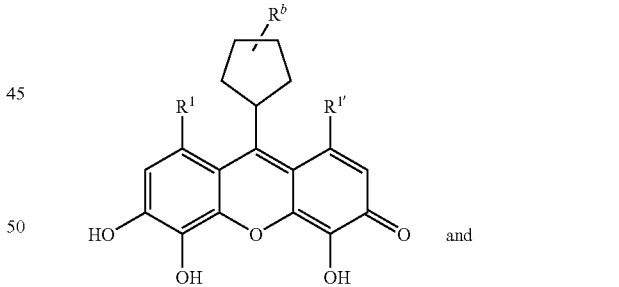

and

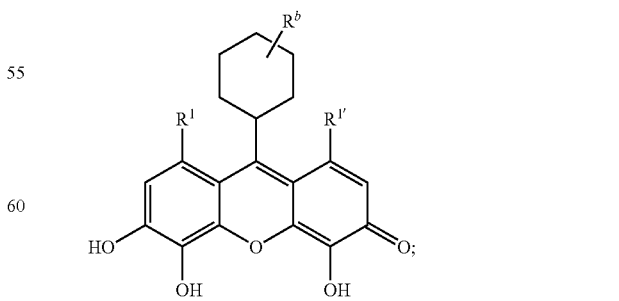

wherein $R^b$ represents one or more optionally present substitutions for hydrogen as defined herein above.

Another category relates to compounds having the formula:

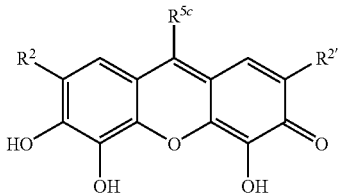

wherein $R^{5c}$ is the same as defined herein above, and $R^2$ and $R^{2'}$ can be hydrogen or a substitution independently chosen from:
 i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);
 ii) $C_6$ and $C_{10}$ substituted or unsubstituted aryl; for example, 4-aminophenyl, 2-sulfamoylphenyl, 3-fluorophenyl, and 2-sulfamoyl-4-aminophenyl;
 iii) —$OR^{201}$; for example, —OH, —$OCH_3$, —$OCH_2CH_3$, —$OCH_2CH_2CH_3$;
 iv) —$C(O)R^{201}$; for example, —$COCH_3$, —$COCH_2CH_3$, —$COCH_2CH_2CH_3$;
 v) —$C(O)OR^{201}$; for example, —$CO_2CH_3$, —$CO_2CH_2CH_3$, —$CO_2CH_2CH_2CH_3$;
 vi) —$C(O)N(R^{201})_2$; for example, —$CONH_2$, —$CONHCH_3$, —$CON(CH_3)_2$;
 vii) —$N(R^{201})_2$; for example, —$NH_2$, —$NHCH_3$, —$N(CH_3)_2$; —$NH(CH_2CH_3)$;
 viii) halogen: —F, —Cl, —Br, and —I;
 ix) —$CH^{m'}X^{n'}$; wherein X is halogen, m' is from 0 to 2, m'+n'=3; for example, —$CH_2F$, —$CHF_2$, —$CF_3$, —$CCl_3$, or —$CBr_3$; and
 x) —$SO_2R^{201}$; for example, —$SO_2H$; —$SO_2CH_3$; —$SO_2C_6H_5$; —$SO_2NH_2$;
wherein each $R^{201}$ is independently hydrogen, substituted or unsubstituted $C_1$-$C_4$ linear, branched, or cyclic alkyl, amino, alkylamino; or two $R^{201}$ units can be taken together to form a ring comprising 3-7 atoms. Examples of this iteration include compound having the formulae:

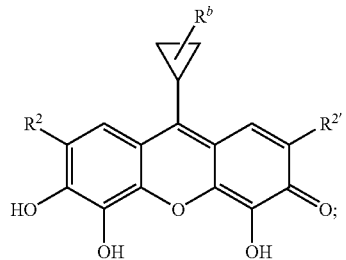

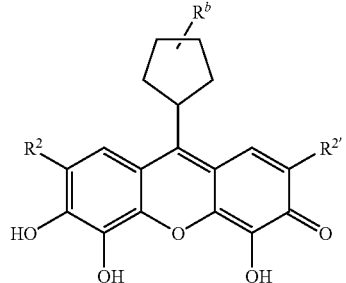

and

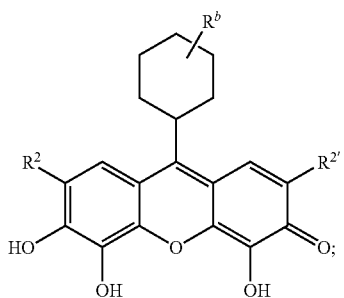

wherein $R^b$ represents one or more optionally present substitutions for hydrogen as defined herein above.

The compounds wherein $R^{5c}$ is a substituted or unsubstituted cycloalkyl ring can have any enantiomeric or diastereomeric form. For example,

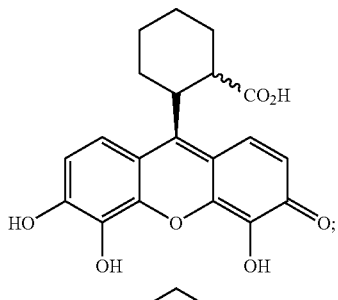

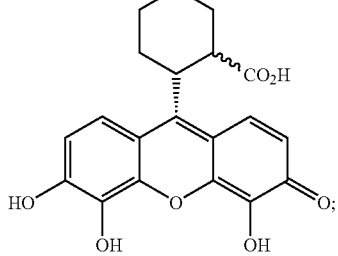

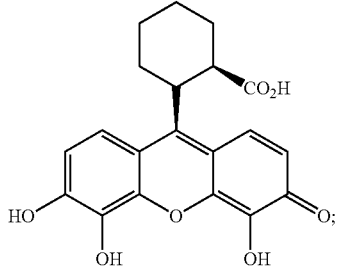

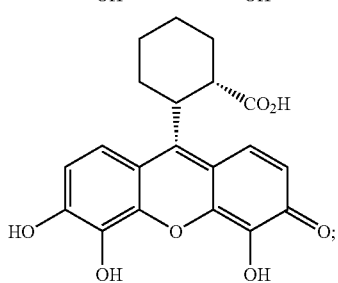

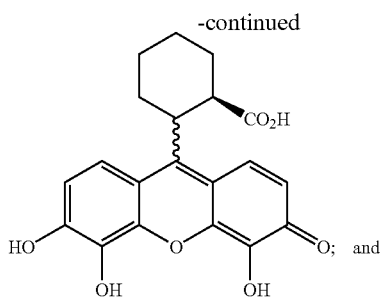

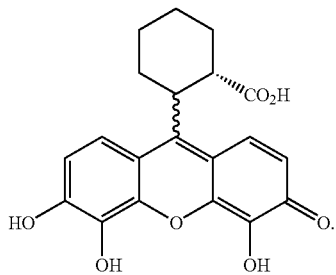

Another category relates to compounds wherein $R^{5c}$ is a substituted or unsubstituted aryl ring. The following are non-limiting examples of substituted aryl $R^{5c}$ units:

2-Carboxyphenyl, 3-carboxyphenyl, 4-carboxyphenyl, 2,3-dicarboxyphenyl, 2,4-dicarboxyphenyl, 2,5-dicarboxyphenyl, 2,6-dicarboxyphenyl, 3,4-dicarboxyphenyl, 3,5-dicarboxyphenyl, 2,3,4-tricarboxyphenyl, 2,3,5-tricarboxyphenyl, 2,3,6-tricarboxyphenyl, 2,4,6-tricarboxyphenyl, 2,3,4,5-tetracarboxyphenyl, 2,3,4,6-tetracarboxyphenyl, 2,3,4,5,6-pentacarboxyphenyl.

2-Fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,3,6-trifluorophenyl, 2,4,6-trifluorophenyl, 2,3,4,5-tetrafluorophenyl, 2,3,4,6-tetrafluorophenyl, 2,3,4,5,6-pentafluorophenyl.

2-Chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,4-trichlorophenyl, 2,3,5-trichlorophenyl, 2,3,6-trichlorophenyl, 2,4,6-trichlorophenyl, 2,3,4,5-tetrachlorophenyl, 2,3,4,6-tetrachlorophenyl, 2,3,4,5,6-pentachlorophenyl.

2-Bromophenyl, 3-bromophenyl, 4-bromophenyl, 2,3-dibromophenyl, 2,4-dibromophenyl, 2,5-dibromophenyl, 2,6-dibromophenyl, 3,4-dibromophenyl, 3,5-dibromophenyl, 2,3,4-tribromophenyl, 2,3,5-tribromophenyl, 2,3,6-tribromophenyl, 2,4,6-tribromophenyl, 2,3,4,5-tetrabromophenyl, 2,3,4,6-tetrabromophenyl, 2,3,4,5,6-pentabromophenyl.

2-Iodophenyl, 3-iodophenyl, 4-iodophenyl, 2,3-diiodophenyl, 2,4-diiodophenyl, 2,5-diiodophenyl, 2,6-diiodophenyl, 3,4-diiodophenyl, 3,5-diiodophenyl, 2,3,4-triiodo-phenyl, 2,3,5-triiodophenyl, 2,3,6-triiodophenyl, 2,4,6-triiodophenyl, 2,3,4,5-tetraiodo-phenyl, 2,3,4,6-tetraiodophenyl, 2,3,4,5,6-pentaiodophenyl.

3-Hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxyphenyl, 3,5-dihydroxyphenyl, 2,3,4-trihydroxyphenyl, 2,3,5-trihydroxyphenyl, 2,3,6-trihydroxy-phenyl, 2,4,6-trihydroxyphenyl, 2,3,4,5-tetrahydroxyphenyl, 2,3,4,6-tetrahydroxyphenyl, 2,3,4,5,6-pentahydroxyphenyl.

2-Methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,6-trimethoxyphenyl, 2,3,4,5-tetramethoxyphenyl, 2,3,4,6-tetra-methoxyphenyl, 2,3,4,5,6-pentamethoxyphenyl.

2-Aminophenyl, 3-aminophenyl, 4-aminophenyl, 2,3-diaminophenyl, 2,4-diaminophenyl, 2,5-diaminophenyl, 2,6-diaminophenyl, 3,4-diaminophenyl, 3,5-diaminophenyl, 2,3,4-triaminophenyl, 2,3,5-triaminophenyl, 2,3,6-triaminophenyl, 2,4,6-triaminophenyl, 2,3,4,5-tetraaminophenyl, 2,3,4,6-tetraaminophenyl, 2,3,4,5,6-pentaaminophenyl.

2-(Dimethylamino)phenyl, 3-(dimethylamino)phenyl, 4-(dimethylamino)phenyl, 2,3-di(dimethylamino)phenyl, 2,4-di(dimethylamino)phenyl, 2,5-di(dimethylamino)-phenyl, 2,6-di(dimethylamino)phenyl, 3,4-di(dimethylamino)phenyl, 3,5-di(dimethyl-amino)phenyl, 2,3,4-tri(dimethylamino)phenyl, 2,3,5-tri(dimethylamino)phenyl, 2,3,6-tri(dimethylamino)phenyl, 2,4,6-tri(dimethylamino)phenyl, 2,3,4,5-tetra(dimethylamino)-phenyl, 2,3,4,6-tetra(dimethylamino)phenyl, 2,3,4,5,6-penta(dimethylamino)phenyl.

One embodiment relates to compounds having the formula:

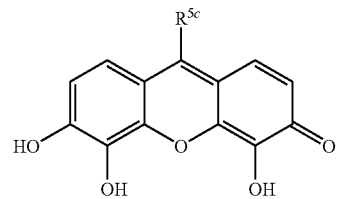

wherein $R^{5c}$ is a substituted or unsubstituted aryl unit, for example, units having the formula:

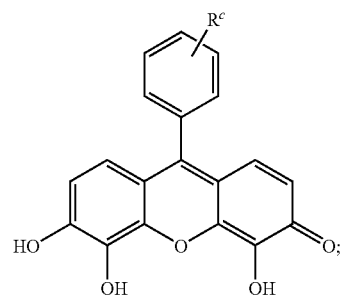

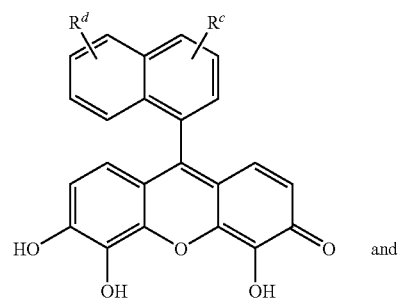

and

-continued

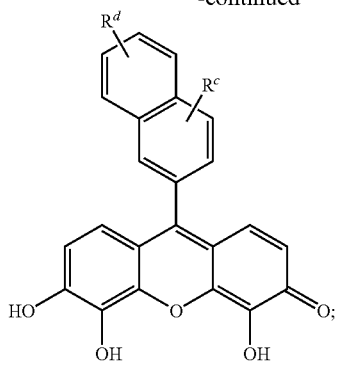

wherein $R^c$ and $R^d$ each represents one or more optionally present substitutions for hydrodgen. Non-limiting examples of $R^c$ and $R^d$ units include units independently chosen from:

i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);

ii) $C_6$ and $C_{10}$ substituted or unsubstituted aryl; for example, 4-aminophenyl, 2-sulfamoylphenyl, 3-fluorophenyl, and 2-sulfamoyl-4-aminophenyl;

iii) —$OR^{202}$; for example, —OH, —$OCH_3$, —$OCH_2CH_3$, —$OCH_2CH_2CH_3$;

iv) —$C(O)R^{202}$; for example, —$COCH_3$, —$COCH_2CH_3$, —$COCH_2CH_2CH_3$;

v) —$C(O)OR^{202}$; for example, —$CO_2CH_3$, —$CO_2CH_2CH_3$, —$CO_2CH_2CH_2CH_3$;

vi) —$C(O)N(R^{202})_2$; for example, —$CONH_2$, —$CONHCH_3$, —$CON(CH_3)_2$;

vii) —$N(R^{202})_2$; for example, —$NH_2$, —$NHCH_3$, —$N(CH_3)_2$, —$NH(CH_2CH_3)$;

viii) halogen: —F, —Cl, —Br, and —I;

ix) —$CH^{m'}X_{n'}$; wherein X is halogen, m' is from 0 to 2, m'+n'=3; for example, —$CH_2F$, —$CHF_2$, —$CF_3$, —$CCl_3$, or —$CBr_3$; and x) —$SO_2R^{202}$; for example, —$SO_2H$; —$SO_2CH_3$; —$SO_2C_6H_5$; —$SO_2NH_2$;

wherein each $R^{202}$ is independently hydrogen, substituted or unsubstituted $C_1$-$C_4$ linear, branched, or cyclic alkyl, amino, alkylamino; or two $R^{202}$ units can be taken together to form a ring comprising 3-7 atoms.

Non-limiting examples of this embodiment includes 2-(4,5,6-trihydroxy-3-oxo-3H-xanthen-9-yl)benzoic acid having the formula:

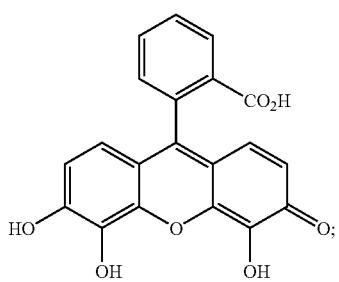 [SMILES: O=C(O)c1ccccc1-c1c2ccc(=O)c(O)c-2oc2c(O)c(O)ccc12]

3-(4,5,6-trihydroxy-3-oxo-3H-xanthen-9-yl)benzoic acid having the formula:

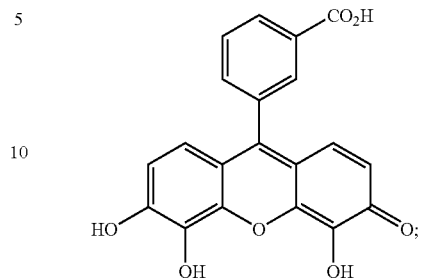

4-(4,5,6-trihydroxy-3-oxo-3H-xanthen-9-yl)benzoic acid having the formula:

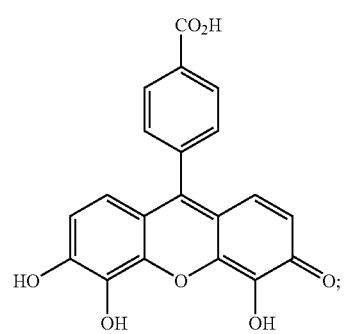 [SMILES: O=C(O)c1ccc(-c2c3ccc(=O)c(O)c-3oc3c(O)c(O)ccc23)cc1]

2-(4,5,6-trihydroxy-3-oxo-3H-xanthen-9-yl)benzamide having the formula:

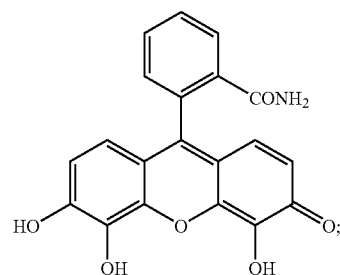

8-(4,5,6-trihydroxy-3-oxo-3H-xanthen-9-yl)-1-naphthoic acid having the formula:

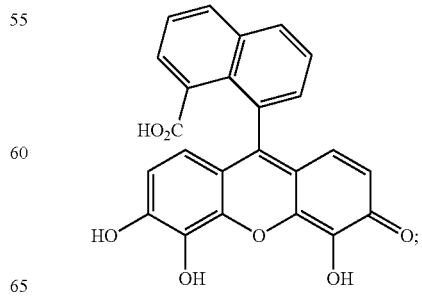

7-(4,5,6-trihydroxy-3-oxo-3H-xanthen-9-yl)-1-naphthoic acid having the formula:

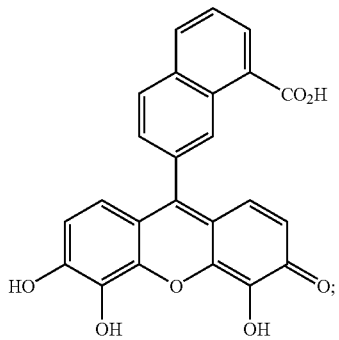 [SMILES: O=C(O)c1cccc2ccc(-c3c4ccc(=O)c(O)c-4oc4c(O)c(O)ccc34)cc12]

and 2-(4,5,6-trihydroxy-3-oxo-3H-xanthen-9-yl)-1-naphthoic acid having the formula:

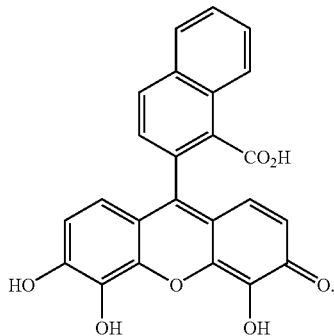 [SMILES: O=C(O)c1c(-c2c3ccc(=O)c(O)c-3oc3c(O)c(O)ccc23)ccc2ccccc12]

Another embodiment relates to compounds having the formula:

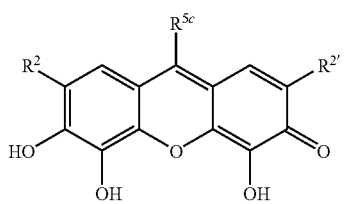

wherein $R^{5c}$ is substituted or unsubstituted aryl, $R^2$ and $R^{2'}$ are the same as defined herein above. Non-limiting examples include:

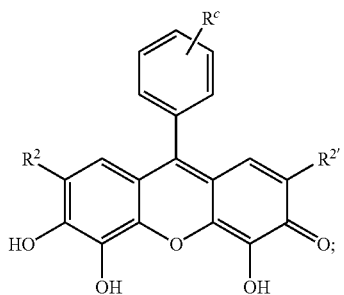

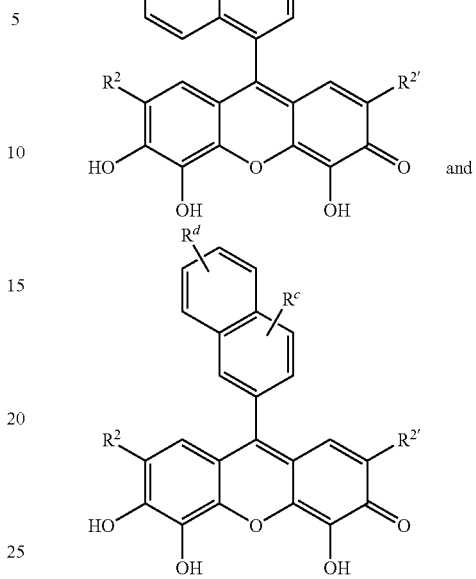

wherein $R^c$ and $R^d$ are the same as defined herein above.

A further embodiment of this category of compounds capable of interacting with at least one amino acid residue of the protein interaction site of the β subunit of a G protein according to the present disclosure relates to compounds wherein $R^{5a}$ and $R^{5b}$ on a carbon atom are taken together to form an exocyclic double bond having the formula =C($R^{5a'}$)($R^{5b'}$), wherein $R^{5a'}$ and $R^{5b'}$ are each independently:
 a) —H;
 b) $C_1$-$C_{12}$ substituted or unsubstituted linear, branched, or cyclic alkyl;
 d) $C_6$ or $C_{10}$ substituted or unsubstituted aryl;
 e) $C_1$-$C_9$ substituted or unsubstituted heterocyclic;
 f) $C_1$-$C_{11}$ substituted or unsubstituted heteroaryl; or
 g) $R^{5a'}$ and $R^{5b'}$ can be taken together to form a substituted or unsubstituted ring having from 3 to 10 carbon atoms and from 0 to 3 heteroatoms chosen from oxygen, nitrogen, and sulfur.

A non-limiting example of a compound within this embodiment is (Z)-9-(3,3-dihydroxyallylidene)-4,5,6-trihydroxy-9,9a-dihydro-3H-xanthen-3-one having the formula:

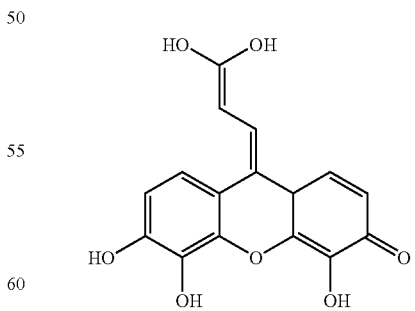

Figure 7:
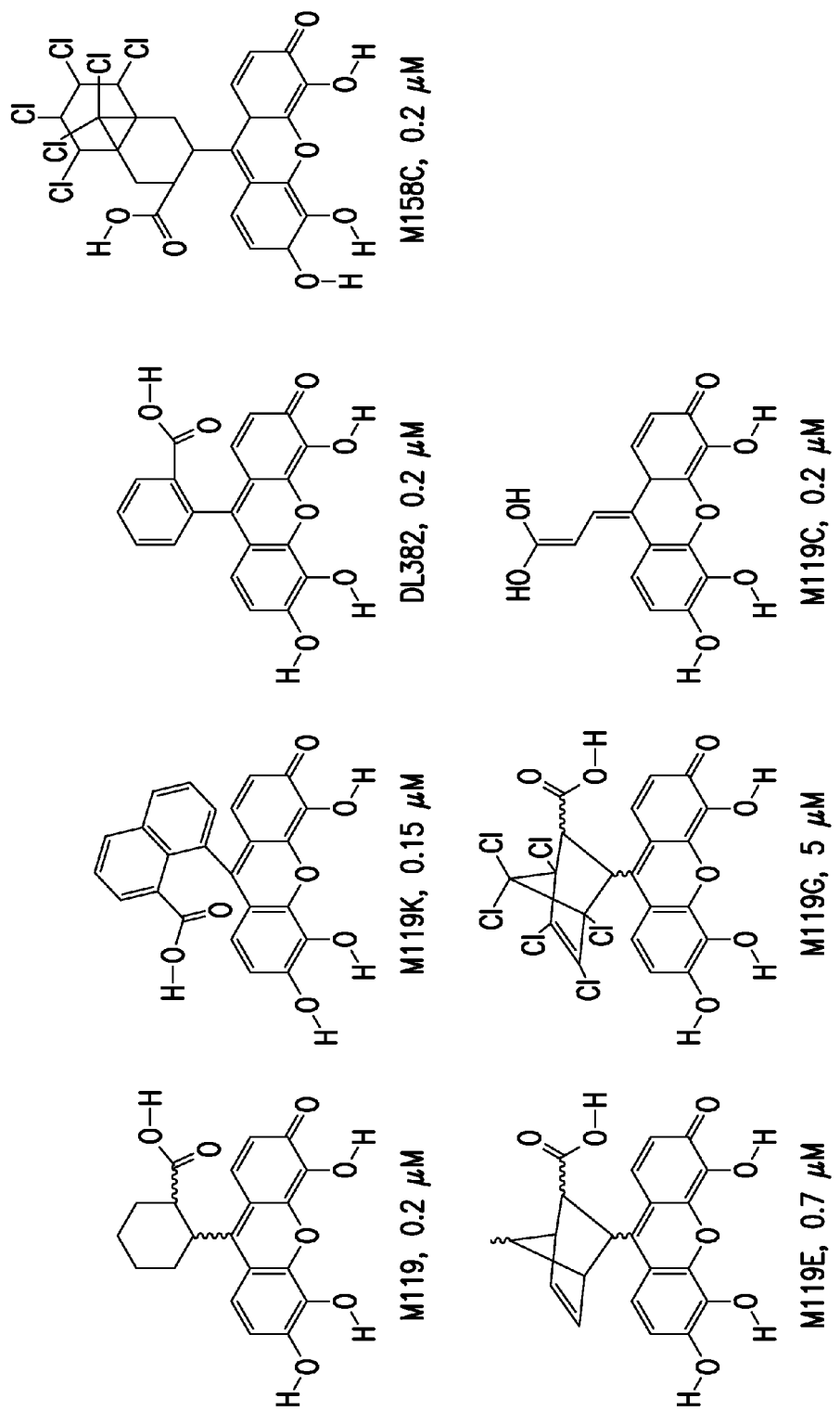
FIG. 7 shows compounds related to M119 that inhibit SIGK binding in the phage ELISA. Shown with each compound is the $IC_{50}$ from the phage ELISA.

Table 6 and FIG. 7 provide SIGK $IC_{50}$ data for non-limiting examples of this category of compounds capable of interacting with at least one amino acid residue of the protein interaction site of the β subunit of a G protein according to the present disclosure.

TABLE 6

| compound | SIGK IC$_{50}$ |
|---|---|
| 2-(4,5,6-trihydroxy-3-oxo-3H-xanthen-9-yl)cyclohexanecarboxylic acid (M119) | 0.2 µM |
| 7-methyl-3-(4,5,6-trihydroxy-3-oxo-3H-xanthren-9-yl)bicyclo[2.2.1]hept-5-ene-2-carboxylic acid | 0.7 µM |
| 1,4,5,6,7,7-hexachloro-3-(4,5,6-trihydroxy-3-oxo-3H-xanthen-9-yl)bicyclo[2.2.1]hept-5-ene-2-carboxylic acid (M119G) | 5 µM |
| 7,8,9,10,11,11-hexachloro-3-(4,5,6-trihydroxy-3-oxo-3H-xanthen-9-yl)tricyclo[4.4.1]-decaline-2-carboxylic acid | 0.2 µM |
| 2-(4,5,6-trihydroxy-3-oxo-3H-xanthen-9-yl) benzoic acid | 0.2 µM |
| 8-(4,5,6-trihydroxy-3-oxo-3H-xanthren-9-yl)-1-naphthoic acid (M119K) | 0.15 µM |
| (Z)-9-(3,3-dihydroxyallylidene)-4,5,6-trihydroxy-9,9a-dihydro-3H-xanthen-3-one (M119C) | 0.2 µM |

However during the course of the work leading to the present disclosure, we further investigated what modifications to the core ring system having the formula:

would provide compounds capable of interacting with at least one amino acid residue of the protein interaction site of the β subunit of a G protein. Disclosed herein above is the compound 7-methyl-3-(4,5,6-trihydroxy-3-oxo-3H-xanthen-9-yl)bicyclo[2.2.1]hept-5-ene-2-carboxylic acid having the formula:

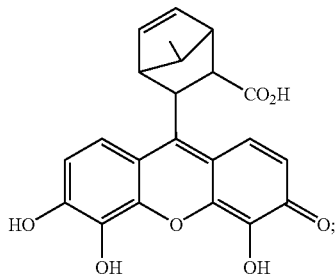 [SMILES: O=C(O)C1C2C=CC(C2)C1c1c2ccc(=O)c(O)c-2oc2c(O)c(O)ccc12]

which was found to bind with at least one amino acid residue of the protein interaction site of the β subunit of a G protein at 700 nM. We attached the $R^{5c}$ unit 7-methyl-bicyclo[2.2.1]hept-5-ene-2-carboxylic acid to the 6-hydroxy-3H-xanthen-3-one ring system having the formula:

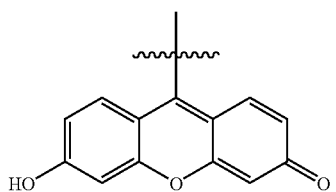 [SMILES: *c1c2ccc(=O)cc-2oc2cc(O)ccc12]

a ring system that was found not to provide compounds eliciting binding with certain $R^{5c}$ units, to prepare 3-(6-hydroxy-3-oxo-3H-xanthen-9yl)bicyclo[2.2.1]hept-5-ene-2-carboxylic acid having the formula:

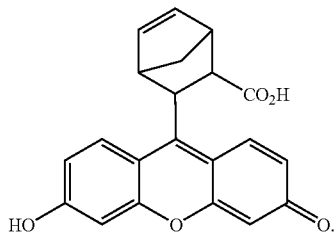

This compound was found to bind at 14 μM.

Another category of compounds capable of interacting with at least one amino acid residue of the protein interaction site of the β subunit of a G protein according to the present disclosure relates to compounds having the formula:

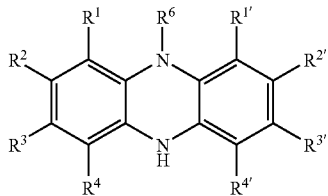

wherein $X^1$ is —[$NR^6$]—, $X^4$ is —[NH]—; $X^2$ and $X^3$ are each —[$CR^{14c}$]=; and the $R^{14c}$ unit from $X^2$ and $X^3$ are taken together to form an aryl ring having 6 carbon atoms.

$R^1$, $R^2$, $R^3$, $R^4$, $R^{1'}$, $R^{2'}$, $R^{3'}$ and $R^{4'}$ are each independently chosen from:
i) —H;
ii) $C_6$ or $C_{10}$ substituted or unsubstituted aryl;
iii) —$OR^{27}$;
  $R^{27}$ is chosen from:
  a) —H;
  b) $C_1$-$C_{12}$ substituted or unsubstituted linear, branched, or cyclic alkyl;
iv) —$N(R^{28a})(R^{28b})$;
  $R^{28a}$ and $R^{28b}$ are each independently chosen from:
  a) —H;
  d) $C_6$ or $C_{10}$ substituted or unsubstituted aryl;
v) halogen;
vi) —$SO_2R^{30}$;
  $R^{30}$ is hydrogen, substituted or unsubstituted $C_1$-$C_4$ linear or branched alkyl.

$R^6$ is phenyl or substituted phenyl, the substitutions for hydrogen on the phenyl ring are each independently chosen from:
i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);
ii) $C_6$ and $C_{10}$ substituted or unsubstituted aryl; for example, 4-aminophenyl, 2-sulfamoylphenyl, 3-fluorophenyl, and 2-sulfamoyl-4-aminophenyl;
iii) —$OR^{100}$; for example, —OH, —$OCH_3$, —$OCH_2CH_3$, —$OCH_2CH_2CH_3$;
iv) —$C(O)R^{100}$; for example, —$COCH_3$, —$COCH_2CH_3$, —$COCH_2CH_2CH_3$;
v) —$C(O)OR^{100}$; for example, —$CO_2CH_3$, —$CO_2CH_2CH_3$, —$CO_2CH_2CH_2CH_3$;
vi) —$C(O)N(R^{100})_2$; for example, —$CONH_2$, —$CONHCH_3$, —$CON(CH_3)_2$;
vii) —$N(R^{100})_2$; for example, —$NH_2$, —$NHCH_3$, —$N(CH_3)_2$, —$NH(CH_2CH_3)$;
viii) halogen: —F, —Cl, —Br, and —I;
ix) —$CH^{m'}X^{n'}$; wherein X is halogen, m' is from 0 to 2, m'+n'=3; for example, —$CH_2F$, —$CHF_2$, —$CF_3$, —$CCl_3$, or —$CBr_3$; and
x) —$SO_2R^{100}$; for example, —$SO_2H$; —$SO_2CH_3$; —$SO_2C_6H_5$; —$SO_2NH_2$;
wherein each $R^{100}$ is independently hydrogen, substituted or unsubstituted $C_1$-$C_4$ linear, branched, or cyclic alkyl, amino, alkylamino; or two $R^{100}$ units can be taken together to form a ring comprising 3-7 atoms. Substituents suitable for replacement of a hydrogen atom are further defined herein below in the iterations and examples.

Non-limiting examples of this embodiment include 3,7-dimethyl-$N^2$-phenyl-10-(4-methylphenyl)-5,10-dihydrophenazine-2,8-diamine having the formula:

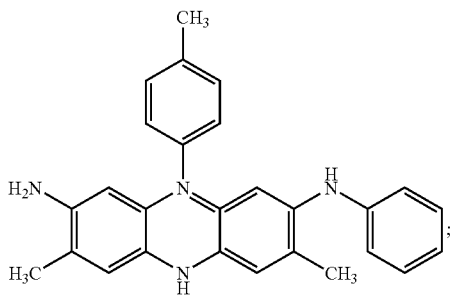

10-phenyl-5,10-dihydrophenazine-2,8-diamine having the formula:

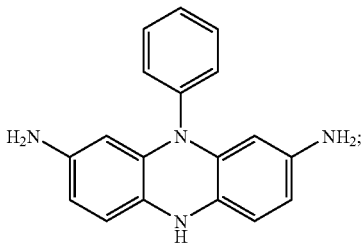 [SMILES: Nc1ccc2c(c1)N(c1ccccc1)c1cc(N)ccc1N2]

and N$^2$,N$^2$-dimethyl-10=phenyl-5,10-dihydrophenazine-2, 8-diamine having the formula:

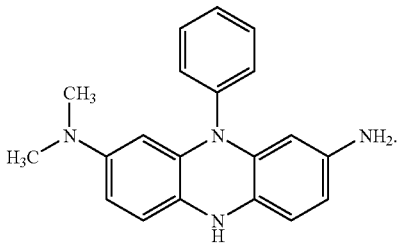 [SMILES: CN(C)c1ccc2c(c1)N(c1ccccc1)c1cc(N)ccc1N2]

A further category of compounds capable of interacting with at least one amino acid residue of the protein interaction site of the β subunit of a G protein according to the present disclosure relates to compounds having the formula:

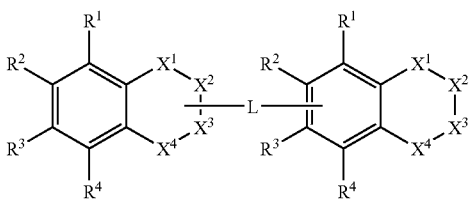

wherein L is a linking group capable of linking a first ring system with a second ring system through any of the R$^1$, R$^2$, R$^3$, R$^4$, X$^1$, X$^2$, X$^3$, or X$^4$ units of each system, L having the formula:

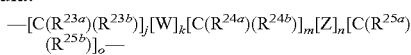

R$^{23a}$, R$^{23b}$, R$^{24a}$, R$^{24b}$, R$^{25a}$, and R$^{25b}$ are each independently chosen from;
  i) —H; or
  ii) C$_1$-C$_4$ substituted or unsubstituted linear or branched alkyl;
  iii) C$_7$-C$_{15}$ substituted or unsubstituted arylalkylene;
W and Z are each independently chosen from:
  i) -M-;
  ii) —C(=M)-;
  iii) —C(=M)M-;
  iv) -MC(=M)-;
  v) -MC(=M)M-;
  vi) -MC(=M)C(=M)M-;
  vii) -MC(=M)MC(=M)M-;
each M is independently chosen from O, S, and NR$^{26}$; R$^{26}$ is hydrogen, hydroxyl, or C$_1$-C$_4$ linear or branched alkyl. The indices k and n are 0 or 1; the indices j, m, and o are from 0 to 12.

One embodiment of compounds that comprise two linked ring systems has the formula:

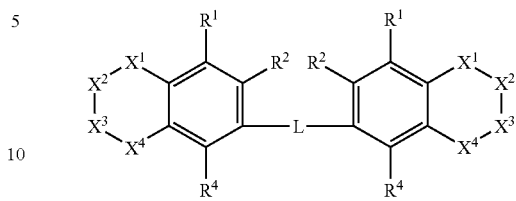

wherein R$^1$, R$^2$, R$^4$, X$^1$, X$^2$, X$^3$, and X$^4$ are the same as defined herein.

A first example of this embodiment relates to compounds wherein L has the formula:

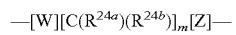

wherein W and Z are each independently chosen from:
  i) —NH—;
  ii) —NHC(O)—; and
  iii) —C(O)NH—.
R$^{24a}$ and R$^{24b}$ are each independently chosen from:
  i) —H; or
  ii) C$_1$-C$_4$ substituted or unsubstituted linear or branched alkyl;
  iii) C$_6$ substituted or unsubstituted aryl; or
  iv) C$_7$-C$_{15}$ substituted or unsubstituted arylalkylene;
the index m is from is from 0 to 6.

A first iteration of this embodiment relates to compounds wherein the index m is equal to 0, W is —NH—, and Z is —C(O)NH—, the linking unit L having the formula:

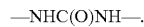

Non-limiting examples of compounds linked via a urea linking unit includes compounds having the formula:

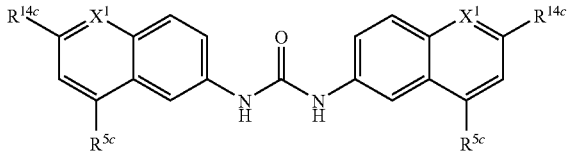

wherein each X$^1$ is CR$^{5c}$ or N; R$^{5c}$ chosen from hydrogen; C$_1$-C$_4$ linear, branched, or cyclic alkyl; —N(R$^{8a}$)(R$^{8b}$), R$^{8a}$ and R$^{8b}$ are each independently hydrogen or C$_1$-C$_4$ linear, branched, or cyclic alkyl; or R$^{8a}$ and R$^{8b}$ can be taken together to form a ring having from 3 to 10 carbon atoms; R$^{14c}$ is hydrogen or C$_1$-C$_4$ linear, branched, or cyclic alkyl.

Specific examples of this iteration includes 1,3-di(quinoline-6-yl)urea having the formula:

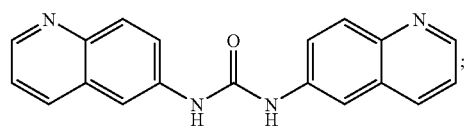 [SMILES: O=C(Nc1ccc2ncccc2c1)Nc1ccc2ncccc2c1]

and 1,3-bis(4-amino-2-methylquinolin-6-yl)urea having the formula:

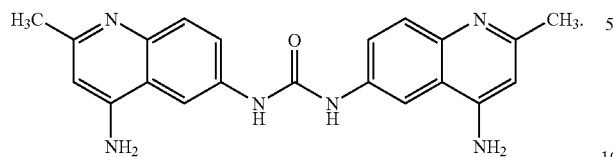

A further embodiment of this category relates to compounds having the formula:

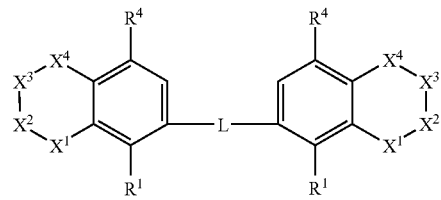

wherein linking unit L has the formula:

—[NHC(O)][C(R$^{24a}$)(R$^{24b}$)]$_m$[C(O)NH]—

R$^{24a}$ and R$^{24b}$ are each independently chosen from:
i) —H; or
ii) C$_1$-C$_4$ substituted or unsubstituted linear or branched alkyl.
the index m is from 1 to 6.

A first iteration of this embodiment relates to compounds having the formula:

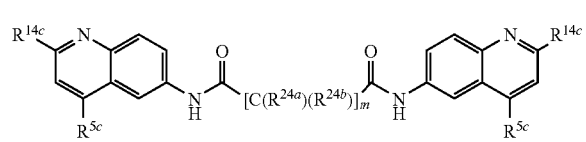

wherein each R$^{5c}$ and each R$^{14c}$ is independently chosen from:

i) hydrogen;
ii) C$_1$-C$_4$ linear, branched, or cyclic alkyl;
iii) —N(R$^{8a}$)(R$^{8b}$); R$^{8a}$ and R$^{8b}$ are each independently hydrogen or C$_1$-C$_4$ linear, branched, or cyclic alkyl; or R$^{8a}$ and R$^{8b}$ can be taken together to form a ring having from 3 to 10 carbon atoms.

Non-limiting examples of this embodiment includes N$^1$,N$^3$-bis(4-amino-2-methylquinolin-6-yl)-2,2-dimethyl-malonamide having the formula:

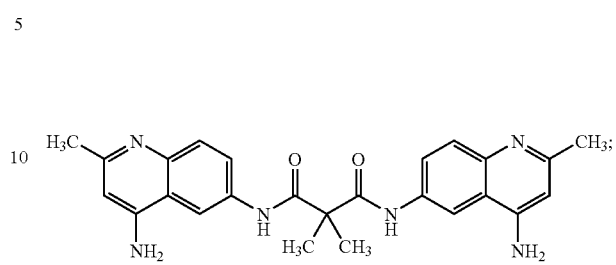

N$^1$,N$^5$-bis(4-amino-2-methylquinolin-6-yl)glutaramide having the formula:

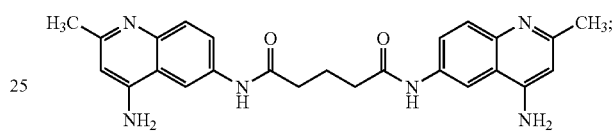

and N$^1$,N$^7$-bis(4-amino-2-methylquinolin-6-yl)heptandiamide having the formula:

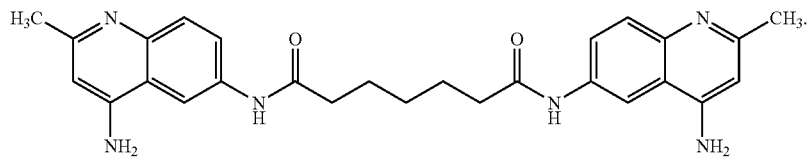 [SMILES: Cc1cc(N)c2cc(NC(=O)CCCCCC(=O)Nc3ccc4nc(C)cc(N)c4c3)ccc2n1]

Another embodiment of compounds that comprise two linked ring systems are compounds wherein the linking group L is —NH—. A non-limiting example of this embodiment includes bis(8-iodo-10-phenyl-5,10-dihydrophenazin-2-yl)amine having the formula:

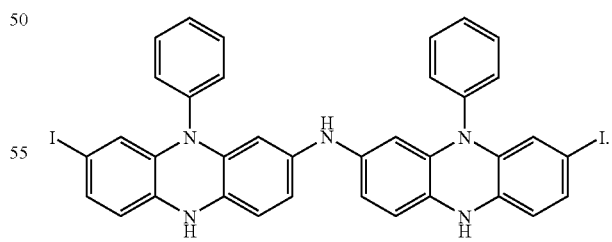

Table 7 provides ELISA IC$_{50}$ data for non-limiting examples of this category of compounds capable of interacting with at least one amino acid residue of the protein interaction site of the β subunit of a G protein according to the present disclosure.

TABLE 7

| compound | ELISA IC$_{50}$ |
|---|---|
| 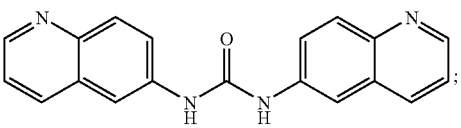  1,3-di(quinoline-6-yl)urea | μM |
| 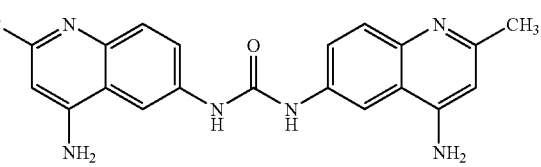  1,3-bis(4-amino-2-methylquinolin-6-yl)urea | 24 μM |
| 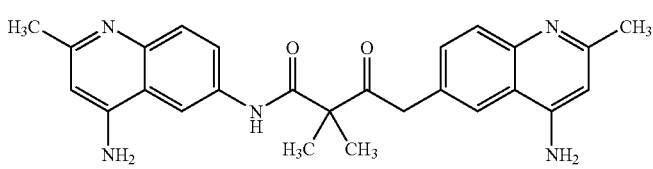  N$^1$,N$^3$-bis(4-amino-2-methylquinolin-6-yl)-2,2-dimethylmalonamide | 74 μM |
| 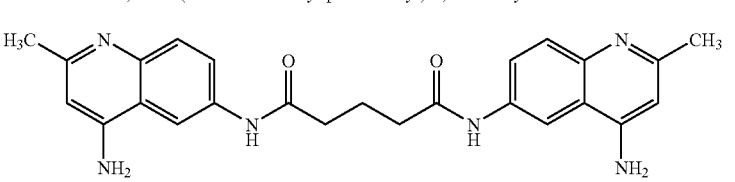  N$^1$,N$^5$-bis(4-amino-2-methylquinolin-6-yl)glutaramide | μM |
| 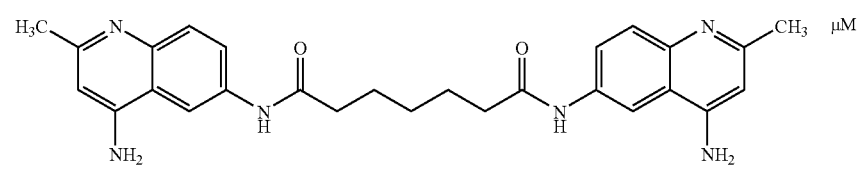  N$^1$,N$^7$-bis(4-amino-2-methylquinolin-6-yl)heptandiamide | μM |
| 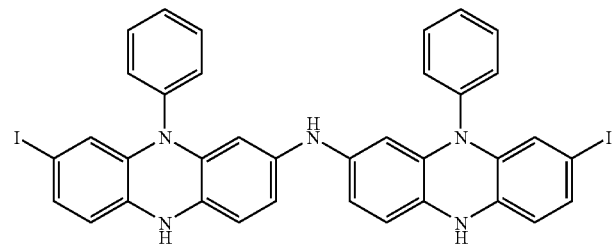 [SMILES: Ic1ccc2c(c1)N(c1ccccc1)c1cc(Nc3ccc4c(c3)N(c3ccccc3)c3cc(I)ccc3N4)ccc1N2]  bis(8-iodo-10-phenyl-5,10-dihydrophenazin-2-yl)amine | 2 μM |

Other compounds which comprise the present disclosure include 1,1'-(5,10-dihydroanthra[9,1,2-cde]benzo[rst]pentaphene-16,17-diyl)bis(azanediyl)dianthracne-9,10-dione having the formula:

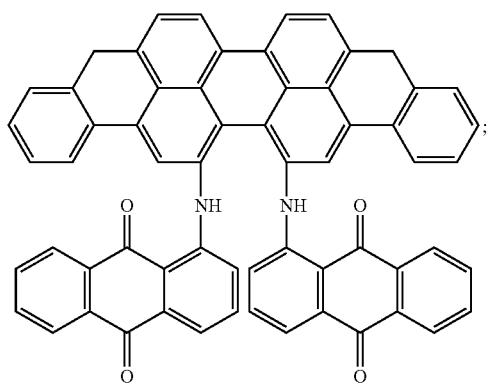
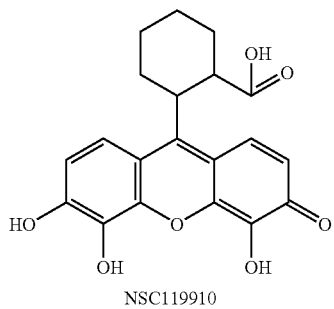
NSC119910
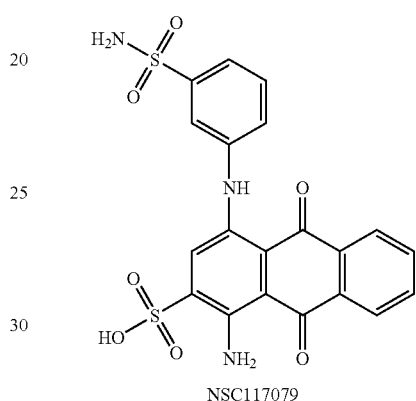
NSC117079
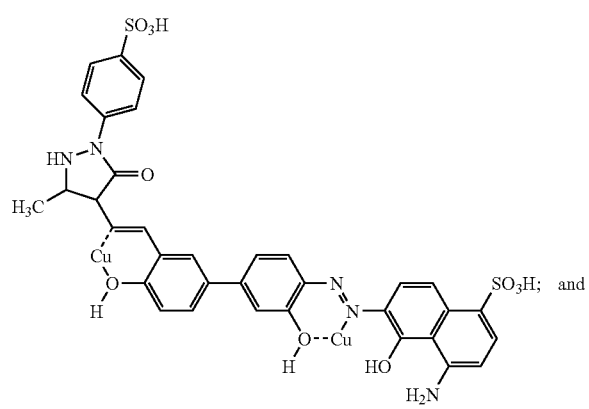
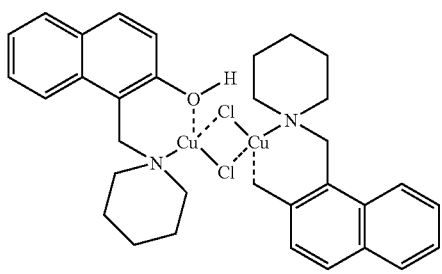
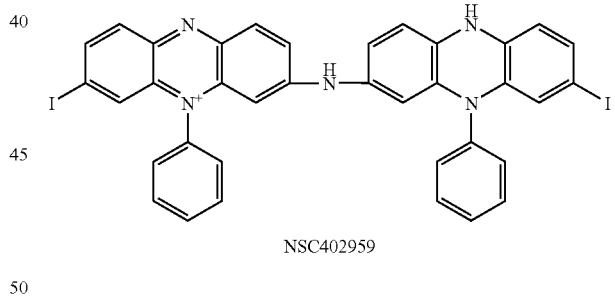
NSC402959
Accordingly, one embodiment of the present invention is a compound having a structure of Formula I:
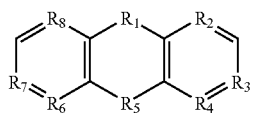
FORMULA I
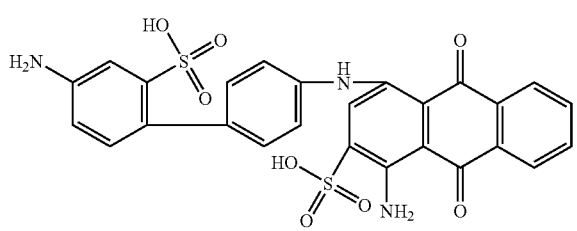
NSC125910
Exemplary compounds having the structure of Formula I which depict various substituent R groups include, but are not limited to, the following:

-continued
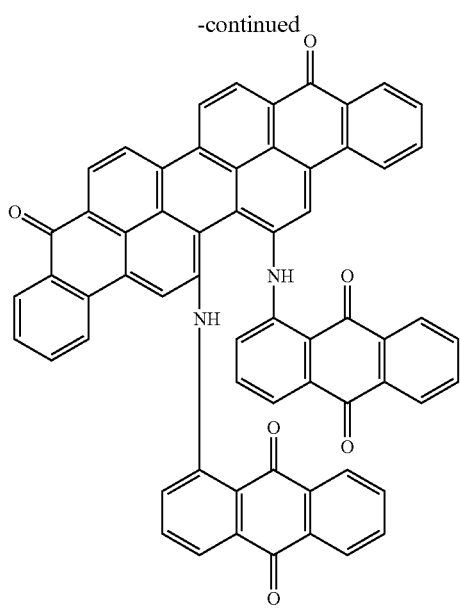
NSC23128
and pharmaceutically acceptable salts and complexes thereof.
Another embodiment of the present invention is a compound having a structure of Formula II:
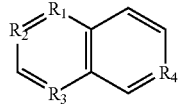
FORMULA II
Exemplary compounds having the structure of Formula II which depict various substituent R groups include, but are not limited to, the following:
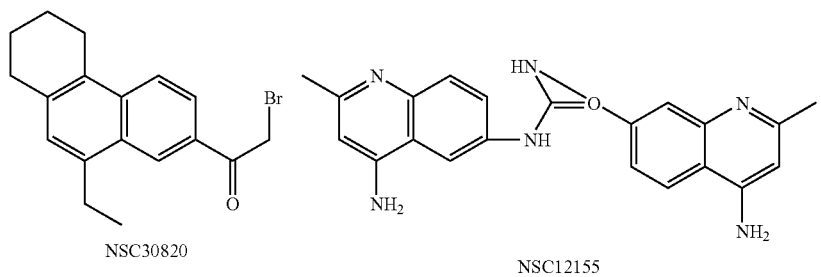
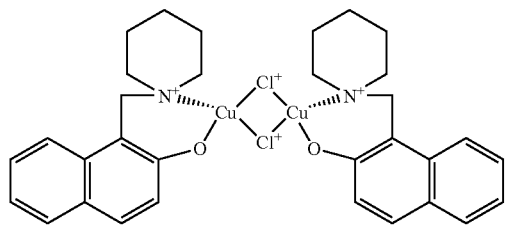
NSC109268
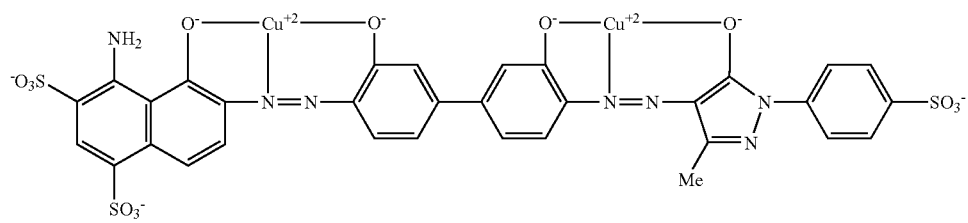
NSC306711 and pharmaceutically acceptable salts and complexes thereof.

Additional exemplary compounds which bind to the protein interaction site of Gβ include, but are not limited to, the following:

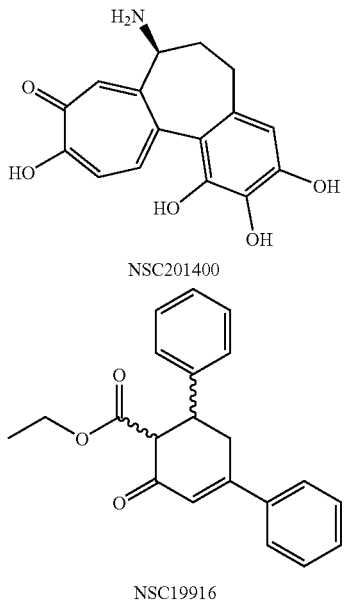

NSC201400

NSC19916 and pharmaceutically acceptable salts and complexes thereof.

Exemplary compounds disclosed herein are intended to include all enantiomers, isomers or tautomers, as well as any derivatives of such compounds that retain the same biological activity as the original compound.

Figure 2:
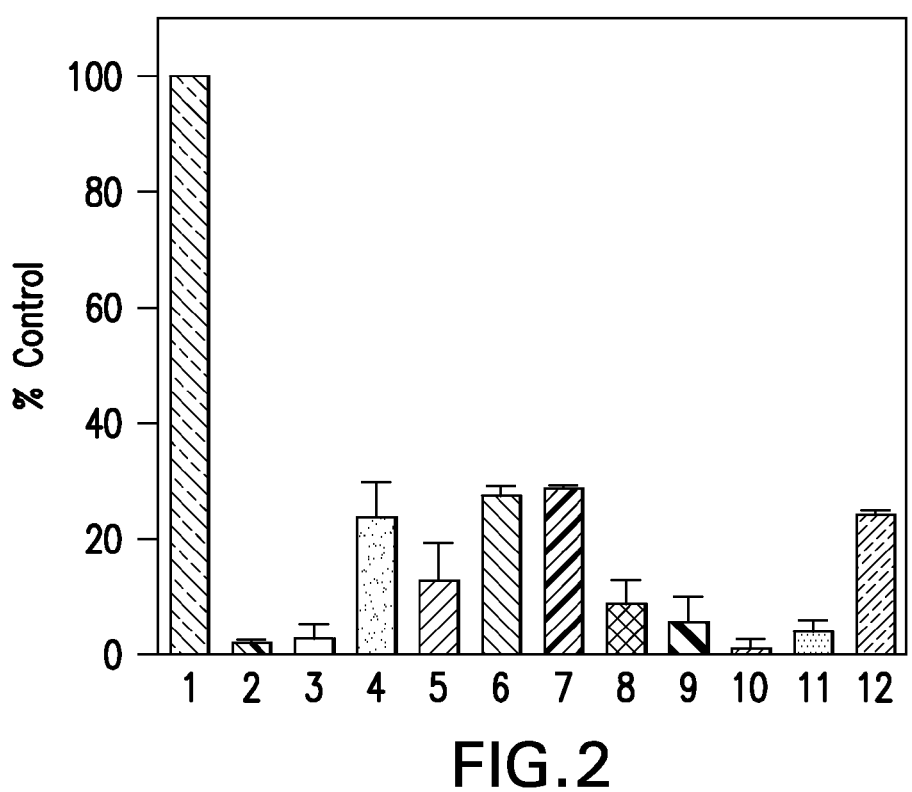

Exemplary compounds of the present invention were initially selected from a computational screen to identify ligands that bind to the novel protein interaction site of Gβ. The computational screen involved using SYBYL molecular modeling software to model the protein interaction site of Gβ as determined in the X-ray structure disclosed herein. The computational docking screen was performed with the National Cancer Institute 1900 compound library wherein the compounds were tested for docking to the protein interaction site of Gβ using FLEXX™ (Tripos, Inc., St. Louis, Mo.) for docking and CSCORE™ (Tripos, Inc.) to evaluate the energetics and fitness of the docked structure. Algorithm-dependent lists of compounds, predicted to interact with the protein interaction site of Gβ and the structural model of the interaction, were generated. Selected compounds were subsequently analyzed in the phage ELISA binding assay disclosed herein to assess whether these compounds could bind to the protein interaction site of Gβ and interfere with protein interactions at this surface. Compounds NSC201400 and NSC119916 had $IC_{50}$ values of .100 nM and 5 μM, respectively, and the remaining compounds were found to bind in the ELISA-based assay to Gβγ with an affinity of at least 50 μM and interfere with peptide interactions at the protein interaction site (FIG. 2). These compounds were further analyzed in the phage ELISA assay and found to have high affinities for the protein interaction site of Gβ and interacted with similar amino acid residues as SIGK.

TABLE 8

| SIGK | NSC30820 | NSC12155 | NSC117079 | NSC23128 | NSC402959 | NSC109268 |
|---|---|---|---|---|---|---|
| Lys57 | Lys57 | | | Lys57 | Lys57 | |
| Tyr59 | Tyr59 | | | Tyr59 | Tyr59 | |
| | Gln75 | | | Gln75 | | |
| Trp99 | Trp99 | | | Trp99 | Trp99 | |
| Val100 | | | | | | |
| Met101 | | | | | | |
| Leu117 | | | | | Leu117 | |
| Tyr145 | | | | | | |
| Asp186 | | | | | | |
| Met188 | | | | | | |
| | | | | | | Cys204 |
| Asp228 | | | | | | Asp228 |
| Asn230 | | Asn230 | Asn230 | | | Asn230 |
| Asp246 | | Asp246 | | | | Asp246 |
| | | Thr274 | | | | |
| | | | | Arg314 | | Arg314 |
| Trp332 | | | | | | |
| $IC_{50}$ | 100 nM | 13 μM | 43 μM | 16 μM | 2 μM | 13 μM |

| SIGK | NSC125910 | NSC119910 | NSC30671 |
|---|---|---|---|
| Lys57 | | Lys57 | Lys57 |
| Tyr59 | Tyr59 | | |
| | | Tyr59 | Tyr59 |
| Trp99 | | | |
| | Trp99 | | |
| Val100 | | Trp99 | Trp99 |
| Met101 | | | |
| | | Val100 | |
| Leu117 | | | |
| Tyr145 | Leu117 | Met101 | |
| Asp186 | | | |
| | | Leu117 | |
| Met188 | | | |
| | | | Met188 |
| Asp228 | | | |
| Asn230 | | | Cys204 |

TABLE 8-continued

| Asp246 | | | Asp228 |
|---|---|---|---|
| | Thr274 | | |
| Trp332 | | | |
| | Trp332 | | |
| | | Ser316 | |
| | | Trp332 | |
| IC$_{50}$ | 68 μM | 100 nM | 7 μM |

Underlined residues indicate residues important for the SIGK*Gβ1γ$_2$ interaction. The last row indicates the IC$_{50}$ value for each compound.

To further illustrate the utility of these compounds, it was demonstrated that NSC119910 blocked interactions of Ga subunit with Gβγ subunits (FIG. 3) and inhibited the ability of Gβγ subunits to inhibit interactions with a physiological target such as PLC β in vitro (FIG. 4) based on a decrease in the enzymatic activity of PLC β. Gβγ-regulated activities of PI3Kγ and PLC-β2/-β3 are important in chemoattractant-induced responses and inflammation. PI3Kγ is involved in the production of TI-Igλ$_L$ and mice deficient in PI3Kγ, lack neutrophil migration (Li, et al. (2000) Science 287:1046-9). The PLC pathway is involved in down-modulation of chemotaxis and in hyperinflammatory conditions (Li, et al. (2000) supra). Therefore, it was determined whether NSC119910 could inhibit the Gβγ/PLC interaction and block PLC activation. Data from fura-2-based experiments demonstrated that the abruptly occurring increase in cytosolic Ca$^{2+}$ in fMLP-stimulated neutrophils, a response which is due to the release of the cation from intracellular stores (Anderson, and Mahomed (1997) Clin. Exp. Immunol. 110:132-138; Geiszt, et al. (1997) J. Biol. Chem. 272:26471-26478), was suppressed by 10 μM NSC119910. Increases in [Ca$^{2+}$] through ATP was not significantly suppressed in the presence of NSC119910, indicating that the effect of the compound on fMLP dependent Ca$^{2+}$ increases are specific. Further, the time taken for fluorescence to decline to half-peak values was not substantially affected. The results indicate that NSC 119910 inhibits PLC/G-protein interactions which lead to activation of PLC in vivo.

Opioid receptors, μ, Δ, and K, couple to Gi and G$_O$ proteins through α and βγ subunits, and regulate a number of signaling pathways. In particular, the efficacy of opioid signal transduction in PLC-β3-deficient mice has been shown to increase, indicating that PLC suppresses opioid signaling by modification of opioid-dependent signaling components (Xie, et al. (1999) Proc. Natl. Acad. Sci. USA 96:10385-10390). Given that PLC-β3 plays a significant role as a negative regulator of opioid responses, it was determined whether NSC119910 could inhibit PLC-β3 activation thereby enhancing morphine-induced analgesia. Mice were intracerebroventricularly injected in accordance with standard protocols (Xu, et al. (1998) J. Pharmacol. Exp. Therapeut. 284:196-201) with 100 nmol of NSC119910 in combination with varying doses (0.1, 0.3, 1, and 3 nmol) of morphine. Mice were tested 20 minutes after the injection for an analgesic response in a 55° C. warm-water tail-flick test (Wells, et al. (2001) J. Pharmacol. Exp. Therapeut. 297:597-605). The ED$_{50}$ value for morphine alone was 0.74 nmol, while the ED$_{50}$ value for NSC119910 plus morphine was 0.065 nmol. The differences in the ED$_{50}$ values showed an 11-fold shift to the left in a morphine dose-response curve (Table 9), indicating that when morphine was administered with NSC119910, less morphine was required to produce a similar analgesic effect. Accordingly, administering opioids in combination with a compound of the instant invention would allow for the use of a lower dose of opioid in patients thereby reducing the development of opioid tolerance.

TABLE 9

| | Percent Antinociception ± S.E.M. | |
|---|---|---|
| Dose of Morphine, nmol | Morphine Alone | Morphine plus NSC119910 |
| 10 | 82.4 ± 11.9 | N/A |
| 3 | 68.0 ± 14.1 | 100 ± 0.0 |
| 1 | 55.6 ± 8.3 | 79.3 ± 9.1 |
| 0.3 | 41.0 ± 10.2 | 64.4 ± 10.0 |
| 0.1 | 21.0 ± 11.1 | 55.3 ± 12.7 |

Having demonstrated that NSC119910 effectively modulates G-protein interactions, a series of structural analogs of NSC119910, identified using modeling software, were analyzed for binding to the protein interaction site of Gβ. These analogs and their corresponding affinities for Gβγ were:

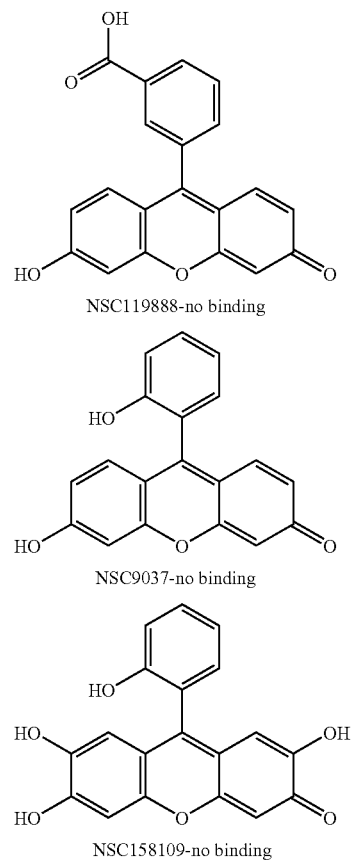

NSC119888-no binding

NSC9037-no binding

NSC158109-no binding

-continued
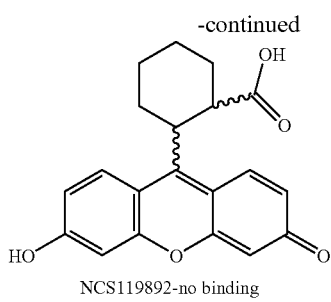
NCS119892-no binding
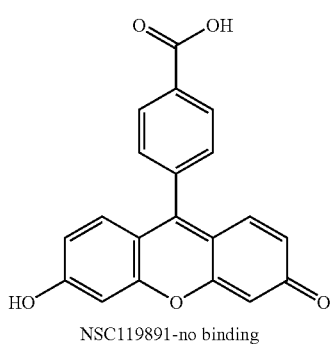
NSC119891-no binding
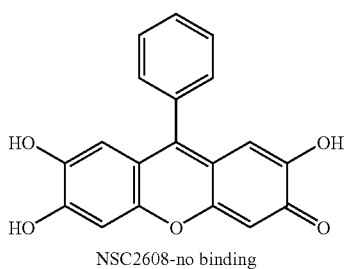
NSC2608-no binding
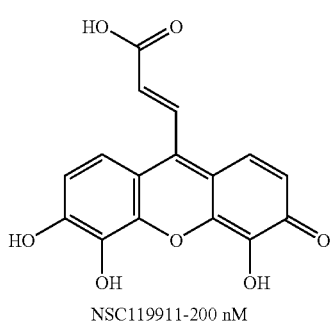
NSC119911-200 nM
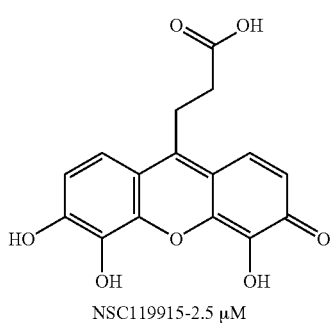
NSC119915-2.5 μM
-continued
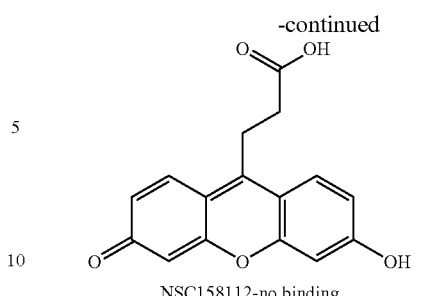
NSC158112-no binding
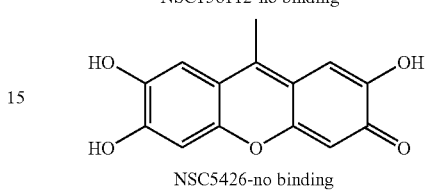
NSC5426-no binding
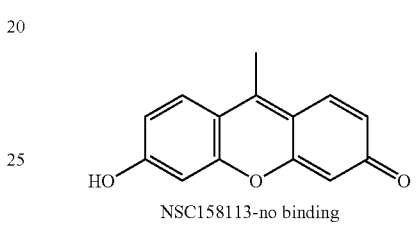
NSC158113-no binding
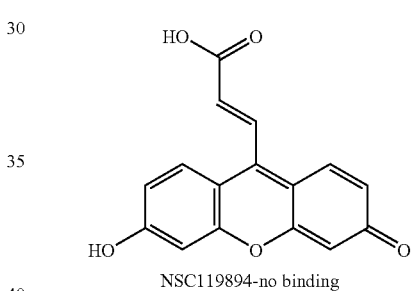
NSC119894-no binding
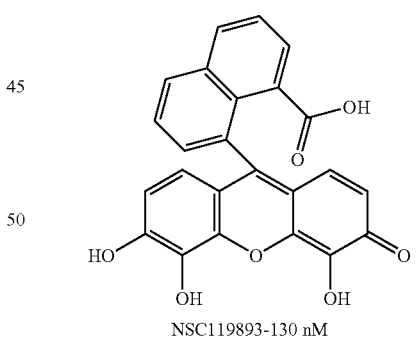
NSC119893-130 nM
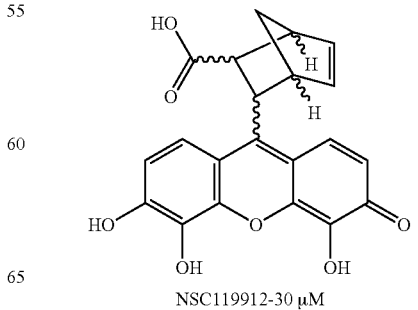
NSC119912-30 μM -continued

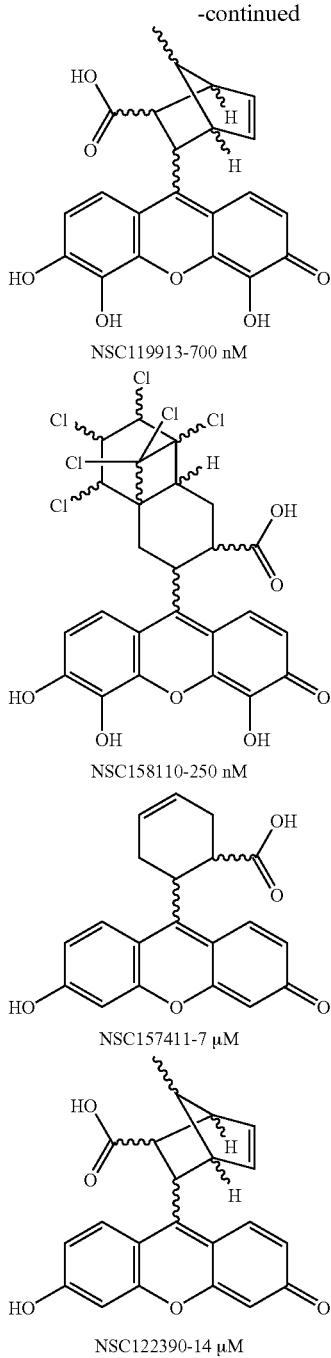

NSC119913-700 nM

NSC158110-250 nM

NSC157411-7 μM

NSC122390-14 μM

From this analysis, a general structure for NSC119910 analogs was identified and is represented as Formula III.

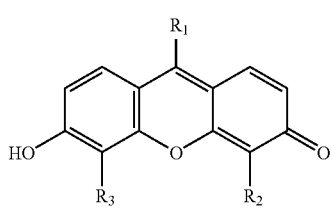

FORMULA III wherein, Ri can be a substituted or unsubstituted alkyl, substituted or unsubstituted alkenyl, substituted or unsubstituted cycloalkyl, or substituted or unsubstituted cycloalkenyl; and $R_2$ and $R_3$ are independently hydrogen or a hydroxyl group. In particular embodiments, $R_2$ and $R_3$ are both hydroxyl.

As used herein, alkyl refers to a straight or branched hydrocarbon chain consisting solely of carbon and hydrogen atoms, containing no saturation, having from one to eight carbon atoms.

Alkenyl is intended to mean an aliphatic hydrocarbon group containing at least one carbon-carbon double bond and which may be a straight or branched chain having from 2 to about 10 carbon atoms.

Cycloalkyl denotes a non-aromatic mono or multicyclic ring system of about 3 to 12 carbon atoms.

As used herein, the term cycloalkenyl refers to a mono or multicyclic ring system containing in the range of about 3 to 12 carbon atoms with at least one carbon-carbon double bond.

Substituents in the substituted alkyl, cycloalkyl, alkenyl or cycloalkenyl groups include, but are not limited to, hydroxy, carboxyl, halogen (e.g., fluorine, chlorine, bromine, or iodine), or substituted or unsubstituted alkyl. With the exception of NSC 157411 and NSC 122390, analogs of NSC119910 generally contained hydroxyl groups in the $R_2$ and $R_3$ positions of Formula III, which appeared to facilitate binding; and a carboxyl-substituted alkyl, cycloalkyl, alkenyl or cycloalkenyl substituent at $R_1$ of Formula III, which appeared to modulate activity, but was not required for binding.

Accordingly, a further embodiment of the present invention is a compound having a structure of Formula III and pharmaceutically acceptable salts and complexes thereof.

C. Methods of Using the Compositions

1. Methods of Treating Disease

Chemoattractant-mediated recruitment of leukocytes is responsible for many of the deleterious effects of chronic inflammatory diseases. Many chemoattractants activate G protein-coupled receptors (GPCRs) coupled to the Gi family of heterotrimeric G proteins in leukocytes. Heterotrimeric G proteins are composed of Gα, Gβ, and Gγ subunits. Ligand binding to receptors catalyzes the exchange of tightly bound GDP for GTP on the Gα subunit, liberating it from the Gβγ subunits. Dissociation of the Gα and Gβγ subunits can allow each to directly bind to downstream effector proteins (Gilman, 1987; Oldham and Hamm, 2006). The free Gβγ subunits released from Gi heterotrimers upon chemoattractant receptor activation initiate critical signaling pathways to direct chemoattractant-dependent neutrophil functions including chemotaxis and superoxide production (Neptune and Bourne, 1997).

Key direct targets of Gβγ subunit binding and activation in neutrophils are phosphoinositide 3-kinase γ(PI3-kinase γ) (Stephens et al., 1994, 1997; Stoyanov et al., 1995), Phospholipase C β (PLCβ) (Wu et al., 2000), and P-Rex (Welch et al., 2002). PI3-kinase γ has been noted to be a central mediator of chemotaxis and plays a pivotal role in leukocyte recruitment to inflamed tissues (Hirsch et al., 2000; Li et al., 2000; Camps et al., 2005). PIP3, produced by PI3-kinase γ catalytic activity, is critical to the development of cell polarity, which is necessary for chemokine-mediated cell motility and directional sensing (Wu et al., 2000). PI3-kinase γ-deficient neutrophils have impaired responses to various chemoattractants, including diminished chemotaxis (Hirsch et al., 2000; Li et al., 2000) and respiratory burst (Li et al., 2000; Sasaki et al., 2000), in response to GPCR activation. Small-molecule inhibitors of PI3-kinase γ catalytic activity have been demonstrated to suppress joint inflammation in mouse models of inflammation (Barber et al., 2005; Camps et al., 2005). The development of selective inhibitors that do not target other PI3-kinase isoforms is important to the success of a method that targets PI3-kinase γ activity as a therapeutic anti-inflammatory approach, because these enzymes are involved in multiple aspects of mammalian cell function (Rückle et al., 2006).

Herein disclosed are novel strategies to inhibit chemoattractant-dependent chemotaxis and inflammation using recently identified compounds that block Gβγ-interactions with effectors, including PI3-kinase γ, by binding to a protein-protein interaction "hot spot" on the Gβ subunit (Bonacci et al., 2006). These compounds block fMLP-dependent PI3-kinase γ activation, Rac1 activation, superoxide production, and neutrophil migration in vitro. Furthermore, when administered in vivo, neutrophil-dependent inflammation is inhibited, demonstrating that suppressing key Gβγ-dependent signaling functions with small molecules has significant anti-inflammatory potential.

Figure 6:
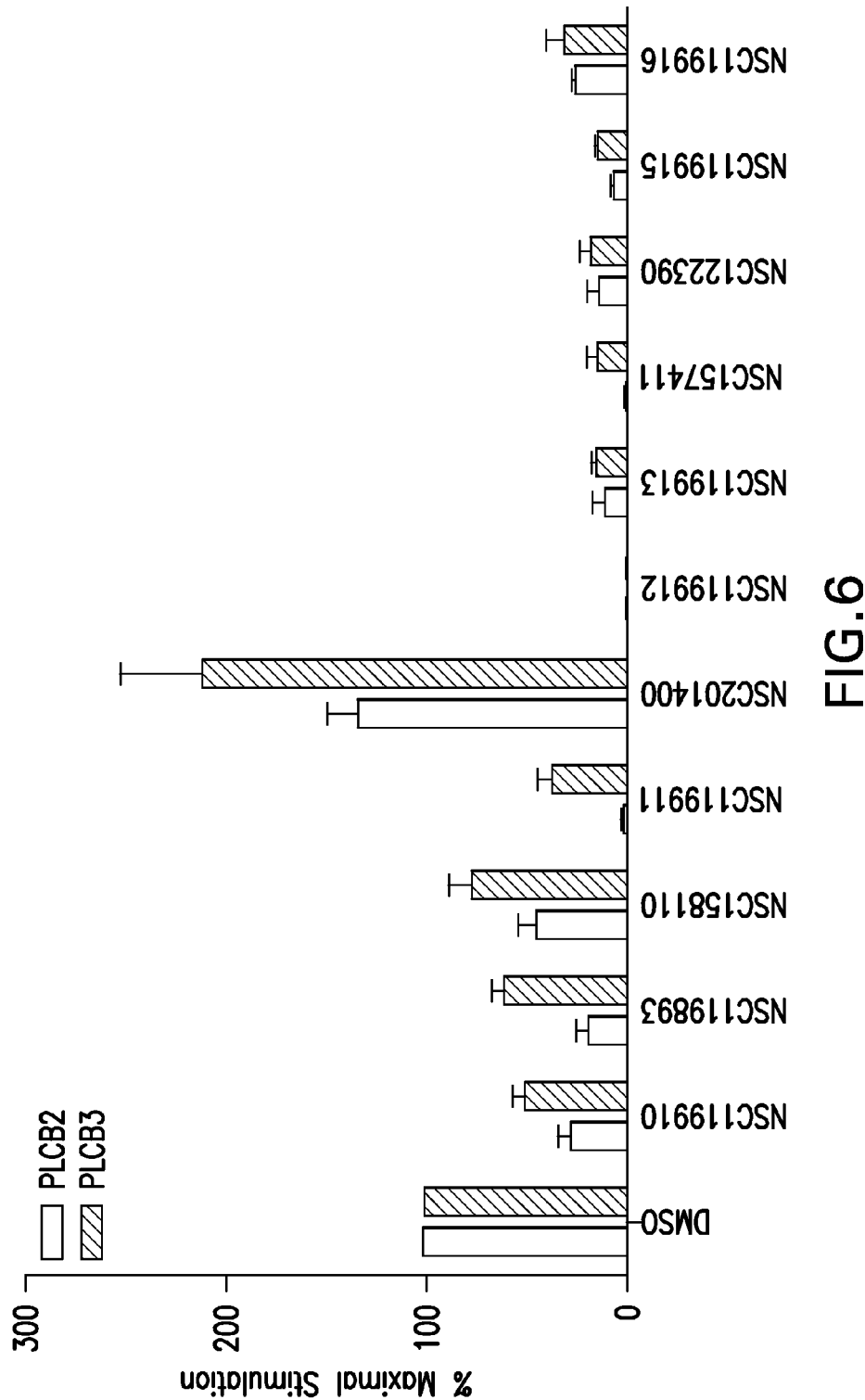
FIG. 6 shows inhibition of PLC-β2 and PLC-β3 activation in the presence of exemplary compounds of the instant invention.

The ability of NSC119910 analogs to selectively modulate activation PLC-β2 and -β3 was analyzed. In this assay, PLC-β2 and PLC-β3 were purified and PLC enzymatic activity was measured in the presence or absence of purified βγ and in the presence or absence of analog. The results of this analysis indicated that NSC119911 appeared to block PLC-β2 activation more effectively than PLC-β3 activation and NSC201400 selectively potentiated PLC-β3 activation despite blocking peptide binding to βγ (FIG. 6). Further, while NSC119910, NSC and analog NSC119893 block $Ca^{2+}$ mobilization, they do so without interfering with fMLP-dependent ERK activation. Likewise, NSC119911, NSC158110, and NSC201400 also do not interfere with fMLP-dependent ERK activation.

The compounds disclosed herein as well as those found to bind to the protein interaction site of Gβ and interfere with protein interactions at this surface can be used in a method for modulating (i.e., blocking or inhibiting, or enhancing or potentiating) at least one activity of a G protein. Such a method involves contacting a G protein either in vitro or in vivo with an effective amount of an agent that interacts with at least one amino acid residue of the protein interaction site of the G protein β subunit so that at least one activity of the G protein is modulated. An effective amount of an agent is an amount which reduces or increases the activity of the G protein by 10%, 20%, 30%, 40%, 50%, 60%, 70%, 80%, 90% or 100%. Such activity can be monitored based on protein-protein interactions or enzymatic assays detecting activity of downstream proteins.

As will be appreciated by one of skill in the art, modulating one or more G protein activities can be useful in selectively analyzing G protein signaling events in model systems as well as in preventing or treating diseases and disorders involving G protein βγ subunit signaling. The selection of the compound for use in preventing or treating a particular disease or disorder will be dependent upon the particular G protein-dependent downstream protein involved in the disease or disorder. For example, a compound which interacts with Lys57, Trp99, Met101, Leu117, Asp186, Asp228, Asp246 and/or Trp332 of Gβ would be useful in preventing or treating adenylyl cyclase-associated diseases or disorders, whereas a compound which interacts with Lys57, Tyr59, Trp99, Met101, Leu117, Tyr146, Met188, Asp246, and/or Trp332 may be more suitable for GRK2-associated diseases or disorders. It is contemplated that this selectivity for specific downstream proteins may reduce side effects associated with antagonists which inhibit all activities associated the G protein βγ subunit signaling.

Prevention or treatment typically involves the steps of first identifying a patient at risk of having or having a disease or disorder involving at least one G protein βγ subunit activity {e.g., congestive heart failure, addiction, hyper- or hypo-inflammation, or opioid tolerance). Once such an individual is identified using, for example, standard clinical practices, said individual is administered a pharmaceutical composition containing an effective of a selective compound disclosed herein or identified in the screening methods of the invention. In most cases this will be a human being, but treatment of agricultural animals, e.g., livestock and poultry, and companion animals, e.g., dogs, cats and horses, is expressly covered herein. The selection of the dosage or effective amount of a compound is that which has the desired outcome of reducing or reversing at least one sign or symptom of a disease or disorder involving G protein βγ subunit signaling in a patient. For example, some of the general signs or symptoms associated with congestive heart failure include increased heart rate, increased respiratory rate, breathing faster and deeper than normal, breathlessness, irritability, restlessness, an unexplained fussiness, swelling, puffiness, edema, sudden weight gain or poor weight gain, decrease in appetite, diaphoresis, cough, congestion or wheezing, a decrease in activity level, fatigue, listlessness, decrease in urine output, or pale, mottled or grayish appearance in skin color. General signs or symptoms associated with addiction include, but are not limited to, changes in attitude, appearance, and relationships with others, whether at home, school or work and other behavioral changes.

When preventing or treating an inflammatory condition, the selective modulation of either the PLC pathway or PI3Kγ will be useful in treating different inflammatory conditions. For example, to reduce neutrophil migration into sites of inflammation (e.g., in arthritis) it is desirable to administer a compound which selectively inhibits the activation of PI3Kγ thereby reducing the injury to tissues that contribute to the pathophysiology of the inflammatory diseases. Conversely, to facilitate an inflammatory response, e.g., to enhance immune responses to bacterial or viral infection, it is desirable to administer a compound which selectively inhibits the activation of the PLC pathway.

By "subject" is meant an individual. Preferably, the subject is a mammal such as a primate, and, more preferably, a human. The term "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

The present methods can also be treat an autoimmune or inflammatory condition. Such conditions include but are not limited to asthma, rheumatoid arthritis, reactive arthritis, spondylarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, ischemia reperfusion injury, Alzheimer's disease, transplant rejection (allogeneic and xenogeneic), thermal trauma, any immune complex-induced inflammation, glomerulonephritis, myasthenia gravis, cerebral lupus, Guillaine-Barre syndrome, vasculitis, systemic sclerosis, anaphylaxis, catheter reactions, atheroma, infertility, thyroiditis, ARDS, post-bypass syndrome, hemodialysis, juvenile rheumatoid, Behcets syndrome, hemolytic anemia, pemphigus, bulbous pemphigoid, stroke, atherosclerosis, and scleroderma.

It is understood and herein contemplated that seizures can be treated using the methods and compounds disclosed herein. There are a numerous causes for seizures known in the art. For example, seizures can be the result of inflammation. For example, the seizures can be associated with hippocampal sclerosis, tuberous sclerosis, or cortical dysplasia. Additionally, seizures are associated with infections diseases such as *Neisseria meningitides, Listeria monocytogenes, Streptococcus pneumoniae*, Lymphocytic choriomeningitis virus, Herpes Simplex virus type-1, West Nile virus, Ebola virus, Marburg virus, Sin Nombre virus, Rift Valley Fever, Hantavirus, Blackcreek canal virus, Lassa virus, Junin virus, Machupo virus, Mumps, Measles, and Influenza. Thus disclosed herein are methods of treating seizures in a subject in need thereof comprising administering to the subject an agent that interacts with at least one amino acid residue of the protein interaction site of the G protein β subunit, and wherein the agent modulates one or more G protein β subunit activities. Also disclosed are methods wherein the seizures are associated with hippocampal sclerosis, tuberous sclerosis, or cortical dysplasia. Also disclosed are methods wherein the seizures are associated with an infectious disease, the infectious disease is selected from the group consisting of *Neisseria meningitides, Listeria monocytogenes, Streptococcus pneumoniae*, Lymphocytic choriomeningitis virus, Herpes Simplex virus type-1, West Nile virus, Ebola virus, Marburg virus, Sin Nombre virus, Rift Valley Fever, Hantavirus, Blackcreek canal virus, Lassa virus, Junin virus, Machupo virus, Mumps, Measles, and Influenza.

The disclosed methods utilize tissue samples from the subject to provide the basis for assessment. Such tissue samples can include, but are not limited to, blood (including peripheral blood and peripheral blood mononuclear cells), tissue biopsy samples (e.g., spleen, liver, bone marrow, thymus, lung, kidney, brain, salivary glands, skin, lymph nodes, and intestinal tract), and specimens acquired by pulmonary lavage (e.g., bronchoalveolar lavage (BAL)). Thus it is understood that the tissue sample can be from both lymphoid and non-lymphoid tissue. Examples of non-lymphoid tissue include but are not limited to lung, liver, kidney, and gut. Lymphoid tissue includes both primary and secondary lymphoid organs such as the spleen, bone marrow, thymus, and lymph nodes.

Heart failure (HF) is the leading cause of death worldwide, the leading cause of hospitalization in the US, and is predicted to be the leading cause of disability by 2020. Five-year survival after HF diagnosis is 50%, and 1-year survival for end-stage HF is only 50%.

Despite therapeutic advances of the past two decades, β-adrenergic receptors (β-AR) play a central role in cardiac contractility, and are dramatically down-regulated and desensitized in end-stage HF. Elevated expression and activity of the G-protein coupled receptor kinase 2 (GRK2, or βARK1), a molecule responsible for chronic β-AR desensitization, is a hallmark of HF and can directly cause HF in animal models. Moreover GRK2 expression and activity correlates with the severity of human HF.

GRK2 is a cytosolic enzyme recruited to membrane-bound Gβγ following β-AR stimulation; the Gβγ-GRK2 interaction is a prerequisite for GRK2-mediated β-AR desensitization. Specific Gβγ-GRK2 inhibitory compounds can be identified by molecular modeling, and a compound named M119 was found that blocks in vitro Gβγ-GRK2 interaction (Bonacci et al, Science, 2006). Large peptide inhibitors of Gβγ and the Gβγ-GRK2 interaction, including the GRK2 C-terminus (βARKct) or truncated phosducin can prevent and reverse HF in animal models by viral gene delivery. β-blockers, standard therapy in medical HF management, are synergistic with βARKct. Thus, M119 inhibition of the Gβγ-GRK2 interaction is a promising therapeutic strategy for HF, and offers distinct size, delivery and specificity advantages over viral gene delivery of large peptides as HF therapy.

The cardiac effects of M119 were investigated in vitro and in vivo. Using adult mouse cardiomyocytes, it was found that M119 reduces β-AR stimulated membrane recruitment of GRK2, and enhances cAMP generation at baseline and in response to β-AR stimulation. Increased cardiomyocyte contractility was demonstrated at baseline and in response to β-AR agonist. Importantly, normalization of cardiac function, morphology and GRK2 expression is demonstrated in an acute animal model of HF.

PI3Kγ, the only PI3K regulated by Gβγ, is involved in β-AR desensitization by GRK2-PI3Kγ complex recruitment to Gβγ. Large peptide disruption of PI3Kγ and its interaction with GRK2 is cardioprotective: genetic ablation of PI3Kγ is not. Compounds were identified that differentially affect Gβγ-GRK2, Gβγ-PI3K, or both. These new chemical tools are used to test whether PI3Kγ regulation of β-AR signaling is Gβγ- and/or GRK2 dependent or independent.

Thus, it is contemplated herein that present methods can also be used to treat conditions associated with heart malfunction. In particular, it is contemplated herein that the heart condition can be a cardiovascular indication associated with heart failure including but not limited to myocardial infarction, restenosis, hypertension, and all primary and secondary cardiomypathies, including but not limited to: dilated, (ischemic, non-ischemic, idiopathic, congestive, diabetic, peripartium, alcoholic, viral, and valvular) hypertrophic, and restrictive. Thus, for example, disclosed herein are methods for treating a disease or condition involving at least one G protein βγ subunit activity comprising administering to a patient having or at risk of having a disease or condition involving at least one G protein βγ subunit activity an effective amount of an agent that interacts with at least one amino acid residue of the protein interaction site of the G protein β subunit so that the at least one activity of the G protein is modulated thereby preventing or treating the disease or condition involving the at least one G protein βy subunit activity, wherein the disease or condition is a associated with heart malfunction and wherein the disease of condition is selected from the group consisting of myocardial infarction, restenosis, hypertension, and all primary and secondary cardiomypathies, including but not limited to: dilated, (ischemic, non-ischemic, idiopathic, congestive, diabetic, peripartium, alcoholic, viral, and valvular) hypertrophic, and restrictive.

Furthermore, it is understood and herein contemplated that diseases affecting the vasculature may affect heart function. Examples of such vaculature diseases include but are not limited to: hypertension of any etiology, atherosclerosis, peripheral vascular disease, restenosis. Thus, disclosed herein are methods for treating a disease or condition involving at least one G protein βy subunit activity comprising administering to a patient having or at risk of having a disease or condition involving at least one G protein βy subunit activity an effective amount of an agent that interacts with at least one amino acid residue of the protein interaction site of the G protein β subunit so that the at least one activity of the G protein is modulated thereby preventing or treating the disease or condition involving the at least one G protein βy subunit activity, wherein the disease or condition is a disease affecting vasculature, wherein in the disease is selected from the vasculature diseases consisting of hypertension of any etiology, atherosclerosis, peripheral vascular disease, and restenosis.

Due to the ability of the present methods to stabilize cardiac function, it is further contemplated herein that the methods and disclosed compositions can be used as an adjunct to therapy or transplantation for any heart dysfunction, including but not limited to: ventricular assist device, implantable defibrillator, ventricular pacemakers, transplantation. Thus it is contemplated herein that the disclosed methods and compositions can be used in conjunction with any method known in the art to treat heart dysfunction. For example, disclosed herein are methods of treating heart dysfunction in a subject comprising administering to the subject an effective amount of an agent that interacts with at least one amino acid residue of the protein interaction site of the G protein β subunit so that the at least one activity of the G protein is modulated and administering to the subject a therapy of transplantation to the subject such as a ventricular assist device, implantable defibrillator, or ventricular pacemaker.

2. Methods Relating to M-Opioid Analgesia and Antinociception

It is understood and herein contemplated that one use for compounds identified by the disclosed methods as well as the compounds and agents disclosed herein relates to the effect of G protein b subunit on μ-opioids such as morphine. In one aspect it is understood that the disclosed compounds can enhance the analgesic effect of μ-opioids. Thus, disclosed herein are methods of screening for an agent that enhances μ-opioid analgesia comprising contacting a G protein β subunit with a test agent and determining whether the agent interacts with at least one amino acid residue of the protein interaction site of the β subunit thereby identifying an agent that enhances μ-opioid analgesia. Also disclosed are methods further comprising measuring the downstream signaling activity of PLCβ3, wherein a decreased activity indicates an agent that enhances μ-opioid analgesia. It is understood that in addition to the ability to relieve pain through enhancing the analgesic properties of μ-opioids, the disclosed compounds and methods can diminish the perception of pain when used in conjunction with μ-opioids. Thus, disclosed herein are method of modulating acute μ-opioid-dependent antinociception in a subject comprising administering to the subject a μ-opioid and an agent that interacts with at least one amino acid residue of the protein interaction site of the G protein β subunit, and wherein the agent modulates one or more G protein β subunit activities. Also disclosed are methods wherein the agent increases the antinociception effects of the μ-opioid. Also disclosed are methods wherein the G protein β subunit activity is the signaling to PLCβ3, and wherein an inhibition of PLCβ3 activity indicates an agent that an agent that increases antinociception.

Enhancing the analgesic and/or antinocicpetive effect of μ-opioids has the benefit of decreasing the amount of a μ-opioid needed to relieve pain. Thus, additional benefits resulting from the disclosed methods and agents when used in conjunction with m-opioids is decreasing tolerance to the μ-opioid and decreasing the risk of dependence (i.e., addiction) on the μ-opioid. Thus disclosed herein are methods of decreasing the risk of dependence on μ-opioids in a subject in need thereof comprising administering to the subject a μ-opioid and an agent that interacts with at least one amino acid residue of the protein interaction site of the G protein β subunit, and wherein the agent modulates one or more G protein β subunit activities. Also disclosed are methods of decreasing tolerance to μ-opioids in a subject in need thereof comprising administering to the subject a μ-opioid and an agent that interacts with at least one amino acid residue of the protein interaction site of the G protein β subunit, and wherein the agent modulates one or more G protein β subunit activities. It is understood and herein contemplated that such agents can also be used as anti-addiction medication.

3. Method of Treating Cancers

The disclosed compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Compounds disclosed herein may also be used for the treatment of precancer conditions such as cervical and anal dysplasias, other dysplasias, severe dysplasias, hyperplasias, atypical hyperplasias, and neoplasias.

D. Homology/Identity

It is understood that one way to define any known variants and derivatives or those that might arise, of the disclosed genes and proteins herein is through defining the variants and derivatives in terms of homology to specific known sequences. For example SEQ ID NO: 1 sets forth a particular sequence of an SIRK peptide. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

E. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

1. Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as SIRK, SIGK, and βARKct into the cell without degradation and include a promoter yielding expression of the gene in the cells into which it is delivered. In some embodiments the SIRK, SIGK, and βARKct s are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

a) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

b) Adenoviral Vectors

The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

c) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

d) Large Payload Viral Vectors

Molecular genetic experiments with large human herpesviruses have provided a means whereby large heterologous DNA fragments can be cloned, propagated and established in cells permissive for infection with herpesviruses (Sun et al., *Nature genetics* 8: 33-41, 1994; Cotter and Robertson, *Curr Opin Mol Ther* 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

2. Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed vectors, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Feigner et al. *Proc. Nail. Acad. Sci USA* 84:7413-7417 (1987); U.S. Pat. No.4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

3. In Vivo/Ex Vivo

As described above, the compositions can be administered in a pharmaceutically acceptable carrier and can be delivered to the subject=s cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

F. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

1. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers f unction to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

2. Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

G. Pharmaceutical Carriers/Delivery of Pharamceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

1. Pharmaceutically Acceptable Carriers

The compositions, including antibodies, can be used therapeutically in combination with a pharmaceutically acceptable carrier.

Suitable carriers and their formulations are described in Remington: *The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides ; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Pharmaceutical compositions can be in the form of pharmaceutically acceptable salts and complexes and can be provided in a pharmaceutically acceptable carrier and at an appropriate dose. Such pharmaceutical compositions can be prepared by methods and contain carriers which are well known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

As will be understood by those of skill in the art upon reading this disclosure, additional compounds to those exemplified herein can be identified routinely in accordance with the screening methods taught herein. Additional compounds for screening can be selected randomly by one skilled in the art, based upon computational prediction, and/or based upon their containing a structure of Formula I, II or III or a structure similar to that of the exemplary compounds disclosed herein.

2. Therapeutic Uses

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

H. Compositions Identified by Screening with Disclosed Compositions/Combinatorial Chemistry

1. Combinatorial Chemistry

The disclosed compositions can be used as targets for any combinatorial technique to identify molecules or macromolecular molecules that interact with the disclosed compositions in a desired way. The nucleic acids, peptides, and related molecules disclosed herein can be used as targets for the combinatorial approaches. For example, SIGK can be used to identify and agent that will disrupt the binding of SIGK to the protein interaction site of Gβ. Also disclosed are the compositions that are identified through combinatorial techniques or screening techniques disclosed herein, such as, for example, M119.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, M119, are also disclosed. Thus, the products produced using the combinatorial or screening approaches that involve the disclosed compositions, such as, M119, are also considered herein disclosed.

It is understood that the disclosed methods for identifying molecules that inhibit the interactions between, for example, Gβγ and bARK1 or Gβγ and SIGK can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. *Proc. Natl. Acad. Sci. USA*, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. *Proc. Natl. Acad. Sci. USA*, 94(23) 12997-302 (1997)).

Another preferred method for combinatorial methods designed to isolate peptides is described in Cohen et al. (Cohen B. A., et al., *Proc. Natl. Acad. Sci. USA* 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972, 719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in interative processes.

2. Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation of Gβγ function. The molecules identified and isolated when using the disclosed compositions, such as, M119, are also disclosed. Thus, the products produced using the molecular modeling approaches that involve the disclosed compositions, such as, M119, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol._Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

I. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. Thus, for example, disclosed herein are kits for identifying an agent that binds at least one amino acid residue of the protein interaction site of the β subunit is also provided. The kit of the invention contains a SIGK peptide or SIGK peptide derivative.

J. Compositions with Similar Functions

It is understood that the compositions disclosed herein have certain functions, such as inhibiting Gβγ activity or binding the protein interaction site of Gβ. Disclosed herein are certain structural requirements for performing the disclosed functions, and it is understood that there are a variety of structures which can perform the same function which are related to the disclosed structures, and that these structures will ultimately achieve the same result, for example stimulation or inhibition Gβγ activity.

K. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Differential Targeting of Gβγ-Subunit Signaling with Small Molecules a) Materials and Methods Peptides were purchased from Alpha Diagnostic International (San Antonio, Tex.) or SIGMA®-Genosys (St. Louis, Mo.), HPLC purified to greater than 90% and masses confirmed by mass spectroscopy. Ni-NTA agarose was from QIAGEN® (Valencia, Calif.). Streptavidin-coated poly-styrene beads were from Spherotec (Libertyville, Ill.). HRP-conjugated anti-M13 antibody was from Amersham Biosciences (Piscataway, N.J.). HRP-conjugated Neutravidin was from Pierce (Rockford, Ill.). All molecular biology reagents were from INVITROGEN™ (Carlsbad, Calif.) unless otherwise indicated.

(1) Expression and Purification of Gβ1Y$_2$ and SIGK Peptide

Baculoviruses harboring cDNA for wild-type bovine Gβ1 and N-terminally (His)$_\epsilon$-tagged bovine Gγ$_2$ were used to produce proteins of the same. High 5 cells (INVITROGEN™, Carlsbad, Calif.; 2×10$^6$ cells/mL) were infected with high titer Gβ1 and Gγ$_2$ baculoviruses. Gβ1γ$_2$ was purified according to standard methods (Kozaza and Gilman (1995) J. Biol. Chem. 270:1734-41), with modifications. All steps were carried out at 4° C. Cells were harvested 60 hours post-infection by centrifugation at 260 Og, then resuspended in 50 mL of lysis buffer (20 rtiM HEPES, pH 8, 150 mM NaCl, 5 mM β-ME, 1 mM EDTA, 1 mL SIGMA® protease inhibitor cocktail P-2714) per liter of cell culture. Cells were lysed by sonication and centrifuged at 2600 gr to pellet the membranes. Resuspension and homogenization of membranes was accomplished by douncing in 100 mL lysis buffer. The membranes were solubilized by adding 1% Lubrol (C12E10, SIGMA®, St. Louis, Mo.) with stirring and the resultant solution clarified by ultracentrifugation at 125,000ˆ. The supernatant was loaded onto Ni-NTA agarose (QIAGEN®, Valencia, Calif.) equilibrated with lysis buffer+ 1% Lubrol. The column was washed and the Lubrol exchanged for sodium cholate using buffers Ni-A (20 mM HEPES, pH 8, 0.4 M NaCl, 5 mM β-ME, 0.5% Lubrol, 0.15% cholate) and Ni—B (20 mM HEPES pH 8, 0.1 M NaCl, 5 mM β-ME, 0.25% Lubrol, 0.3% cholate). Gβ1γ2 eluted in Ni—C (20 mM HEPES pH 8, 0.01 M NaCl, 5 mM β-ME, 1% cholate, 200 mM imidazole). The eluate was loaded onto a HITRAP™ Q (Amersham Biosciences, Piscataway, N.J.) column pre-equilibrated with QA (20 mM HEPES, pH 8, 5 mM β-ME, 0.7% CHAPS, 1 mM EDTA). Gβ1γ$_2$ eluted in a gradient using QB (QA+1.0 M NaCl). Fractions containing Gβ1γ$_2$ were analyzed by SDS-PAGE and pooled. Gel filtration was performed using a tandem SEPHADEX® 75:SEPHADEX® 200 column (Amersham Biosciences, Piscataway, N.J.) equilibrated with buffer GF+CHAPS (20 mM HEPES, pH 8, 150 mM NaCl, 10 mM β-ME, 1 mM EDTA, 0.7% CHAPS). The purified yield was typically 1 mg Gβ1γ$_2$ per liter of cell culture.

SIGK peptide (Ser-Ile-Gly-Lys-Ala-Phe-Lys-Ile-Leu-Gly-Tyr-Pro-Asp-Tyr-Asp; SEQ ID NO: 2) was synthesized using well-established methods. No modifications were made to the peptide termini; purification was by reverse phase-HPLC chromatography on a VYDAC® C4 semi-preparative column.

(2) Crystallography

SIGK peptide was added to β1γ$_2$ in 1.5 molar excess, and the Gβ1γ$_2$<<SIGK complex was used at 7 mg/mL for crystallization. Crystals were grown by vapor diffusion using equal volumes (2 μL) of protein and reservoir solution (15-17% PEG 4000, 100 mM HEPES, pH 7.5, 0.01-0.05 M Na-Acetate, 10% glycerol) at 20° C. Crystals attained dimensions of 150 μm×50 μm×20 μm within one week. Crystals were cryoprotected in 15% glycerol and frozen in liquid nitrogen.

Native crystals of Gβ1γ$_2$*SIGK were screened at Advanced Light Source (ALS) beamlines 8.2.1 and 8.2.2 (Berkeley, Calif.) and at the Advanced Photon Source (APS) beamline BM-19 (Chicago, Ill.). A dataset from ALS 8.2.2 was used to determine the structure. Over 100 crystals were screened; diffraction limits varied from 7A to the 2.7A dataset used for structure determination. Diffraction data were indexed, integrated, and scaled using the software package HKL2000 (Otwinowski and Minor (1997) In: Methods in Enzymology, Vol. 276:307-326) (Table 10). The space-group of the crystals was P2$_1$2$_1$2$_1$.

TABLE 10

| Data Collection | | | |
|---|---|---|---|
| Space Group | P2$_1$2$_1$2$_1$ | Unique Reflections | 9729 |
| Unit Cell | | Redundancy [1] | 3.5 (1.8) |
| a (Å) | 45.468 | Completeness (%) [1] | 90.1 (56.2) |
| b | 74.669 | <I/σ> [1] | 13.5 (1.6) |
| c | 108.023 | Rsym [1, 2] | 8.7 (41.4) |
| α (°) | 90 | Mosaicity (°) | 2.3 |
| β | 90 | Wilson B-factor (Å) | 61.8 |
| γ | 90 | | |
| D$_{min}$ (Å) | 2.7 | | |

TABLE 10-continued

| L. Refinement | | | |
|---|---|---|---|
| Resolution (Å) | 45.4-2.7 | R.m.s Deviations | |
| Number of atoms [3] | | Bond lengths (Å) | 0.006 |
| Protein | | Bond Angles (°) | 1.3 |
| Water | | | |
| R$_{work}$ (%) [4] | | R.m.s. B factors (Å$^2$) | |
| R$_{free}$ (%) [5] | | Bonded main chain | 1.29 |
| | | Bonded side chain | 18.1 |
| | | Average B-factor (Å) [6] | 46.3 |

The final model contains residues 2-340 of Gβ1 (of 340), 7-52 of Gγ2 (of 68), 1-13 of SIGK (of 15), and 37 water molecules.
[1] Numbers in parentheses correspond to the highest resolution shell, 2.8-2.7 A.
[2] R$_{sym}$ = Σ$_h$ Σi |Ii(h) − <I(h)>|/Σ$_h$ Σi Ii (h), where Ii (h) and <I (h)> are the i$^{th}$ and mean measurement of the intensity of reflection h, respectively.
[3] The final model contains residues 2-340 of Gβ1 (of 340), 7-52 of Gγ2 (of 68), and 1-13 of SIGK (of 15).
[4] Rwork = Σ$_h$ I I F$_0$ (h) I − |F$_c$(h)|/Σ$_h$ |F$_o$(h)|, where F$_0$ (h) and F$_c$ (h) are the observed and calculated structure factors, respectively. An J/o cutoff was not used in the final calculations of R-factors.
[5] Rfree is the R-factor obtained for a test set of reflections consisting of a randomly selected 8% of the data.
[6] B-factors at the N-termini, including Gβ1 residues 2-41 and Gγ2 residues 7-13, are greater than 80 A$^2$.

The structure of the Gβ1γ$_2$*SIGK complex was solved by the molecular replacement method using the program PHASER (Storoni, et al. (2004) Acta Crystallogr. D Biol. Crystallogr. 60:432-8; Read (2001) Acta Crystallogr. D Biol. Crystallogr. 57:1373-82). The coordinates of Gβ1γ$_2$ in the Gβχγ$_2$>>GRK2 complex (10 MW, 100% sequence identity) were used as the search model. After rigid body refinement using the maximum likelihood minimization target in CNS version 1.1 (Adams, et al. (1997) Proc. Natl. Acad. Sci. USA 94:5018-23; Brunger, et al. (1998) Acta Crystallographica Section D 54:905-921), the model was further refined by using a combination of simulated annealing, Powell minimization, and B factor refinement. The sigma A-weighted 2Fo-Fc electron density map computed with refined phases revealed clear main chain density for ten residues of the SIGK peptide along with identifiable side chain density for several SIGK residues. Subsequent model building was performed in O (Jones, et al. (1991) Acta Crystallographica Section A 47:110-119) followed by simulated annealing, energy minimization, and B factor refinement using CNS. PROCHECK (Laskowski, et al. (1993) J. Appl. Crystallography 26:283-291) analysis indicates that all residues exhibit main chain conformations in most favored or additional allowed regions of φ, ψ space (Table 10). Calculations of surface accessibility, Gβ1γ$_2$<<SIGK contacts and RMSD between structures were carried out using programs in the CNS suite.

(1) Construction and Partial Purification of Biotinylated Gβ1γ$_2$ (b-βγ) and b-βγ Mutants Wild-type Gβ1 and Gp$_1$ mutants were made in the baculovirus vector PDW464 which encodes a biotinylation site at a lysine upstream of the amino terminus of Gβ1 (Goubaeva, et al. (2003) supra). Mutants were generated by overlap extension PCR using standard protocols. The wild-type and mutant Gβ1 constructs consisted of a 20 amino acid biotin acceptor peptide (BAP) sequence fused in-frame with the amino-terminus of rat Gβ1 subunit. When coexpressed with biotin holoenzyme synthetase (BirA) in Sf9 cells, the Gβ1 subunit becomes covalently biotinylated in vivo at the specific lysine acceptor residue in the BAP. Using this approach, 1-2 mg protein of purified protein can be obtained per liter of Sf9 insect cells. As 45 ng of protein is used in the phage ELISA assay, a single purification is sufficient for 10,000 to 30,000 binding assays.

Baculoviruses were generated via the BAC-TO-BAC® system following the manufacturer's instructions (GIBCO/BRL, Gaithersburg, Md.). Sf9 cells (200 tnL) were triply infected with 0.5 mL baculovirus encoding (His) 6-Gαu, 4 mL of Gγ$_2$ virus, and 4 mL of either wild-type or mutated Gβ1 virus. Gβ1γ$_2$ dimers were purified 60 hours postinfection using a well-established method with modifications as indicated (Kozasa and Gilman (1995) supra). Cell pellets were lysed in 4 mL lysis buffer (50 mM HEPES, pH 8.0, 3 πiM MgCl$_2$, 10 mM β-mercaptoethanol, 1 mM EDTA, 100 mM NaCl, 10 μM GDP, and protease inhibitors) by four freeze-thaw cycles in liquid nitrogen. Membranes were solubilized using 1% sodium cholate, clarified by ultracentrifugation at 100,00 Og for 20 minutes, diluted into buffer containing 0.5% lubrol, and mixed with Ni-NTA resin. After washing thoroughly, Gβ1γ$_2$ subunits were eluted from bound Gαi by mixing beads with buffer containing 50 mM MgCl$_2$, 10 mM NaF, 10 μM AlCl$_3$, 1% cholate, and 5 mM imidazole at room temperature for one hour. The concentrations of b-βγ and b-βγ mutants were analyzed by comparative immunoblotting and chemiluminescence. Proteins were separated by SDS-PAGE, transferred to nitrocellulose, and probed with HRP-neutravidin (Pierce, Rockford, Ill.). The chemiluminescent signal was measured using an EPI-CHEM II™ darkroom system (UVP Bioimaging Systems, Upland, Calif.). Concentrations of eluted b-βγ dimers were determined by comparing to a standard curve of fully purified 100% biotinylated Gβ1γ2 from at least two separate gels.

(2) b-βγ Binding Assay

Phage ELISA assays used to assess peptide binding to wild-type and mutant b-βγ were performed according to standard methods (Smrcka and Scott (2002) Methods Enzymol. 344:557-76). Briefly, 1 μg streptavidin was immobilized in the well of a 96-six well plate overnight at 4° C. The wells were blocked with 100 μL of 2% bovine serum albumin (BSA) in Tris-buffered saline (TBS) for 1 hour at 4° C. followed by three washes of IX TBS/0.5% TWEEN®. Forty μL of 25 nM bGβ1γ$_2$ in TBS/0.5% TWEEN® was added to each well and incubated at 4° C. for 1.5 hour. The wells were washed, followed by the addition of IxIO$^6$ to IxIO$^{10}$ phage particles and incubated at 4° C. for 3 hours. The wells were then washed six times with TBS/0.5% TWEEN® followed by addition of 40 μL of 1:5000 dilution of anti-M13 antibody (Pharmacia, Uppsala, Sweden) and incubated at room temperature for 1 hour. The wells were washed, followed by the addition of 40 μL of (2,2'-Azino-bis (3-ethylbenzthiazoline)-6-sulfonic acid (ABTS) and the colorimetric reaction was monitored at 405 nm. Nonspecific binding was subtracted for each reading.

Signals obtained with partially purified b-βγ subunits were similar to signals obtained from fully purified b-βγ subunits. Blocking of Gαi$^{>>}$Gβ1γ$_2$ binding was assessed by simultaneously adding 200 pM FITC-Gαi with or without SIGK to 50 pM immobilized b-βγ and measuring the amount of FITC-Gαi bound to the beads by flow cytometry according to standard methods (Ghosh, et al. (2003) supra; Sarvazyan, et al. (1998) J. Biol. Chem. 273:7934-40).

b) Results (1) Architecture of the Gβ1γ$_2$<<SIGK Complex

Unless indicated otherwise, amino acid residues having the prefix "s" are indicative of SIGK residues.

Gβ1 is a β-propeller composed of seven four-stranded β-sheets ("blades") and an N-terminal extended helix that interacts extensively with Gγ$_2$. Each sheet is composed of WD-40 repeats connected by loops of variable length. Residues 2-340 of Gβ1 are included in the model. B factors throughout the core of Gβ1 are less than 40 Å$^2$. Residues with B factors>60 Å$^2$ are found in three loop regions: Lys127-Ser136 in blade two, Arg214-Met217 in blade four, and Ser265-Ile269 in the loop connecting blades six and seven. Gγ$_2$ forms a helix with a kink made by residues Asn24-Lys29 and a coil region beginning at residue His44. The average B factor within the Gγ$_2$ molecule is 44 Å$^2$. No electron density was observed for the N-terminal seven residues and the C-terminal sixteen residues of Gγ$_2$ or the prenyl lipid modification at the C-terminus of Gγ$_2$.

SIGK forms an α-helical structure broken by a glycine at position 10. The C-terminal three residues form an extended structure that stretches away from the Gβ$_1$ molecule and is supported by crystal contacts between sPro12 and sAsp13 with Thr47 and Lys337 from a symmetry-related Gβ1 molecule. The B factors for the N- (sSer1, sIle2) and C-terminal (sGly1O-sAsp13) residues of SIGK are greater than 50 Å$^2$; those for all other residues are between 30-50 Å$^2$. The electron density for the main chain atoms in residues 1-13 is well-defined; three of the SIGK side chains that do not contact Gβ1 (sIle2, sLys7, and sAsp13) are disordered. The peptide binds across the "top" face of Gβ1 and is buried 970 Å$^2$ total solvent-accessible surface area. The peptide makes no contact with the Gγ$_2$ subunit, which is bound to the "bottom" surface of the Gβ1 torus.

The SIGK contact surface on Gβ1 was separated into two regions: an acidic region on Gβ1 that interacts with the N-terminus of the peptide, and a largely nonpolar region that interacts with the C-terminus of the peptide. In total, thirteen Gβ1 residues directly contact SIGK, contributed by six of the seven blades of the β-propeller (Table 11).

TABLE 11

| Gβ$_1$-Interacting Residues | | SIGK-Interacting Residues | | Distance (Å) | Type of Interaction |
|---|---|---|---|---|---|
| Lys57 | Cε | Leu9 | O | 3.35 | Nonpolar |
|  | Cε | Gly10 | Cα | 3.99 | Nonpolar |
| Tyr59 | OH | Leu9 | O | 2.66 | Polar |
|  | Cε | Ile8 | O | 3.87 | Nonpolar |
| Trp99 | Nε1 | Tyr11 | OH | 2.81 | Polar |
|  | Cδ1 | Leu9 | Cδ2 | 3.59 | Nonpolar |
| Val100 | O | Leu9 | Cδ2 | 3.75 | Nonpolar |
| Met101 | Cε | Ile8 | Cγ2 | 3.46 | Nonpolar |
|  | Cε | Ala5 | O | 3.52 | Nonpolar |
|  | Cε | Leu9 | Cδ2 | 3.54 | Nonpolar |
| Leu117 | Cδ1 | Ile2 | Cγ2 | 3.46 | Nonpolar |
|  | Cδ2 | Ala5 | Cβ | 3.68 | Nonpolar |
|  | Cδ2 | Leu9 | Cδ1 | 3.80 | Nonpolar |
| Tyr145 | Cε2 | Ser1 | O | 3.19 | Nonpolar |
|  | OH | Lys4 | Cγ | 3.45 | Nonpolar |
|  | Cδ2 | Ala5 | Cβ | 3.81 | Nonpolar |
| Asp186 | Oδ2 | Ser1 | O | 3.03 | Polar |
| Met188 | Cε | Ile8 | Cδ1 | 3.31 | Nonpolar |
|  | Cε | Lys4 | Cε | 3.48 | Nonpolar |
| Asp228 | Oδ2 | Lys4 | Nζ | 3.23 | Polar |
| Asn230 | Nδ2 | Lys4 | Nζ | 2.82 | Polar |
| Asp246 | Oδ2 | Lys4 | Nζ | 3.05 | Polar |
| Trp332 | Cζ2 | Ile8 | O | 3.12 | Nonpolar |
|  | CH2 | Gly10 | Cα | 3.57 | Nonpolar |

The N-terminal binding surface is centered on an electrostatic interaction in which sLys4 projects into a negatively charged binding pocket on Gβ1γ$_2$ where it forms hydrogen-bonded or charge interactions with Asp228, Asn230, and Asp246. A hydrogen bond between the carbonyl oxygen of Asp228 and the main chain nitrogen of Asp246 stabilizes the three acidic residues on Gβ1. Met188 participates in van der Waals interactions with the alkyl chain of sLys4, and Asp186 forms a polar contact with the carbonyl oxygen of sSer1 and also makes a hydrogen bond to the amide of Cys204. Additionally, Tyr145 forms van der Waals interactions with the main chain oxygen of sSer1, the sLys4 side chain, and the Cβ atom of sAla5, and forms a hydrogen bond with the nearby amide of Gly162. The side chain of Leu117 is within van der Waals contact distances of the side chains of sIle2 and sAla5.

Together, these nine Gβ1 residues form a surface that tethers SIGK to Gβ1 using charged and nonpolar interactions. Mutational analysis of SIRK and SIGK peptides can now be interpreted in the context of the SIGK*Gβ1γ$_2$ structure (Scott, et al. (2001) supra; Goubaeva, et al. (2003) supra). Wild-type SIRK peptide inhibits the activation of PLC β2 by Gβ1γ$_2$ with an IC$_{50}$ of 5 μM. Substitution of sLys4 with alanine in the SIRK peptide lowers the IC$_{50}$ of the peptide 12-fold, and mutation of sAla5 to glycine lowers the IC$_{50}$ by 13-fold. Mutation of sIle2 to alanine reduces IC$_{50}$ of the peptide by 4-fold, and mutation of sSer1 to alanine has no effect on IC$_{50}$ (Scott, et al. (2001) supra). The SIGK$^{>>}$Gβ1γ$_2$ structure indicates that the main chain of sSer1 and the side chains of sIle2, sLys4, and sAla5 contact multiple resides on Gβ, thereby explaining this mutational data.

To measure the contribution of the Gβ1 residues observed at the Gβ1γ$_2$>>SIGK interface to the binding energy for the complex, two approaches were utilized. First, an ELISA assay was used to measure binding of immobilized Gβ1γ$_2$ subunits to phage displaying the SIGK sequence (Table 12). The ELISA binding data were then correlated with IC$_{50}$ values for SIGK as a competitor of Gβχγ$_2$ association with Gαu (Table 13). Both assays were then carried out with Gβ1γ$_2$ heterodimers containing mutations in the Gβ$_1$ subunit. In the N-terminal binding surface, mutation of Gβ$_1$ Asn230 to alanine decreased the affinity of Gβ$_1$γ$_2$ for peptide 10-fold (Table 12). Single mutation of Gβ1 residues Asp186, Met188, Tyr145, and Leu117 to alanine also resulted in Gβχγ$_2$ dimers with drastically decreased affinity for SIGK (Table 12). Gβ1mutants in which either Asp228 or Asp246 were substituted with alanine did not dimerize with Gγ$_2$ and therefore were not analyzed. However, a mutant in which Asp228 was substituted with serine caused only a slight loss in binding affinity for SIGK peptide (Table 12). Thus, many of the Gβ1 residues that create the N-terminal SIGK binding interface contribute strongly to the energy of binding.

TABLE 12

| Gβ$_1$γ$_2$ Mutation | % of Wild-Type Signal (mean ± SD) |
|---|---|
| Lys57Ala | 18.6 ± 4.6 |
| Tyr59Ala | 24.7 ± 15.2 |
| His62Ala | 111.2 ± 11.3 |
| Trp99Ala | 66.0 ± 7.7 |
| Met101Ala | 32.2 ± 15.5 |
| Leu117Ala | 2.1 ± 2.4 |
| Tyr145Ala | 0.8 ± 0.9 |
| Asp186Ala | 13.0 ± 13.1 |
| Met188Ala | 2.5 ± 3.7 |
| Asn230Ala | 22.4 ± 4.2 |
| Asp246Ser | 66.5 ± 7.5 |
| Phe292Ala | 109.1 ± 21.4 |
| His311Ala | 94.3 ± 18.9 |
| Arg314Ala | 50.2 ± 5.0 |
| Trp332Ala | 7.1 ± 3.7 |

Amino acids that contact the SIGK peptide were individually mutated to alanine (or serine for Asp246) and binding to peptide was assayed using a phage ELISA. Immobilized b-βγ was incubated with phage displaying SIGK peptide. Phage binding was detected using an α-phage antibody; the raw data was absorbance at 405 nm. Data shown are the mean ± SD of triplicate determinations from three independent experiments.

TABLE 13

| Log | % Maximal Fα Binding (±SD) | | | |
|---|---|---|---|---|
| [SIGK] M | Wild-Type | Met188Ala | Trp332Ala | Arg314Ala |
| −7 | 100.0 ± 0.0 | 100.0 ± 0.0 | 100.0 ± 0.0 | 100.0 ± 0.0 |
| −5.7 | 55.0 ± 10.8 | 101.3 ± 7.6 | 72.7 ± 2.3 | 65.3 ± 5.8 |
| −5 | 45.7 ± 16.3 | 80.7 ± 7.6 | 57.3 ± 7.2 | 47.0 ± 11.1 |
| −4.7 | 17.3 ± 3.8 | 72.7 ± 11.2 | 33.0 ± 3.5 | 30.7 ± 4.2 |
| −4.4 | 13.3 ± 1.5 | 40.0 ± 7.1 | 24.7 ± 3.5 | 21.0 ± 0.0 |
| −4.1 | 5.8 ± 4.8 | 33.0 ± 7.2 | 16.7 ± 1.2 | 13.0 ± 3.0 |

SIGK competition for FITC-Gαiiβiγ$_2$ interactions with representative Gp$_1$ subunit mutants. SIGK and FITC-αn were simultaneously added to streptavidin beads coated with wild-type or mutant b-βγ protein and the amount of FITC-αn bound to the beads was assayed by flow cytometry. Data are shown as the mean of triplicate determinants +/− standard deviation of a representative experiment.
The experiment was repeated two (Met188A) or three (wild-type, Arg314A, Trp332A) times with similar results. Comparison of the two assays over a selection of mutants that spanned the range of SIGK binding affinities indicates that a 50% loss of binding translates into a five-fold increase in IC$_{50}$, a 75% loss of binding corresponds to a 10-fold increase, a 90% loss is a 20-fold shift and a 98% loss is a 50-fold shift. The IC$_{50}$ values are as follows: wild-type = 0.47 μM, Arg314A = 1.5 μM, Trp332A = 9 μM, and Met188A = 22 μM.

The second area of binding involves most of the C-terminal residues of SIGK (sAla5-sGly11), which pack against a largely hydrophobic pocket on Gβ1. This pocket extends HA from Trp332 on blade seven to Met188 in blade two. Eight Gβ1 residues are in direct contact with the C-terminal surface of SIGK, and two more Gβ1 residues support the residues directly involved in the SIGK interaction. Met188, which interacts with sLys4 in the N-terminal interface, is also within contact distance of the side chain of sLeu8. SIGK residues sAla5, sLeu6 and sLeu9 are complimented by van der Waals interactions with Leu117, Met101, Trp99, Tyr59 and the alkyl chain of Lys57. The main chain oxygen of Val100 interacts with the side chain of sLeu9. The indole imine of Trp99 forms a hydrogen bond with the hydroxyl group of sTyr11 and the side chain of Trp332 makes contact with the main chain oxygen of sIle8 and the Cα of sGly10. The side chains of Lys57 and Arg314 are positioned on either side of Trp332 and support its orientation in the binding site. Arg314 also forms a hydrogen bond with Trp332, and Lys57 with the nitrogen of Gln75, further stabilizing this interaction surface on Gβ1. Data from alanine scanning of the peptide (Scott, et al. (2001) supra; Goubaeva, et al. (2003) supra) validate these structural observations. Mutation of sIle6, sLeu9 or sGly10 to alanine increases the IC$_{50}$ for inhibition of PLC activation by 40-fold (5 μM to 200 μM), 60-fold and 12-fold, respectively (Scott, et al. (2001) supra). The same mutation of sLeu9 also blocks the ability of SIRK to enhance ERK1/2 phosphorylation in RASM cells (Goubaeva, et al. (2003) supra). Mutation of amino acids in Gβ1 that constitute the SIGK C-terminal binding surface caused a loss in affinity for the SIGK peptide, although to different extents. Mutation of Leu117, Met188, or Trp332 to alanine nearly abrogated SIRK binding; mutants of Lys57, Tyr59, Met101, and Arg314 had more modest effects (Table 12 and Table 14). The Trp99 mutation resulted in a 4-fold decrease in affinity. A summary of all the Gβ1 mutations (i.e., conversions to alanine) presented herein and their effects on SIGK binding affinity is listed in Table 14.

TABLE 14

| | Loss in Affinity for SIGK Peptide | | | | |
|---|---|---|---|---|---|
| | 75-100% | 50-75% | 25-50% | 0-25% | No Effect |
| Gβ$_1$ Residue | Lys57 | Met101 | Trp99 | His311 | His62 |
| | Tyr59 | Arg314 | Asn246 | | Phe292 |
| | Leu117 | | | | |
| | Tyr145 | | | | |
| | Asp186 | | | | |
| | Met188 | | | | |
| | Asn230 | | | | |
| | Trp332 | | | | |

Considering all of the data for the N-terminal and C-terminal SIGK binding interfaces, seven of the fifteen residues of the SIGK peptide and ten of the twelve Gβ residues tested contribute significant binding energy to the interface, in good correlation with the structural model.

The binding surface of Gβ1 in the Gβ1γ$_2$>>SIGK complex is not significantly changed upon SIGK binding. The RMSD between the core residues of Gβ1 in the Gβ1γ$_2$<<SIGK complex and that in the uncomplexed Gβ1γ$_x$ heterodimer (ITBG (Sondek, et al. (1996) Nature 379:369-74); Val40-Asn340, Ca only) is 0.88 A. However, the side chains of Trp99, Tyr59, Asp228, Leu117 and Met101 rotate to accommodate SIGK such that atoms within these residues undergo maximum displacements of 4.0 A, 3.6 A, 2.9 A, 2.8 A and 2.3 A, respectively, relative to their positions in uncomplexed Gβ1. The B factors for residues in the SIGK binding surface are close to the overall average for the complex. However, the B factor for Trp99 is reduced two-fold upon binding to SIGK, as indicated by comparison of normalized B factors of the respective structures. In this analysis, there are no large conformational changes or disorder to order transitions in Gβ upon SIGK binding. The SIGK$^>$$^>$Gβ1γ$_2$ complex may be compared to those of five Gβ1γ$_2$ complexes with protein targets: the Gβ1γ$_2$'Gαii heterotrimer (1GG2) (Wall, et al. (1995) supra; Wall, et al. (1998) supra) and the Gβ1Yi'Gαt/1 heterotrimer (IGOT) (Lambright, et al. (1996) supra), the Gβ1γi<<phosducin complex (IAOR and 2TRC) (Loew, et al. (1998) supra; Gaudet, et al. (1996) supra), and the Gβ1γ$_2$>>GRK2 complex (10 MW) (Lodowski, et al. (2003) supra). Superposition of the Gβ1Y$_2$#SIGK complex with each of these structures yields average RMS deviations for Gβ1 residues 40-340 of less than 1.0 A (Ca only). With the exception of a few residues involved in the Gβ1Yi'phosducin complex, the Gβγ heterodimer does not undergo significant structural rearrangement in order to bind protein targets, nor does it in the Gβ$_1$γ$_2$<<SIGK structure.

(2) Measurement of α-βγ Interactions via Flow Cytometry

Fluorescein-labeled Ga^ (Fan) was prepared in accordance with standard methods (Sarvazyan, et al. (1998) supra). Assays were used to determine peptide effects on Gα-Gβγ interactions included competition and dissociation assays (Ghosh, et al. (2003) supra). Briefly, for competition-based assays, 100 pM Fan and indicated concentrations of peptides were added to 50 pM b-Gβ1γ$_2$ immobilized on 10$^s$ beads per mL and incubated at room temperature for 30 minutes to reach equilibrium. The bead-associated fluorescence was then recorded in a BD Biosciences FACSCALXBUR™ flow cytometer. Data was corrected for background fluorescence and fit with a sigmoid dose response curve using Graph Pad Prism 4. To measure dissociation of Fan from b-Gβαγ$_2$, 100 pM of Fa^ was incubated with 50 pM immobilized b-Gβ1γ$_2$ at room temperature for 15-20 minutes. The fluorescence of bound Fαii subunit was measured, followed by the addition of a 200-fold excess of unlabeled Gcx±$_x$ or peptides and the amount of Fan remaining bound to the beads was measured at the indicated times.

(3) Molecular Recognition at the Protein Interaction Site

Having demonstrated that the interface for SIGK peptide binding was divided into two broad interactions; a C-terminal binding interface, which contacts the hydrophobic core of the peptide (amino acids 8-10, Ile-Leu-Gly), and an N-terminal interface, which associates with the N-terminus (Lys4 primarily) of the peptide, the molecular basis for recognition of the peptide was determined. Accordingly, amino acids of the common binding surface of Gβ1 were individually alanine substituted to determine which amino acids were most critical for the interaction of Gβ1γ$_2$ with nine different SIGK peptide derivatives (Table 15).

TABLE 15

| Phage Name | Sequence* | SEQ ID NO: | Group |
|---|---|---|---|
| 3.14 | SIGKALFILGYPDYD | 5 | I |
| 2F | LCSKAYLLLGQTC | 6 | |
| C1 | SCKRTKAQILLAPCT | 7 | |
| C14 | WCPPKAMTQLGIKAC | 8 | II |
| 3C | SCGHGLKVQSTIGACA | 9 | |
| C4 | SCEKRYGIEFCT | 10 | III |
| C5 | SCEKRLGVRSCT | 11 | |
| C8 | SCARFFGTPGCT | 12 | |
| C2 | WCPPKLEQWYDGCA | 13 | IV |

*Underlined residues denote the lysine residue contacting the N-terminus, and the hydrophobic core residues.

The nine peptides were selected to represent the different consensus groups of peptides previously identified (See Scott et al. (2001) supra; Table 15) and to compare binding characteristics within and between consensus groups. Binding of phage displaying these peptides to wild-type Gβ1γ$_2$ gave ELISA signals that were different, but fell within a similar range (25 to 100% binding relative to phage 3.14). As disclosed herein, the binding signal obtained in the ELISA assay was correlated to a loss in affinity by comparing the results to behavior of the peptide in a solution based assay. For example, a mutant displaying an 80% loss of binding in an ELISA had a corresponding 10-fold shift in peptide affinity in solution. For the purposes of present disclosure, any substitution that decreased the binding to less than 20% of the wild-type binding was considered to be a critical binding contact for that peptide. Data obtained from this analysis is presented in Table 16.

TABLE 16

| | % of Wild-Type Signal | | | | | | |
|---|---|---|---|---|---|---|---|
| | C-Terminal Interface | | | | Shared | | |
| Peptide | Trp332 | Lys57 | Tyr59 | Trp99 | Leu117 | Met101 | Met188 |
| Group I | | | | | | | |
| 3.14 | 7.1 ± 3.7 | 18.6 ± 4.6 | 24.7 ± 15.2 | 66.0 ± 7.7 | 2.1 ± 2.4 | 26.8 ± 12.5 | 2.5 ± 3.7 |
| 2F | −1.5 ± 3.6 | −4.5 ± 6.2 | −2.0 ± 9.5 | 32.6 ± 26.3 | 2.1 ± 5.5 | 6.0 ± 5.1 | 8.5 ± 5.2 |
| C1 | −0.3 ± 2.5 | 0.1 ± 1.6 | 0.3 ± 0.7 | 1.2 ± 2.7 | 5.2 ± 3.1 | 70.5 ± 35.3 | 4.0 ± 3.4 |
| Group II | | | | | | | |
| C14 | 1.6 ± 2.4 | 3.0 ± 5.0 | 3.6 ± 2.0 | 10.1 ± 3.3 | 3.8 ± 9.2 | 1.1 ± 4.9 | 9.9 ± 3.8 |
| 3C | −0.3 ± 1.7 | 3.6 ± 7.5 | 8.5 ± 6.4 | −0.5 ± 5.9 | 10 ± 13.3 | −4.2 ± 5.5 | −5.7 ± 5.6 |

TABLE 16-continued

| Group III | | | | | | | |
|---|---|---|---|---|---|---|---|
| C4 | 1.7 ± 3.0 | −0.2 ± 1.9 | 7.6 ± 9.6 | 67.0 ± 15.2 | 18.4 ± 7.1 | 61.2 ± 30.9 | 127.5 ± 22.4 |
| C5 | 3.2 ± 3.7 | 5.6 ± 5.3 | 73.8 ± 16.6 | 39.0 ± 3.8 | 28.5 ± 5.2 | 47.8 ± 18.9 | 97.2 ± 14.2 |
| C8 | 0.7 ± 2.4 | 14.2 ± 9.8 | 4.0 ± 6.2 | −0.8 ± 2.7 | 24.7 ± 12.5 | 23.6 ± 8.5 | 122.6 ± 26.2 |
| Group IV | | | | | | | |
| C2 | 4.7 ± 6.2 | −1.2 ± 4.5 | −1.7 ± 4.8 | −1.0 ± 5.1 | 1.5 ± 5.5 | 157.1 ± 51.5 | −0.7 ± 2.5 |

| | % of Wild-Type Signal | | | | | |
|---|---|---|---|---|---|---|
| | N-Terminal Interface | | | | Indirect | |
| Peptide | Asn230 | Asp246 | Tyr145 | Asp186 | His311 | Arg314 |
| Group I | | | | | | |
| 3.14 | 22.4 ± 4.2 | 66.5 ± 7.5 | 0.8 ± 0.9 | 14.4 ± 13.4 | 93.4 ± 21.5 | 50.2 ± 5.0 |
| 2F | 27.6 ± 19.1 | 0.6 ± 2.5 | 0.1 ± 6.5 | 2.4 ± 3.5 | 23.6 ± 46.0 | 2.4 ± 3.9 |
| C1 | 19.8 ± 12.3 | 2.3 ± 3.0 | 88.0 ± 29.9 | 1.4 ± 1.7 | 3.0 ± 4.0 | 2.8 ± 1.6 |
| Group II | | | | | | |
| C14 | 60.0 ± 26.5 | 6.3 ± 13.9 | 1.9 ± 5.9 | 3.6 ± 1.9 | 6.1 ± 3.4 | 3.9 ± 7.9 |
| 3C | 4.1 ± 4.4 | 2.0 ± 2.7 | 2.7 ± 10.5 | 35.0 ± 17.2 | 30.5 ± 18.9 | 8.3 ± 3.6 |
| Group III | | | | | | |
| C4 | 11.5 ± 6.0 | 35.8 ± 7.4 | 4.4 ± 3.8 | 51.3 ± 15.0 | 36.5 ± 8.3 | 1.4 ± 1.0 |
| C5 | 33.5 ± 7.2 | 56.3 ± 4.1 | 16.7 ± 4.8 | 45.7 ± 5.2 | 58.7 ± 14.4 | 76.5 ± 6.7 |
| C8 | 74.8 ± 14.8 | 60.8 ± 14.4 | 17.5 ± 7.8 | 124.9 ± 29.1 | 51.6 ± 13.2 | 20.8 ± 11.1 |
| Group IV | | | | | | |
| C2 | 0.0 ± 3.3 | 5.9 ± 5.7 | 4.5 ± 8.1 | 267.2 ± 40.6 | 11.7 ± 8.0 | 1.3 ± 3.1 |

Wild-type or alanine-substituted biotinylated Gβχγ₂ subunits were immobilized on a streptavidin-coated 96-well plate, followed by the addition of phage. Phage binding was assessed as described herein. Data was corrected for nonspecific binding of phage to the plate and is represented as a percent wild-type binding. Data shown are mean ± SD of duplicate determinations from three independent experiments.

Unexpectedly, each of the peptides utilized unique combinations of amino acids within the SIGK binding surface for its particular interaction. A dominant feature amongst the peptides was a strong requirement for Trp332, within the C-terminal interface. Lys57, Tyr59, Leu117, also within this interface, generally contributed significantly to binding the peptides, though there were cases where their effects were not absolutely required. The remainder of the amino acids had more variable effects on binding of each peptide. For example, SIGK has a minimal requirement for Trp99 while Ser~Cys-Lys-Arg~Thr-Lys-Ala-Gln-Ile-Leu-Leu-Ala-Pro-Cys-Thr (Cl; SEQ ID NO: 7) absolutely requires Trp99 for binding. The reverse is true for Tyr145 where SIGK binding has an absolute requirement for Tyr145 and Ser-Cys-Lys-Arg-Thr-Lys-Ala-Gin-He-Leu-Leu-Ala-Pro-Cys-Thr (Cl; SEQ ID NO: 7) binding is not affected by this mutation.

The N-terminus of SIGK interacts with the Gβ subunit through two main contacts: sSer1 interactions with βAsp188 and βTyr145 residues, and sLys4 interactions with βMet188 through a Van der Waals interaction and βAsn230, βAsp246 and βAsp228 through hydrogen bonded or charged interactions. In the expression system utilized herein, Asp228Ala and Asp246Ala did not dimerize with gamma and could not be purified; however, Asp246Ser was expressed and purified. In general, peptides in groups I, II and IV have a substantial requirement for binding to the N-terminal region, reflected by an almost complete loss of binding to the Met188Ala and Asp246Ser (except SIGK) mutants and various requirements for Asn230.

Peptides in groups I, II and IV have a conserved motif where a lysine is spaced three amino acids away from a hydrophobic core motif (see Table 15). This motif in SIGK provides the appropriate spacing in a single alpha-helical turn between the lysine that interacts with the N-terminal binding surface and the Ile-Leu-Gly motif that interacts with the C-terminus. It is believed that some of the other peptides adopt a similar α-helical structure that may make this spacing critical. The peptides in group III bind the C-terminal interaction region, but lack a requirement for Met188 and have minimal requirements for Asn230 and Asp246, indicating they do not use the N-terminal binding surface for their interaction with β.

Two amino acids that do not apparently bind directly to SIGK were also analyzed, Arg314 and His311. Replacement of Arg314 results in a modest decrease in SIGK binding; however, for other peptides, Arg314 is absolutely required indicating that they may directly interact with this amino acid. His311 lies well outside the SIGK peptide binding site but was mutated because of its potential involvement in a conformation change in βγ subunits (Gaudet, et al. (1996) supra; Loew, et al. (1998) supra). The imidazole side chain of His311 is 13 A from the guanido nitrogen of Arg314, the closest amino acid that apparently interacts with any of the peptides. It is unlikely that His311 could directly interact with amino acids from the phage display-derived peptides. Nevertheless, mutation of His311 to alanine affected binding of various peptides to varying extents. Peptides whose binding was affected by His311A also required Arg314 for binding, an effect possibly due to an alteration in the position of Arg314.

It has been demonstrated that two peptides predicted to bind at the Gα-Gβγ interface, βARK-ct peptide (amino acids 643-670) and QEHA, blocked heterotrimer formation but could not promote heterotrimer dissociation (Ghosh, et al. (2003) supra). The crystal structure of the GRK2 (βARK)-Gβγ complex reveals that the surface interacting with the βARK-ct peptide partially overlaps with the SIGK and Gα-switch II binding site (Lambright, et al. (1996) supra; Wall, et al. (1995) supra; Lodowski, et al. (2003) supra). In particular, amino acids Trp99, Trp332, and Try59 within the hydrophobic pocket are common interaction sites in all three structures. The SIGK peptide and α switch II have a lysine residue occupying nearly identical positions on Gβ. Although the βARK-ct peptide has a lysine residue in a similar position, the geometry and nature of the interaction is different. βARK interacts only with Asp228 whereas SIGK and Gα interact with Asp228, Asp246, Asn230 and Met188. Based on this difference, it was determined whether the specific interactions of SIGK at this interface were critical for promoting dissociation.

To examine subunit dissociation, the SCAR peptide, another peptide derived from the phage display screen, was used. Amino acids within the N-terminal interaction interface, Asn230, Asp246 and Met188, contacting sLys4 of SIGK, are not important for binding SCAR. SCAR lacks a lysine residue with the correct positioning relative to the hydrophobic core motif to reach the lysine-binding N-terminal surface (Table 15). Therefore, SCAR would not be able to promote subunit dissociation. Both SIGK and SCAR can compete with Gα± for binding to Gβχγ$_2$, with IC$_{50}$'s of 0.5 and 1.7 μM, respectively. However, unlike the SIGK peptide, saturating concentrations of SCAR peptide could not promote dissociation of a preformed heterotrimer. Concentrations of up to 160 μM SCAR, (four times the saturating concentration) did not cause dissociation. The inability of SCAR to promote heterotrimer dissociation was not due to its lower binding affinity since SIRK has a similar affinity and promotes dissociation. These results indicate that peptide binding to the N-terminal interface is necessary for acceleration of heterotrimer dissociation.

To more directly assess the importance of peptide binding to the N-terminal peptide binding interface, the sLys4 residue of SIRK was mutated to alanine, eliminating the key contact to the N-terminal binding pocket. This peptide had a markedly lower affinity than SIRK (IC$_{50}$=60 μM vs 1.4 μM) for blocking Gα-Gβγ interactions; however, at high concentrations, it blocked to levels near that of SIRK. Despite blocking Gα-Gβγ interactions, SIRK (Lys4Ala) failed to accelerate heterotrimer dissociation. The apparent off-rate of Faü appears slower for SIRK(LyS4Ala) relative to the intrinsic dissociation rate. This could be because SIRK(Lys4Ala) is low affinity blocker, and is not effective at preventing rebinding of Fan. To confirm that the low affinity of SIRK(Lys4Ala) was not responsible for the inability to accelerate dissociation, a peptide with comparable affinity to SIRK (Lys4Ala), SIRK(GIyIOAIa) (IC$_{50}$~80 μM), was tested. This peptide has Lys4 but Ala is substituted for Gly at position 10, thus SIRK (GIyIOAIa) retains binding to the N-terminal interface but has a reduced affinity due to decreased interactions with the C-terminal region. SIRK(GIyIOAIa) blocked heterotrimer formation at high peptide concentrations and despite having a low affinity for Gβγ, could still accelerate heterotrimer dissociation. SIGK binds to Gβ$_α$ at a region occupied by the switch II domain of Gα subunits in the heterotrimer. The crystal structure of the heterotrimer reveals the switch interface (composed of switch I and switch II) of Gα buries approximately 1,800 A of Gβ through numerous contacts (Lambright, et al. (1996) supra; Wall, et al. (1995) supra) ; however, the effects of mutations of β subunit amino acids at this interface on α subunit binding have not been measured in direct binding assays near the K$_d$ for Gα-Gβγ interactions. Switch I and switch II undergo large conformational changes upon GTP binding and it is thought these changes mediate heterotrimer dissociation.

Gβ1 subunit mutants disclosed herein were isolated from insect cells as a complex with Gγ$_2$ and hexa-histidine-tagged Gαii indicating that many of these contacts between the subunits predicted from the crystal structures were not individually critical for Ga subunit binding. To determine which amino acids were contributing to the ability of peptides to enhance dissociation rate constants, the dissociation rate constant (k$_{off}$) for Fαii from each of the individually substituted b-βiγ$_2$ mutants was measured. The intrinsic off-rate for wild-type was 0.123 s-1, corresponding well with previous measurements (Sarvazyan, et al. (1998) J. Biol. Chem. 273:7934-7940). Data from all of these mutants are shown in Table 17.

TABLE 17

| Mutation | K$_{off}$** |
|---|---|
| Wild-Type | 0.123 ± 0.0429 min$^{-1}$ |
| Lys57Ala | 0.144 ± 0.0441 min$^{-1}$ |
| Tyr59Ala | 0.181 ± 0.0726 min$^{-1}$ |
| Trp99Ala | 0.288 ± 0.0547 min$^{-1}$ |
| Met101Ala | 0.114 ± 0.0175 min$^{-1}$ |
| Leu117Ala | 0.361 ± 0.0258 min$^{-1}$ |
| Tyr145Ala | 0.155 ± 0.0423 min$^{-1}$ |
| Asp186Ala | 0.160 ± 0.0429 min$^{-1}$ |
| Met188Ala | 0.122 ± 0.0380 min$^{-1}$ |
| Asn230Ala | 0.148 ± 0.0488 min$^{-1}$ |
| Asp246Ser† | — |
| Arg314Ala | 0.118 ± 0.0246 min$^{-1}$ |
| Trp332Ala | 0.301 ± 0.0420 min$^{-1}$ |

**Mean + SD from four independent experiments.
Statistically significant as compared to wild-type (p < 0.05) as determined by a one-way ANOVA followed by independent linear contrasts.
†k$_{Off}$ could not be measured because significant stable binding of F-αi was not detectable.

The results showed that of the 12 mutants tested, Trp99Ala, Leu117Ala, and Trp332Ala were statistically different from wild-type with relatively minor increases in k$_{off}$. On the other hand, Asp246Ser, despite being able to be purified based on 6HisGαi binding (although in low yield from a large culture), was unable to stably bind F-α$_{ij}$ in the flow cytometry assay at the low concentrations used for this assay. This indicates that interactions with Asp246 are critical for stable Ga subunit interactions, while individual interactions in the primarily hydrophobic C-terminal interface are not as important.

(4) Small Molecule Library Screen

A phage ELISA assay was used to determine whether small molecules identified in the computational screen could interact with the Gβγ protein interaction surface. Phage displaying the SIGK peptide were used in accordance with established methods (Scott, et al. (2001) supra; Smrcka and Scott (2002) supra). The screen was based on a reduction in the optical density (OD) of wells containing Gβγ subunits and phage. In each plate, three wells contained positive controls for binding that included b-βγ subunits, SIGK-phage, and the appropriate amount of vehicle. Three background wells contained no βy subunits.

As disclosed herein, biotinylated Gβy subunits were immobilized on the surface of a 96-well plate coated with streptavidin, phage displaying Gβγ-binding peptides were subsequently added and binding in the presence and absence of test compounds detected with an anti-phage antibody.

(5) Inhibition of Gβγ Signaling in Neutrophils

Ca$^{2+}$ fluxes were measured using two 35 mL cultures of differentiated HL-60 neutrophil cultures (0.2×10$^6$ cells/mL). Cells were cultured for three days with in DMSO (1.2%), washed in HSS and resuspended in 2 mL HBSS at a concentration of 7×10$^5$ cells/mL. Addition of DMSO to the growth medium induces differentiation of these cells into morphologically and functionally mature neutrophils (Collins, et al. (1978) Proc. Natl. Acad. Sci. USA 75:2458; Collins, et al. (1979) J. Exp. Med. 149:969). Neutrophils were preloaded with fura-2 (1 μM), a fluorescent Ca$^{2+}$-sensitive indicator (Suh, et al. (1996) J. Biol. Chem. 271:32753), for 45 minutes, washed with HBSS and resuspended in 2 mL of indicator-free HBSS. An 140 μL aliquot of cells was added to a total of 2 mL HBSS. Fluorescence ratios were taken by dual excitation at 340 and 380 nm and emission at 510 nm. After a stable baseline was established, either DMSO or NSC119910 was added and incubated for 5 minutes. Subsequently, either fMLP or ATP agonists were added to activate release of $Ca^{2+}$ from intracellular stores.

2. Example 2

Pharmaceutical Manipulation of G Protein βγ Subunit Signaling a) Analysis of Selectivity Profiles of βγ-Binding Compounds.

The specificity of compounds are further characterized in vitro with respect to effector functions by analyzing effects on βγ-dependent regulation of adenylyl cyclase I and II, N-type $Ca^{2+}$ channels and inwardly rectifying $K^+$ channels. Since βγ subunits are critical components of receptor-G protein coupling, compound effects on the receptor stimulated GTP binding and turnover are evaluated, and determined if compound binding kinetics affects the ability to influence receptor G protein coupling. Selectivity of compounds for G protein βγ subunit subtypes is also evaluated. Medium throughput assays are developed that are used to predict effector selectivity and potentially therapeutic efficacy of new compounds without laborious screening in enzymatic assays. These experiments form the basis for connecting specificity characteristics with biophysical binding characteristics.

b) Determination of the Molecular Basis for Binding and Selectivity of Gβγ-Binding Compounds.

Small molecules binding directly to G protein βγ subunits selectively alter individual protein-protein interactions by binding to different subsites of the G protein βγ subunit "hot spot", but compound chemistry and/or binding kinetics impart some degree of selectivity. Compounds predicted to bind to the same site but with different chemistries are tested for effector selectivity in vitro. Surface plasmon resonance is used to measure binding kinetics and dissociation constants for individual selective compounds coupled with site-directed mutagenesis to understand binding characteristics and define binding sites for individual selective compounds. Specific compounds are co-crystallized with Gβγ to give a detailed picture of the interactions between selective compounds and Gβγ.

c) Computational Prediction of βγ Binding Specificity and Screening of New Libraries.

A specific binding subsite for a specific selective compound, defined by either X-ray structure determination or mutagenesis, is used as the specific target in a computation screen of a 50,000 compound diversity library. The top 100 compounds are analyzed in each of 7 scoring functions with the hypotheses that: 1) a single scoring function will emerge as the best scoring function for that site which will simplify further screening. 2) Compounds predicted to bind to that site have selectivity for βγ-effector interactions that resemble other compounds that bind to that subsite.

d) Analysis of Specificity and Efficacy in Neutrophil Based Models of Inflammation.

Specific selective compounds are analyzed for selective functional effects in neutrophils as a model for inflammation. A particular focus is on compounds that modify the βγ-dependent regulation of phosphoinsotide 3 kinase γ (PI3Kγ). Specifically, compounds are tested for specific effects on regulation of fMLP or IL-8 dependent signaling pathways in an HL60 neutrophil model cell line and in primary human neutrophils. Compounds that are selective for effects on neutrophil signaling are assayed for selective effects on neutrophil chemotaxis, superoxide production and extracellular matrix adhesion.

e) Background (1) Interactions Between βγ Subunits, α Subunits, and Effectors.

(a) Structure of the Heterotrimer:

Three dimensional crystal structures have been solved for G proteins yielding information about the interaction interfaces between α and βγ subunits and between these subunits and their effectors (Lambright et al., 1996; Noel et al., 1993; Tesmer et al., 1997; Wall et al., 1995). The β subunit belongs to the WD-40 β propeller family of proteins. The N terminus of the gamma subunit forms a coiled coil interaction with the N-terminus of β that extends away from the β propeller while the C terminal portion of γ forms an α helix that packs against the β subunit at blade 5 of the propeller. The α subunit has extensive interactions with a portion of the top of the β subunit and the amino terminal α helix of the α subunit interacts with the side of βγ at blades 1 and 7. There are no interactions between the α subunit and the γ subunit in these three dimensional models. βγ subunits have also been crystallized in a complex with phosducin, a molecule that binds to βγ subunits in the visual signal transduction system (Gaudet et al., 1996). Comparison of the phosducin structure with the heterotrimer structure reveals that the binding site on βγ subunits for phosducin overlaps extensively, but not completely, with the binding site for α. This suggests that effector-binding sites on βγ may only partially correspond to the α subunit-binding site. On the other hand, in the recently solved structure of βγ subunits in a complex with G protein coupled receptor kinase 2 (GRK2), the main contacts of βγ with the pleckstrin homology domain of GRK2 were very similar to the contacts with α subunits (Lodowski et al., 2003).

(b) Mutagenesis to Identify Protein Interaction Surfaces on βγ Subunits.

Different surfaces of βγ subunits are involved in interactions with different effectors and target proteins. Evidence from a variety of laboratories supports this view. To examine the functional role of the α subunit binding interface of βγ subunits in effector activation, a series of alanine mutants were made in the β subunit at amino acids involved in contacts with the α subunit (Ford et al., 1998). These mutants were tested for activation of effectors, and it was found that many of the mutants were incapable of activating $K^+$ channels, phospholipase C (PLC) β, and adenylyl cyclase (AC). Interestingly, distinct sets of amino acids at the α subunit interface seemed to be important for activation of different effectors. Putative effector binding sites have been identified in yeast β and γ subunits. These sites map to regions on β and γ subunits that do not correspond to the α subunit-binding site (Leberer et al., 1992). A site for interaction of PLC β2 with the amino terminus of β subunits that does not overlap with the α subunit binding site was identified using chemical crosslinking and mutagenesis (Yoshikawa et al., 2001). All of these experiments indicate that proteins bind to βγ subunits with distinct but overlapping sets of interactions allowing for binding and regulation. Disclosed herein, peptides were identified that selectively block activation of effectors by βγ subunits in vitro, supporting this idea (Scott et al., 2001) and have more recently identified small molecule binders with even greater specificity that are the subject of this proposal.

(2) Physiological Significance of βγ Activation.

G protein βγ subunit-mediated activation of effectors has diverse roles in regulation of cell physiology. Some examples of cellular processes regulated by βγ subunits are briefly described here. In excitable cells, including neurons and cardiac myocytes, βγ subunits that are released from $G_i$ regulate inwardly-rectifying $K^+$ channels modulating membrane potential or heart rate (Clapham and Neer, 1997). In immune cells, chemokine receptors, such as the IL-8 receptor and the co-receptors for entry of the AIDS virus into leukocytes, are coupled to the release of βγ subunits from $G_i$ (Kuang et al., 1996; Littman, 1998). Several mouse knockout studies implicate βγ regulated effectors in various physiological functions. For example, mouse neutrophils, with βγ-responsive PLCβ2 eliminated by gene-targeting, displayed increased chemotaxis in response to chemotactic peptides, and the mice were more resistant to viral infection (Jiang et al., 1997). In knockout mice lacking βγ-regulated PLCβ3, morphine acting at $G_i$ linked opioid receptors produced painkilling effects at much lower doses (Xie et al., 1999). In a similar set of studies, genetic deletion of βγ-regulated PI3Kγ resulted in decreased neutrophil migration and a reduction in inflammation.

Activation of multiple $G_i$ and $G_q$-coupled receptors, including thrombin, lysophosphatidic acid (LPA), and acetylcholine receptors, results in a mitogenic response in several cell types. MAP kinases are critical components in the growth-promoting pathways regulated by these receptors. βγ subunits indirectly activate MAP kinase, indicating that βγ subunits may mediate the growth-promoting effects of many G protein-coupled receptors (Gutkind, 2001; Luttrell et al., 1997). Sequestering βγ in smooth muscle cells inhibits serum stimulated growth and vascular restenosis (Iaccarino et al., 1999).

(3) G Protein βγ Subunits as a Target for Therapeutic Development.

The diverse functionality of Gβγ signaling in cellular physiology indicated that manipulating G βγ function has significant therapeutic potential. On the other hand Gβγ is known to be required for the functioning of all G protein coupled receptors so blocking all G βγ functions might be predicted to have some side effects. The therapeutic usefulness of targeting Gβγ signaling has been investigated extensively using the carboxy terminus of GRK2 (GRK2ct) (Bookout et al., 2003; Iaccarino et al., 1999; Iaccarino and Koch, 2003; Koch et al., 1995; Rockman et al., 1998) and to a lesser extent with other βγ binding peptides such as QEHA (Yao et al., 2002). GRK2ct, despite binding at the α/βγ "hot spot" interface interferes with βγ signaling to downstream targets without disrupting GPCR dependent G protein activation in general. The basis for this selectivity is unclear. This has strong implications for small molecule development, indicating that a strategy that targets the α/βγ interface "hot spot" is successful at blocking downstream βγ signaling without disrupting G protein signaling in general.

(4) βγ and Inflammation.

Data with knockouts of βγ effectors as described in "physiological significance of βγ activation" indicate that targeting βγ-effector interactions is a viable therapeutic strategy. Of particular interest is the demonstration that deletion of PI3Kγ in mice inhibits neutrophil migration in response to chemoattractants. PI3Kγ activity is directly regulated by Gβγ released from chemokine and chemotactic peptide receptors and is relatively selectively expressed in monocytic cells, indicating that blocking βγ-regulation of PI3Kγ is an effective strategy for treating inflammatory diseases (Li et al., 2000). Because of their roles in neutrophil recruitment, chemokines and chemokine receptors have been the subject of anti-inflammatory pharmaceutical development (Barnes et al., 1998; Gong et al., 1997; Halloran et al., 1999; Ogata et al., 1997; Plater-Zyberk et al., 1997; Podolin et al., 2002; Yang et al., 2002). A potential problem is the overwhelming complexity of these signaling molecules (multiple chemokines, chemokine receptors, and redundancy) making it difficult to know which specific receptors to target for conditions such as arthritis. Polychemokine (Carter, 2002) or combinations of different chemokine (al Mughales et al., 1996) antagonists have been suggested, but there may be chemokines that act as an agonist at one receptor and an antagonist at another (Xanthou et al., 2003). An alternate approach that is currently being investigated is specific pharmacological targeting of PI3K catalytic activity with inhibitors that are relatively selective for PI3Kγ relative to other PI3K isoforms (Camps et al., 2005). In this approach, blocking PI3Kγ circumvents the problem with chemokine receptor redundancy by blocking a common signaling target of chemokines. The small molecule inhibitors that were developed inhibit βγ-dependent activation of PI3Kγ indicating an alternate approach to selectively blocking PI3Kγ relative to other PI3K isoforms since these isoforms are not regulated primarily by Gβγ.

f) Results

Small molecules can be developed that by virtue of their small size, differentially affect activity of effectors that bind to the Gβγ "hot spot". As discussed in Background and Significance, each effector has a unique footprint on the Gβγ surface with an overlapping binding surface at the βγ "hot spot". Herein it is disclosed that effector/pathway-selective molecules have been developed that appear to function by targeting the Gβγ "hot spot" in different ways. This represents a totally new approach to manipulation of G protein signaling but the true mechanisms underlying selectivity remain to be defined.

(1) Amino Acid Sequence Characteristics of Peptides that Accelerate Heterotrimer Dissociation.

SIGK accelerates G protein subunit dissociation from a preformed heterotrimer leading to G protein activation, while other peptides that interfered with α/βγ interactions did not (Ghosh et al., 2003). Therefore, the specific interactions of SIGK at this interface were critical determinants of the ability of a peptide to promote dissociation of Gβγ from Gα·GDP. To test this idea the ability of SCAR, which uses unique binding determinants for interactions with Gβγ, was examined to promote subunit dissociation. In an equilibrium binding experiment, both SIGK and SCAR peptide competed for binding of fluorescently labeled $α_{i1}$ ($Fα_{i1}$) to βγ in a flow cytometry based binding assay (FIG. 1B) (see (Ghosh et al., 2003; Sarvazyan et al., 1998) for details the method). The ability of peptides to dissociate a preformed hetero-trimer was assessed by comparing the rates of $Fα_{i1}$ dissociation from $Fα_{i1}β_1γ_2$ with excess unlabeled $α_{i1}$ competitor (intrinsic dissocia-tion rate) and in the presence of a saturating concentration of peptide. In FIG. 1C, it can be seen that in the presence of SIGK the rate of dissociation of $Fα_{i1}$ is faster than the intrinsic rate of dissociation, (i.e. with excess $α_{i1}$) while with SCAR the rate is the same as the intrinsic rate. Thus two peptides that bind to the same interface but use unique contacts within the interface have two different effects on subunit dissociation.

In summary, these data reinforce the idea that Gβγ functions can be selectively altered by targeting the "hot spot" with peptides. The fact that the selective peptides that were developed bind to the "hot spot" switch II interface, indicates that reagents that bind this surface can be selective for Gβγ subunit interactions. Thus, for SIGK, the selectivity for effectors results from some Gβγ targets having key interactions outside the "hot spot" (Scott et al., 2001). The new data demonstrating that peptides have unique binding determinants within the hot spot that may dictate selectivity for α subunit interactions indicates that selectivity can be achieved within the "hot spot" that can be pharmacologically exploited to develop selective drugs.

(2) Virtual Screening of the NCI Diversity Library.

Figure 3A:
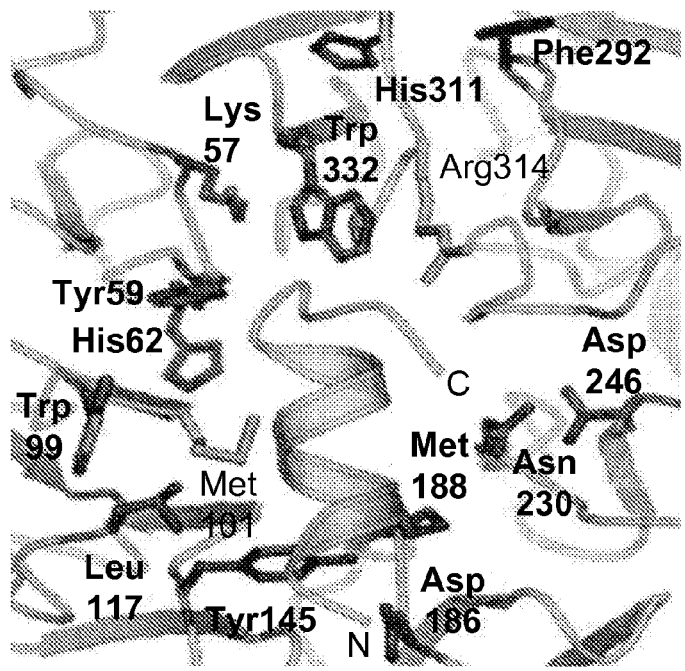

Given the ability to develop peptides selective for G protein functions within a single binding site, when small molecules are found that bind within this site, an even higher level of selectivity is achieved. Since peptides are relatively large, it can be more difficult to selectively sterically modify protein-protein interactions within the hot spot. To find small molecules that bind to this site the NCI diversity library of 1990 compounds was obtained from the Developmental Therapeutics program at the National Cancer Institute that represents a larger library of 250,251 compounds. A virtual version of this library was screened for binding to the Gβγ "hot spot" using Sybyl/FlexX virtual docking software. For the purposes of this screen the "hot spot" was defined as the surface area of Gβγ within 6.5 Å of the peptide binding site (FIG. 3A). FlexX computationally poses the molecule in the "hot spot" and each of the selected poses is evaluated with five scoring functions (D-score, G-score, F-score, chemscore, and PMF score (Wang et al., 2003) and two consensus scores. Eighty five compounds representing the top 1% from each scoring function were selected and tested for interaction with Gβγ in the competitive phage ELISA described below.

(3) Selected Compounds Inhibit SIGK Peptide Binding.

Figure 3B:
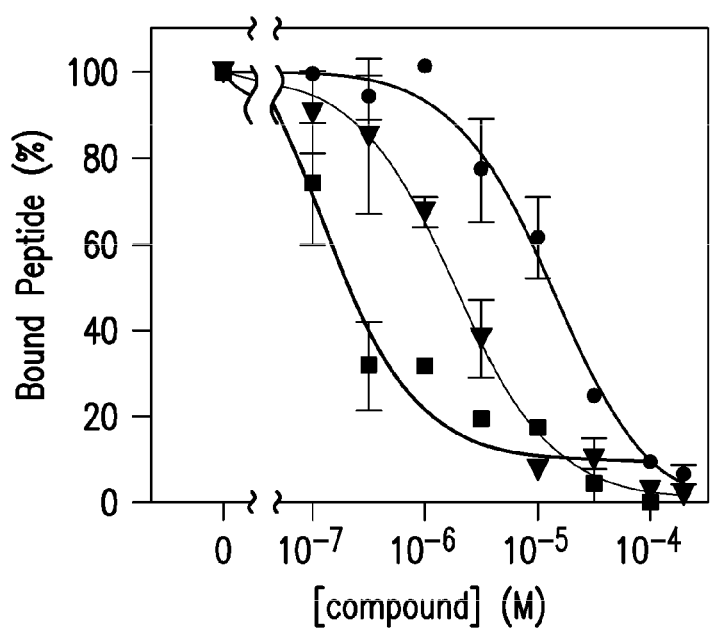

Here, compounds identified as potential binders computationally were tested to determine whether they would compete for binding of a phage displaying SIGK. Since the binding of SIGK to Gβγ has been structurally defined, compounds that compete for SIGK binding were selected as compounds that bound to the "hot spot" on Gβγ. The phage ELISA assay was used to rapidly screen the ability of compounds to bind to the protein interaction "hot spot" based on the method of Scott et. al (Scott et al., 2001). This assay is performed in the presence of detergent (0.5% Tween) to eliminate non-specific compound aggregation artifacts. Because of the assay's simplicity, compounds that influence the binding are likely to be directly affecting βγ. Compounds that blocked SIGK-phage binding were then titrated to determine their affinity for Gβγ (FIG. 3B). Initial screening identified 9 candidate compounds that inhibited SIGK binding with $IC_{50}$'s ranging from 100 nM to 60 µM (Table 18).

TABLE 18

Compounds identified in Elisa screen

| Compound (NSC#) | MW | $IC_{50}$ µM |
|---|---|---|
| M119 (119910) | 370 Da | 0.2 |
| M306 (306711) | 1001 Da | 7 |
| M308 (308820) | 319 Da | 0.1 |
| M117 (117079) | 437 Da | 56 |
| M121 (12155) | 445 Da | 13 |
| M231 (23128) | 899 Da | 16 |
| M402 (402959) | 779 Da | 2 |
| M125 (125910) | 566 Da | 18 |
| M109 (109268) | 679 Da | 4 |

(4) Structure Activity Relationships.

Figure 3C:
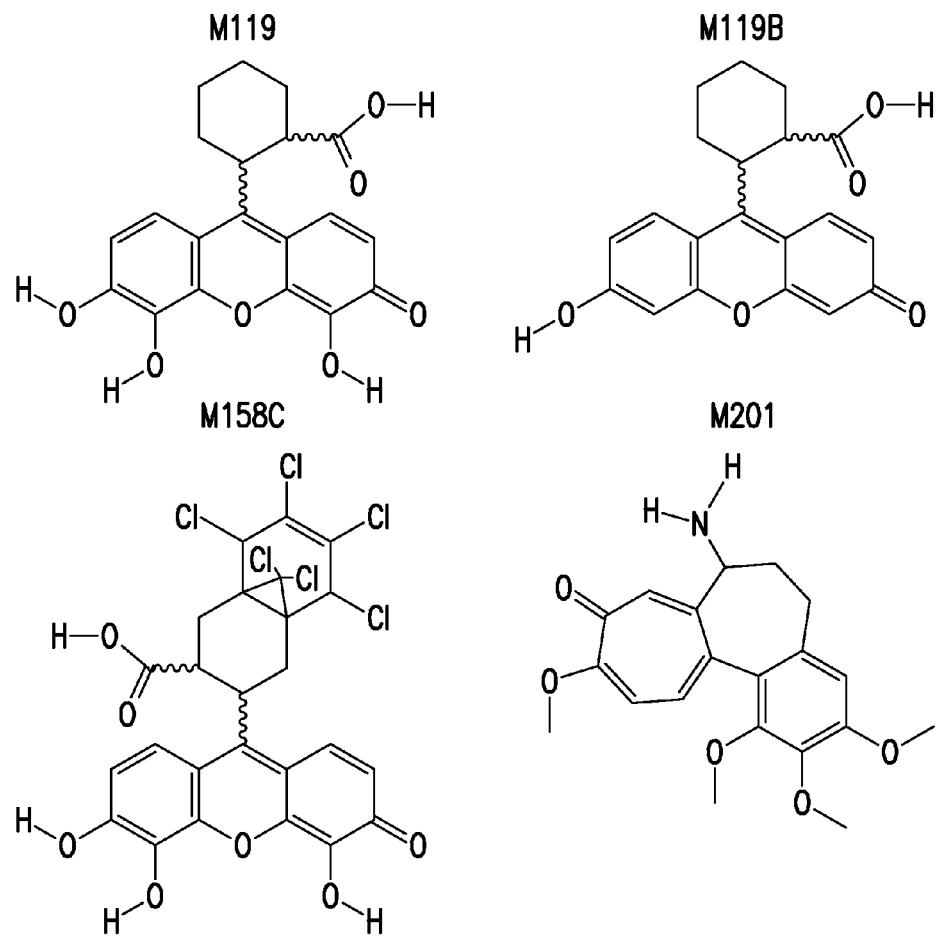

One compound, M119, with high "apparent" affinity for $G\beta_1\gamma_2$ (ELISA $IC_{50}$=200 nM) (FIGS. 3B and C) was selected as a lead to define structure-activity requirements (SAR) for binding to $G\beta_1\gamma_2$. M308, which also had a very high "apparent" affinity for Gβγ was found to act via a βγ-dependent oxidation mechanism and was not pursued further in this analysis. The NCI library was searched for compounds similar to M119 using Sybyl/Unity data base searching software. This software creates a two dimensional chemical fingerprint, taking into account the number of hydrogen bond donors and acceptors and other physiochemical parameters, and used this fingerprint to search the 250,000 compound NCI library. 21 compounds from the NCI library with similar structures to M119 were tested for relative $G\beta_1\gamma_2$ binding affinities (See FIG. 18 for representative binders). For example, the apparent affinity of M119B for $G\beta_1\gamma_2$ is $\frac{1}{1000}$ that of M119 with the key chemical difference being the loss of 2 hydroxyl groups (FIG. 3C). Thus, specific chemical characteristics are required for interactions with the Gβγ hotspot.

(5) α-Subunit Interactions.

Figure 3D:
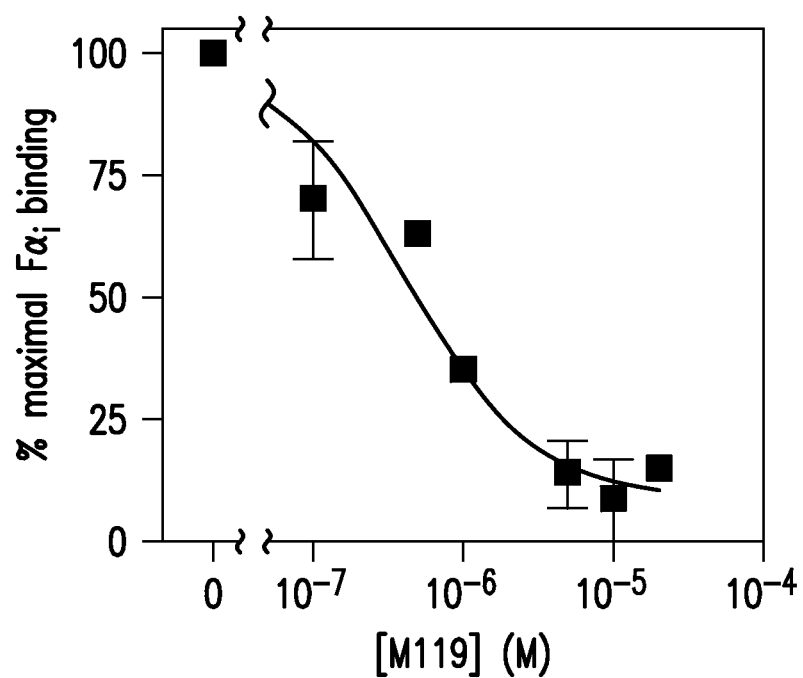

While the compounds inhibited interactions between $G\beta_1\gamma_2$ and the peptide SIGK, it is thought to be relatively difficult for small compounds to disrupt true protein-protein interactions. Whether M119 could disrupt protein interactions was tested with a bona fide Gβγ binding partner, $G\alpha_{i1}$. The 'hot spot' for protein interaction overlaps with the Gα switch II binding surface on Gβγ. The overall $G\alpha_{i1}$-βγ interaction surface spans 1800 Å$^2$ (Lambright et al., 1996; Wall et al., 1995) and the dissociation constant ($K_d$) for $G\alpha_{i1}$ binding to Gβγ is approximately 1 nM (Sarvazyan et al., 1998). M119 competed with FITC-$\alpha_{i1}$ (F$\alpha_i$) for binding to b$G\beta_1\gamma_2$ with an $IC_{50}$ value of 400 nM (FIG. 3D). However, unlike SIGK and related peptides that bind to this surface (Ghosh et al., 2003), M119 did not promote dissociation of $G\alpha_i$ from Gβγ (Bonacci et al., 2006).

(6) Effect of Compounds on in vitro PI3Kγ, PLCβ2/3 and GRK2 Regulation and Binding by Gβγ.

Figure 4A:
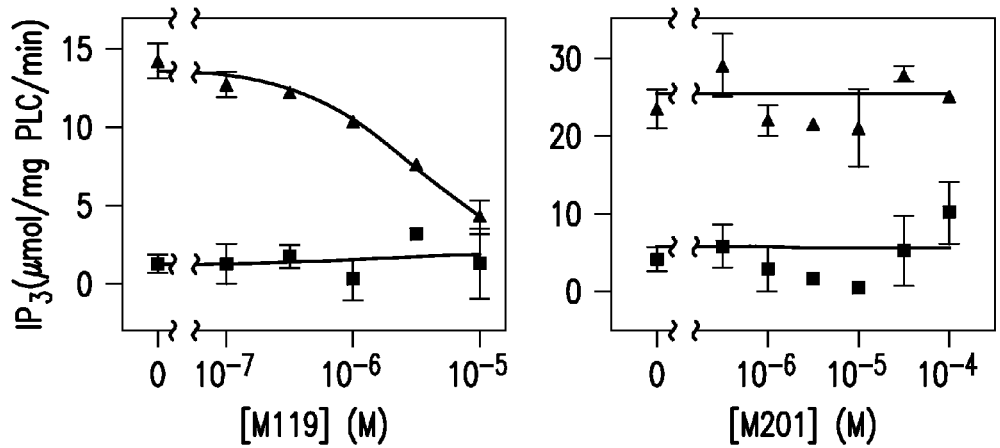
Figure 4B:
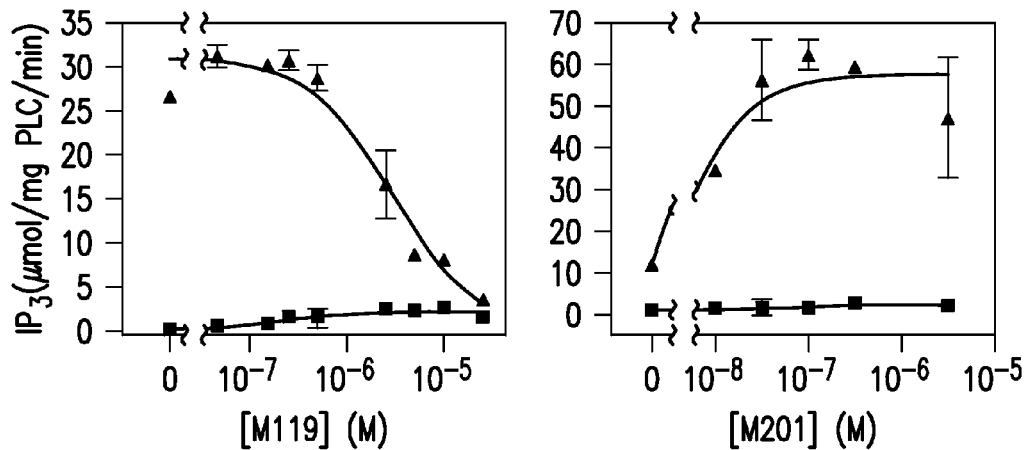
Figure 4C:
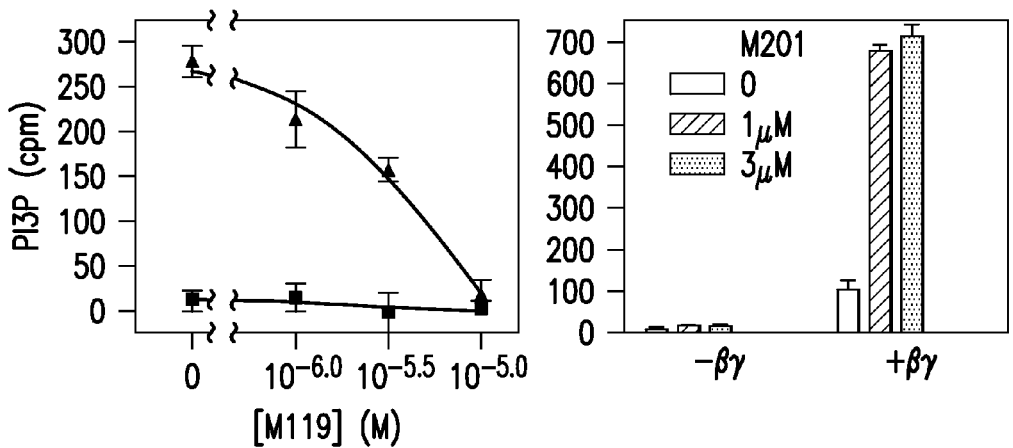
Figure 4D:
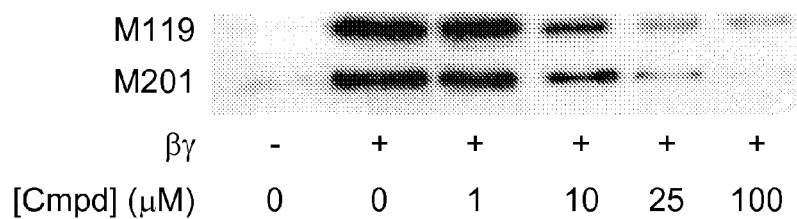
Figure 4E:
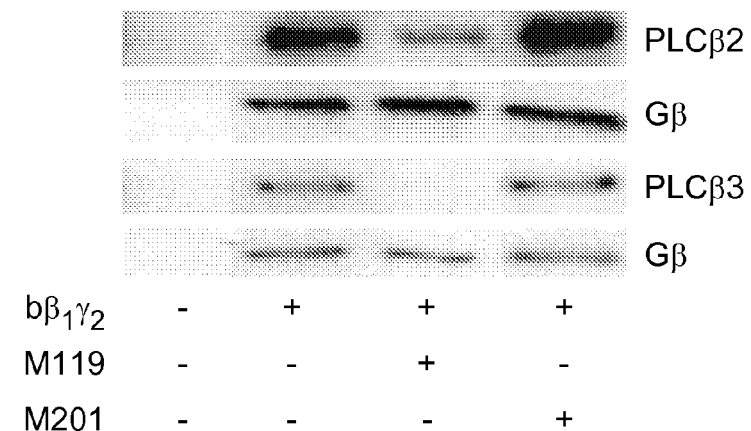
Figure 4F:
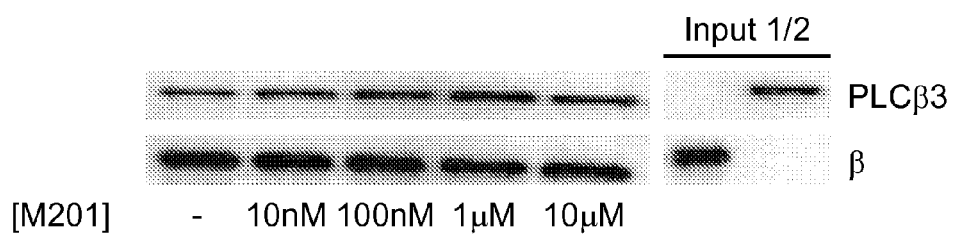

FlexX docking software predicted that compounds M201 and M119 (FIG. 3C) bound to distinct subsurfaces in the 'hot spot', but M201 did not compete for SIGK binding. Nevertheless, M119 and M201 were tested in in vitro reconstitution assays of Gβγ-dependent activation of PLCβ2, PLCβ3 and PI3Kγ and binding to GRK2. M119 attenuated $G\beta_1\gamma_2$-dependent activation of PLCβ2 ($IC_{50}$ value of 3 µM), PLCβ3 and PI3Kγ (FIG. 4A-C left panels). M201, on the other hand, did not affect PLCβ2 activation by $G\beta_1\gamma_2$ but potentiated $G\beta_1\gamma_2$-dependent activation of both PLCβ3 and PI3Kγ (FIGS. 4A-C right panels). M119 also inhibited direct binding of b$G\beta_1\gamma_2$ to PLCβ2 and PLCβ3, while M201 did not block binding of PLCβ2 and enhanced binding of PLCβ3 to $G\beta_1\gamma_2$ (FIGS. 4E and F). M119 and M201 both inhibited GRK2 binding to b$G\beta_1\gamma_2$ with similar $IC_{50}$ values of approximately 5 µM (FIG. 4D). A weakly binding compound M119B (FIG. 3C) did not have effects in these assays (Bonacci et al., 2006). These data show that small molecules differentially modulate Gβγ interactions with effectors. These are only two of multiple diverse compounds identified, indicating potential for multiple modes of Gβγ-dependent target modulation by these small molecules.

TABLE 19

| Compound | ELISA (µM) | PLCb2 (µM) | PLCb3 (µM) | PI 3-Kg (µM) |
|---|---|---|---|---|
| M119 | 0.2 | 3 | 3 | 8 |
| 115360 (M360) | 12 | 12 | 75 | 2.5 |
| 115372 (M372) | 19 | 14 | 15 | 6 |
| 402959 (M402) | 2 | NE | NE | 12 |
| 23128 (M231) | 27 | 167 | NE | 13.5 |

Summary of effector IC50's. n ≥ 2 (each in duplicate). NE = No effect.

Table 19 shows the IC50's of compounds found to be relatively selective for inhibition of βγ-dependent regulation of PI3Kγ relative to regulation of PLCβ23 and β3. Compounds were tested for βγ-dependent regulation of these enzymes in in vitro enzyme assays as described earlier.

(7) Biophysical Analysis of Ligand Binding by SPR.

The competition ELISA is a valuable medium throughput method that implies efficacy and localizes the binding site, but the apparent $K_d$'s estimated from $IC_{50}$ values in the ELISA assay do not give a true measure of binding affinity because it relies on competition with multivalent peptide binding. To understand the protein binding characteristics of compounds a surface plasmon resonance (SPR) method was developed for monitoring direct small molecule binding to Gβγ subunits using a Reichert SPR instrument. In addition to binding affinity, binding kinetics can be obtained from this analysis. Given an $IC_{50}$ in the range of 1 µM, it was suspected that M119 binds with relatively rapid on/off kinetics. To obtain the data in herein, 3000 refractive index units (RIU) of $Gβ_1γ_2$ was immobilized to maximize detection of small molecule binding (Karlsson et al., 2006; Markgren et al., 2001; Rich et al., 2001) and compounds were injected at 75 µl/min and changes in bulk refractive index were accounted for in a reference flow cell. No non-specific binding of the compound to the sensor surface in the absence of Gβγ was detected. In the analysis of M119 binding to Gβγ SPR, the results indicate that $k_{on}$ and $k_{off}$ are much slower than expected (global fitting analysis gave estimated $k_{on}$ $2×10^3$ $M^{-1}s^{-1}$, $k_{off}$ $2×10^{-4}$ $s^{-1}$, $K_d$ 100 nM). This data demonstrates that small molecule binding to Gβγ by SPR can be detected and analyzed. This method is used to analyze compound binding kinetics and calculate equilibrium binding constants to test the mechanisms of action and selectivity of various "hot spot" binding compounds.

(8) Analysis of Compound Efficacy and Selectivity in Intact Cells.

Figure 5A:
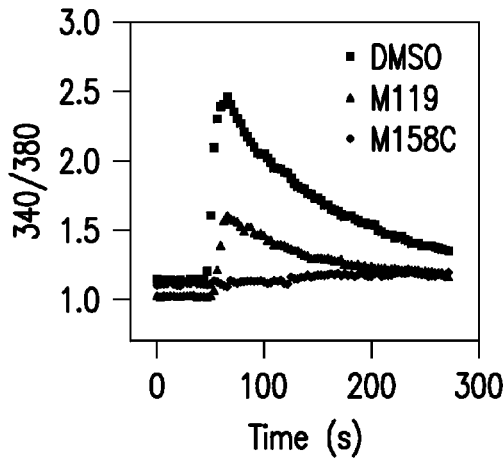
Figure 5B:
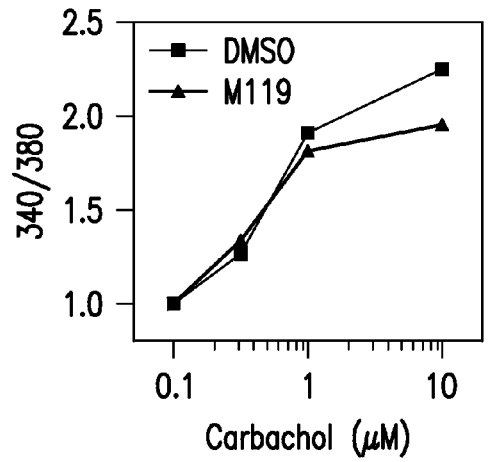
Figure 5C:
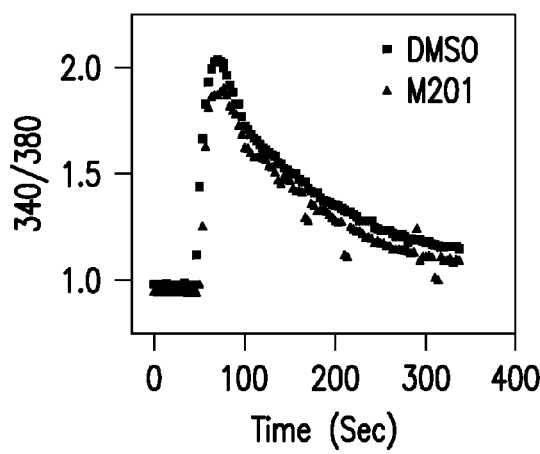
Figure 5D:
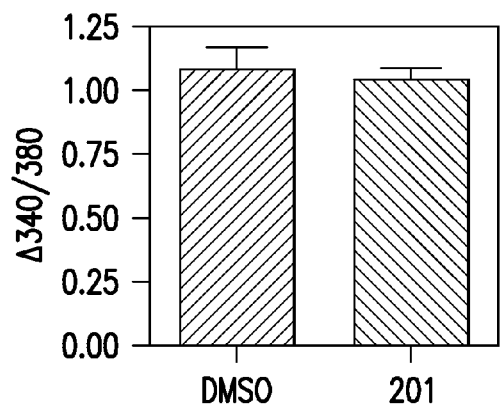
Figure 5E:
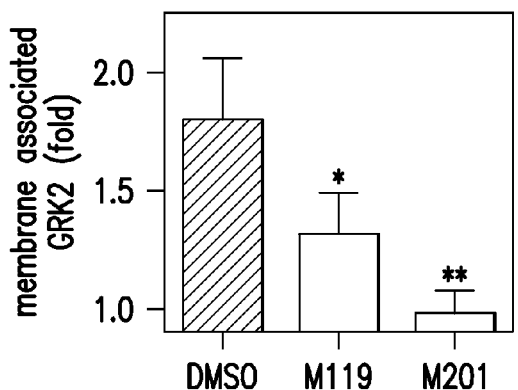

To test the effects of differentially targeting Gβγ on GPCR signaling in intact cells, M119 (and a similar compound M158C) (See FIG. 3C) and M201 were tested for their ability to modulate fMLP receptor-dependent signaling in differentiated HL60 leukocytes. The fMLP receptor couples to Gi in these cells and activates PLCβ2 (PLCβ3 is a minor isoform in these cells), PI3Kγ, and ERK through Gβγ signaling (Li et al., 2000; Neptune and Bourne, 1997). Pre-treatment of differentiated HL60 cells with M119 and M158C (FIGS. 5A), but not M201 (FIGS. 5C and D), attenuated fMLP-induced $Ca^{2+}$ increases. M119 had no effect on carbachol-dependent increases in $Ca^{2+}$ in HEK293 cells stably expressing the Gq-linked M3-muscarinic receptor, confirming a specific effect of M119 on Gβγ-dependent $Ca^{2+}$ mobilization (FIG. 5B). fMLP-dependent GRK2 translocation to the membrane fraction of HL60 cells on the other hand was substantially inhibited by incubation with either M119 or M201 (FIG. 5E). Thus M119 and M201 differentially modulate PLCβ2 regulation by Gβγ, yet both inhibit GRK2 binding in intact cells.

Figure 5F:
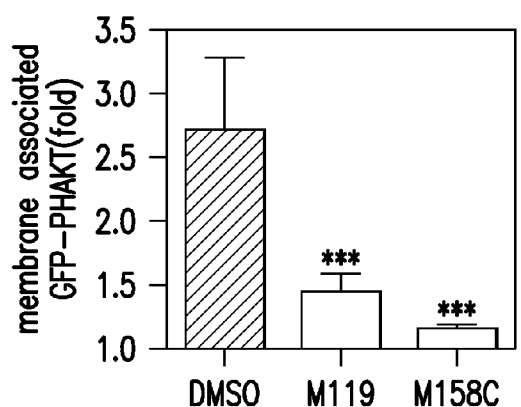

To assess the ability of M119 and M158C to inhibit fMLP receptor-dependent regulation of PI3Kγ activation, HL60 cells were stimulated stably over-expressing a GFP tagged PH domain from Akt (Servant et al., 2000) with fMLP, and assessed translocation of the GFP-PHAkt to the membrane by subcellular fractionation and Western blotting. The PH domain from Akt binds to $PIP_3$ produced by PI3K activity at the membrane. Pre-treatment of the cells with 10 µM of M119 or M158C inhibited fMLP-dependent translocation of GFP-PHAkt to the membrane (FIG. 5F), consistent with the ability of these compounds to inhibit activation of PI3Kγ by Gβγ.

Figure 5G:
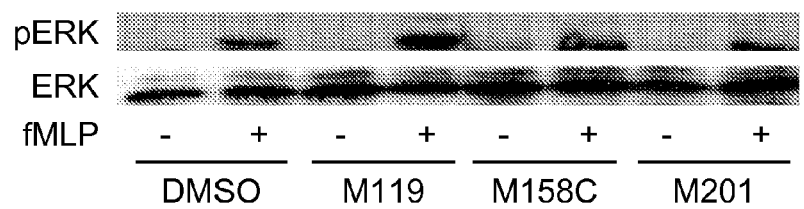

Stimulation of differentiated HL60 cells with fMLP also results in pertussis toxin sensitive activation of various MAP kinases including ERK1 and ERK2, p38 and JNK (Rane et al., 1997). However, pretreatment of HL60 cells with M119, M158C or M201 did not block fMLP-induced activation of ERK1 and ERK2 (FIG. 5G).

(9) Characterization of Novel Compound Binding to Gβγ

Previous studies identified multiple compounds that blocked effector binding to Gβγ. A lead compound, M119, inhibited Gβγ-dependent PI3-kinase γ and PLCβ activation in vitro and blocked chemoattractant/PI3-kinase-dependent GFP-PH-Akt translocation to membranes as well as Ca2+ release (Bonacci et al., 2006). A related compound, galleon (DL382), was identified that differs from M119 by the substitution of a benzene carboxylic acid for cyclohexane carboxylic acid at the 9 position of the core xanthene (FIG. 8A). Gallein is commercially available at high purity as a single isomer and in quantities necessary for in vivo analysis, so the Gβγ binding properties of gallein were compared with M119. Gallein effectively competed for binding of SIGK peptide to Gβγ in a phage ELISA assay with an IC50 comparable with that of M119 (FIG. 8B). Herein is shown that compounds that block peptide binding in this assay are effective competitors of many Gβγ protein-protein interactions.

To determine direct binding equilibrium and kinetic constants for gallein binding to Gβγ, surface plasmon resonance (SPR) measurements were performed with streptavidin-immobilized biotinylated Gβ1γ2. Binding and dissociation of gallein was monitored as a function of concentration and time. Data were fit to one site association and dissociation models to calculate association and dissociation rate constants from which affinity constants were derived (FIG. 8C, Table 21). Based on the SPR analysis, gallein bound to Gβ1γ2 (FIG. 8C) with a Kd value of approximately 400 nM (Table 21), in relatively close agreement with the IC50 of 200 nM observed in the competition ELISA assay. The control compound, fluorescein, which did compete for SIGK binding in the competition ELISA, did not have detectable binding by SPR (Table 21). It is noteworthy that binding and dissociation rates for gallein were relatively slow (FIG. 8C). These data confirm that gallein binds directly to Gβγ, and resulting effects on competition for effector binding are likely to result from direct binding to Gβγ with high affinity. Based on these data, gallein has similar effects to M119 when tested in in vitro and in vivo assays.

Figure 9A:
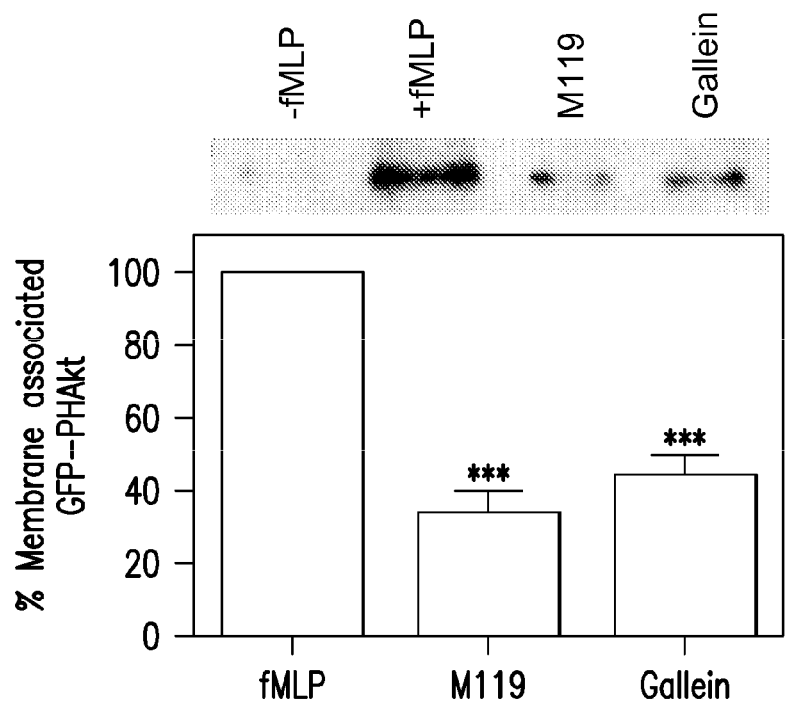

(10) Inhibition of G Protein-Dependent Chemotactic Peptide Signaling with Small Molecules As discussed in background and significance Gβγ-dependent activation of PI3kγ in neutrophils is important in directing neutrophil migration in response to chemoattractants. Activation of this receptor system leads to a gradient of $PIP_3$ production with enhanced accumulation at the leading edge of the cell that is important for polarizing the cells in the direction of the chemo-attractant (Servant et al., 2000; Wang et al., 2002). In animal models of neutrophil chemotaxis, deletion of PI3kγ results in defects in neutrophil accumulation and reduced inflammation (Hirsch et al., 2000; Li et al., 2000). To determine if blocking Gβγ-depend-ent activation of PI3Kγ in neutro-phils would affect chemotaxis, the Boyden chamber assay was used to quantitate chemotaxis. fMLP enhanced migration and inclusion of 10 µM M119 with fMLP significantly blunted migration (FIG. 10E), supporting the idea that blocking Gβγ dependent signaling (likely PI3K activation) in HL60 cells inhibits migration. The same assay with M119 without fMLP did not induce motility and the inactive control M119B had no effect on migration. To determine whether galleon (DL382) (see FIG. 8 for structure), like M119, modulates the receptor-dependent activation of PI3-kinase, HL60 cells expressing GFP-PH-Akt were pretreated with compound and challenged with fMLP. Gallein inhibited fMLP-dependent GFP-PH-Akt translocation in differentiated HL60 cells with an efficacy comparable with that of M119 (FIG. 9A).

Figure 9B:
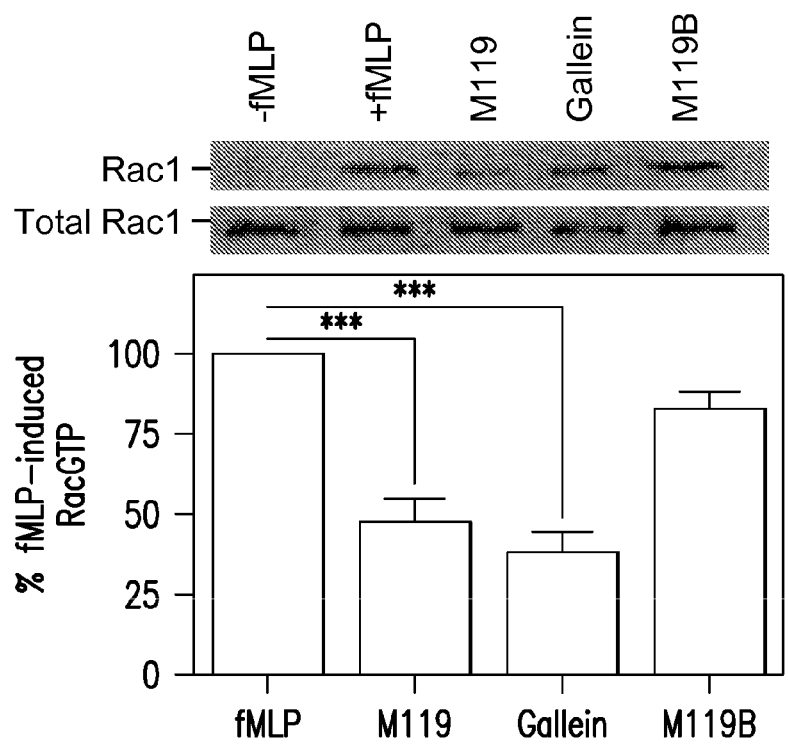

Activation of Rac in neutrophils is critical for fMLP-dependent activation of NADPH-oxidase and subsequent superoxide production and is dependent on Gβγ- and PIP$_3$-dependent activation of the Rac-specific exchange factor P-Rex. Herein is shown that M119 inhibited P-Rex1 activation by fMLP suggesting the compounds could inhibit Rac activation (Zhao et al., 2007). It was determined whether Gβγ-binding compounds would inhibit receptor-dependent activation of Rac1. Rac1 GTP levels were measured in cytosolic extracts of HL60 cells that had been pretreated with compounds before stimulation with fMLP. M119 and gallein inhibited fMLP-induced Rac1 activation in differentiated HL60 cells, whereas the negative control compound M119B had little effect (FIG. 9B).

(11) Gβγ Inhibitors Blocked fMLP-Dependent Superoxide Production and Neutrophil Chemotaxis.

The ability of these small molecules to block fMLP-induced chemotaxis and superoxide production was assessed to determine whether the compounds can block relevant cellular functions downstream of PI3-kinase γ and Rac. Both of these functions are critical to the inflammatory process and inhibition of both processes can contribute to anti-inflammatory effects of Gβγ inhibitors.

Figure 9C:
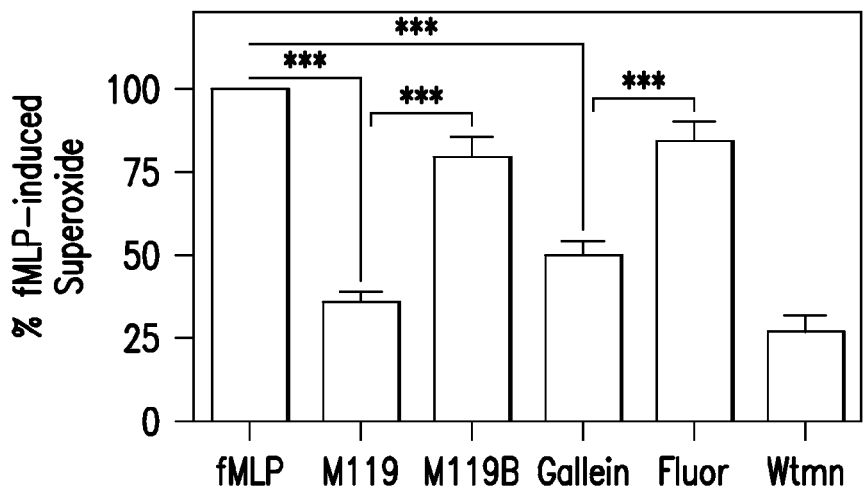
Figure 9D:
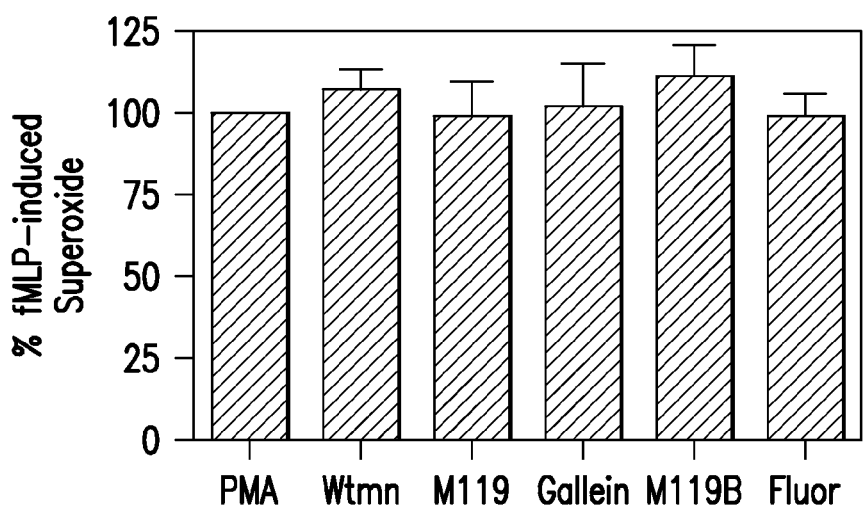
Figure 10A:
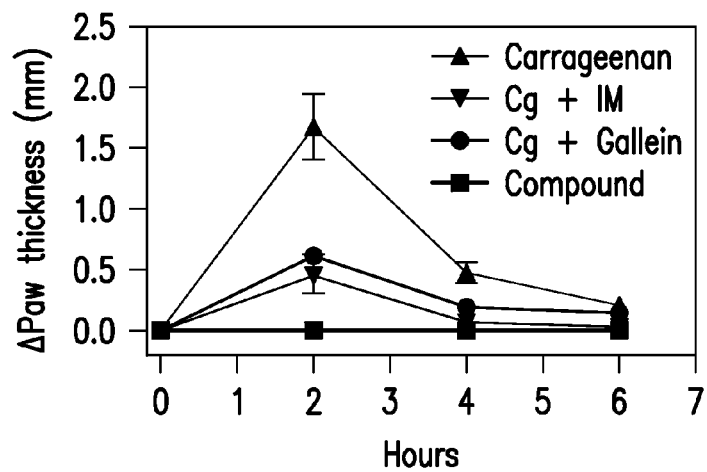
Figure 10B:
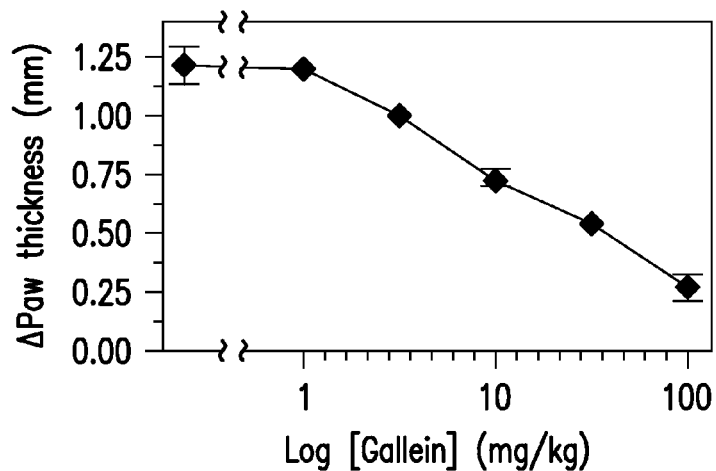

M119 and gallein both significantly inhibited fMLP-dependent superoxide production. Control compounds M119B and fluorescein did not significantly affect this response (FIG. 9C). Wortmannin also blocked fMLP-dependent superoxide production, indicating that the pathway was a PI3-kinase-dependent pathway. PMA-dependent superoxide production, a process not dependent on Gβγ was also examined. PMA-dependent superoxide production was not inhibited by any of the Gβγ binding compounds or controls (FIG. 9D), indicating that the compounds specifically inhibited the Gβγ-dependent pathway to superoxide production.

fMLP-dependent chemotaxis was assessed in a Boyden Chamber. M119 and gallein inhibited fMLP-induced chemotaxis in differentiated HL60 cells with similar efficacy (FIG. 10A). Neither M119 nor gallein had any effects on chemokinesis measured in the transwell assay with fMLP in both the upper and lower chambers (data not shown). To support the idea that the mode of action of these compounds is dependent on Gβγ heterodimers liberated from Gα$_i$-coupled chemokine receptors, cells were challenged with GM-CSF. Chemotaxis induced by GM-CSF is partly dependent on PI3-kinase activity in human neutrophils but is independent of Gβγ-stimulation of PI3-kinase (Gomez-Cambronero et al., 2003). If the small molecules were acting directly on PI3-kinase or by a nonspecific mechanism, they would be expected to block GM-CSF-induced chemotaxis. Neither M119 nor gallein blocked GM-CSF-induced chemotaxis in differentiated HL60 cells (FIG. 10B). These data demonstrate two key points: 1) the general chemotaxis machinery in HL60 cells is not affected by these compounds and 2) the compounds selectively inhibited GPCR-dependent chemotaxis, consistent with inhibition of Gβγ signaling.

Figure 10C:
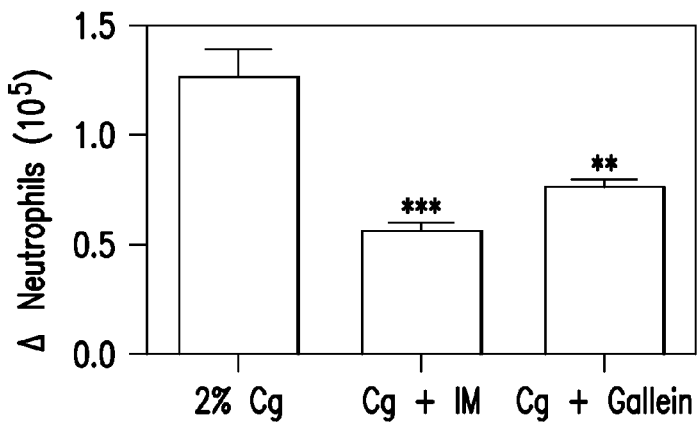

The inhibitory properties of these compounds in potentially more clinically relevant isolated primary human neutrophils were also evaluated. Again, both M119 and gallein significantly inhibited fMLP-induced chemotaxis (FIG. 10C). Wortmannin, a general PI3-kinase inhibitor (Okada et al., 1994), also blocked chemotaxis (FIG. 10C). Conversely, M119B binds only weakly to the Gβγ "hot spot" (Table 21 in Bonacci et al., 2006) and had no affect on cell motility (FIG. 10C), suggesting that the observed effects on chemotaxis are dependent on small-molecule-binding to the Gβγ "hot spot." IL-8 regulated chemotaxis was also blocked by M119 and gallein (FIG. 10C) extending the findings to other G$_i$ coupled chemoattractants and supporting the idea that the mechanism of action of these compounds is to inhibit Gβγ subunit signaling down-stream of chemoattractant/chemokine receptors.

Figure 10D:
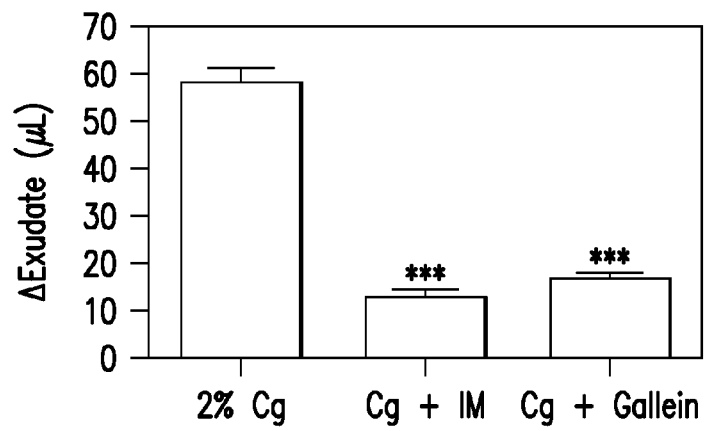
Figure 10E:
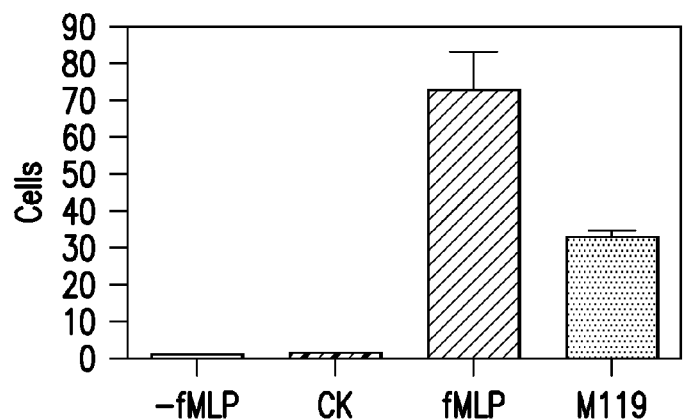
Figure 10F:
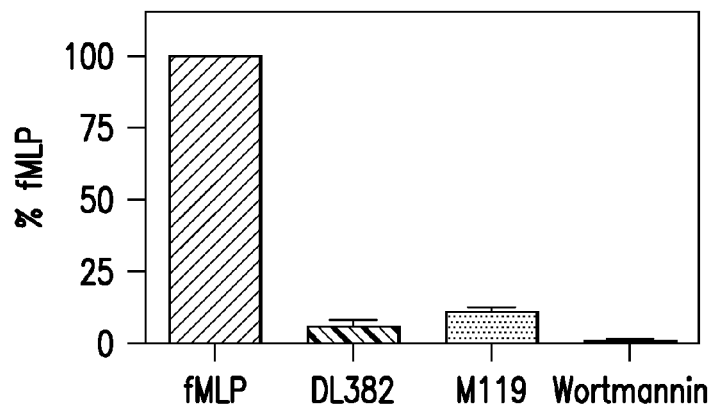

To assess the potency of gallein for inhibition of chemotaxis, primary human neutrophils were treated with a range of concentrations and assayed for fMLP-dependent chemotaxis. Gallein blocked fMLP-dependent chemotaxis with an IC$_{50}$ of approximately 5 μM (FIG. 10D). Thus, small molecules that bind to Gβγ and block Gβγ-dependent PI3-kinase γ regulation in vitro and in HL60 cells potently inhibit GPCR-dependent neutrophil chemotaxis with an IC$_{50}$ comparable with what has been published for direct PI3-kinase catalytic inhibitors on chemokine-dependent monocyte chemotaxis (Camps et al., 2005).

(12) Gallein Attenuates Inflammation and Neutrophil Recruitment in Vivo.

Figure 11A:
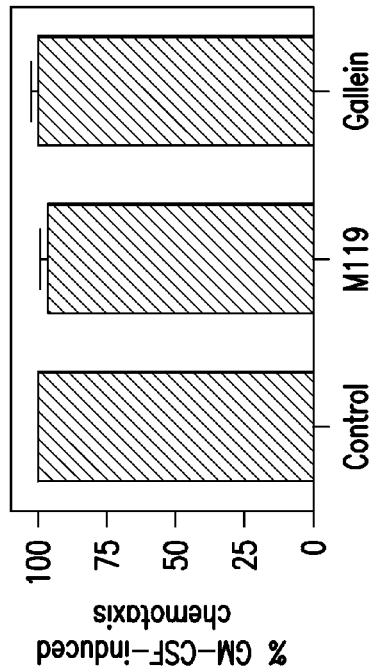
Figure 11B:
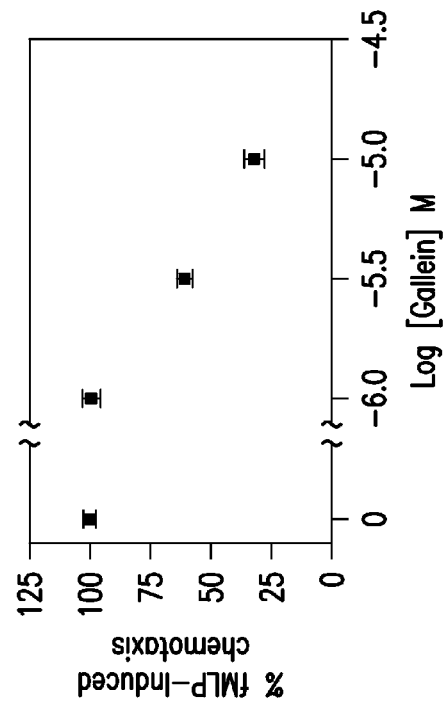
Figure 11C:
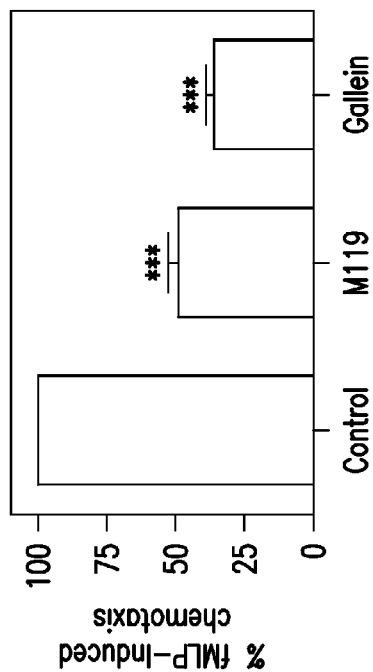
Figure 11D:
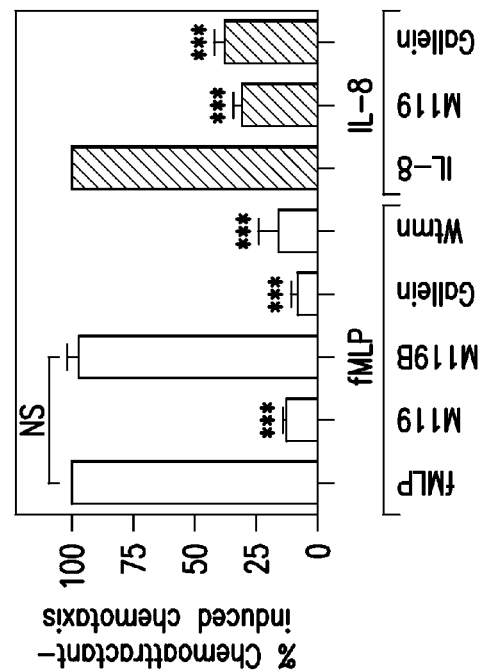

Inhibition of chemoattractant-dependent chemotaxis of neutrophils would be predicted to inhibit neutrophil-dependent inflammation based on data from PI3-kinase γ knock-out mice (Hirsch et al., 2000; Li et al., 2000). To assess the in vivo efficacy of Gβγ-binding small molecules in blocking neutrophil chemotaxis gallein was tested in the carrageenan paw edema model. Carrageenan, when injected into the glabrous tissue of the hind paw, leads to rapid acute inflammation characterized by infiltration of neutrophils (Siqueira-Junior et al., 2003). Gallein or vehicle control was delivered by intraperitoneal injection 1 h before injection of carrageenan into the paw. Peak paw edema was observed 2 h after carrageenan injection (FIG. 11A). Indomethacin, a nonselective nonsteroidal anti-inflammatory drug that inhibits cyclooxygenases 1 and 2 (Siqueira-Junior et al., 2003), is the drug of choice for comparative in vivo efficacy studies. Pretreatment with indomethacin sharply reduced paw edema. It is noteworthy that prophylactic administration of 100 mg/kg gallein reduced paw edema to levels comparable with that of indomethacin. Injection with gallein in the absence of carrageenan had no effect on paw thickness (data not shown). Additional experimentation determined that the ED$_{50}$ value of gallein for inhibiting paw edema to be approximately 20 mg/kg (FIG. 11B). Acute phase inflammation, as seen in the carrageenan-induced paw edema model, is characterized by neutrophil infiltration (Siqueira-Junior et al., 2003; Posadas et al., 2004). To confirm that neutrophil infiltration was inhibited, the number of neutrophils in paw exudates was quantified. Pretreatment with 100 mg/kg gallein reduced the number of neutrophils in the edematous fluid by approximately half to levels comparable with that seen with indomethacin (FIG. 11C). These data correlated well with the actual volume of exudate fluid. Pretreatment with indomethacin and gallein also reduced exudate volume by approximately 75% (FIG. 11D).

Oral administration of gallein (30 mg/kg) in mice 1 h before carrageenan challenge also significantly reduced paw swelling by 40% comparable with that of indomethacin (FIG. 12). These data demonstrate that gallein is absorbed into systemic circulation, is bioavailable, and systemically impairs neutrophil recruitment. To support the conclusion that the observed reduction in paw swelling was Gβγ-dependent, the M119B-like compound fluorescein was tested under identical experimental conditions. Fluorescein differs from M119B only by the substitution of an aromatic benzene ring for a cyclohexane at the 9 position of the core xanthene (FIG. 8A) and binds Gβγ very weakly if at all (Table 21). Fluorescein did not reduce paw swelling under identical experimental conditions (FIG. 12), which indicates that the observed reduction in paw swelling and neutrophil infiltration was correlated with the ability of the small molecules to bind to Gβγ. Based on this data and other published structure activity data one key structural requirements for activity resides in the core xanthene scaffold with requirements for hydroxylation at the 3,4,5 and 6 positions of the xanthene ring system.

g) Discussion

Herein a novel strategy for treatment of inflammation that targets interactions between G protein βγ subunits and effectors that are critical for neutrophil migration in response to activation of chemoattractant receptors was presented. Gβγ-responsive PI3-kinase γ production of $PIP_3$ is critical to neutrophil functions, including superoxide production, chemotaxis, and cellular polarization (Hirsch et al., 2000; Li et al., 2000). It was shown that Gβγ-binding small molecules inhibit interactions between Gβγ and PI3-kinase γ. These same molecules block PI3-kinase and Rac1 activation in HL60 cells, chemoattractant-dependent superoxide production and chemotaxis in differentiated HL60 cells. These findings were extended to inhibition of chemoattractant-dependent chemotaxis in primary human neutrophils and ultimately neutrophil-dependent inflammation in vivo.

PI3-kinases play diverse roles in normal cellular physiology, including cell motility and survival (Cantley, 2002). Camps and colleagues identified and characterized small-molecule inhibitors of PI3-kinase γ that are competitive with ATP (Camps et al., 2005). These small molecules were efficacious in mouse models of rheumatoid arthritis and systemic lupus, providing further rationale for pharmacological targeting of the pathway as therapeutic strategy (Barber et al., 2005; Camps et al., 2005). However, a concern with inhibitors of this class is that because many kinases of the same family have significant homology, there may be difficulty in developing inhibitors that are selective for PI3-kinase γ, although some progress has been made in this area (Rückle et al., 2006). The strategy presented here selects for a single isoform of the PI3-kinase family because PI3-kinase γ is the only PI3-kinase isoform that uses $G_i$βγ-dependent activation as a major mechanism for regulation (Stephens et al., 1994, 1997; Hirsch et al., 2000).

Compounds such as M119 and gallein also inhibit interactions between Gβγ and other targets that are critical for chemoattractant-dependent directed migration or reactive oxygen species production by neutrophils or other monocytes. For example, M119 blocks membrane translocation of P-Rex, a $PIP_3$- and Gβγ-regulated Rac2 exchange factor, in human neutrophils, which is due in part to directly blocking P-Rex binding to Gβγ in addition to blocking $PIP_3$ production by PI3-kinase (Zhao et al., 2007). It has recently been shown that Ras is required for full PI3-kinase γ activation in neutrophils (Suire et al., 2006). It is possible that the inhibitors block Gβγ-dependent activation of Ras and in part act to block PI3-kinase γ activation in cells indirectly through inhibition of Ras activation. In *Dictyostelium discoideum*, both PI3-kinase and phospholipase $A_2$ activities downstream of G protein activation are important for chemotaxis (Chen et al., 2007). Other studies have shown chemoattractant-dependent chemotaxis becomes PI3-kinase-independent under certain conditions (Ferguson et al., 2007). Thus, a broad-spectrum Gβγ inhibitor is more effective, in some cases, than selective PI3-kinase γ inhibitors because they can block other Gβγ interactions besides PI3-kinase-γ, a property that contributes to therapeutic efficacy. Nevertheless, because of the wide roles of Gβγ in regulation of cell physiology, development of Gβγ binding small molecules that are more selective for PI3-kinase γ inhibition relative to other Gβγ-dependent pathways is an important direction.

Inflammation is a central mediator of many human conditions, including atherosclerosis, allergic reactions, psoriasis, virus-induced myocarditis, ischemia-reperfusion injury, and rheumatoid arthritis. The inflammatory process involves complex signaling cascades partly coordinated by chemokines, which recruit leukocytes, including large numbers of neutrophils, to sites of inflammation (Wu et al., 2000). Targeting chemokines with antibodies or binding proteins as well as targeting chemokine receptors has been attempted as a therapeutic strategy (Gong et al., 1997; Ogata et al., 1997; Plater-Zyberk et al., 1997; Barnes et al., 1998; Halloran et al., 1999; Matthys et al., 2001; Podolin et al., 2002; Yang et al., 2002) However, the overwhelming complexity of these signaling molecules (multiple chemokines, chemokine receptors, and redundancy) is a significant hurdle. Polychemokine (Carter, 2002) or combinations of different chemokine (al Mughales et al., 1996) antagonists have been suggested, but there are chemokines that act as an agonist at one receptor and an antagonist at another (Xanthou et al., 2003). Despite this complexity, these chemokine receptors and ligands represent a tantalizing therapeutic target because of their integral role in the inflammatory process. Targeting PI3-kinase γ has been suggested as strategy for blocking a common signal downstream of chemokine receptors (Camps et al., 2005; Rückle et al., 2006). The data presented herein indicate that targeting Gβγ also circumvents the redundancy of the chemokine system and can offer some advantages to direct targeting of PI3-kinase γ.

h) Additional Methods (1) Analysis of Selectivity of Gβγ-Binding Compounds.

Herein, the selectivity of G protein βγ-binding compounds is examined at 3 levels of G protein signaling: 1) effector selectivity, 2) effects on GPCR coupling to G protein-dependent nucleotide cycling, and 3) selectivity for G protein βγ subtypes. All of these factors contribute to the potential utility of this novel class of compounds as therapeutic agents. The data demonstrate the therapeutic efficacy of this approach with a relatively general inhibitor of Gβγ-effector function (M119), but the more selective a particular compound for a particular function, the greater the potential for selective efficacy in vivo. These studies provide the critical basis for evaluating the significance of the biophysical measurements. Understanding the nature of the selectivity is important for evaluating structurally how selectivity is generated at a molecular level.

A second series of experiments involves development of a new assay that provides a rapid method for analysis of selectivity without testing each compound in individual reconstitution assays. After fully characterizing the selectivity and efficacy of these compounds on various G protein effector systems, the results are correlated with selectivity defined in two rapid screening assays. These assays provide a tool for rapid prediction of effector selectivity. Since inhibition of specific effector systems may correlate with therapeutic utility (for example, inhibition of Gβγ-dependent PI3Kγ regulation might be useful in treating inflammatory diseases), this analysis provides a faster approach for identification of compounds with specific therapeutic predictable therapeutic applications.

(2) Effector Specificity of Gβγ Binding Compounds.

Disclosed herein, a focused comparison of M119 and M201 was presented in Gβγ-effector selectivity to demonstrate the concept that effector selectivity can be achieved with this small molecule approach. Here, this analysis is extended to other effector systems and to other compounds that have not been tested for specificity.

(3) New Compounds.

Several other lead compounds (besides M119 and M201) were identified that block SIGK binding to Gβγ in the low to mid μM range (Table 18). The effector selectivity of these molecules is characterized as was done with M119 and M201, and further as described below for new effector systems. It is understood and herein contemplated that unique specificity profiles for different compounds are identified. Since many of these compounds appear to bind in the low μM range, it is desirable to identify related compounds that bind with higher affinity. As discussed for M119, similarity searches were performed for all of the lead compounds in Table 18 to identify compounds structurally related to the lead compounds in the NCI library. These compounds were obtained from the NCI and tested in the phage ELISA and by SPR binding analysis as described herein. To control for nonspecific effects compounds containing metal ions are avoided, and activities are measured in the presence reducing agents such as DTT and metal chelators such as EDTA. For example, it was found that the activity one of the compounds in Table 18, M308 is blocked by DTT and is thus is likely acting via a redox mechanism, and it is no longer be considered in this analysis. Thus, a family of compounds with unique specificity profiles that bind with relatively high affinity is collected.

(4) New Effectors.

Experiments presented herein focused on compound selectivity for Gβγ-dependent PLCβ2, PLCβ3, PI3Kγ and GRK2 as proof of principle. The effector specificity analysis can be expanded to other major Gβγ-dependent effector systems including adenylyl cyclase type I and type II, N-type $Ca^{2+}$ channels, inwardly rectifying potassium (GIRK) channels and ERK activation.

Compound effects on Gβγ-dependent regulation of ACI and ACII are tested using Sf9 cell membranes expressing either of these two isoforms as previously described (Scott et al., 2001; Taussig et al., 1994). ACI expressing membranes (10 μg) in the presence of forskolin, and ACII expressing membranes in the presence of added 50 nM GsαGTPγS, with or without 100 nM Gβ$_1$γ$_2$ subunits, are assayed for cAMP production. Compounds are titrated around their apparent $K_d$ estimated from their ELISA $IC_{50}$'s. When the compound affects forskolin (ACI) or Gsα (ACII) stimulated activity in the absence of Gβγ the effects are considered non-specific and are be pursued further.

Effects on GIRK channels and N-type $Ca^{2+}$ channels are assessed in primary rat superior cervical ganglion (SCG) neurons (Kammermeier et al., 2000; Ruiz-Velasco and Ikeda, 1998). Norepinephrine inhibits N-type $Ca^{2+}$ channels through a Gβγ dependent mechanism in SCG neurons and activates GIRK channels when they are heterologously expressed. Neurons are pretreated with varying concentrations of compounds (either in the bath or included in the patch pipette), and NE dependent inhibition of N-type $Ca^{2+}$ channels are measured in the whole cell patch clamp configuration. Initial analysis indicates that this pathway is unaffected by M119. When compounds are found that block inhibition of $Ca^{2+}$ channels, it is confirmed that the effects are reproduced in a prepulse facilitation protocol in the presence of heterologously expressed Gβγ to confirm that the compounds are acting at the level of Gβγ. N-type Calcium currents (CaV 2.1) directly inhibited by Gβγ exhibit slowed activation kinetics and voltage dependence such that strong depolarizing steps can partially reverse the inhibition. This voltage dependence is diagnostic of Gβγ-mediated modulation. The "facilitation" ratio of the postpulse current to the prepulse current (during which inhibition is strong) provides a quantitative measure of the degree of Gβγ modulation. Uninhibited currents generally have a facilitation ratio around 1 so cells pretreated with compounds that inhibit Gβγ interactions with the channel causes the facilitation ratio to approach 1. The effects on responses to other receptors such as transfected μ-opioid receptors or endogenous M4 muscarinic receptors are also examined. GIRK channel regulation is assessed by microinjecting GIRK1/2 subunits in SCG neurons and measuring $K^+$ channel regulation by NE at varying concentrations of compound. Basal $K^+$ channel activity and $Ca^{2+}$ channel activity is assessed to look for non-specific effects of Gβγ blockers. Outcomes from these experiments are that the compounds block both of these currents or compounds are identified that selectively modulate one or the other of the currents. When compounds have no effect on either $Ca^{2+}$ channel or $K^+$ channel regulation, this is interesting and indicates that the compound inhibits some effectors but not these channels.

Gβγ-dependent ERK activation is measured in two cellular systems that were examined previously using both a physiological agonist and a direct activator of Gβγ signaling. In primary rat arterial smooth muscle cells (RASM) and in Chinese hamster ovary (CHO) cells, lysophosphatidic acid (LPA) activates ERK in a PTX-sensitive manner that involves Gβγ. In RASM cells LPA promotes cell division in culture, and vascular restenosis in vivo in a Gβγ- and ERK-dependent manner (Iaccarino et al., 1999). A cell permeable Gβγ-binding peptide (mSIRK) that activates ERK signaling in both cell types through a nucleotide exchange independent G protein subunit dissociation mechanism (Goubaeva et al., 2003; Malik et al., 2005) are also tested. This peptide allows assessment of Gβγ-dependent ERK activation more directly than with LPA. Cells are treated with compounds at their apparent $IC_{50}$ or above for 10 min followed by addition of 5 nM LPA or 10 μM mSIRK. Control, inactive compounds such as M119B are used where appropriate and cells treated with compound alone (no LPA or mSIRK) are also analyzed. ERK activation is measured with p-42/p44 phospho-ERK immunoblotting. Compounds found to affect ERK activation are further characterized for dose dependence and specificity.

(5) Effects of Compounds on Receptor-G Protein Coupling.

Figure 14A:
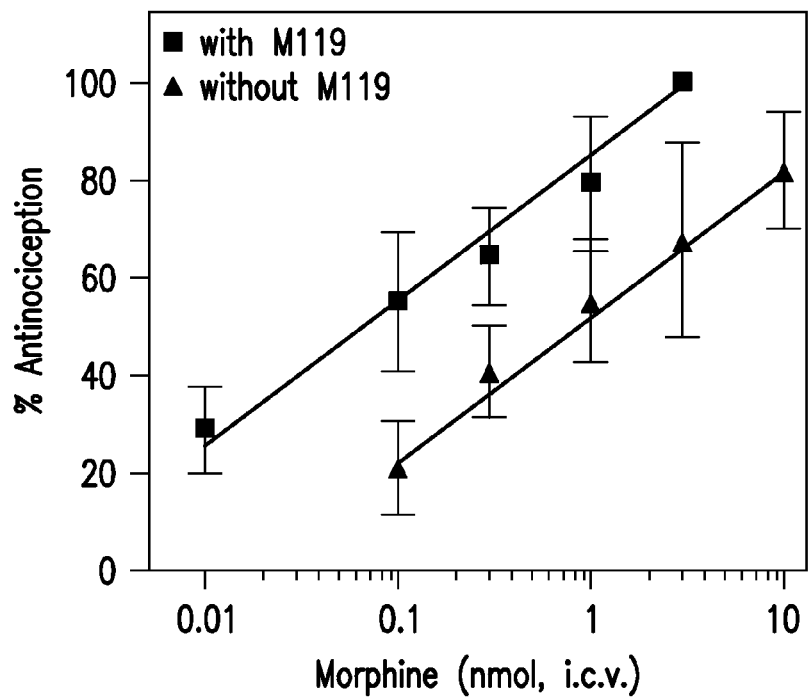

Receptor coupling to G proteins requires interaction between G protein α and βγ subunits. M119 blocks interaction between Gα and Gβγ subunits in an equilibrium binding assay (See FIG. 3D), but does not promote subunit dissociation. Compounds that bind at the Gα/βγ interface also interfere with receptor-dependent G protein activation, yet this does not appear to be the case in vivo or in cells since some aspects of receptor-effector coupling appears to be intact in systems where M119 is otherwise blocking Gβγ functions (FIGS. 5G and 14A). A receptor-G protein reconstitution system is used to determine if the different compounds alter the ability of receptors to stimulate GTPγS binding to G protein α subunits or GTP hydrolysis by α subunits. The receptor reconstitution systems developed by John Northup (Hellmich et al., 1997) and Peter Chidiac (Cladman and Chidiac, 2002) are used to accomplish this. The system developed by Northup measures [$^{35}$S]-GTPγS binding to purified G protein subunits added back to urea stripped Sf9 cell membranes expressing specific GPCRs, while the system developed by Chidiac examines GTP hydrolysis by G proteins coexpressed with receptors in Sf9 membranes. Both GTPγS binding and GTP hydrolysis assays are important for this analysis. GTPγS binding is dependent on a single round of G protein activation while GTP hydrolysis can involve several rounds of GTP binding and hydrolysis. Compounds like M119 do not interfere with receptor-dependent GTPγS binding because the compound does not have access to the binding site in the heterotrimer and because no reassociation of Gα and Gβγ is required in the single round of nucleotide exchange. With receptor stimulated GTP hydrolysis, there are multiple rounds of dissociation and reassociation. Under these conditions M119 or other compounds gain access to the Gβγ/α interface and inhibit receptor stimulated GTP hydrolysis. This is dependent upon the kinetics of G protein dissociation and reassociation as well as the on and off rates for compound binding to Gβγ.

Sf9 insect cells are infected with viruses expressing M2 muscarinic receptors (or other receptors as below), membranes are prepared from these cells and the endogenous G proteins are inactivated by treatment with 7M urea. Purified $G\alpha_{i1}$ and $\beta_1\gamma_2$ proteins are reconstituted with the membranes, and carbachol and Gβγ-dependent binding of [$^{35}$S]-GTPγS to $G\alpha_{i1}$ are measured in the presence of multiple concentrations of compound. It has been previously demonstrated that in this assay, Gβγ subunits are required for agonist stimulated activities (Goubaeva et al., 2003; Hellmich et al., 1997).

Rather than the compounds simply interfering with Gα/βγ interactions, they can also interfere with direct interactions between Gβγ subunits and receptors. There is evidence for direct interactions between receptors and Gβγ that can influence G protein activation and signaling (Mahon et al., 2006; Taylor et al., 1996; Wu et al., 2000). Coupling of a variety of receptors to G proteins is assessed in the Sf9 membrane reconstitution assay. When compounds interfere with determinants on G protein Gβγ subunits that interact directly with receptors, the compound inhibits receptor dependent-activation but can be selective for certain receptors. When the compounds act by inhibiting Gα/βγ interactions they block activation of all receptors tested. A variety of Gi coupled receptors are tested including $\alpha_2$-adrenergic receptors and μ-opioid receptors and look for selectivity for different receptors. When there is a selective effect on different GPCRs, it means that the compounds are interfering with specific interactions between the receptor and the G protein.

(6) G Protein βγ Subtype Selectivity.

A major question in the field of G protein βγ subunit signaling is the significance of Gβγ subunit diversity. Multiple G protein βγ subunit combinations are assembled in vivo although the functional significance of this diversity is unclear. Many of the amino acids in the "hot spot" are 100% conserved between different G protein β subtypes. Since the "hot spot" was targeted with the screen, no subtype selectivity is predicted. When there was selectivity for subunit subtypes, in vivo selectivity is much greater. The simplest approach is to use SPR to measure interactions of specific compounds with purified G protein βγ subtypes. Specific Gβγ subtypes are purified from Hi5 insect cells. Purified $G\beta_1\gamma_2$, $G\beta_2\gamma_2$, $G\beta_1\gamma_5$ and $G\beta_1\gamma_7$ have been acquired. Other Gβγ combinations containing $G\beta_3$ and $G\beta_4$ are also purified. These are immobilized on a biosensor chip via primary amine coupling as described herein, and individual compounds are titrated, on and off rate constants determined and $K_d$'s calculated from SPR data as described in specific aim 2 and compared between the different Gβγ subtypes.

(7) Global Prediction of Gβγ-Dependent Pathway Specificity.

The goal of this subaim is to develop methods to determine Gβγ-dependent pathway selectivity of individual compounds in a single assay rather than testing each compound in individual effector assays. Disclosed herein are two alternative approaches to this.

(a) Signatures in the Peptide Competition Assay.

Here the phage ELISA assay is used to explore compound inhibition signatures which are correlated with known effector specificity profiles established in in vitro biochemical assays. This approach depends on the observation that each individual phage displayed peptide has unique requirements for specific amino acids in the G protein βγ "hot spot" as discussed herein (Davis et al., 2005). When individual compounds each have their own unique binding requirements, they differentially affect the binding of different peptides in a way that is correlated with selectivity for effector binding. Each compound is screened against 9 different phage displaying peptides each with unique binding requirements as described in (Davis et al., 2005) and obtain an inhibition profile. Compounds are tested at a concentration corresponding to their $IC_{50}$ for inhibition of SIGK phage binding and their $IC_{50}$'s for each peptide are determined. This profile is compared between compounds and the specific inhibition patterns correlated with known effector profile specificity. For example, groups of compounds that are relatively selective inhibitors of Gβγ-dependent PI3Kγ regulation have a similar peptide inhibition profile distinct from more global inhibitors of Gβγ function or inhibitors with different effector selectivities.

(b) Evaluation of Compound Efficacy in a Focused GPCR Array.

Alternatively, gene expression downstream of GPCRs is examined in a whole-cell system to evaluate the effects of selective compounds on GPCR dependent signal transduction. For these experiments a specific GPCR focused pathway array developed by GE Super Array Bioscience that has been utilized to analyze GPCR signaling pathways is used (Gesty-Palmer et al., 2005; Lee et al., 2005). In this array, 60 mer oligonucleotides representing 96 human genes known to be regulated downstream of specific GPCR activated pathways have been filter arrayed. The genes have been selected to represent genes downstream of pathways including $Ca^{2+}$, cAMP, PKC and PI3K. RNA is isolated from stimulated cells and labeled cRNA probes are created that are hybridized with the array and detected by chemiluminescence imaging. First, this system is used to analyze selective effects of compounds on signaling downstream of the chemotactic peptide receptor (fMLP) in HL60 human neutrophil like cells. Gene expression profiles in differentiated HL60 cells are analyzed with different doses of fMLP for 5 min, 30 min, 1 h and 4 h to establish conditions with significant alterations in gene expression relevant to key signaling pathways. Responses of specific pathways are validated with specific pathway inhibitors. Wortmannin is used to block PI3K pathways, U73122 is used to validate PLC responsive genes and H-89 or Rp-cAMPs are used to validate cAMP responsive gene expression. With this assay optimized, the specificity and efficacy of individual Gβγ inhibitors is evaluated by adding saturating concentrations of compound prior to and during fMLP stimulation. Effects of compounds in the absence of fMLP stimulation are also determined. Specific effects on gene expression are predictable based on their established effector specificity profiles.

(8) Determination of the Molecular Basis for Binding and Selectivity of Gβγ Binding Compounds.

(a) Effector Selectivity of M119 Derivatives.

This series of experiments is designed to test the "chemical hypothesis" by examining compounds that bind to the same subsurface of Gβγ but have different chemical characteristics. The premise of this example is that when selectivity is observed for compounds that bind to the same subsurface of Gβγ it is the chemistry of the compound that is responsible for the selectivity. Structure activity relationships for compounds related to M119 were examined in the phage ELISA and it was found a series of binding compounds as was discussed herein and shown in FIG. 8. All the active compounds contain a rigid xanthene moiety as a core binding structure and the majority contains hydroxyl groups at the 4 and 5 positions that appear to be required for binding. Associated with this core structure are a variety of chemical structures substituted at the 9 position of the xanthene ring. Since all these compounds contain the core xanthene ring and the required 4 and 5 hydroxyl groups, they bind to a similar location within the Gβγ "hot spot". Computational modeling indicates that 5 of these compounds with diverse substitutions at the 9 position bind to Gβγ at the same site. Thus far, this series of compounds has only been evaluated for competition with SIGK binding in the phage ELISA.

Here, the specificity of these compounds predicted to bind to the same site are examined in the "hot spot" for different effectors as described herein. Specifically the concentration dependence for each compound is examined for Gβγ-dependent PLCβ2, PLCβ3, PI3Kγ and GRK2 regulation in in vitro reconstitution assays with purified components.

When the compounds all have similar selectivity profiles, it indicates that the chemical structure does not strongly influence the selectivity and that steric occupation of specific binding surfaces within the "hot spot" is what drives specificity. On the other hand, when there is a difference in the selectivity profiles for these compounds it indicates that the chemical nature of the binding compound presented at the Gβγ/effector interface contributes to effector selectivity.

Further evaluation and definition of this concept depends on results from other assays described herein that more directly evaluate the nature of binding of the compounds to Gβγ. For example, when selectivity for different effectors is shown by this series of compounds, confirmation that they bind to the same site either by mutagenesis or X-ray crystallography can be performed as described below. Additionally, binding kinetics are evaluated by SPR to determine if differences in $k_{on}$ and $k_{off}$ contributes to the observed specificity.

(9) Evaluation of Ligand-Gβγ Binding Kinetics and Affinities by SPR and ITC.

1) The assays used thus far to evaluate the binding of small molecules to Gβγ have relied on competition analysis to evaluate apparent affinities. The primary assay has been a phage ELISA competition assay where compounds are tested for competition with binding of SIGK peptide binding to Gβγ. This assay has the advantage that it determines if a compound binds to Gβγ, most likely at the "hot spot" and gives an estimate of apparent affinity from the $IC_{50}$. In some cases it was found that the $IC_{50}$ in the ELISA correlates well with the $IC_{50}$ for competition with effectors and in other cases it does not.

2) Evaluation of $k_{on}$ and $k_{off}$ allows verification that the kinetics of compound binding contributes to selectivity for Gβγ function. As discussed herein, the on and off rate constants for M119 binding to Gβγ were very slow. This has implications for the mechanism of action of M119 and might form the basis for some level of selectivity. For example, despite binding at the Gα/βγ interface M119 does not disrupt GPCR dependent G protein activation which is thought to require Gα/βγ interactions. One possible basis for this selectivity relies on the rapid cycle of subunit dissociation that may occur upon activation of many G protein systems. M119 may not interfere with this cycle because the slow $k_{on}$ limits access to the Gα/βγ heterotrimer (Ross and Wilkie, 2000). In cases where free βγ accumulates to a significant level, this free Gβγ may no longer be participating in G protein cycling and is accessible to inhibition by slowly binding compounds.

SPR is used to measure binding kinetics and equilibrium binding constants for all of the binding molecules identified in the screens and similarity searches. This method has the advantage that direct binding can be measured to give both the $K_d$ and kinetics of the interaction. A second advantage of the method is that relatively low amounts of protein are required (relative to ITC for example) which is important for analysis of binding to Gβγ mutants as described below. Some disadvantages include the necessity for immobilization of the target Gβγ, and that binding of low molecular weight molecules is difficult to detect by SPR due to the nature of the method. SPR monitors the alterations in refractive index as a function of mass binding at a surface with immobilized target molecule. As the ligand binds to the target the mass bound to the surface increases and changes the refractive index. This method is ideally suited to monitoring protein-protein interactions because the binding of relatively high molecular weight materials at the surface causes significant alterations in mass and thereby refractive index. Lower molecular weight molecules such as peptides and low molecular weight organic molecules are more problematic because the binding causes only a small change in refractive index. Nevertheless, SPR has been used to monitor small molecule interactions with immobilized protein and it has been successfully applied here. The key to detecting small molecule binding is to immobilize the target at higher densities than is required for monitoring protein-protein interactions so that significant accumulation of the ligand occurs at the sensor surface.

As discussed herein, an SPR method for binding of small molecule ligands to Gβγ has ben established. This method was used to measure binding of the "hot spot" peptide SIGK. Gβγ was immobilized directly via primary amine coupling to a hydroxylated surface for this analysis. It had previously been indicated that primary amine coupling of Gβγ to dextran coated SPR chips results in inactivation of Gβγ subunits for α subunit binding (Willard and Siderovski, 2006). It was found that small molecule and peptide binding to the "hot spot" is retained. Some possible reasons for this are that primary amine coupling may affect binding of larger molecules to Gβγ but the binding site for small molecules remains intact. Also, a dextran surface is not used herein for immobilization but rather the surface of the chip is coated with a PEG array (Lahiri et al., 1999). An advantage of this surface is the very low non-specific binding. Additionally, because the density of reactive OH groups in the array is lower than with dextran, the likelihood of immobilization by single linkages rather than multiple linkages is greater. As the number of amines on the protein react with the surface the chances increase for inactivation of the protein. Regardless, the $K_d$ obtained from the analysis is consistent with what was obtained from other analyses.

To complement the SPR analysis, isothermal titration calorimetry (ITC) is used to determine binding constants. Advantages of this method over SPR include a lack of need for immobilization of the target molecule, the sensitivity is independent of the mass of the ligand, and additional information about enthalpy can be obtained.

Expected results and interpretation: These analyses provide further evidence that the compounds are directly binding to Gβγ and give a direct determination of the affinity. Knowing the direct binding affinity gives a base from which to evaluate $IC_{50}$ values from competition analysis between Gβγ subunits and effectors and allows for the evaluation of the effects of Gβγ mutants on compound binding as discussed below.

(10) Mutagenesis of G Protein βγ Subunits and X-ray Structure Determination to Define Compound Binding Modes With direct binding assays for small molecule interactions with Gβγ established, each selective compound can be investigated to determine that a unique binding interaction determines effector selectivity. Computational modeling predicts unique binding interactions for many compounds, but these models require validation.

(a) Mutagenesis:

A series of individual alanine substituted mutants of the G protein β subunit were created and these mutants were used to determine the unique binding requirements for individual peptides that bind to the "hot spot". Here, these mutants are screened for effects on binding to small molecules using the SPR assay. Individual purified mutants are immobilized on biosensor chips and affinity constants calculated based on $k_{on}$ and $k_{off}$ determined for binding of each compound and compared with wt Gβγ. An initial focus is on M119 and M201 since these have such disparate effects on effector interactions. The predicted result from this experiment is that distinct sets of amino acids are required for interaction of these molecules with Gβγ. Alanine substituted mutants for the majority of the amino acids in the "hot spot" have been created (Davis et al., 2005). These compounds bind within this region. These mutants have been analyzed extensively in other assays that confirm the functional folding and viability (α subunit and peptide binding analysis) (Davis et al., 2005). M119 and M201 experiments establish evidence, but this analysis is performed on the entire panel of binding compounds to date to create a binding map for each compound. Unique binding maps correlate with specific effector specificities.

(b) X-ray Crystallographic Determination of Ligand Binding to Gβγ.

The most definitive approach to defining the binding interactions of these small molecules with Gβγ is three dimensional structural analysis with X-ray crystallography. This process is relatively straight-forward because Gβγ has already been crystallized either alone or in complexes with α subunits, effectors or peptides (Davis et al., 2005; Gaudet et al., 1996; Sondek et al., 1996; Wall et al., 1995). The focus is to obtain M119 or M201 Gβγ complexes. This is accomplished either by co-crystallizing Gβγ with compounds using conditions established for crystallization of Gβγ alone (Sondek et al., 1996), or by screening new conditions, which are necessary when binding of the compounds affects crystal lattice formation. A second approach is to soak preformed crystals with compounds; this is tractable when binding sites are not already occupied by crystal lattice contacts. The crystal lattice in the structure of $G\beta_1\gamma_1$ and found relatively few crystal contacts with the "hot spot". Additionally, there appeared to be extensive solvent channels in the lattice that allow diffusion of a small molecule in to the "hot spot". This indicates a crystal soaking approach is successful.

The determination of such structures is relatively straightforward using either difference Fourier methods or molecular replacement that employ known coordinates of Gβγ as a starting or search model. The initial co-crystallization efforts have focused on Gβγ with a $\gamma_2$C68S mutation and a 6His-tag at the amino terminus of $\gamma_2$. The $\gamma_2$C68S mutation prevents post-translational geranyl-geranylation of the γ subunit that targets Gβγ subunits to membranes. This soluble protein is easy to purify in relatively high quantities (up to 10 mg/L) from the soluble fraction of Hi5 insect cell lysates using sequential Ni-NTA-agarose, HiTrap Q ion exchange and Superdex Gel filtration chromatography. The preparation is monodisperse by dynamic light scattering. Hanging drop crystal screens were based on previous communications with Dr Sprang and were based on conditions of 12-18% PEG 6K and 0.1M Tris-HCl pH 7-8.5 using protein concentrations between 2-8 mg/mL and conditions were expanded to include different types of PEGs, as well as a broader range of protein concentrations, pH's and PEG percentages. Crystal formation was observed at a protein concentration of 5 mg/mL with pH 8.4 using 15% PEG 6K. Random screens were also setup to obtain possible alternate conditions for crystal formation and these were based on commercially available crystal screens from Qiagen®. In this screen a new crystal form was identified from 50% (v/v) PEG 200, 0.2 M NaCl buffered by 0.10 M Na+/K+ phosphate pH 6.2. Screening is also underway to co-crystallize $G\beta_1\gamma_2$ with compounds M119 and M201 using the conditions previously stated as optimal for native $G\beta_1\gamma_2$(C68S) crystal growth. Alternatively geranylgeranylated $\beta_1\gamma_2$ (with amino terminal 6His-tag on γ) purified from the membrane fraction of Hi5 cells can be utilized. The yield is lower and the preparation more difficult but it is still a tractable system. 6His-tagged geranylgeranylated $\beta_1\gamma_2$ has been co-crystalized with the SIGK peptide.

This analysis allowa definitive identification of the site of interaction of a given Gβγ binding molecule. Combined with SPR and ITC analysis, a thorough understanding of the interaction is achieved. Individual compounds that have selective actions such as M201 and M119 have distinct binding sites within the "hot spot" surface that can be correlated with selectivity for different effectors.

(11) Computational Prediction of Gβγ Binding Specificity and Screening of New Libraries.

Selectivity for specific Gβγ-target interactions is based on differential occupation of the "hot spot" surface. Thus, computational screening strategies can specifically target particular biological problems. The current strategy is to screen the entire "hot spot" for binders and to test these for competition with peptide followed by systematic screening with several potential effector targets. Herein is described potential "global analysis" approaches that streamline evaluation of small molecules for selectivity. Because targeting a subsurface of the "hot spot" correlates with specific interrogation of a particular pathway/biology, then a structurally defined subsurface (by X-ray crystallography or mutagenesis) can be targeted specifically for screening with computational prediction methods. In broader terms, computational screens can be focused to target particular diseases by focusing the screen to a discrete subsurface of the "hot spot".

By developing a global screen for compound selectivity as described herein, there is no need to target a specific "hot spot" subsite with computational screening. The "hot spot" is computationally screened as was already done and use the global specificity screen to identify selective binders. One issue is that the global specificity screen has not yet been developed. Secondly, by targetting a particular subsite a priori screening occurs more efficiently for the following reason: In the current screening strategy using any single scoring function is not the most efficient at evaluating the quality of docked poses and predicting high affinity binding of small molecules to the "hot spot". Thus seven different scoring functions are used, each differing in approach to evaluating the quality of the docked models. Differences in the scoring function include whether the functions are based on training set of docked ligands or rely on first principles modeling of force field interactions (Brooijmans and Kuntz, 2003; Kitchen et al., 2004). In general, for a smaller binding site, one of these scoring functions tends to be the best at predicting true binders because a smaller site has a more limited set of interactions to be considered by the particular scoring function. The reason that this is not true for the "hot spot" is that this large surface consists of many binding sites, each of which has unique physicochemical properties, so no one scoring function can predict the binding accurately. The logical extension of this argument is that focussing the screening to a unique binding site as defined by X-ray crystallography or mutagenesis enables the use of a single scoring function to identify binders for a particular "hot spot" subsurface. Using the current approach, compounds are tested that are highly ranked in each of the seven scoring functions. When small libraries are screened such as the NCI diversity set (2000 compounds) this is not an issue, but when screening larger diversity sets, such as the 50,000 compound diversity set from Chembridge, it is more of a problem. For each computational screen, at least the top 1% of compounds predicted by each scoring function are tested. For a 2000 compound diversity set with 7 scoring functions this would be a maximum of 140 molecules but for the 50,000 compound library this expands to 3500 molecules. Use of a single scoring function reduces the number of molecules that would have to be tested by as much as seven-fold and reduces the screening to only 500 molecules.

Once a defined unique binding sites has been found, either by X-ray crystallography or mutagenesis, a computational screen is performed using the Chembridge diversity set, focusing on one particular binding site identified for a selective PI3Kγ inhibitor. First the top 100 compounds are screened from each scoring function (~700 compounds) at a concentration of 100 μM in the ELISA assay for inhibition of SIGK binding and potential inhibitors are titrated to determine an $IC_{50}$. This number of compounds can be screened manually in a few weeks. When the compounds bind to a single site it is understood that one particular scoring function will be particularly well suited to evaluating compound binding to that site and therefore one scoring function can predict a high proportion of compounds that bind with relatively high affinity. Binders that are identified are relatively selective for PI3Kγ inhibition. The binders are tested for selective inhibition of PI3Kγ in assays that have been described in herein.

(12) Evaluation of Small Molecule Inhibitor Selectivity in a Cellular Model of Inflammation.

The previous specific aims were designed to understand the mechanisms for selectivity of Gβγ-binding compounds. One effector system of particular interest is PI3Kγ. PI3Kγ is relatively selectively expressed in neutrophils and several groups have shown that genetic deletion of PI3Kγ results in impaired neutrophil migration in response to chemoattractants. Studies of neutrophil motility suggest that primary events that regulate directional neutrophil migration include Gβγ-dependent activation of PI3Kγ. These studies have attracted the attention of the pharmaceutical industry who have developed selective catalytic inhibitors of PI3Kγ relative to other PI3K isoforms as a potential anti-inflammatory strategy (Camps et al., 2005). An alternative approach to selective inhibition of PI3Kγ in neutrophils through inhibition of PI3Kγ interactions with Gβγ is disclosed herein since the other isoforms of PI3K are primarily regulated by interaction with tyrosine kinase receptors and/or ras, not through Gβγ. Indeed data indicates that blocking Gβγ with an M119 related compound that blocks PI3Kγ regulation, (DL382), inhibits fMLP-dependent neutrophil chemotaxis and inhibits inflammation in an animal model.

Herein, potentially selective PI3Kγ inhibitors that have been identified using the methods disclosed herein are tested. Data indicate that such compounds can be identified. For example, analysis indicates compound 402959 (Table 18) binds to and inhibits peptide binding to Gβγ with an $IC_{50}$ of 2 μM, does not affect Gβγ-dependent regulation of PLCβ2 or β3 but inhibits Gβγ-dependent PI3Kγ regulation with an $IC_{50}$ of 12 μM. Novel compounds are identified that specifically inhibit Gβγ-dependent regulation of PI3Kγ, such as 402959, and test them in various assays of neutrophil function in differentiated HL60 cells and primary human neutrophils as described below. Compounds that affect other signaling processes such as GRK2 translocation or PLC activity but not PI3Kγ are also tested. fMLP and IL-8 dependent regulation of PI3Kγ and PLC are examined in neutrophils followed by assessment of neutrophil biological functions. Selective PI3Kγ inhibitors identified in vitro block PI3K activation in neutrophils and are effective blockers of chemotaxis but do not affect $Ca^{2+}$ signaling in neutrophils or neutrophil adhesion. Identification of compounds that block neutrophil chemotaxis but do not affect $Ca^{2+}$ signaling by fMLP are valuable anti-inflammatory inhibitors with limited effects on other Gβγ-dependent signaling pathways.

(13) Intracellular Signal Transduction:

(a) PLC Activity.

PLC activity can be addressed by measuring receptor-dependent $IP_3$ production and/or calcium efflux. Analysis of $IP_3$ production in the presence and absence of compounds is conducted as described (Goubaeva et al., 2003). Briefly, differentiated HL60 cells are incubated overnight in inositol-free medium with 1 μCi [$^3$H]inositol. Cultures are preincubated with individual compounds for 5 minutes prior to addition of fMLP and incubated for 30 minutes at 37° C. $IP_3$ production is determined by scinitillation counting and reported as percent fMLP induced $IP_3$.

Cytoplasmic calcium release is monitored in differentiated HL60 cells and human neutrophils loaded with FURA-2 and resuspended in HEPES buffered saline solution containing EGTA in the absence of extracellular $Ca^{2+}$ (as described in FIG. 5). M119 attenuates fMLP-induced $Ca^{2+}$ release in HL60 cells (FIG. 5A). Compounds that exhibit intrinsic fluorescence are deemed unsuitable for this assay. Compounds not anticipated to affect calcium levels or structurally similar compounds with low affinity for Gβγ are used as negative controls. To control for non specific effects on $Ca^{2+}$ signaling compounds are also tested for effects on ionomycin-dependent $Ca^{2+}$ release to ensure that this is not affected.

(b) PI3Kγ Activity.

PI3Kγ activity is assessed by evaluating translocation of GFP tagged Akt pleckstrin homology domain fusion protein (GFP-PHAkt) in stably transfected HL60 cells (as described in FIG. 5 and (Servant et al., 2000)). Subcellular fractionation rather than microscopy has been selected since it is a more objective evaluation. In agreement with in vitro studies, M119 inhibited GFP-PHAkt membrane translocation in HL60 cells (FIG. 5F). An alternative approach is to measure phospho-Akt with a specific phospho-Akt antibody.

(14) Neutrophil Function:

This subaim is designed to test the ability of compounds to modulate processes that are dependent on PI3Kγ and PLCβ2/3 activity in intact cells including superoxide production, chemotaxis and adhesion.

(a) Superoxide Production.

PLCβ2/3 and PI3Kγ have both been demonstrated to be involved in superoxide production (Li et al., 2000). Therefore, compounds that inhibit either or both PLCβ2 and PI3Kγ are screened for effects on superoxide production in HL60 cells and human neutrophils. Superoxide production is measured as described (Vlahos et al., 1995). Briefly, cells are plated in a 96-well plate in HEPES buffered saline solution containing cytochrome c to which compounds/DMSO or PMA (positive control (Li et al., 2000)) is added. After a 5 minute preincubation, fMLP is added and incubated for 5 minutes. Superoxide production is reported as superoxide (nM/min) as determined by absorbance at 550 nm over a 5 minute time period. Compounds that inhibit both PLCβ and PI3Kγ are more potent than compounds that inhibit one or the other selectively and that these compounds do affect PMA stimulated superoxide production.

(b) Chemotaxis.

Given the defined role of PI3Kγ in neutrophil chemotaxis (Curnock et al., 2002; Li et al., 2000; Sasaki et al., 2000), compounds that inhibit in vitro PI3Kγ activity are evaluated for effects on fMLP-induced chemotaxis in the Boyden chamber as described (Hannigan et al., 2002), and in data FIGS. 10E and F. Wortmannin is used as a positive control for inhibition of chemotaxis. It is important to note that certain compounds may prevent neutrophil chemotaxis (directed migration in a gradient of stimulus), but the neutrophils may still undergo chemokinesis (random, stimulus-dependent migration). Recent literature demonstrated that PI3Kγ deficient neutrophils are unable to translocate up the chemotactic gradient, but still undergo chemokinesis (Li et al., 2000). Therefore, to control for chemokinesis fMLP is added to both chambers and cells that translocate through the membrane are considered chemokinetic.

(c) Cell Adhesion.

In these assays, neutrophil adhesion to extracellular matrix is measured in response to chemokine stimulation. In these assays, endothelial ligands are presented in conjunction with immobilized chemokines (IL-8). In the absence of IL-8, no adhesion is observed indicting that activation of the GPCR dependent pathway known to involve Gi and Gβγ is required for the observed adhesion. Results indicate that wortmannin does not block this process indicating that pathways other than PI3Kγ activation are responsible for adhesion. This allows for testing the selective compounds to determine influence on adhesion or chemotaxis.

Specific adhesion method: A dual micropipette micromanipulation system is used to measure adhesion probability between cells (neutrophils, principally) and target beads coated with specified endothelial ligands (typicaly ICAM-1) (Lomakina and Waugh, 2004; Lomakina and Waugh, 2006). One pipette is used to hold the target bead, and one is used to hold the cell, and the operator manually brings the cell and bead into repeated contact. Detection of adhesive events depends on visual observation of the cell surface as the cell and bead are separated. An adhesive event is detected as a small deformation of the cell surface during separation. The probability of adhesion is simply the number of adhesive contacts out of the total number of contacts between the cell and bead. Typically 25 contacts are used for an individual determination. Alternatively, adhesion probability can be monitored continuously to observe the time course of the change in cell adhesiveness after stimulation.

Compounds that identified that are selective for blocking Gβγ-dependent PI3Kγ activation or with other selectivity have similar selectivity profiles for signal transduction pathways in intact cells and block the expected physiological response of the neutrophil. For example, an inhibitor that selectively blocks Gβγ-dependent regulation of PI3Kγ blocks chemotaxis but does not block $Ca^{2+}$ signaling or IL-8 dependent neutrophil adhesion. Compounds that block GRK2 regulation or PLCβ do not to affect chemotaxis but other processes such as neutrophil adhesion or superoxide production are affected. In order to be considered a selective regulator of intracellular signaling, the compound must be shown to inhibit some intracellular function to be sure that the compound is indeed cell permeable and effective.

(15) Compounds and Libraries:

All of the compounds that were used to generate data and are used in the experiments described herein have been obtained through the Developmental Therapeutics Program at the National Cancer Institute. The NCI diversity set library contains 1990 compounds in 200 μl DMSO at 10 mM in a 96 well format. The diversity set was assembled to represent chemical diversity in the larger 250,000 compound NCI library. As lead compounds are identified from screening the diversity set, structurally related compounds identified by similarity searching were obtained in crystalline form for all of the lead compounds in Table 18 in 10 mg quantities which is more than sufficient for all of the proposed experiments. These compounds have been freely available in the past, but more recently have become freely available only if a cancer related justification can be provided. Since G protein signaling has roles in mitogenesis and cancer cell migration, this justification has not been difficult. Additionally, some of the compounds such as M201 and DL382 are available in high purity and quantity from commercial vendors. A potential issue with many of the compounds in the diversity set is the level of purity of the compounds. In all cases, the biological efficacy and potency of identified compounds have been confirmed with fresh preparation from the crystalline form and in some cases with further confirmation of efficacy and potency with pure preparations from other sources. Compounds that have not been analyzed for purity are analyzed for purity and identity by HPLC and GC-MS analysis. Another issue is that many of the compounds in this library contain metals that are redox active might give false positive results. For all compounds screened oxidation dependent activity was assayed for by adding DTT to the assay and metal ion dependent activity using metal chelators. Compounds that appear to work through these mechanisms are not considered further.

It is contemplated herein that other libraries such as the Chembridge 50,000 compound DIVERSet collection can be screened. This set represents the compounds in a larger 435,000 compound express-PICK library.

(16) Human Neutrophil Preparation.

Whenever possible, neutrophils are selected directly from whole blood samples dispersed into low endotoxin buffers. They are easily identified by their size and multilobular nuclear structures. When necessary, purified neutrophil populations are isolated from whole blood by density separation. Venous blood drawn from healthy donors is placed over a layer of 1-Step Polymorphs (Accurate Chemical & Scientific Corporation, Westbury, N.Y.). After centrifugation at 1500 rpm for 45 minutes, the band of polymorphonuclear cells is visible. Neutrophils are harvested by pipette, then washed in 4% FCS in Hanks Balanced Salt Solution (HBSS, BioWhittaker, Walkersville, Md.), containing 10 mM N-(2-Hydroxyethyl)piperazine-N'-(2-ethanesulfonic acid) (HEPES, Sigma, Saint Louis, Mo.) without $Ca^{2+}$ and $Mg^{2+}$, and brought to final concentration $5 \times 10^6$ cells/ml. Measurements are completed within six hours after phlebotomy.

(17) Fluorescence Screening for Gbg "hot spot" Molecules

Two new assays have been developed that allow more effective screening for Gβγ "hot spot" molecules. Both involve using a fluorescently labeled version of SIGK with fluorescein attached at the amino terminus. The first is a fluorescence polarization anisotropy (FP) assay where binding of Gβγ to the peptide increases the anisotropy of the fluorescence due to rotational slowing of peptide motions. The second is a fluorescence quenching method where binding of the peptide to Gβγ quenches peptide fluorescence by an unknown method. Both methods are highly amenable to HTS screening in a homogeneous single addition assay format where the assay would screen for compounds that block Gβγ peptide interactions by assaying for compound ability to reduce anisotropy or fluorescence quenching.

i) Materials and Methods (1) Small Molecules.

Compounds for this study were kindly provided by the National Cancer Institute repository except when indicated otherwise. Compound abbreviations are as follows: M119 (NSC119910) and M119B (NSC119892). Gallein (Acros Organics, Geel, Belgium), fluorescein, and wortmannin were obtained from Sigma Aldrich (St. Louis, Mo.).

(2) Competition ELISA and Structure Activity Relationships.

Binding of small molecules to $Gβ_1γ_2$ was assessed by competition with phage displaying the SIGK peptide as described previously (Scott et al., 2001 ♦ ; Bonacci et al., 2006). In brief, $Gβ_1γ_2$ (25 nM), with biotin incorporated via an N-terminal acceptor peptide on $Gβ_1$, was immobilized in a 96-well plate coated with streptavidin. Compounds/DMSO and $0.1×10^{10}$ phage were added simultaneously and subsequently incubated for 1 h at room temperature. Plates were then washed with 1× Tris-buffered saline/0.5% Tween 20 and incubated with anti-M13, HRP-conjugated antibody (Amersham, Chalfont St. Giles, Buckinghamshire, UK). Phage binding was determined by monitoring $A_{405}$ upon addition of 2,2'-azino-bis(3-ethylbenzothiazoline-6-sulfonic acid) (Sigma Aldrich).

(3) Surface Plasmon Resonance.

Direct binding of "hot spot" binding small molecules was assessed using the Reichert SR7000 Surface Plasmon Resonance dual chamber instrument equipped with an autosampler (Reichert, Depew, N.Y.). To activate the sensor chip surface, a mixture of 0.1 M 1-ethyl-3-(3-dimethylaminopropyl) carbodiimide hydrochloride and 0.05 M N-hydroxysuccinimide was injected (flow rate 5 μl/min) over the sensor surface. Streptavidin (100 μg/ml; prepared in 20 mM sodium acetate buffer, pH 5.5) was coupled to the sensor chip surface followed by quenching the remaining activated carboxyl groups with 1 M ethanolamine, pH 8.5. $bGβ_1γ_2$ was conjugated to the streptavidin-coated chip in running buffer (50 mM HEPES, pH 7.6, 1 mM EDTA, 100 mM NaCl, 0.1% $C_{12}E_{10}$, and 1 mM dithiothreitol) to achieve 2000 microrefractive index units. A second reference cell was treated similarly, but $bGβ_1γ_2$ was excluded. Direct binding of small molecules was tested out at room temperature with a flow rate of 75 μl/min. Compounds were prepared in running buffer and injected for 10 min followed by a dissociation phase of 10 min. The obtained sensorgrams were corrected for nonspecific background by running the same experiment in series over an identical sensor surface with immobilized streptavidin, blocked with biotin, without bGβγ. Binding rates and constants were independent of flow rate over a wide range and did not fit mass transport limited models, indicating that mass transport was not limiting association or dissociation rates. Best fit kinetic parameters were determined using kinetic titration model and ClampXP ver. 3.5, which accounts for incomplete dissociation between injections (Karisson et al., 2006).

(4) GFP-PH-Akt Translocation in Differentiated HL60 Cells.

HL60 cells stably overexpressing GFP-PH-Akt (Servant et al., 2000) were maintained and differentiated as described previously (Bonacci et al., 2006). Cells ($0.2×10^6$ cells/ml) were differentiated by incubation with 1.2% DMSO for 5 days. Cells were washed with serum-free RPMI 1640 (Invitrogen, Carlsbad, Calif.). Cells ($2×10^5$; 100 μl) were transferred to a 1.8-ml Beckman ultracentrifuge tube. Cells were pretreated with DMSO or compounds for 10 min at room temperature and stimulated with 250 nM fMLP (Sigma Aldrich) for 2 min. at 37° C., snap-frozen in liquid nitrogen, and thawed in the presence of 100 μl of 2× lysis buffer (100 mM HEPES, pH 8.0, 6 mM $MgCl_2$, 0.2 mM EDTA, 200 mM NaCl, 100 μM$Na_3VO_4$, and protease inhibitors). Membranes were harvested by centrifugation 100,000 g for 20 min after four freeze-thaw cycles. All treatments contained the same final concentration of DMSO. Pellets were washed once with 100 μl of lysis buffer (50 mM HEPES, pH 8.0, 3 mM $MgCl_2$, 0.1 mM EDTA, 100 mM NaCl, 50 μM $Na_3VO_4$, and protease inhibitors), pelleted as above, and boiled in 2× sample loading buffer. Samples were resolved by 12% SDS-PAGE, transferred to nitrocellulose, and probed with anti-GFP antibody (1:1000; Roche) followed by incubation with goat anti-mouse HRP-conjugated secondary antibody (1:5000, Bio-Rad Laboratories, Hercules, Calif.). Chemiluminescence was analyzed using a charge-coupled device camera in a UVP Epi-Chem II Darkroom imaging system. All samples had background subtracted and were normalized to the fMLP-induced signal set at 100%.

(5) Cell Motility Analysis.

Chemotaxis was assayed using a Boyden chamber (Neuro Probe, Gaithersburg, Md.) using 3-μm polyvinylpyrrolidone-free polycarbonate filters (Neuro Probe). HL60 cells (differentiated for 4 days) were washed with and resuspended in HBSS containing 1% bovine serum albumin to a final concentration of $1×10^6$ cells/ml. Primary human neutrophils were washed and resuspended in NaCl buffer (140 mM NaCl, 4 mM KCl, 10 mM D-glucose, 10 mM HEPES, pH 7.4, 1 mM $MgCl_2$, and 1 mM $CaCl_2$) to a final concentration of $1×10^6$ cells/mi. Chemoattractant [1 μM granulocyte-macrophage-colony stimulating factor (GM-CSF), 10 nM IL-8, or 250 nM fMLP; Sigma Aldrich] was added to the bottom chamber in HBSS containing 1% bovine serum albumin. Cell suspensions ($0.2×10^6$ cells/well) were added to the top wells of the Boyden chamber and allowed to migrate for 1 h at 37° C. When applicable, cell suspensions were preincubated for 10 mM with small-molecule inhibitors (in DMSO) at the indicated concentrations, and the bottom chamber was adjusted to the same concentration of small molecule. All treatments contained the same final concentration of DMSO. Filters were processed according to the manufacture's recommendations and stained using DifQuik (VWR Scientific, West Chester, Pa.). Chemotactic HL60 cells were scored by counting three microscope fields and subtracting the number of cells from fMLP wells as background. All samples had background subtracted and were normalized to the fMLP-induced signal set at 100%. For all the small molecules, effects of the compounds on chemokinesis was analyzed by measuring chemotaxis in the presence of 250 nM fMLP in both the upper and lower chambers of the Boyden Chamber and measuring changes in transwell migration. Unless otherwise indicated, none of the compounds had effects on chemokinesis.

(6) Measurement of Superoxide Production.

The nitro blue tetrazolium (NBT) method was used to assess the effects of Gβγ inhibitors on NADPH oxidase activity. HL60 cells (differentiated for 4 days) were washed with and resuspended in HBSS containing calcium and magnesium (Cellgro; Mediatech, Herndon Va.) to a final concentration of $2×10^6$ cells/ml. Cells ($1×10^6$/reaction) were pretreated with 10 μMGβγ inhibitor compound (in DMSO) or 100 nM wortmannin (Sigma Aldrich) for 10 min at 37° C. before the addition of NBT (25 μl of 10 mg/ml in methanol) and then incubated or an additional 5 min at 37° C. All treatments contained the same final concentration of DMSO. Cells were then activated with either 250 nM fMLP (Sigma Aldrich) or PMA (Sigma Aldrich) for 30 min in a 37° C. water bath. Reactions were stopped by the addition of 500 µl of 1.2 N HCl, and cells were collected by centrifugation at 12,000 g for 5 min. Cell pellets were then resuspended in 200 µl of DMSO, transferred to a 96-well plate, and absorbance was measured at 540 nM. All treatments and controls contained the same concentration of DMSO. All samples had background subtracted and were normalized to the fMLP-induced signal set at 100%.

(7) Evaluation of Rac-1 Activation.

HL60 cells (differentiated for 4 days) were washed with and resuspended in NaCl buffer to a final concentration of $20 \times 10^6$ cells/ml. Cells ($10 \times 10^6$/reaction) were pretreated with 10 µM Gβγ inhibitor (in DMSO) for 10 min before challenge with 1 µM fMLP for 90 s in a 37° C. water bath and then immediately transferred to an ice-water bath. Cells were recovered by centrifugation at 500 g and washed two times with ice-cold Tris-buffered saline, pH 7.4. The Rac1 activation assay kit (Upstate Cell Signaling Solutions, Billerica, Mass.) was used to prepare cell extracts and evaluate Rac1 activation according to the manufacturer's instructions. Affinity-purified GTP-Rac1 was resolved by 15% SDS-polyacrylamide gel electrophoresis, transferred to nitrocellulose, probed with anti-Rac1 monoclonal antibody followed by detection with HRP-conjugated secondary antibody in accordance with the manufacturer's recommendations. Chemiluminescence was analyzed using a charge-coupled device camera in a UVP Epi-Chem II Darkroom imaging system. Results were expressed as percent fMLP-stimulated GTP Rac1 normalized to total Rac1 with the background subtracted.

(8) Carrageenan-Induced Paw Edema and Neutrophil Abundance.

Male Swiss-Webster mice (35-40 g b.wt.; Taconic Farms, Germantown, N.Y.) were randomized and acclimated for 1 week in a 12-h light/dark cycle. Food and water were provided ad libitum. Animals were labeled with unique identifiers on their tails using indelible marker. One hour before challenge with carrageenan, mice were administered compounds (dissolved in PBS) or vehicle (PBS) either by intraperitoneal (300 µl with 27.5 gauge needle) injection or by oral gavage (100 µl with 1.5", steel ball-tipped feeding needle; Popper and Sons, New Hyde Park, N.Y.). Indomethacin (2.5 mg/kg) stock solution was prepared in methanol and diluted into PBS (Mediatech), small-molecule inhibitor (concentration as indicated in appropriate figure legend) was prepared in PBS. Mice were anesthetized by intraperitoneal injection with ketamine hydrochloride (175 mg/kg) and xylazine (7 mg/kg) using a 26 gauge needle. Mice were tested for pain reflex to ensure sedation and then injected subcutaneously into the plantar region of the hind paw with 25 µl of 2% carrageenan using a precision engineered ⅝" 25 gauge Hamilton syringe (hypodermic needle; Hamilton Co., Reno, Nev.). Carrageenan (CarboMer, Inc., San Diego, Calif.) was suspended in PBS at 50° C. for 10 min with stirring the night before experimentation. The contralateral paw was injected with vehicle as control. Mice were then transferred to bedded cages to minimize pain associated with the carrageenan injections. Dorsal-plantar swelling was measured using an electronic digital caliper (±0.03 mm; VWR Scientific) at time 0 and every 2 h thereafter. To ensure measuring and injection consistency, the dorsal and plantar surface of the test paw and contralateral paws of each animal were marked with indelible marker. Each paw was measured two times at each time point and averaged. At the conclusion of the experiment, animals were euthanized in accordance with the University of Rochester and American Veterinary Medical Association standards by carbon dioxide narcosis and cervical dislocation. Paw edema was determined by subtracting the thickness of the contralateral paw from that of the carrageenan-injected paw at each time point.

Paws were amputated 2 h after carrageenan injection to determine the number of neutrophils present in the edematous fluid. Paws were transferred to prepared Eppendorf tubes, and the exudates were collected by centrifugation for 2 min. The paws were removed and the tubes re-weighed to determine the mass of the exudates, which was then converted to volume. The volume in the contralateral untreated control paw was subtracted from the cardgeenan-treated paw volume. To remove erythrocytes by hypertonic lysis, the exudate was resuspended in 250 µl of 1× PBS to which 50 µl of water was added. At the conclusion of a 30-s incubation, 75 µl of 4.5× PBS was added to return the solution to normal salt levels. The number of neutrophils present was determined by manual counting, and the small number of neutrophils in the control contralateral paw was subtracted.

(9) Isolation of Primary Human Neutrophils.

Human blood obtained by venous puncture from consenting, healthy adult donors, in accordance with University of Rochester standards, and collected in sterile vacutubes containing sodium heparin (BD Biosciences, San Jose, Calif.). Neutrophils were layered over PolymorphprepT11 (Accurate Chemical and Scientific Co., Westbury, N.Y.) and isolated by centrifugation (470 g for 50 mM at room temperature). Trace erythrocytes were removed by hypertonic treatment followed by centrifugation. Isolated neutrophils were stored in HEPES-buffered saline solution (146 mM NaCl, 5 mM KCl, 5.5 mM D-glucose, 10 mM HEPES, 1 µM $CaCl_2$, and 1 mM $MgSO_4$) at pH 7.4.

(10) Data Analysis.

Ligand competition curves were determined by nonlinear regression using Prism software (GraphPad Software, Inc., San Diego, Calif.). Statistical significance was evaluated by one-way analysis of variance and Bonferroni's multiple comparison test. Statistical significance was defined as *, $P<0.05$; , $P<0.01$; *, $P<0.001$.

3. Example 3

A Novel Gβγ-Subunit Inhibitor Selectively Modulates Acute µ-Opioid-Dependent Antinociception and Attenuates Morphine-Induced Antinociceptive Tolerance and Dependence Opioid analgesics, such as morphine, are clinically important for the treatment of moderate to severe pain. Molecular cloning experiments led to the identification of the mu (µ), delta (δ), and kappa (κ) opioid receptors (Evans et al., 1992; Kieffer et al., 1992; Chen et al., 1993). All three types of opioid receptor are GPCRs (G protein coupled receptors) that activate $G_i$ resulting in inhibition of adenylyl cyclase activity (Childers, 1991; Sharma et al., 1977), activation of inwardly rectifying $K^+$ channels (Armstrong et al., 1992; North et al., 1987), inhibition of voltage-activated $Ca^{2+}$ channels, (Moises et al., 1994; Schroeder et al., 1991), the activation of the MAP kinase (mitogen activated protein kinase), Erk-1/2 (extracellular signal-regulated kinases) (Law et al, 2004) and phosphatidylinositol (PI) specific phospholipase C (PLC) (PI-PLC) (Xie et al., 1999). Recently, the importance of Gβγ-mediated activation of PI-PLC in the potentiation of opioid analgesia has been examined (Xie et al., 1999, Galeotti et al., 2006).

Activation of PLC results in hydrolysis of phosphatydilinositol 4,5-bisphosphate (PIP$_2$) to inositol 1,4,5, triphosphate (IP$_3$), which mobilizes Ca$^{2+}$ from intracellular stores, and diacylglycerol (DAG), which activates protein kinase C (PKC) (Rebecchi et al., 2000). PLCβ2 and PLCβ3 isoforms are activated by Gβγ and are responsible for PI hydrolysis stimulated by G$_i$ coupled receptors, with PLCβ2 being expressed primarily in hematopoetic cells (Rhee et al., 1997).

Data indicated that pharmacological inhibition of PLCβ3 enhanced opioid-induced antinociception. In these experiments with PLCβ3 knock-out mice, deletion of PLCβ3 resulted in a 10-fold potentiation in analgesic response in mice treated with morphine, compared to control animals, in the 55° C. warm-water tail-flick assay. This was one of the first indications that this pathway is an important regulator of opioid signaling and subsequent analgesic responsiveness, and indicated that targeting PLCβ3 or PLCβ3 regulation pharmacologically influenced opioid efficacy.

From screening of a small molecule library (NCI diversity set) several compounds were found that bound to Gβγ subunits and selectively inhibited Gβγ subunit signaling in vitro (Table 20). The lead compound in the series, M119, had high affinity for the Gβγ subunit and was an inhibitor of PLCβ3 signaling in vitro. In vivo, co-administration of M119 (100 nmol, i.c.v.) with graded doses of morphine (i.c.v.) resulted in a 10-fold leftward shift in the morphine dose-response curve (Bonacci, et al., 2006). This same shift is observed in PLCβ3 knock-out mice that have been treated with morphine alone (Bonacci et al., 2006; Xie et al., 1999). Administration of M119 with morphine in the PLCβ3 knock-out mice had no additional effect (Bonacci et al., 2006), further supporting the hypothesis that the mechanism of action for M119 was through the attenuation of opioid-induced activation of PLCβ3 by Gβγ. It is important to note that morphine still produced an analgesic response in the animals which had been administered M119, indicating that regulation of other Gβγ targets was still intact.

TABLE 20

Structure-Activity Relationship (SAR) of M119 based on competition ELISA analysis for SIGK binding.

| Compound* | IC$_{50}$ ELISA |
|---|---|
| M119 (119910) | 0.2 μM |
| M119B (119892) | >300 μM |
| M119C (119911) | 0.2 μM |
| M119D (119912) | 30 μM |
| M119E (119913) | 0.7 μM |
| M19F (119915) | >300 μM |
| M119G (11916) | 5 μM |
| M119H (119888) | >300 μM |
| M119I (119891) | NB |
| M119J (119894) | >300 μM |
| M119K (119893) | 0.13 μM |
| M122 (122390) | 14 μM |
| M157 (157411) | 70 μM |
| M158 (158109) | NB |
| M158B (158113) | NB |
| M158C (158110) | 0.25 μM |
| M158D (158112) | >300 μM |
| M260 (2608) | 300 μM |
| M542 (5426) | NB |
| M903 (9037) | >300 μM |

*NCI identification numbers in parentheses. NB- No inhibition at 300 μM. Data are from Bonacci et al. (2006).

Selectively inhibiting downstream signaling from the Gβγ subunit, with a small molecule inhibitor, is a novel approach to targeting only a pathway of interest, while leaving the rest of the signaling machinery intact. To take this concept a step further, the goal of this current study was to determine the effect M119 would have in vivo, not only on antinociception mediated by all three opioid receptors, but also in models of acute analgesic tolerance and dependence.

a) Materials and Methods (1) Animals

Male, ICR mice (20-30 g) (Harlan Industries, Indianapolis, Ind.) were housed in groups of five with food and water available ad libitum before any procedures. Animals were maintained on a 12-hr light/dark cycle in a temperature-controlled animal colony. Studies were carried out in accordance with the Policies on the Use of Animals in Neuroscience Research.

(2) Chemicals

M119 (cyclohexanecarboxylic acid, 2-(4,5,6-trihydroxy-3-oxo-3H-xanthen-9-yl)-(9cl)) (FIG. 3C) was obtained from the chemical diversity set from the Developmental Therapeutics Program from the NCI/NIH. M119 is compound 119910 within that series. Morphine sulfate was purchased from Mallinckrodt (Saint Louis, Mo.). [D-Ala$^2$, N-Me-Phe$^4$, Gly$^5$-ol]-enkephalin (DAMGO), [D-Pen$^2$,D-Pen$^5$]enkephalin (DPDPE), [D-Ala$^2$]-Deltorphin II (Deltorphin II), (trans)-3,4-dichloro-N-methyl-N-[2-(1-pyrrolidinyl)-cyclohexyl]benzeneacetamide methane-sulfonate hydrate (U50,488), β-FNA and naloxone were purchased from Sigma Chemical Co. (Saint Louis, Mo.). Scintisafe was purchased from Fisher Scientific (Pittsburgh, Pa.).

(3) Inositol Phosphate Assay Using hMOR-CHO, hKOR-CHO, and hDOR-CHO Cells.

Chinese hamster ovary (CHO) cells stably expressing either the human κ (hKOR-CHO), δ (hDOR-CHO)(L. Toll, Stanford Research Institute, Palo Alto, Calif.) or μ (hMOR-CHO)(G. Uhl, National Institute on Drug Abuse, Baltimore, Md.) opioid receptor were used in the experiments. Cells in 6-well plates were labeled by adding 4 μCi of [$^3$H]inositol for 24 hr in inositol-free F-10 media, without serum. After labeling, LiCl was added directly to the labeling media at a final concentration of 10 mM. Ligands or peptides were added at the same time. The final volume of each well was 1 mL. The plates were put back in to the incubator at 37° C. for 30 min after which time the medium was aspirated and the plates were washed twice with 1× PBS. Ice-cold 50 mM formic acid, 1 mL, was added to the plates which were placed in the cold room at 4° C. for 30 min. After the incubation, the contents of the plates were applied to Dowex AG1-X8 columns and allowed to flow all the way through the column. The columns were washed, twice each, with 50 and 100 mM formic acid, for a total of four washes, followed by elution of the IP-containing fraction with 3 mL of 1.2 M ammonium formate/0.1 M formic acid. The eluted fraction was mixed with Scintisafe scintillation fluid, for high salt, and counted. The data are represented as the fold increase over control in total inositol phospates. All experiments were repeated three times and performed in duplicate. Control cells for each experiment were labeled with [$^3$H]inositol and LiCl, in the same manner as the treatment groups.

(4) Drug Solutions and Injections

For intracerebroventricular (i.c.v.) injections, M119 was initially solubilized in DMSO and all subsequent dilutions were in distilled water. For systemic injections intraperitoneal (i.p.), M119 was initially solubilized in a small volume of NaOH and brought to volume in phosphate buffered saline (PBS) to approximately pH 7.5. Vehicle was prepared in a similar manner without the drug. Additional compounds used in these studies were dissolved in the same vehicle as M119 for both i.c.v. and systemic injections. Intracerebroventricular injections were made directly into the lateral ventricle according to the modified method of Haley and McCormick (1957). The mouse was lightly anesthetized with ether, an incision was made in the scalp, and the injection was made 2 mm lateral and 2 mm caudal to bregma at a depth of 3 mm using a 10-μl Hamilton syringe. The volume of all i.c.v. injections was 5 μl.

(5) Antinociceptive Testing

Antinociception was assessed using the 55° C. warm-water tail-flick test. For the tail-flick test, the latency to the first sign of a rapid tail-flick was taken as the behavioral endpoint (Jannsen et al., 1963). Each mouse was first tested for baseline latency by immersing its tail in the water and recording the time to response. Mice not responding within 5 sec were excluded from further testing. Mice were then administered the test compound and tested for antinociception 20 min after the injection. A maximum score was assigned (100%) to animals not responding within 15 sec to avoid tissue damage. Antinociception was calculated by the following formula: % antinociception=100×(test latency−control latency)/(15−control latency).

(6) Effects of M119+ Receptor-Selective Agonists

Mice were treated concomitantly with M119 (100 nmol, i.c.v.) and graded doses of receptor selective agonists (DAMGO, U50,488, DPDPE, and Deltorphin II). Control mice received a vehicle injection (i.c.v., −20 min). Antinociception was assessed 20 min after agonist injection. To test the effects of M119 systemically, mice received M119 (100 mg/kg, i.p.) followed immediately by graded doses of morphine subcutaneous (s.c.). Antinociception was tested 20 min following the agonist injection.

(7) Acute Antinociceptive Tolerance

For quantitative measurements of acute opioid tolerance, a standardized state of tolerance was induced by administration of morphine at times 0, 2 hr, 4 hr, and 6 hr. The degree of tolerance was calculated from the shift in $ED_{50}$ value from the non-tolerant state to the tolerant condition (Way et al., 1969). All injections were i.c.v. and antinociception was assessed 20 min after each injection. Mice were lightly anesthetized prior to each injection. Previous reports have indicated that this dosing schedule induced acute morphine tolerance (Jiang et al., 1995). To assess the role of M119 in acute morphine tolerance M119 and morphine were administered concomitantly at times 0, 2 hr, 4 hr, and 6 hr. Time 0 is defined as the first injection of agonist.

(8) Acute Physical Dependence

To assess development of acute morphine physical dependence (Yano and Takemori, 1977; Bilsky et al., 1996, Wang et al., 1999) mice were pretreated with a single injection of morphine (100 mg/kg, s.c., −4 hr). Prior to the administration of naloxone (30 min) mice were injected with vehicle, i.c.v. Withdrawal was precipitated by an injection of the opioid antagonist, naloxone (10 mg/kg, i.p.). Mice were immediately placed in a clear cylinder and observed for 15 min. The number of vertical jumps was recorded during this time. To test if M119 affected morphine physical dependence, the same treatment as described above was used with M119 (100 nmol, i.c.v.) being administered 30 min prior to the administration of naloxone.

(9) Statistical Analysis

Data from dose-response experiments were fitted to a sigmoidal dose-response model using nonlinear regression analysis, and $ED_{50}$ values were calculated. A shift in the dose-response curve was determined from the $ED_{50}$ values. To assess if the $ED_{50}$ values for 2 dose-response curves were significantly different, an F-test was performed (GraphPad Prims 4.03). Values are reported as two-tailed p values. Statistical significance was set at $P<0.05$. All data points are the mean of 7-10 mice, with standard error of the mean represented by error bars. Statistical analysis of the acute dependence data and inositol phosphate data used the Student's t test.

b) RESULTS (1) The Gβγ Inhibitor, M119, Potentiated μ-Mediated Antinociception.

Figure 14B:
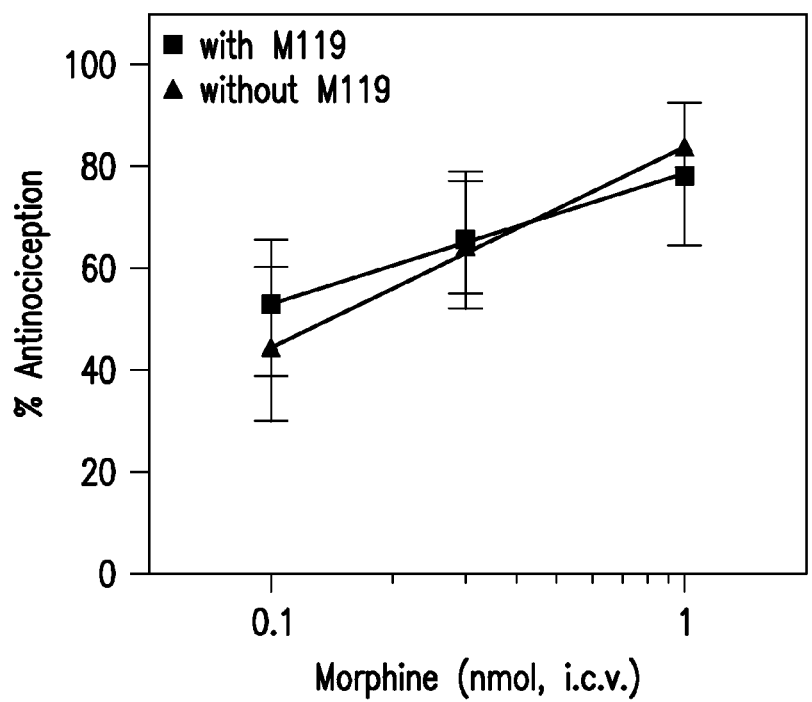

The efficacy of the compounds were tested in an in vivo model. Compared to wild type animals, PLCβ3 −/− mice are 10-fold more sensitive to the antinociceptive effects of the μ-agonist morphine (Xie et al., 1999). Since M119 blocks Gβγ-dependent activation of PLCβ3 it was determined whether co-administration of M119 with morphine would also increase morphine-induced antinociception. Co-administration of M119 with morphine intracerebroventricularly (i.c.v) resulted in an 11-fold increase in the analgesic potency of morphine (FIG. 14A) [$ED_{50}$ values and 95% confidence limits: 0.069 (0.023-0.201) nmol and 0.743 (0.341-1.62) nmol respectively], whereas administration of 100 nmol M119 alone had no effect on baseline antinociception. M119 also had no effect on morphine-dependent antinociception in PLCβ3 −/− mice (FIG. 14B). These data highlight the specificity of M119 actions and the selective nature of M119 both in vitro and in vivo. Gβγ subunits regulate many aspects of signaling critical for the actions of opioid agonists (Connor and Christie, 1999). If M119 were globally blocking Gβγ subunit functions, it is expected that morphine-induced antinociception would have been attenuated rather than potentiated with M119 co-administration.

Data disclosed herein demonstrated that PLCβ3, a Gβγ subunit-regulated enzyme, was a negative modulator of μ opioid-dependent signaling. Therefore, it was predicted that inhibiting βγ-dependent PLCβ3 activation would potentiate μ opioid-mediated antinociception, in a manner similar to the PLCβ3 knock-out studies (Xie et al., 1999, Bonacci et al., 2006). Additionally, it was observed that co-administration of M119 (FIG. 3C) with morphine resulted in a significant (p<0.001), 10-fold potentiation in morphine-mediated antinociception (Bonacci et al., 2006) (FIG. 14). To determine if the effects of M119 were specific to morphine, M119 was also administered with agonists selective for the μ, κ, and δ receptors. Co-administration of M119 and the μ-selective agonist, DAMGO, resulted in a 7-fold leftward shift in the DAMGO dose-response curve when compared to DAMGO alone (p<0.001). DAMGO alone produced an $ED_{50}$ value and 95% CL of 0.07 nmol (0.03-0.17 nmol) while DAMGO and M119 resulted in an $ED_{50}$ value and 95% CL of 0.01 nmol (0.005-0.03 nmol). A modest, 2-fold, shift was observed in the dose-response curve of the κ-selective agonist, U50,488, when administered with M119 (p<0.01). The $ED_{50}$ values for U50, 488 alone and U50,488 with M119 were 37 nmol (29-47 nmol) and 17 nmol (9.4-31) nmol, respectively. M119 did not potentiate antinociception mediated through either $\delta_1$ or $\delta_2$ receptor. The $ED_{50}$ values for the $\delta_1$-specific agonist, DPDPE, alone or with M119 did not change significantly, 6.5 nmol (2.6-16 nmol) and 5.4 nmol (2.6-11 nmol), respectively. The $\delta_2$-selective agonist, Deltorphin II, produced an $ED_{50}$ value of 11 nmol (5.5-23 nmol) which was unchanged in the presence of M119, 11 nmol (5.1-23 nmol). Administration of M119 alone had no effect on baseline tail-withdrawal latancies (Bonacci et al., 2006). These experiments demonstrated that, in vivo, M119 selectively potentiated μ opioid-dependent antinociception.

To determine if M119 would be effective after systemic administration, M119 was administered i.p. followed immediately with a s.c. injection of morphine. Systemic administration of morphine alone produced an $ED_{50}$ value of 5.0 mg/kg (2.9-8.4 mg/kg) which was shifted 4-fold to the left in the presence of M119, producing an $ED_{50}$ value of 1.3 mg/kg (0.59-2.8 mg/kg) ($p<0.001$).

(2) M119 Selectively Inhibited Inositol Phosphate Generation Mediated Through The IA Receptor.

It is disclosed herein that the potentiation in morphine-induced antinociception was due to M119 inhibition of βγ-dependent PLCβ3. To demonstrate that M119 blocked μ-opioid-receptor-dependent PLC activation, morphine and DAMGO-dependent total inositol phosphate (IP) production were measured in hMOR-CHO cells. Both DAMGO (10 μM) and morphine (10 μM) significantly increased total IP measured as compared to control, with a 4- and 3-fold increase respectively ($p<0.01$) (FIG. 15A). This increase was significantly attenuated with the addition of the βγ-inhibitor, M119 (10 μM) ($p<0.05$) while M119 had no effect by itself. The μ-receptor selective antagonist, β-FNA (β-funaltrexamine), attenuated DAMGO and morphine-dependent IP production (FIG. 15A) ($p<0.05$). The κ-selective agonist, U50,488 (10 μM) and the δ-selective agonist, DPDPE (10 μM) had no effect on IP production alone or in the presence of M119 in the hMOR-CHO cells (data not shown). These data demonstrate that the μ opioid receptor can stimulate PLC activation and that this coupling is blocked by M119.

To determine if other opioid receptors couple to PLC activation, opioid receptor-dependent IP generation was examined in hKOR-CHO and hDOR-CHO cells. Treatment with U50,488 (10 μM), with or without M119 (10 μM) or nor-BNI (10 μM), the κ-selective antagonist, in the hKOR-CHO cells had no significant effect on IP production over control treated cells (FIG. 15B). In the hDOR-CHO cells neither DPDPE (10 μM) (FIG. 15C) nor Deltorphin II (10 μM) (FIG. 15D) significantly increased IP generation over control treated cells. Treatment with M119 (10 μM) and the δ-selective antagonist, naltrindole (100 μM) also had no significant effect (FIGS. 23C and 23D). Importantly, the levels of opioid receptors were the same for all three cell lines ($B_{max}$ values not significantly different, data not shown). These in vitro data correlate with the effects of M119 in vivo where only in the mice treated with the p-preferring compounds was a significant potentiation in antinociception observed. Thus, the selective effects of M119 observed in vivo on μ opioid receptor-dependent antinociception can be the result of selective coupling of μ opioid receptor to Gβγ-dependent PLC activation.

(3) M119 Attenuated Acute Morphine Antinociceptive Tolerance.

As an initial in vivo test of the efficacy of M119 in reducing the development of morphine antinociceptive tolerance, an acute tolerance assay was performed. This assay was used to measure tolerance because it requires considerably less compound than traditional tolerance paradigms, while still yielding reliable results. The antinociceptive effect of repeated (0, 2 hr, 4 hr, 6 hr) doses (1-10 nmol) of morphine and the development of acute antinociceptive tolerance are shown herein. Morphine produced dose-dependent antinociception in the 55° C. warm-water tail-flick assay. The $ED_{50}$ value (95% CL) for i.c.v. morphine at time 0 was 0.59 nmol (0.16-2.2 nmol). After repeated administration, acute morphine antinociceptive tolerance developed by 4 hr with a significant shift in the $ED_{50}$ value ($p<0.01$). At 4 hr, the $ED_{50}$ value had shifted 8-fold, 4.9 nmol (1.8-13 nmol) and by 6 hr, the $ED_{50}$ value had shifted 16-fold, 9.6 nmol (3.2-29 nmol) ($p<0.001$). Co-administration of M119 with morphine greatly attenuated acute morphine antinociceptive tolerance. The $ED_{50}$ values remained virtually unchanged, with no statistical difference, from time 0, 0.16 nmol (0.02-1.3 nmol) to the 6 hr time-point, 0.22 nmol (0.008-5.7 nmol). Control mice were treated under the same injection protocol, however, received only vehicle. No significant change from baseline tail-withdrawal values were observed for any of the control mice at any of the times tested, indicating that the procedure employed in the acute tolerance protocol was not contributing to the data which was observed.

(4) Pre-treatment With M119 Attenuated Acute Morphine Physical Dependence.

In an acute model of morphine dependence, mice were treated with morphine (100 mg/kg, s.c., −4 hr), vehicle (i.c.v.) 30 min prior to naloxone, then administered naloxone (10 mg/kg, i.p.) which resulted in withdrawal jumping. These mice jumped an average of 71±12 times in the 15-min counting period. To test if M119 would attenuate acute morphine withdrawal, mice were treated with morphine (100 mg/kg, s.c., −4 hr) and administered M119 (100 nmol, i.c.v.) 30 min prior to the administration of naloxone (10 mg/kg, i.p.). Under this test condition, mice jumped significantly less times in the 15-min counting period, an average of 23±14 compared to 71±12 for the control mice. This indicates that M119 blocks the development of physical symptoms associated with opiate dependence. Post hoc analysis (Student's t-test) indicated that co-administration of M119 with naloxone produced significantly less vertical jumps than naloxone alone ($p<0.05$).

c) Discussion

Herein, the novel approach of using a Gβγ-inhibitor to influence the efficacy and potency of morphine in several animal models of μ-opioid receptor function is disclosed. The mechanism of action of this compound is based on studies demonstrating that the Gβγ-dependent enzyme, PLCβ3, was a negative modulator of μ opioid-receptor signaling both in PLCβ3 knock-out mice and in dorsal root ganglion neurons. It was demonstrated herein that the Gβγ inhibitor, M119, inhibited PLCβ3 in vitro and that concomitant administration of this novel drug with morphine in vivo resulted in a 10-fold shift in morphine analgesic potency, virtually identical, to data from the PLCβ3 knock-out studies (Xie et al., 1999, Bonacci et al., 2006). Herein, the specificity and underlying mechanisms of action of M119 in potentiating analgesia are further explored. Additionally, evidence was presented extending the therapeutic efficacy of this approach.

M119 Displayed μ Receptor-Selective Specificity In Vivo. Increased analgesic potency was observed in mice treated with M119 and morphine and also M119 and the receptor-selective agonist, DAMGO. Minimal effects were observed with κ- and δ-selective agonists, U50,488, DPDPE, and Deltorphin II. These studies indicated that M119 was selective, in vivo, for the potentiation of μ-mediated analgesia. Similar results were obtained from the in vitro IP assay, with only the μ-agonists, DAMGO and morphine, stimulating IP generation which was inhibited by M119. The κ and δ opioid receptors do not activate the same PLC isoforms, or are not acting in the same brain regions, and therefore are not inhibited by the same PLC-dependent feedback pathway observed for the μ-opioid receptor and it is for this reason that that M119 lacks efficacy with these receptors.

Galeotti and colleagues (2006) recently demonstrated the importance of PLCβ3 in opposing morphine analgesia utilizing antisense phosphodiester oligonucleotides specifically to PLCβ3. In mice treated both with morphine and the antisense oligonucleotide, a potentiation in analgesic response was observed (Galeotti et al., 2006). The same group also demonstrated localization of PLCβ3 in regions of the brain important for nociceptive transmission which have been previously shown to also express the μ opioid receptor (Galeotti et al., 2006).

(1) Downstream Signaling And The Role Of Phospholipids In Tolerance and Dependence.

There is evidence that the PLC pathway can influence the development of opioid tolerance and dependence. Inhibitors of PLC (Smith et al., 1999), IP$_3$ receptors (Smith et al., 1999), and PKC (Bilsky et al., 1996; Smith et al., 1999; Bohn et al., 2002) all attenuated morphine tolerance. PKC knock-out animals also exhibited attenuated morphine tolerance (Zeitz et al., 2001). It has also been suggested that generation of IP$_3$ and DAG along with activation of PKC may be important for the development of opioid-dependence (Fundytus and Coderre, 1996; Smith et al., 1999). Herein, it was shown that M119 attenuated both acute antinociceptive tolerance and dependence but which of these specific mechanisms downstream of βγ-dependent PLCβ3 regulation are responsible for these effects remains to be defined.

4. Example 4

Small Molecule Targeting of G-Protein Beta Gamma in Cardivoscular Disease

Bioavailable Gβγ-GRK2 inhibitory compounds with exciting data have been identified. Therefore, selective small molecule compound targeting of Gβγ-GRK2 is a novel therapeutic paradigm for HF, and selective Gβγ compounds elucidates important β-AR-Gβγ pathways in HF.

Heart failure (HF) continues to be the leading cause of death worldwide, having surpassed infectious disease in the 1990s: it has recently been predicted that HF will also become the leading cause of all disability by 2020(Murray C J, Lopez A D. Lancet 1997; 349(9064):1498-1504). Current data indicate that 5-year survival following the diagnosis of HF is 50%, and that 1-year survival for those with end-stage disease is only 50% (Califf R M, et al. Am Heart J. 1997; 134:44-54), despite substantial therapeutic advances in the past two decades. HF is the leading cause for hospitalization in the U.S. at the cost of $300 billion per year. For patients with end-stage HF, there are few options for effective treatment. Although cardiac transplantation is the most effective treatment for end-stage HF, substantial limitations of this surgical intervention include an extremely limited supply of acceptable donor hearts, reaching a plateau of ~2000/year in the USA, <3000/year worldwide.

(1) β2-Adrenergic Receptor Signaling in the Heart

G-protein coupled receptors (GPCRs) play an important role in both local and systemic regulation of heart function. In particular, β-adrenergic receptors (β-AR) play a critical role in regulating cardiac contractility, including both chronotropy and inotropy. HF is associated with chronic down-regulation and desensitization of cardiac β-ARs, due in part to chronic agonist stimulation(Bristow M R, et al. N Engl J Med. 1982; 307:205-211; Rodman H A, et al. Nature. 2002; 415(6868):206-212). Attenuation and desensitization of β-AR signaling and responsiveness is mediated by the β-AR kinase ((βARK1). βARK1 is a member of the G protein-coupled receptor (GPCR) kinase (GRK) family, and is also known as GRK2. GRK2 is a cytosolic enzyme that targets and phosphorylates agonist-occupied GPCRs, including myocardial β-ARs, via recruitment by and binding to the βγ-subunits of heterotrimeric G-proteins (Gβγ) following GPCR agonist stimulation (Koch W J, et al. Annu Rev Physiol. 2000; 62:237-26). Agonist-stimulated Gβγ-GRK2 interaction is a prerequisite for GRK2-mediated GPCR (including β-AR) phosphorylation, homologous receptor desensitization and subsequent internalization and degradation (Bristow M R, et al. N Engl J Med. 1982; 307:205-211).

Elevated expression and activity of the G-protein coupled receptor kinase (GRK2, a.k.a. β-AR kinase, βARK1) is a hallmark of human and experimental animal HF (Rockman H A, et al. Nature. 2002; 415(6868):206-212; Hansen J L, et al. Trends Cardiovasc Med. 2006; 16(5):169-177). Furthermore, cardiac targeted overexpression of GRK2 can directly cause HF in experimental animal models (Koch W, et al. Science. 1995; 268:1350-1353). Importantly, levels of GRK2 expression and activity from cardiac tissue and circulating lymphocytes correlate directly with the severity of human HF: it was found GRK2 expression and activity were elevated in end-stage HF, and were normalized following salutary left ventricular assist device (LVAD) support (FIG. 16 and (Blaxall B C, et al. J Am Coll Cardiol. 2003; 41(7):1096-1106; Hata J A, et al. J Card Fail. 2006; 12(5):360-368).

(2) A Role for G βγ Subunit Inhibition in the Heart

Since Gβγ binding is a critical prerequisite for GRK2-mediated GPCR desensitization, several approaches have been explored to interdict the Gβγ-GRK2 interaction. GRK2 possesses three general domains, including an N-terminal RGS and protein recognition domain, a central kinase domain, and a C-terminal region encoding the Gβγ binding domain. To study the role of the Gβγ binding domain in the functional regulation of GRK2, the C-terminal 197 amino acids encoding the GRK2 Gβγ binding domain (βARKct) was expressed in cells as a Gβγ peptide inhibitor of GRK2, where it attenuated homologous γ-AR desensitization in a GPCR-specific manner (Koch W J, et al. J Biol Chem. 25 1994; 269(8):6193-6197). Subsequently, transgenic mice were created with myocardial targeted expression of βARKct, which demonstrated enhanced basal cardiac function and response to isoproterenol (Koch W J, et al. Science. 1995; 268(5215):1350-1353). Mating of the cardiac-targeted βARKct mice with the GRK2 overexpressing mice normalized cardiac function, providing direct evidence that the mechanism responsible for the phenotype in these mice was βARKct inhibition of G$_{βγ}$-mediated signaling, including GRK2 activity(Koch W, et al. Science. 1995; 268:1350-1353; Akhter S A, et al. Circulation. 1999; 100(6):648-653).

To determine the direct role of GRK2 and the Gβγ-GRK2 interaction in the pathogenesis of HF, the cardioprotective potential of βARKct has been assessed in animal models of HF. The data repeatedly demonstrate a salutary, cardioprotective effect of βARKct both by transgenesis in genetic models of HF, as well as through adenoviral delivery in surgical models of HF (Blaxall B C, et al. Physiol Genomics. 2003; 15(2):105-114; Rockman H A, et al. Proc Natl Acad Sci USA. 1998; 95(12):7000-7005; Koch W J. Mol Cell Biochem. 2004; 263(1-2):5-9). Notably, βARKct has not only normalized cardiac function, but has also normalized aspects of β-AR signaling(Blaxall B C, et al. Physiol Genomics. 2003; 15(2):105-114; Rockman H A, et al. Proc Natl Acad Sci USA. 1998; 95(12):7000-7005; Harding V B, et al. Proc Natl Acad Sci USA. 2001; 98(10):5809-5814). Furthermore, βARKct was shown to be synergistic with β-AR blockers (standard medical therapy for HF) in the cardiac calsequestrin overexpressor (CSQ) mouse model of HF. Importantly, βARKct has also been shown to normalize contractile function of failing human cardiac mycoytes (Williams M L, et a;. Circulation. 2004; 109(13):1590-1593). Thus, inhibition of the Gβγ-GRK2 interaction possesses great therapeutic promise.

The therapeutic possibilities of targeting Gβγ signaling in the pathogenesis of HF were further validated in a recent report by the Ungerer group(Li Z, et al. Gene Ther. 2003; 10(16):1354-1361). This group investigated an alternative dominant-negative peptide approach to interdicting Gβγ signaling in direct comparison to βARKct. Phosducin is a Gβγ binding protein first discovered in retinal tissue following activation of the GPCR transducin, with phosducin homologues now described in several tissues. Like βARKct, phosducin also translocates from cytosol to membrane upon GPCR activation, binds Gβγ subunits with high affinity, and inhibits subsequent Gβγ signaling events, including GRK2 recruitment (Bauer P H, et al. Nature. 1992; 358(6381):73-76; Gaudet R, et al. Cell. 1996; 87(3):577-588; Hekman M, et al. FEBS Lett. 1994; 343(2):120-124; Schulz R. Pharmacol Res. 2001; 43(1):1-10). Prior reports had indicated more stable high affinity of an ~200 amino acid N-terminally truncated version of phosducin (nt-del-phd). Viral gene delivery of either βARKct or nt-del-phd delivered after pacing-induced HF in rabbits equally normalized cardiac function in vivo. Both transgenes also normalized contractility of isolated failing cardiomyocytes, with some differences in their effects on β-AR signaling. Taken together, the above data strongly indicate the therapeutic potential of targeting Gβγ signaling in HF.

(3) β-AR-Gβγ-PI3Kγ Signaling in the Heart

Cardiac Gβγ signaling results in activation of downstream pathways beyond GRK2, including phosphoinositide 3-kinase g (PI3Kγ), the only PI3K regulated in part by Gβγ signaling[5]. Following β-AR stimulation, cytosolic GRK2 interacts with phosphoinositide 3-kinase γ (PI3Kγ). Gβγ-mediated membrane recruitment of GRK2 appears to recruit PI3Kγ to the membrane proximal to β-AR, where both the protein and lipid kinase activity of PI3K are required for the pathologic β-AR receptor desensitization and downregulation observed in HF (Naga Prasad S V, Nat Cell Biol. 2005; 7(8):785-796; Naga Prasad S V, et al. J Cell Biol. 2002; 158(3):563-575; Naga Prasad S V, et al. J Biol Chem. 2001; 276(22):18953-18959; Perrino C, et al. Vascul Pharmacol. 2006; 45(2):77-85).

A growing body of evidence demonstrates that displacement of PI3Kγ from the GRK2 complex is cardioprotective, in part through reducing β-AR desensitization and downregulation. Experiments have included cardiac-targeted expression of a kinase-inactive PI3Kγ (PI3Kγ$_{inact}$)(Nienaber J J, et al. J Clin Invest. 2003; 112(7):1067-1079; Perrino C, et al. J Am Coll Cardiol. 2005; 45(11):1862-1870; Perrino C, et al. J Clin Invest. 2006; 116(6):1547-1560) or a large peptide inhibitor of the protein kinase domain of PI3K(Perrino C, et al. J Am Coll Cardiol. 2005; 45(11):1862-1870; Curcio A, et al. Am J Physiol Heart Circ Physiol. 2006; 291(4):H1754-1760; Perrino C, et al. Circulation. 2005; 111(20):2579-2587). Both large peptides disrupt the cytosolic GRK2-PI3Kγ interaction and normalize β-AR signaling and cardiac function both in vivo and in isolated cardiomyocytes from chronic HF models. Despite early suggestions of mild cardioprotection in PI3Kγ null animals (Crackower M A, et al. Cell. 2002; 110(6):737-749; Oudit G Y, et al. Circulation. 2003; 108(17): 2147-2152), subsequent experiments have convincingly demonstrated their increased susceptibility to β-AR abnormalities and cardiac injury in multiple HF models. Concurrent experiments showed that PI3Kγ$_{inact}$ and PIK domain animals were cardioprotective and normalized β-AR signaling in these HF models. These experiments suggest that β-AR-Gβγ-GRK2-PI3Kγ interactions in the heart lead to cardiac pathophysiology, yet there are important aspects of PI3Kγ signaling in the heart that should be maintained. In summary, the β-AR-Gβγ-GRK2-PI3Kγ cascade plays an important role in cardiac pathophysiology and pathologic β-AR abnormalities. What remains unclear is whether PI3Kγ-mediated regulation of β-AR signaling is Gβγ- and/or GRK2 dependent or independent.

Targeting Gβγ signaling has proven a promising therapeutic paradigm in the treatment of HF. Unfortunately, despite vast efforts in both academia and industry, therapeutic targeting of cardiac Gβγ in HF to date has only been achieved by ~200 amino acid peptides that can only be administered via transgenesis or viral gene therapy, which faces substantial hurdles in development as a therapeutic modality. Identification of selective and differential small molecule compounds targeting Gβγ signaling in the pathogenesis of HF provides valuable new research tools to dissect the β-AR-Gβγ-GRK2-PI3Kγ signaling pathway(s), and may provide novel and readily bioavailable therapeutics for cardiovascular disease.

b) Results

The cardioprotective peptide inhibitors described above (βARKct, nt-del-phd, PI3Kγ$_{inact}$) function in part by inhibiting aspects of Gβγ signaling, including recruitment of GRK2 (and PI3K) to Gβγ following β-AR agonist stimulation (a requisite step in GRK2-mediated desensitization of agonist occupied β-ARs). These data highlight the therapeutic potential of Gβγ inhibitors in HF, but are hampered by the fact that all are peptides requiring viral vector delivery for therapeutic efficacy. Thus, identification of small molecule compounds that inhibit Gβγ is a promising and effective therapeutic approach for HF.

(1) Chemical Gβγ Inhibitor Studies in Isolated Adult Mouse Cardiomyocytes

Data obtained with purified proteins indicated that one of the high affinity Gβγ binding compounds, M119, could inhibit the Gβγ-GRK2 interaction (Bonacci T M, et al. Science. 2006; 312(5772):443-446). Subsequently, it was found that M119 demonstrated the capability to reduce GRK2 membrane recruitment following fMLP stimulation of leukocyte cells. Thus, it was tested whether M119 could block GRK2 recruitment to membrane-bound Gβγ subunits upon agonist stimulation of β-AR in cardiomyocytes, similar to what had been observed in vitro with the peptide inhibitors described above. Indeed M119 reduced β-AR-mediated recruitment of GRK2 to membranes of isolated adult mouse cardiomyocytes, with a mild reduction of membrane associated GRK2 at baseline.

To assess whether the M119 inhibition of Gβγ-mediated GRK2 recruitment resulted in downstream effects on β-AR signaling, β-AR mediated activation of adenylyl cyclase and subsequent cAMP generation was determined in isolated adult mouse cardiomyocytes. Isolated cardiomyocytes were treated with vehicle (V) or 100 nM isoproterenol (I) for 15 minutes in the presence or absence of a 5 minute pre-treatment with 10 μM M119 (M). Forskolin treatment, which directly activates adenylyl cyclase, was used as a control. It was found that M119 concomitantly reduced GRK2 recruitment to the membrane and enhanced cAMP generation both at baseline and in response to the β-AR agonist isoproterenol. These data indicated that M119 was blocking Gβγ-mediated GRK2 recruitment, and was effecting changes similar to those found with the salutary Gβγ inhibitory peptides.

The above data led to investigations that M119 plays a positive functional role in the heart, due in part to its inhibition of Gβγ-GRK2 interactions. Prior to pursuing in vivo studies with M119, the role of M119 affecting contractility was evaluated by assessment of isolated adult mouse cardiomyocyte contractility at baseline and in response to β-AR stimulation. In agreement with the signaling data, it was found that M119 enhanced cardiomyocyte contractility both at baseline and in response to β-AR treatment with the β-AR agonist isoproterenol.

In addition to cardiomyocyte contractility studies with M119, contractility studies were also conducted with the inactive form of M119 (M119b). M119b demonstrated no effect on cardiomyocyte contractility at baseline or in response to contraction elicited by isoproterenol treatment. Furthermore, a compound closely related to M119, referred to as both DL-382 and its trade name Gallein, was investigated in these contractility studies. These molecules bear a similar chemical scaffold with minor differences in the fourth ring structure. The studies demonstrated that closely related compounds to M119, such as Gallein, produce significant positive effects on isolated cardiomyocyte contractility at concentrations similar to M119.

(2) Chemical Gβγ inhibitor Studies in an Acute Mouse Model of HF

Based on the positive cardiomyocyte data, the cardiac effects of M119 were tested in vivo. The NCI compound database and chemical library was originally assembled to investigate these compounds utilizing both a yeast high-throughput screening assay as well as in vivo compound delivery to mice for 1-2 weeks. The NCI had delivered M119 at a dose of 250 mg/kg/day to animals for two weeks with no reported overt evidence of toxicity. Based on this data, the effects of M119 were investigated on an acute model of HF representative of the chronic catecholamine stress and adrenergic dysfunction found in human HF. Wild type mice were implanted with mini-osmotic pumps filled with either vehicle or the non-selective β-AR agonist isoproterenol. These pumps release a constant fluid volume, and 30 mg/kg/day of isoproterenol (Iso) has been used to attain pathologic cardiac hypertrophy and dysfunction in one week Immediately following mini-osmotic pump implantation of vehicle or Iso (30 mg/kg/day), mice from each group were injected intraperitoneal (IP) once daily with equal volumes of either vehicle or a moderate dose of M119 (100 mg/kg) for seven days. Conscious echocardiography and post-mortem morphology demonstrated that M119 alone had no effect on cardiac function or morphology. The Iso pumped animals indeed suffered a decrease of cardiac function coupled with pathologic hypertrophy. Excitingly, the Iso pumped animals treated for one week with daily intraperitoneal injections of M119 demonstrated near normalization of cardiac function and morphology (FIG. 17), and a reduction in interstitial cardiac fibrosis. Finally, it was found that M119 treatment nearly normalized GRK2 expression in the Iso HF model (FIG. 18). Together, these data further validate an important role for Gβγ signaling in the heart, and indicate the therapeutic potential of Gβγ inhibitory compounds in the treatment of HF.

(3) Other Compounds

Compound M119 appears to block Gβγ-activated GRK2 and PI3K binding and activity in vitro. In contrast, compound M201 appears to block Gβγ-GRK2 interactions, but potentiates PI3K activity in vitro (Bonacci T M, et al. Science. 2006; 312(5772):443-446). Importantly, compounds were found that differentially block Gβγ interactions with GRK2 and/or PI3K in vitro. These compounds offer substantial delivery, size (~400 Da, vs. ~35 kDa peptides) and specificity advantages over the large peptides, and provide powerful tools to dissect the β-AR-Gβγ-GRK2-PI3K signaling pathway and define the role of specific components in pathologic β-AR desensitization and HF.

In summary, the data demonstrate that Gβγ-GRK2 inhibitory compounds are a very promising therapeutic paradigm for the treatment of HF. In particular, the bioavailable and cell permeable M119 Gβγ binding/blocking compound can: 1) reduce GRK2 membrane recruitment upon β-AR stimulation in isolated adult cardiomyocytes; 2) enhance basal and β-AR mediated cAMP generation in isolated adult cardiomyocytes; 3) enhance both basal and β-AR stimulated isolated cardiomyocyte contractility; 4) reduce pathologic hypertrophy in a chronic β-AR agonist model of HF; and 5) normalize cardiac function as measured by echocardiography in this model of HF. Herein, newly identified Gβγ-signal specific chemical inhibitors are tested to determine whether Gβγ-sensitive PI3K regulation of β-AR signaling is GRK2 dependent or independent (FIG. 19).

(4) Toxicity

Toxicity studies of M119 were undertaken where a one week dosing regimen of 100 mg/kg/day of M119 delivered by intraperitoneal injection. Here, no overt toxicity was observed nor any overt toxicity in intact animals or upon histological examination of lung, liver, brain, heart and kidney following two weeks of daily Gallein injections at doses of 10, 30 and 100 mg/kg/day.

(5) Alpha2-Adrenergic Receptors and Catecholamine Release

A beneficial effect of inhibiting G-protein-beta-gamma mediated desensitization of alpha2-adrenergic receptors in the adrenal gland has been shown. Inhibiting this desensitization restores a normal feedback inhibition of catecholamine release that is disrupted in advanced heart failure. Not only are the methods presented herein capable of investigating adrenal chromaffin cell catecholamine release, but also M119 can reduce or prevent alpha2-adrenergic receptors in these cells, thus restoring normal levels of catecholamine release from the adrenal gland. Thus, dual inhibition of cardiac and adrenal adrenergic receptor desensitization with a systemically delivered agent is dually efficacious in the treatment of heart failure.

c) Methods (1) Determine in vivo Efficacy of M119 in Chronic Animal Models of HF, Including Effects on β-AR Signaling HF is associated with chronic β-AR desensitization and down-regulation, due in part to Gβγ-mediated recruitment of GRK2, which demonstrates enhanced expression and activity in HF. Compounds, including M119, have been identified which inhibit the Gβγ-GRK2 interaction in vitro. Using adult mouse cardiomyocytes, it was found that M119 reduces β-AR stimulated membrane recruitment of GRK2, and enhances cAMP generation at baseline and in response to β-AR stimulation. Also demonstrated was increased cardiomyocyte contractility at baseline and in response to β-AR agonist. Importantly, normalization of cardiac function, morphology and GRK2 expression was shown in an acute animal model of HF. Previously, large peptide inhibition of the Gβγ-GRK2 interaction with βARKct has enhanced baseline and Iso-stimulated in vivo hemodynamics. Further, βARKct has normalized cardiac function and β-AR signaling in both the cardiac calsequestrin (CSQ) overexpressor HF mouse as well as following transverse aortic constriction, and has demonstrated similar mortality benefit to and synergy with β-blocker therapy, current standard treatment for HF patients (Harding V B, et al. Proc Natl Acad Sci USA. 2001; 98(10): 5809-5814; Tachibana H, et al. Circulation. 2005; 111(5): 591-597). Importantly, CSQ animals replicate hallmark β-AR abnormalities seen in human HF. Disclosed herein, M119 can normalize β-AR-Gβγ signaling and cardiac function in vivo and in a long-term HF model, both alone and in combination with β-blocker therapy.

(a) Hemodynamic Characterization of M119 in Basal wt Animals

To determine the hemodynamic response of wt mice in response to M119, invasive in vivo hemodynamics are determined both at baseline and in response to increasing doses of the β-AR agonist Iso, in the absence and presence of a 100 mg/kg IP dose of M119 delivered four hours prior to hemodynamic assessment, or with bolus M119 (10 mg/kg) delivered concurrent with the hemodynamic studies at baseline and in response to increasing doses of Iso. Also disclosed herein M119 enhancesbasal and Iso-induced cardiac contractility.

(b) Investigation of M119 in a Chronic HF Model

Cardiac-specific calsequestrin (CSQ) mice provide a close representation of the development and progression of human HF, including progressive dilated cardiomyopathy and associated β-AR dysfunction.

The CSQ mice develop dramatic dilated cardiomyopathy by 10-14 weeks. The animals are treated with the β1-AR selective β-blocker metoprolol 2 mg/mL in drinking water (~350 mg/kg/day) for breeding purposes, and have found no adverse effects. These are the same concentrations utilized in the experiments that compared metoprololol to βARKct in the CSQ mice[16]. To test the in vivo effects of M119 alone or in combination with β-blocker therapy, four groups of male CSQ mice are tested beginning at one month of age: 1) regular drinking water; daily vehicle injection IP, 2) 2 mg/mL metoprololol in drinking water, daily IP vehicle injection, 3) regular drinking water, daily M119 injection (100 mg/kg/day) IP, and 4) 2 mg/mL metoprololol in drinking water, daily M119 injection (100 mg/kg/day) IP. Additionally, M119 demonstrates greater effects than metoprolol on β-AR signaling, cardiac dysfunction and survival, and that M119 is synergistic with metoprolol in improving these parameters.

(c) Serial Echocardiography.

Conscious echocardiography is non-invasive, can be performed in serial fashion, and provides excellent data regarding in vivo cardiac morphology and function. Furthermore, the echocardiography data indicate M119 is cardioprotective in an acute model of HF. Mice are analyzed at baseline at one month of age and weekly for the duration of the pharmacological treatments described above.

(d) Heart Weight and LV to Body Weight Ratio.

To determine the extent of hypertrophy/dilation heart weight, and LV (mg) divided by body weight (g) ratio are examined upon sacrifice of animals after 1 month of treatment, and normalized with M119 in all conditions.

(e) Analysis of Fetal Gene Expression.

Heart failure is associated with the expression of a variety of the genes present in the heart during embryonic development. These genes include ANF, BNP, α-skeletal actin, and β-MHC. The expression of these genes are analyzed in mice using real-time PCR analysis (5 mice per group).

(f) β-AR Binding and Adenylyl Cyclase Assays.

To determine the β-AR effect of M119 in HF, alone or in combination with metoprolol, the total and sub-type specific membrane β-AR expression and adenylyl cyclase activity is assessed in LV homogenates (Specific Methods), and anticipate normalization of both with M119.

(g) GRK2 Expression and Activity.

Elevated expression and activity of GRK2 is a hallmark of HF, and concordance between these parameters and the severity of HF has been demonstrated, including response to therapy (Hata J A, et al. J Card Fail. 2006; 12(5):360-368). Total GRK2 expression and activity is determined in LV homogenates, and anticipate normalization with M119.

(h) Histochemistry.

HF in the CSQ model is associated with structural myocardial abnormalities and increased fibrosis. To assess the role of M119 in these parameters, and to corroborate parameters found by echocardiography, hematoxylin and eosin staining (H&E), is performed and wall thickness determined, as well as, myocyte structure and cross-sectional area. To assess fibrosis, the Masson's Trichrome and total collagen stain are used.

(i) Apoptosis.

Apoptotic cell death contributes to the heart remodeling and development of dilated cardiomyopathy, particularly after myocardial infarction. The impact of M119 expression on cardiac apoptosis is determined using two different methods: Tunel staining on heart sections, and determine caspase-3 activity in LV homogenates with a colorimetric assay, as well as Bax expression and Caspase 3 cleavage by Western Blot.

(2) Determine the Role of Targeted, Specific Small Molecule Gβγ Blockade of GRK2 or PI3Kγ Alone or in Combination in β-AR Signaling and Cardiomyocyte Contractility.

Several lines of evidence indicate that β-AR-Gβγ-GRK2-PI3Kγ interactions and signaling in the heart lead to β-AR dysfunction and cardiac pathophysiology, and that there are important aspects of PI3Kγ signaling in the heart that should be maintained. The data, derived almost exclusively from large peptide interference, has indicated an important role for Gβγ-mediated GRK2 recruitment to the membrane, and for PI3Kγ recruitment to GRK2, prior to their role in pathologic β-AR desensitization. What remains unclear is the specificity of these large peptide inhibitors, whether blockade of Gβγ binding to GRK2 or PI3Kγ alone can prevent β-AR dysfunction and HF, and whether PI3Kγ-mediated regulation of β-AR signaling is Gβγ- and/or GRK2 dependent or independent. Compounds were identified in vitro that offer substantial delivery, size (~400 Da, vs. ~35 kDa peptides) and potential specificity advantages over large peptide inhibitors. These compounds, at similar $EC_{50}$ concentrations of 1-12 μM: 1) block Gβγ-binding and activation of GRK2 and PI3K (M119), 2) block Gβγ-GRK2 binding and activity, but do not block Gβγ-PI3K, and actually potentiate PI3K activity (M201 (Bonacci T M, et al. Science. 2006; 312(5772):443-446)), 3) block only Gβγ-GRK2 binding and interaction with no effect on PI3Kγ binding or activity, 4) block only Gβγ-mediate PI3Kγ activity with no effect on GRK2, and 5) block neither GRK2 nor PI3Kγ binding nor activity associated with Gβγ (M119b (Bonacci T M, et al. Science. 2006; 312(5772): 443-446).

Experiments in this aim test the hypothesis that targeted Gβγ-GRK2 inhibition is key to the normalizing β-AR signaling and cardiac contractility. The Gβγ-signal specific chemical inhibitors are used to test whether Gβγ-sensitive PI3K regulation of β-AR signaling is GRK2 dependent or independent. These experiments provide new tools to dissect β-AR-Gβγ-GRK2-PI3K signaling.

(3) Determination of Gβγ-GRK2 and Gβγ-PI3Kγ Signal-Specific Effects on Chronic β-AR Signaling To assess cardiomyocyte-specific effects of the specific compounds β-AR signal transduction, the signal specific effects of each of the compounds are examined in neonatal rat ventricular myocytes (NRVM), where it was demonstrated pathologic β-AR dysfunction following chronic β-AR agonist treatment with Iso(Ding B, et al. Circulation. 2005; 111 (19):2469-2476; Ding B, et al. Proc Natl Acad Sci USA. 2005; 102Milano C A, et al. Proc Natl Acad Sci USA. 1994; 91(21):10109-10113:14771-14776). NRVMs are isolated, cultured, then treated with 10 μM Iso for 10 minutes (localization studies) or 24 hours to produce pathologic β-AR desensitization and down-regulation, in the presence and absence of the following compounds at concentrations of 1 and 10 μM: 1) M119, (blocks Gβγ-binding and activation of GRK2 and PI3K), 2) M201 (blocks Gβγ-GRK2 binding and activity, Gβγ-PI3K: potentiates PI3K activity), 3) Mcmpd (blocks only Gβγ-GRK2 binding and interaction with no effect on PI3Kγ binding or activity), 4) Mcmpd (blocks only Gβγ-mediated PI3Kγ activity with no effect on GRK2), and 5) M119b (blocks neither GRK2 nor PI3Kγ binding nor activity associated with Gβγ). In parallel, NRVMs are adenovirally infected with GRK2, βARKct, PIK, or PI3Kγ$_{inact}$ (kindly provided by Drs. Walter Koch and Howard Rodman, see letters) and treated in the presence and absence of 10 μM Iso for comparison of effect and specificity. Following 24 hours of treatment, cells undergo characterization described below.

(a) β-AR Binding.

Total and sub-type specific membrane β-AR is determined in membrane isolates of NRVMS following 24 hrs treatment described above (Specific Methods).

(b) Whole Cell Adenylyl Cyclase.

Cells are harvested after 24 hrs, and whole cell adenylyl cyclase assays determine β-AR-, NaF- and forskolin-stimulated cAMP generation (Specific Methods).

(c) GRK2 Expression, Localization and Activity.

Whole cell lysates are used to assess effects on total GRK2 expression after 24 hours of treatment by Western Blotting. Membrane and cytosolic fractionation are performed to assess GRK2 membrane localization following either 10 minutes or 24 hours of treatment by Western Blotting. GRK2 activity is determined after 24 hrs of treatment (Specific Methods).

(d) Membrane- and GRK2-Associated PI3K Activity.

Following 24 hrs treatment, membrane fractions are utilized to determine total membrane-associated PI3K activity. Membrane fractions are immunoprecipitated with anti-GRK2 antibody to assess GRK2-associated PI3K activity (Specific Methods).

(4) Determination of Gβγ-GRK2 and Gβγ-PI3Kγ Signal-Specific Effects Cardiomyocyte Contractility (a) Adult Mouse Cardiomyocyte Contractility.

To assess effects of the signal-specific Gβγ-inhibitory compounds described above, the established method of contractility assessment is used in isolated adult mouse cardiomyocytes. Following isolation and plating, contractile assessment of cardiomyocytes is performed in the absence and presence of the β-AR agonist Iso (100 nM), in the absence and presence of the individual Gβγ inhibitory compounds described above at 1 and 10 μM (Specific Methods).

(b) Morphological and Histological Characterization of Transgenic Mouse Hearts:

Morphological and histological examination as previously described (Rockman H A, et al. Proc Natl Acad Sci USA. 1998; 95(12):7000-7005; Milano C A, et al. Proc Natl Acad Sci USA. 1994; 91(21):10109-10113; Jaber M, et al. Proc Natl Acad Sci USA. 1996; 93(23):12974-12979; Maekawa N, et al. Circulation. May 22 2006; Maekawa N, et al. J Am Coll Cardiol. 2002; 39(7):1229-1235; Itoh S, et al. Circulation. 2006; 113(14):1787-1798), including hematoxylin and eosin (H&E) Masson's trichrome and total collagen staining following standard techniques (Rockman H A, et al. Proc Natl Acad Sci USA. 1998; 95(12):7000-7005; Kypson A P, et al. J Thorac Cardiovasc Surg. 1998; 115(3):623-630).

(c) Determination of β-AR Density:

Myocardial membranes are prepared, assayed with [$^{125}$I]-CYP, non-specific binding determined with 1 μM alprenolol. Specific binding ($B_{max}$) is normalized to membrane protein concentration (Koch W J, et al. Science. 1995; 268(5215): 1350-1353; Milano C A, et al. Proc Natl Acad Sci USA. 1994; 91(21):10109-10113). Sub-type specific β-AR density is determined by competition binding, % of high affinity and low-affinity receptors is determined (Koch W J, et al. Science. 1995; 268(5215):1350-1353).

(d) Adenylyl Cyclase Assays:

Myocardial membranes are prepared as described above. Adenylyl cyclase activity under basal conditions and in response to 100 μM isoproterenol, 10 mM NaF or 100 mM forskolin is determined as described(Koch W J, et al. Science. 1995; 268(5215):1350-1353; Milano C A, et al. Proc Natl Acad Sci USA. 1994; 91(21):10109-10113). Whole cell adenylyl cyclase assays (cardiomyocyte) are performed with Assay Designs cAMP generation colorimetric (EIA) kit (Ann Arbor, Mich.) per manufacturer instructions.

(e) In vivo Hemodynamic Measurements:

Performed as previously described (Wang H, et al. Circ Res. 2005; 97(12):1305-1313). Adult mice are anesthetized and intubated. Hemodynamic measurements are recorded using a 1.0F high-fidelity micromanometer Millar carotid catheter secured in the LV. Pressure recordings are taken at baseline and 45 to 60 s after injection of 50 uL saline or incremental doses of Iso via jugular cannulation.

(f) Conscious Echocardiography:

Performed as previously described. Briefly, the chest of conscious mice is shaved, the mice are restrained, acclimatized and transthoracic echochardiography performed with the VisualSonics Vevo 770 system (VisualSonics, Toronto, ON) designed specifically for rodent studies(Ng C M, et al. J Clin Invest. 2004; 114(11):1586-1592; Zhou Y Q, et al. Physiol Genomics. 2004;18(2):232-244).

(g) GRK Activity Assay:

Extracts are prepared from tissue samples as described above. GRK activity is assessed in membrane and cytosolic fractions (100 to 150 mg protein) by light-dependent phosphorylation of rhodopsin-enriched rod outer segment membranes, phospho-rhodopsin is visualized by autoradiography (Iaccarino G, et al. Eur Heart J. 2005; 26(17):1752-1758; Iaccarino G, et al. Circulation. 1998; 98(17):1783-1789).

(h) PI3K Activity Assay:

Assays were performed as described previously (Nienaber J J, et al. J Clin Invest. 2003;112(7):1067-1079). Membrane fractions are assayed directly or following GRK2 immunoprecipitation for GRK2-associated PI3K. In vitro lipid kinase assays are performed using PtdIns-4,5-P2, lipids are extracted, spotted on TLC plates and resolved chromatographically and subjected to autoradiography.

(i) Neonatal Rat Ventricular Cardiomyocyte Isolation.

Performed as described previously (Ding B, et al. Circulation. 2005; 111(19):2469-2476; Ding B, et al. Proc Natl Acad Sci USA. 2005; 102 Milano C A, et al. Proc Natl Acad Sci USA. 1994; 91(21):10109-10113:14771-14776). More than 90% of cells were NRVM (positive for α-actinin). Adenovirus-mediated transfection efficiency in all the cardiomyocytes is 90% to 95% at MOI 0.1-1.

(j) Adult Cardiomyocyte Isolation:

Adult cardiomyocytes are isolated from collagenase digested hearts as described previously (O'Connell T D, et al. Methods Mol Biol. 2006; 357:271-296). Briefly, the heart is excised, cannulated, perfused and digested with collagenase II, myocytes are filtered, sedimented, calcium is re-introduced followed by plating on laminin coated dishes.

(k) Cardiomyocyte Contractility and $Ca^{++}$ Assessment:

Mechanical properties of ventricular myocytes are assessed by an IonOptix Myocam system (IonOptix Inc., Milton, Mass., U.S.A.). Myocytes are superfused (at 25° C.) with Tyrodes, cells are pre-loaded in culture medium for 20 minutes with Fura-2, for concurrent calcium flux and myocyte contractility following field stimulation at 0.5 Hz.

(5) Statistical Analysis:

For single biochemical/physiological observations, students t-test are applied to compare animal treatments. Multiple responses of various physiological and biochemical and assays are analyzed using one-way or repeated measures ANOVA. Post-hoc analysis (ie. Newman-Keuls) is performed if significance is achieved, using P<0.05 for all tests.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

M. References

2001 *Heart and Stroke Statistical Update*. Dallas: American Heart Association; 2001.

Akhter S A, Eckhart A D, Rodman H A, et al. In vivo inhibition of elevated myocardial beta-adrenergic receptor kinase activity in hybrid transgenic mice restores normal beta-adrenergic signaling and function [see comments]. *Circulation*. 1999;100(6):648-653.

al Mughales, J., Blyth, T. H., Hunter, J. A., and Wilkinson, P. C. (1996). The chemoattractant activity of rheumatoid synovial fluid for human lymphocytes is due to multiple cytokines. Clin. Exp Immunol. 106, 230-236.

Arkin, M. R. and Wells, J. A. (2004). Small-Molecule Inhibitors of Protein-Protein Interactions: Progressing Towards the Dream. Nat Rev Drug Discov 3, 301-317.

Armstrong D L and White R E (1992) An enzymatic mechanism for potassium channel stimulation through pertussis-toxin-sensitive G proteins. Trends Neurosci 15:403-408.

Atwell, S., Ultsch, M., Devos, A. M., and Wells, J. A. (1997). Structural plasticity in a remodeled protein-protein interface. Science 278, 1125-1128.

Barnes, D. A., Tse, J., Kaufhold, M., Owen, M., Hesselgesser, J., Strieter, R., Horuk, R., and Daniel Perez, H. (1998). Polyclonal Antibody Directed Against Human RANTES Ameliorates Disease in the Lewis Rat Adjuvant-induced Arthritis Model. J. Clin. Invest. 101, 2910-2919.

Bauer P H, Muller S, Puzicha M, et al. Phosducin is a protein kinase A-regulated G-protein regulator. *Nature. Jul. 2* 1992; 358(6381):73-76.

Bilsky E J, Bernstein R N, Wang Z, Sadee W, and Porreca F (1996) Effects of naloxone and D-Phe-Cys-Tyr-D-Trp-Arg-Thr-Pen-Thr-NH$_2$ and the protein kinase inhibitors H7 and H8 on acute morphine dependence and antinociceptive tolerance in mice. J Pharmacol Exp Ther 277:484-490.

Blaxall B C, Spang R, Rockman H A, et al. Differential myocardial gene expression in the development and rescue of murine heart failure. *Physiol Genomics. Nov.* 17 2003; 15(2):105-114.

Blaxall B C, Tschannen-Moran B M, Milano C A, et al. Differential gene expression and genomic patient stratification following left ventricular assist device support. *J Am Coll Cardiol. May* 2 2003; 41(7):1096-1106.

Bohn L M, Lefkowitz R J, and Caron M G (2002) Differential mechanisms of morphine antinociceptive tolerance revealed in (beta)arrestin-2-knock-out mice. J Neurosci 22:10494-10500.

Bonacci T M, Mathews J L, Yuan C, et al. Differential targeting of Gbetagamma-subunit signaling with small molecules. Science. Apr. 21 2006; 312(5772):443-446.

Bookout, A. L., Finney, A. E., Guo, R., Peppel, K., Koch, W. J., and Daaka, Y. (2003). Targeting Gβγ Signaling to Inhibit Prostate Tumor Formation and Growth. J Biol. Chem. 278, 37569-37573.

Bristow M R, Ginsburg R, Minobe W, et al. Decreased catecholamine sensitivity and beta-adrenergic-receptor density in failing human hearts. *N Engl J Med.* 1982; 307(4): 205-211.

Brooijmans, N. and Kuntz, I. D. (2003). Molecular Recognition and Docking Algorithms. Ann. Rev. Biophys. and Biomol. Struc. 32, 335-373.

Califf R M, Adams K F, McKenna W J, et al. A randomized controlled trial of epoprostenol therapy for severe congestive heart failure: The Flolan International Randomized Survival Trial (FIRST). *Am Heart J.* 1997;134(1):44-54.

Camps, M., Ruckle, T., Ji, H., Ardissone, V., Rintelen, F., Shaw, J., Ferrandi, C., Chabert, C., Gillieron, C., Francon, B., Martin, T., Gretener, D., Perrin, D., Leroy, D., Vitte, P. A., Hirsch, E., Wymann, M. P., Cirillo, R., Schwarz, M. K., and Rommel, C. (2005). Blockade of PI3Kγ suppresses joint inflammation and damage in mouse models of rheumatoid arthritis. Nat Med 11, 936-943.

Carter, P. H. (2002). Chemokine receptor antagonism as an approach to anti-inflammatory therapy: 'just right' or plain wrong? Current Opinion in Chemical Biology 6, 510-525.

Chen Y, Mestek A, Liu J, and Yu L (1993) Molecular cloning of a rat κ-opioid receptor reveals sequence similarities to the μ and δ opioid receptors. Biochem J 295:625-628.

Childers S R (1991) Opioid receptor-coupled second messenger systems. Life Sci 48:1991-2003.

Cladman, W. and Chidiac, P. (2002). Characterization and Comparison of RGS2 and RGS4 as GTPase-Activating Proteins for m2 Muscarinic Receptor-Stimulated Gi. Mol Pharmacol 62, 654-659.

Clapham, D. E. and Neer, E. J. (1997). G Protein βγ subunits. Ann. Rev. Pharmacol. Toxicol. 37, 167-203.

Connor, M. and Christie, M. J. (1999). Opioid Receptor Signaling Mechanisms. Clin. Exp. Pharmacol. and Physiol. 26, 493-499.

Crackower M A, Oudit G Y, Kozieradzki I, et al. Regulation of myocardial contractility and cell size by distinct PI3K-PTEN signaling pathways. *Cell. Sep.* 20 2002; 110(6):737-749.

Curcio A, Noma T, Naga Prasad S V, et al. Competitive displacement of phosphoinositide 3-kinase from beta-adrenergic receptor kinase-1 improves postinfarction adverse myocardial remodeling. *Am J Physiol Heart Circ Physiol. October* 2006; 291(4):H1754-1760.

Curnock, A. P., Logan, M. K., and Ward, S. G. (2002). Chemokine signalling: pivoting around multiple phosphoinositide 3-kinases. Immunology 105, 125-136.

Davis T L, Bonacci T M, Sprang S R, et al. Structural and molecular characterization of a preferred protein interaction surface on G protein beta gamma subunits. *Biochemistry. Aug.* 9 2005; 44(31):10593-10604.

Davis, T., Bonacci, T. M., Sprang, S. R., and Smrcka, A. V. (2005). Structural Definition of a Preferred Protein Interaction Site in the G protein β1γ2 heterodimer. Biochem. 44, 10593-10604.

Delano, W. L. (2002). Unraveling hot spots in binding interfaces: progress and challenges. Curr. Opin. Struct. Biol. 12, 14-20.

Delano, W. L., Ultsch, M. H., de Vos, A. M., and Wells, J. A. (2000). Convergent solutions to binding at a protein-protein interface. Science 287, 1279-1283.

Di Rosa, M., Giroud, J. P., and Willoughby, D. A. (1971). Studies on the mediators of the acute inflammatory response induced in rats in different sites by carrageenan and turpentine. J Pathol. 104, 15-29.

Ding B, Abe J, Wei H, et al. A positive feedback loop of phosphodiesterase 3 (PDE3) and inducible cAMP early repressor (ICER) leads to cardiomyocyte apoptosis. *Proc Natl Acad Sci USA. Oct.* 11 2005; 102(41):14771-14776.

Ding B, Abe J, Wei H, et al. Functional role of phosphodiesterase 3 in cardiomyocyte apoptosis: implication in heart failure. *Circulation*. May 17 2005; 111(19):2469-2476.

Evans C J, Keith D E, Morrison H, Bagendzo K, and Edwards R H (1992) Cloning of a delta opioid receptor by functional expression. Science 258:1952-1955.

Fairbrother, W. J., Christinger, H. W., Cochran, A. G., Fuh, G., Keenan, C. J., Quan, C., Shriver, S. K., Tom, J. Y., Wells, J. A., and Cunningham, B. C. (1998). Novel peptides selected to bind vascular endothelial growth factor target the receptor-binding site. Biochem. 37, 17754-17764.

Ford, C. E., Skiba, N. P., Bae, H., Daaka, Y., Reuveny, E., Shektar, L. R., Rosal, R., Weng, G., Yang, C.-S., Iyengar, R., Miller, R., Jan, L. Y., Lefkowitz, R. J., and Hamm, H. E. (1998). Molecular basis for interactions of G protein βγ subunits with effectors. Science 280, 1271-1274.

Fundytus M E and Coderre T J (1996) Chronic inhibition of intracellular Ca++ release of protein kinase C activation significantly reduces the development of morphine dependence. Eur J Pharmacol 300:173-181.

Galeotti N, Stefano G B, Guarna M, Bianchi E, and Ghelardini C (2006) Signaling pathway of morphine induced acute thermal hyperalgesia in mice. Pain, doi:10.1016/j.pain.2006.03.008.

Gaudet R, Bohm A, Sigler P B. Crystal structure at 2.4 angstroms resolution of the complex of transducin betagamma and its regulator, phosducin. *Cell. Nov.* 1 1996; 87(3):577-588.

Gesty-Palmer, D., She, H. E., Kohout, T. A., and Luttrell, L. M. (2005). β-Arrestin 2 Expression Determines the Transcriptional Response to Lysophosphatidic Acid Stimulation in Murine Embryo Fibroblasts. Journal of Biological Chemistry 280, 32157-32167.

Ghosh, M., Peterson, Y. K., Lanier, S. M., and Smrcka, A. V. (2003). Receptor and nucleotide exchange independent mechanisms for promoting G protein subunit dissociation. J. Biol. Chem. 273, 34747-34750.

Gierse, J. K., Zhang, Y., Hood, W. F., Walker, M. C., Trigg, J. S., Maziasz, T. J., Koboldt, C. M., Muhammad, J. L., Zweifel, B. S., Masferrer, J. L., Isakson, P. C., and Seibert, K. (2005). Valdecoxib: Assessment of Cyclooxygenase-2 Potency and Selectivity. J Pharmacol Exp Ther 312, 1206-1212.

Gilman, A. G. (1987). G proteins: transducers of receptor-generated signals. Ann. Rev. Biochem. 56, 615-649.

Gong, J. H., Ratkay, L. G., Waterfield, J. D., and Clark-Lewis, I. (1997). An Antagonist of Monocyte Chemoattractant Protein 1 (MCP-1) Inhibits Arthritis in the MRL-1pr Mouse Model. J. Exp. Med. 186, 131-137.

Goubaeva, F., Ghosh, M., Malik, S., Yang, J., Hinkle, P. M., Griendling, K. K., Neubig, R. R., and Smrcka, A. V. (2003). Stimulation of cellular signaling and G protein subunit dissociation by G protein βγ subunit binding peptides. J. Biol. Chem. 278, 19634-19641.

Gutkind, J. S. (2001). Regulation of mitogen-activated protein kinase signaling networks by G protein-coupled receptors. Sci STKE. 2000, RE1.

Haley T J and McCormick W G (1957) Pharmacological effects produced by intracerebral injection of drugs in the conscious mouse. Br J Pharmacol Chemother 12:12-15.

Halloran, M. M., Woods, J. M., Strieter, R. M., Szekanecz, Z., Volin, M. V., Hosaka, S., Haines, G. K., III, Kunkel, S. L., Burdick, M. D., Walz, A., and Koch, A. E. (1999). The Role of an Epithelial Neutrophil-Activating Peptide-78-Like Protein in Rat Adjuvant-Induced Arthritis. J Immunol 162, 7492-7500.

Hamm, H. E. (1998). The many faces of G protein signaling. J. Biol. Chem. 273, 669-672.

Hannigan, M., Zhan, L., Li, Z., Ai, Y., Wu, D., and Huang, C. K. (2002). Neutrophils lacking phosphoinositide 3-kinase gamma show loss of directionality during N-formyl-Met-Leu-Phe-induced chemotaxis. Proc. Natl. Acad. Sci U.S.A. 99, 3603-3608.

Hansen J L, Theilade J, Aplin M, et al. Role of G-protein-coupled receptor kinase 2 in the heart—do regulatory mechanisms open novel therapeutic perspectives? *Trends Cardiovasc Med. July* 2006; 16(5):169-177.

Harding V B, Jones L R, Lefkowitz R J, et al. Cardiac beta ARK1 inhibition prolongs survival and augments beta blocker therapy in a mouse model of severe heart failure. *Proc Natl Acad Sci USA. May* 8 2001; 98(10):5809-5814.

Hata J A, Williams M L, Schroder J N, et al. Lymphocyte levels of GRK2 (betaARK1) mirror changes in the LVAD-supported failing human heart: lower GRK2 associated with improved beta-adrenergic signaling after mechanical unloading. *J Card Fail. June* 2006; 12(5):360-368.

Hekman M, Bauer P H, Sohlemann P, et al. Phosducin inhibits receptor phosphorylation by the beta-adrenergic receptor kinase in a PKA-regulated manner. *FEBS Lett. Apr.* 25 1994; 343(2):120-124.

Hellmich, M. R., Battey, J. F., and Northup, J. K. (1997). Selective reconstitution of gastrin-releasing peptide receptor with Gαq. Proc. Natl. Acad. Sci U.S.A. 94, 751-756.

Hirsch, E., Katanaev, V. L., Garlanda, C., Azzolino, O., Pirola, L., Silengo, L., Sozzani, S., Mantovani, A., Altruda, F., and Wymann, M. P. (2000). Central Role for G Protein-Coupled Phosphoinositide 3-Kinaseγ in Inflammation. Science 287, 1049-1053.

Iaccarino G, Barbato E, Cipolletta E, et al. Elevated myocardial and lymphocyte GRK2 expression and activity in human heart failure. *Eur Heart J. September* 2005; 26(17): 1752-1758.

Iaccarino G, Tomhave E D, Lefkowitz R J, et al. Reciprocal in vivo regulation of myocardial G protein-coupled receptor kinase expression by beta-adrenergic receptor stimulation and blockade. *Circulation. Oct.* 27 1998; 98(17):1783-1789.

Iaccarino, G. and Koch, W. J. (2003). Transgenic mice targeting the heart unveil G protein-coupled receptor kinases as therapeutic targets. Assay. Drug Dev. Technol. 1, 347-355.

Iaccarino, G., Smithwick, L. A., Lefkowitz, R. J., and Koch, W. J. (1999). Targeting Gβγ signaling in arterial vascular smooth muscle proliferation: a novel strategy to limit restenosis. Proc. Natl. Acad. Sci. USA 96, 3945-3950.

Itoh S, Ding B, Shishido T, et al. Role of p90 ribosomal S6 kinase-mediated prorenin-converting enzyme in ischemic and diabetic myocardium. *Circulation. Apr.* 11 2006; 113 (14):1787-1798.

Jaber M, Koch W J, Rodman H, et al. Essential role of beta-adrenergic receptor kinase 1 in cardiac development and function. *Proc Natl Acad Sci USA.* 1996; 93(23):12974-12979.

Jadot, G., Michelson, A. M., and Puget, K. (1986). Anti-inflammatory activity of superoxide dismutases: inhibition of carrageenan induced edema in rats. Free Radic. Res Commun. 1, 395-403.

Jannsen P A J, Niemegeers C J E, and Dorg J G H (1963) The inhibitory effects of fentanyl and other morphine-like analgesics on the warm water-induced tail-withdrawal reflex in rats. Arzneim-Forsch 13:502-505.

Jiang Q, Seyed-Mozaffari A, Sebastian A, Archer S, and Bidlack J M (1995) Preventing morphine antinociceptive tolerance by irreversible mu opioid antagonists before the onset of their antagonism. J Pharmacol Exp Ther 273:680-688.

Jiang, H., Kuang, Y., Wu, Y., Xie, W., Simon, M. I., and Wu, D. (1997). Roles of phospholipase C β2 in chemoattractant-elicited responses. Proc. Natl. Acad. Sci. USA 94, 7971-7975.

Kammermeier, P. J., Ruiz-Velasco, V., and Ikeda, S. R. (2000). A Voltage-Independent Calcium Current Inhibitory Pathway Activated by Muscarinic Agonists in Rat Sympathetic Neurons Requires Both Gα q/11 and Gβγ. J. Neurosci. 20, 5623-5629.

Karlsson, R., Katsamba, P. S., Nordin, H., Pol, E., and Myszka, D. G. (2006). Analyzing a kinetic titration series using affinity biosensors. Analytical Biochemistry 349, 136-147.

Kieffer Bl, Befort K, Gaveriaux-Ruff C, and Hirth C G (1992) The δ-opioid receptor: isolation of a cDNA by expression cloning and pharmacological characterization. Proc Natl Acad Sci USA 89:12048-12052.

Kitchen, D. B., Decornez, H., Furr, J. R., and Bajorath, J. (2004). Docking and Scoring in Virtual Screening for Drug Discovery: Methods and Applications. Nat Rev Drug Discov 3, 935-949.

Kleuss, C., Scherübl, H., Hescheler, J., Schultz, G., and Wittig, B. (1993). Selectivity in Signal Transduction Determined by γ Subunits of Heterotrimeric G Proteins. Science 259, 832-834.

Kleuss, C., Scherubl, H., Heschler, J., Schultz, G., and Wittig, B. (1992). Different β-subunits determine G-protein interaction with transmembrane receptors. Nature 358, 424-426.

Koch W, Rockman H, Samama P, et al. Cardiac function in mice overexpressing the b-adrenergic receptor kinase or a bARK inhibitor. *Science.* 1995; 268:1350-1353.

Koch W J, Hawes B E, Inglese J, et al. Cellular expression of the carboxyl terminus of a G protein-coupled receptor kinase attenuates G beta gamma-mediated signaling. *J Biol Chem.* Feb. 25 1994; 269(8):6193-6197.

Koch W J, Lefkowitz R J, Rockman H A. Functional consequences of altering myocardial adrenergic receptor signaling. *Annu Rev Physiol.* 2000; 62:237-260.

Koch W J. Genetic and phenotypic targeting of beta-adrenergic signaling in heart failure. *Mol Cell Biochem.* August 2004; 263(1-2):5-9.

Kuang, Y., Wu, Y., Jiang, H., and Wu, D. (1996). Selective G protein coupling by C-C chemokine receptors. J. Biol. Chem. 271, 3975-3978.

Kypson A P, Peppel K, Akhter S A, et al. Ex vivo adenovirus-mediated gene transfer to the adult rat heart. *J Thorac Cardiovasc Surg.* 1998; 115(3):623-630.

Lahiri, J., Isaacs, L., Tien, J., and Whitesides, G. M. (1999). A strategy for the generation of surfaces presenting ligands for studies of binding based on an active ester as a common reactive intermediate: a surface plasmon resonance study. Anal. Chem. 71, 777-790.

Lambright, D. G., Sondek, J., Bohm, A., Skiba, N. P., Hamm, H. E., and Sigler, P. B. (1996). The 2.0 Å crystal structure of a heterotrimeric G protein. Nature 379, 311-319.

Law P Y, Loh H H, and Wei L N (2004) Insights into the receptor transcription and signaling: implications in opioid tolerance and dependence. Neuropharmacology 4:300-311.

Leberer, E., Dignard, D., Hougan, L., Thomas, D. Y., and Whiteway, M. (1992). Dominant-negative mutants of a yeast G-protein β subunit identify two functional regions involved in pheromone signalling. EMBO J. 11, 4805-4813.

Lee, M. J., Tasaki, T., Moroi, K., An, J. Y., Kimura, S., Davydov, I. V., and Kwon, Y. T. (2005). RGS4 and RGS5 are in vivo substrates of the N-end rule pathway. Proc. Natl. Acad. Sci U.S.A. 102, 15030-15035.

Li Z, Laugwitz K L, Pinkernell K, et al. Effects of two Gbetagamma-binding proteins—N-terminally truncated phosducin and beta-adrenergic receptor kinase C terminus (betaARKct)—in heart failure. *Gene Ther.* August 2003; 10(16):1354-1361.

Li, Y., Sternweis, P. M., Charnecki, S., Smith, T. F., Gilman, A. G., Neer, E. J., and Kozasa, T. (1998). Sites for G-α binding on the G protein β subunit overlap with sites for regulation of phospholipase C β and adenylyl cyclase. J. Biol. Chem. 273, 16265-16272.

Li, Z., Jiang, H., Xie, W., Zhang, Z., Smrcka, A. V., and Wu, D. (2000). Roles of PLC-2 and -3 and PI3K in Chemoattractant-Mediated Signal Transduction. Science 287, 1046-1049.

Littman, D. R. (1998). Chemokine receptors: keys to AIDS pathogenesis? Cell 93, 677-680.

Lodowski, D. T., Pitcher, J. A., Capel, W. D., Lefkowitz, R. J., and Tesmer, J. J. G. (2003). Keeping G Proteins at Bay: A Complex Between G Protein-Coupled Receptor Kinase 2 and Gβγ. Science 300, 1256-1262.

Lomakina, E. B. and Waugh, R. E. (2004). Micromechanical Tests of Adhesion Dynamics between Neutrophils and Immobilized ICAM-1. Biophys. J. 86, 1223-1233.

Lomakina, E. B. and Waugh, R. E. (2006). Dynamic of Increased Neutrophil Adhesion to ICAM-1 after Contacting Immobilized IL-8. Annals Biomed. Engineer. 34, 1553-1563.

Luttrell, L. M., van Biesen, T., Hawes, B. E., Koch, W. J., Krueger, K. M., Touhara, K., and Lefkowitz, R. J. (1997). G-protein-coupled receptors and their regulation: activation of the MAP kinase signaling pathway by G-protein-coupled receptors. Adv. Second Messenger Phosphoprotein Res. 31, 263-277.

Maekawa N, Abe J I, Shishido T, et al. Inhibiting p90 Ribosomal S6 Kinase Prevents Na+-H+ Exchanger-Mediated Cardiac Ischemia-Reperfusion Injury. *Circulation.* May 22 2006.

Maekawa N, Wada H, Kanda T, et al. Improved myocardial ischemia/reperfusion injury in mice lacking tumor necrosis factor-alpha. *J Am Coll Cardiol.* Apr. 3 2002; 39(7):1229-1235.

Mahon, M. J., Bonacci, T. M., Divieti, P., and Smrcka, A. V. (2006). A Docking Site for G Protein βγ Subunits on the Parathyroid Hormone 1 Receptor Supports Signaling through Multiple Pathways. Mol Endocrinol 20, 136-146.

Malik, S., Ghosh, M., Bonacci, T. M., Tall, G. G., and Smrcka, A. V. (2005). Ric-8 Enhances G Protein β=-Dependent Signaling in Response to βγ-Binding Peptides in Intact Cells. Mol Pharmacol 68, 129-136.

Markgren, P. O., Lindgren, M. T., Gertow, K., Karlsson, R., Hamalainen, M., and Danielson, U. H. (2001). Determination of Interaction Kinetic Constants for HIV-1 Protease Inhibitors Using Optical Biosensor Technology. Analytical Biochemistry 291, 207-218.

Milano C A, Dolber P C, Rodman H A, et al. Myocardial expression of a constitutively active alpha 1B-adrenergic receptor in transgenic mice induces cardiac hypertrophy. *Proc Natl Acad Sci USA*. 1994; 91(21):10109-10113.

Moises H C, Rusin K I, and Macdonald R L (1994) Mu- and kappa-opioid receptors selectively reduce the same transient components of high-threshold calcium current in rat dorsal root ganglion sensory neurons. J Neurosci 14:5903-5916.

Murray C J, Lopez A D. Alternative projections of mortality and disability by cause 1990-2020: Global Burden of Disease Study. *Lancet. May* 24 1997; 349(9064):1498-1504.

Naga Prasad S V, Barak L S, Rapacciuolo A, et al. Agonist-dependent recruitment of phosphoinositide 3-kinase to the membrane by beta-adrenergic receptor kinase 1. A role in receptor sequestration. *J Biol Chem. Jun.* 1 2001; 276(22):18953-18959.

Naga Prasad S V, Jayatilleke A, Madamanchi A, et al. Protein kinase activity of phosphoinositide 3-kinase regulates beta-adrenergic receptor endocytosis. *Nat Cell Biol. August* 2005; 7(8):785-796.

Naga Prasad S V, Laporte S A, Chamberlain D, et al. Phosphoinositide 3-kinase regulates beta2-adrenergic receptor endocytosis by AP-2 recruitment to the receptor/beta-arrestin complex. *J Cell Biol. Aug.* 5 2002; 158(3):563-575.

Neptune, E. R. and Bourne, H. R. (1997). Receptors induce chemotaxis by releasing the βγ subunit of Gi, not by activating Gq or Gs. Proc. Natl. Acad. Sci U.S.A. 94, 14489-14494.

Ng C M, Cheng A, Myers L A, et al. TGF-beta-dependent pathogenesis of mitral valve prolapse in a mouse model of Marfan syndrome. *J Clin Invest*. December 2004; 114(10: 1586-1592.

Nienaber J J, Tachibana H, Naga Prasad S V, et al. Inhibition of receptor-localized PI3K preserves cardiac beta-adrenergic receptor function and ameliorates pressure overload heart failure. *J Clin Invest. October* 2003; 112(7):1067-1079.

Noel, J. P., Hamm, H. E., and Sigler, P. B. (1993). The 2.2 Å crystal structure of transducin-α complexed with GTPγS. Nature 366, 654-663.

North R A, Williams J T, Surprenant A and Christie M J (1987) Mu and delta receptors belong to a family of receptors that are coupled to potassium channels. Proc Natl Acad Sci USA 84:5487-5491.

O'Connell T D, Rodrigo M C, Simpson P C. Isolation and culture of adult mouse cardiac myocytes. *Methods Mol Biol*. 2006; 357:271-296.

Ogata, H., Takeya, M., Yoshimura, T., Takagi, K., and Takahashi, K. (1997). The role of monocyte chemoattractant protein-1 (MCP-1) in the pathogenesis of collagen-induced arthritis in rats. J Pathol. 182, 106-114.

Oudit G Y, Crackower M A, Eriksson U, et al. Phosphoinositide 3-kinase gamma-deficient mice are protected from isoproterenol-induced heart failure. *Circulation*. Oct. 28 2003; 108(17):2147-2152.

Panchenko, M. P., Saxena, K., Li, Y., Charnecki, S., Sternweis, P. M., Smith, T. F., Gilman, A. G., Kozasa, T., and Neer, E. J. (1998). Sites important for PLC-β2 activation by the G protein βγ subunit map to the sides of the propeller structure. J. Biol. Chem. 273, 28298-28304.

Perrino C, Naga Prasad S V, Mao L, et al. Intermittent pressure overload triggers hypertrophy-independent cardiac dysfunction and vascular rarefaction. *J Clin Invest. June* 2006; 116(6):1547-1560.

Perrino C, Naga Prasad S V, Patel M, et al. Targeted inhibition of beta-adrenergic receptor kinase-1-associated phosphoinositide-3 kinase activity preserves beta-adrenergic receptor signaling and prolongs survival in heart failure induced by calsequestrin overexpression. *J Am Coll Cardiol. Jun.* 7 2005; 45(11):1862-1870.

Perrino C, Naga Prasad S V, Schroder J N, et al. Restoration of beta-adrenergic receptor signaling and contractile function in heart failure by disruption of the betaARK1/phosphoinositide 3-kinase complex. *Circulation*. May 24 2005; 111(20):2579-2587.

Perrino C, Rockman H A, Chiariello M. Targeted inhibition of phosphoinositide 3-kinase activity as a novel strategy to normalize beta-adrenergic receptor function in heart failure. *Vascul Pharmacol*. August 2006; 45(2):77-85.

Plater-Zyberk, C., Hoogewerf, A. J., Proudfoot, A. E. I., Power, C. A., and Wells, T. N. C. (1997). Effect of a CC chemokine receptor antagonist on collagen induced arthritis in DBA/1 mice. Immunology Letters 57, 117-120.

Podolin, P. L., Bolognese, B. J., Foley, J. J., Schmidt, D. B., Buckley, P. T., Widdowson, K. L., Jin, Q., White, J. R., Lee, J. M., Goodman, R. B., Hagen, T. R., Kajikawa, O., Marshall, L. A., Hay, D. W. P., and Sarau, H. M. (2002). A Potent and Selective Nonpeptide Antagonist of CXCR2 Inhibits Acute and Chronic Models of Arthritis in the Rabbit. J Immunol 169, 6435-6444.

Rane, M. J., Carrithers, S. L., Arthur, J. M., Klein, J. B., and McLeish, K. R. (1997). Formyl peptide receptors are coupled to multiple mitogen-activated protein kinase cascades by distinct signal transduction pathways: role in activation of reduced nicotinamide adenine dinucleotide oxidase. J Immunol 159, 5070-5078.

Rebecchi M J and Pentyala S N (2000) Structure, function, and control of phosphoinositide-specific phospholipase C. Physiol Rev 4:1291-1335.

Rhee S G and Bae Y S (1997) Regulation of phosphoinositide-specific phospholipase C isozymes. J Biol Chem 272:15045-15048.

Rich, R. L., Day, Y. S. N., Morton, T. A., and Myszka, D. G. (2001). High-Resolution and High-Throughput Protocols for Measuring Drug/Human Serum Albumin Interactions Using BIACORE. Anal. Biochem. 296, 197-207.

Rioja, I., Ubeda, A., Terencio, M. C., Guillen, I., Riguera, R., Quintela, J. M., Peinador, C., Gonzalez, L. M., and Alcaraz, M. J. (2000). An anti-inflammatory ditriazine inhibiting leukocyte functions and expression of inducible nitric oxide synthase and cyclo-oxygenase-2. Eur. J. Pharmacol. 397, 207-217.

Rockman H A, Chien K R, Choi D J, et al. Expression of a beta-adrenergic receptor kinase 1 inhibitor prevents the development of myocardial failure in gene-targeted mice. *Proc Natl Acad Sci USA*. 1998; 95(12):7000-7005.

Rockman H A, Koch W J, Lefkowitz R J. Seven-transmembrane-spanning receptors and heart function. *Nature. Jan.* 10 2002; 415(6868):206-212.

Ross, E. M. and Wilkie, T. M. (2000). GTPase-activating proteins for heterotrimeric G proteins: regulators of G protein signaling (RGS) and RGS-like proteins. Annu. Rev. Biochem. 69, 795-827.

Ruiz-Velasco, V. and Ikeda, S. R. (1998). Heterologous expression and coupling of G protein-gated inwardly rectifying K+ channels in adult rat sympathetic neurons. J Physiol (Lond) 513, 761-773.

Sarvazyan, N. A., Remmers, A. E., and Neubig, R. R. (1998). Determinants of Giα and βγ binding: Measuring high affinity interactions in a lipid environment using flow cytometry. J. Biol. Chem. 273, 7934-7940.

Sasaki, T., Irie-Sasaki, J., Jones, R. G., Oliveira-dos-Santos, A. J., Stanford, W. L., Bolon, B., Wakeham, A., Itie, A., Bouchard, D., Kozieradzki, I., Joza, N., Mak, T. W., Ohashi, P. S., Suzuki, A., and Penninger, J. M. (2000). Function of PI3K in Thymocyte Development, T Cell Activation, and Neutrophil Migration. Science 287, 1040-1046.

Schroeder J E, Fischbach P S, Zheng D and McCleskey E W (1991) Activation of mu opioid receptors inhibits transient high- and low-threshold Ca2+ currents, but spares a sustained current. Neuron 6:13-20.

Schulz R. The pharmacology of phosducin. *Pharmacol Res.* January 2001; 43(1):1-10.

Scott, J. K., Huang, S. F., Gangadhar, B. P., Samoriski, G. M., Clapp, P., Gross, R. A., Taussig, R., and Smrcka, A. V. (2001). Evidence that a protein-protein interaction 'hot spot' on heterotrimeric G protein βγ subunits is used for recognition of a subclass of effectors. EMBO J. 20, 767-776.

Servant, G., Weiner, O. D., Hezmark, P., Balla, T., Sedat, J. W., and Bourne, H. R. (2000). Polarization of Chemoattractant Receptor Signaling During Neutrophil Chemotaxis. Science 287, 1037-1040.

Sharma S K, Klee W A, and Niremberg M (1977) Opiate-dependent modulation of adenylate cyclase. Proc Natl Acad Sci USA 74:3365-3369.

Siqueira-Junior, J. M., Peters, R. R., Brum-Fernandes, A. J., and Ribeiro-do-Valle, R. M. (2003). Effects of valeryl salicylate, a COX-1 inhibitor, on models of acute inflammation in mice. Pharmacological Research 48, 437-443.

Smith F L, Lohmann A B, and Dewey W L (1999) Involvement of phospholipid signal transduction pathways in morphine tolerance in mice. Br J Pharmacol 128:220-226.

Smrcka A V and Sternweis P C (1993) Regulation of purified subtypes of phosphatidylinositol-specific phospholipase C beta by G protein alpha and beta gamma subunits. J Biol Chem 268:9667-9674.

Smrcka, A. V. and Scott, J. K. (2002). Discovery of ligands for βγ subunits from phage-displayed peptide libraries. Methods Enzymol. 344:557-76., 557-576.

Sondek, J., Bohm, A., Lambright, D. G., Hamm, H. E., and Sigler, P. B. (1996). Crystal structure of a G-protein βγ dimer at 2.1 Å resolution. Nature 379, 369-374.

Sprang, S. R. (1997). G protein mechanisms:Insights from structural analysis. Ann. Rev. Biochem. 66, 639-678.

Tachibana H, Naga Prasad S V, Lefkowitz R J, et al. Level of beta-adrenergic receptor kinase 1 inhibition determines degree of cardiac dysfunction after chronic pressure overload-induced heart failure. *Circulation.* Feb. 8 2005; 111 (5):591-597.

Taussig, R., Tang, W.-J., Hepler, J. R., and Gilman, A. G. (1994). Distinct Patterns of Bidirectional Regulation of Mammalian Adenylylcyclases. J. Biol. Chem. 259, 6093-6100.

Taylor, J. M., Jacob-Mosier, G. G., Lawton, R. G., VanDort, M., and Neubig, R. R. (1996). Receptor and membrane interaction sites on Gβ. A receptor-derived peptide binds to the carboxyl terminus. J. Biol. Chem. 271, 3336-3339.

Tesmer, J. J., Sunahara, R. K., Gilman, A. G., and Sprang, S. R. (1997). Crystal structure of the catalytic domains of adenylyl cyclase in a complex with Gsα-GTPγS. Science 278, 1907-1916.

Ueda, N., Lee, E., Smrcka, A. V., Robishaw, J. D., and Gilman, A. G. (1994). G protein βγ subunits: Simplified purification and properties of novel isoforms. J. Biol. Chem. 269, 4388-4395.

Vlahos, C. J., Matter, W. F., Brown, R. F., Traynor-Kaplan, A. E., Heyworth, P. G., Prossnitz, E. R., Ye, R. D., Marder, P., Schelm, J. A., and Rothfuss, K. J. (1995). Investigation of neutrophil signal transduction using a specific inhibitor of phosphatidylinositol 3-kinase. J Immunol 154, 2413-2422.

Wall, M. A., Coleman, D. E., Lee, E., Iniguez-Lluhi, J. A., Posner, B. A., Gilman, A. G., and Sprang, S. R. (1995). The structure of the G protein heterotrimer $Gi\alpha_1\beta_1\gamma_2$. Cell 83, 1047-1058.

Wang H, Oestreich E A, Maekawa N, et al. Phospholipase C epsilon modulates beta-adrenergic receptor-dependent cardiac contraction and inhibits cardiac hypertrophy. *Circ Res.* Dec. 9 2005; 97(12):1305-1313.

Wang Z, Bilsky E J, Wang D, Porreca F, and Sadee W (1999) 3-Isobutyl-methylxanthine inhibits basal mu-opioid receptor phosphorylation and reverses acute morphine tolerance and dependence in mice. Eur J Pharmacol 371:1-9.

Wang, F., Herzmark, P., Weiner, O. D., Srinivasan, S., Servant, G., and Bourne, H. R. (2002). Lipid products of PI(3)Ks maintain persistent cell polarity and directed motility in neutrophils. Nat Cell Biol 4, 513-518.

Wang, R., Lu, Y., and Wang, S. (2003). Comparative Evaluation of 11 Scoring Functions for Molecular Docking. J Med Chem 46, 2287-2303.

Way E L, Loh H H, and Shen F (1969) Simultaneous quantitative assessment of morphine tolerance and physical dependence. J Pharmacol Exp Ther 167:1-8.

Wells, J. A. and Devos, A. M. (1996). Hematopoietic receptor complexes. Annu. Rev. Biochem. 65, 609-634.

Wickman, K. D., Iñiguez-Lluhi, J. A., Davenport, P. A., Taussig, R., Krapivinsky, G. B., Linder, M. E., Gilman, A. G., and Clapham, D. E. (1994). Recombinant G-protein βγ-subunits activate the muscarinic-gated atrial potassium channel. Nature 368, 255-257.

Willard, F. S. and Siderovski, D. P. (2006). Covalent immobilization of histidine-tagged proteins for surface plasmon resonance. Analytical Biochemistry 353, 147-149.

Williams, M. L., Hata, J. A., Schroder, J., Rampersaud, E., Petrofski, J., Jakoi, A., Milano, C. A., and Koch, W. J. (2004). Targeted {beta}-Adrenergic Receptor Kinase (βARK1) Inhibition by Gene Transfer in Failing Human Hearts. Circulation 109, 1590-1593.

Wu, G. Y., Bogatkevich, G. S., Mukhin, Y. V., Benovic, J. L., Hildebrandt, J. D., and Lanier, S. M. (2000). Identification of Gβγ binding sites in the third intracellular loop of the M-3-muscariinic receptor and their role in receptor regulation. J Biol. Chem. 275, 9026-9034.

Xanthou, G., Duchesnes, C. E., Williams, T. J., and Pease, J. E. (2003). CCR3 functional responses are regulated by both CXCR3 and its ligands CXCL9, CXCL10 and CXCL11. Eur. J Immunol. 33, 2241-2250.

Xie, W., Samoriski, G. M., McLaughlin, J. P., Romoser, V., Smrcka, A., Hinkle, P. M., Bidlack, J. M., Gross, R. A., Jiang, H., and Wu, D. (1999). Genetic alteration of phospholipase Cβ3 expression modulates behavioral and cellular responses to μ opioids. Proc. Natl. Acad. Sci. USA 96, 10385-10390.

Yang, Y. F., Mukai, T., Gao, P., Yamaguchi, N., Ono, S., Iwaki, H., Obika, S., Imanishi, T., Tsujimura, T., Hamaoka, T., and Fujiwara, H. (2002). A non-peptide CCR5 antagonist inhibits collagen-induced arthritis by modulating T cell migration without affecting anti-collagen T cell responses. Eur. J Immunol. 32, 2124-2132.

Yano I and Takemori A E (1977) Inhibition by naloxone of tolerance and dependence in mice treated acutely and chronically with morphine. Res Commun Chem Pathol Pharmacol 16:721-734.

Yao, L., Arolfo, M. P., Dohrman, D. P., Jiang, Z., Fan, P., Fuchs, S., Janak, P. H., Gordon, A. S., and Diamond, I. (2002). βγ Dimers mediate synergy of dopamine D2 and adenosine A2 receptor-stimulated PKA signaling and regulate ethanol consumption. Cell 109, 733-743.

Yao, L., Fan, P., Jiang, Z., Mailliard, W. S., Gordon, A. S., and Diamond, I. (2003). Addicting drugs utilize a synergistic molecular mechanism in common requiring adenosine and Gi-βγ dimers. Proc. Natl. Acad. Sci U.S.A. 100, 14379-14384.

Yoshikawa, D. M., Bresciano, K., Hatwar, M., and Smrcka, A. V. (2001). Characterization of a phospholipase C β2-binding site near the amino terminal coiled-coil of G protein βγ subunits. J. Biol. Chem. 276, 11246-11251.

Zeitz K P, Malmberg A B, Gilbert H, and Basbaum A I (2001) Reduced development of tolerance to the analgesic effects of morphine and clonidine in PKC gamma mutant mice. Pain 102:245-253.

Zhou Y Q, Foster F S, Nieman B J, et al. Comprehensive transthoracic cardiac imaging in mice using ultrasound biomicroscopy with anatomical confirmation by magnetic resonance imaging. *Physiol Genomics*. Jul. 8 2004; 18(2): 232-244.

What is claimed is:

1. A method for treating a disease or condition involving at least one G protein βγ subunit activity in a patient having the disease or condition, the method comprising administering to the patient an effective amount of an agent that interacts with at least one amino acid residue of the protein interaction site of the G protein β subunit, whereby the at least one activity of the G protein is modulated and the disease or condition is treated in the patient, wherein the disease or condition is selected from the group consisting of an inflammatory condition, a cardiovascular disease or condition, and a vascular disease or condition, wherein the agent comprises a compound of:

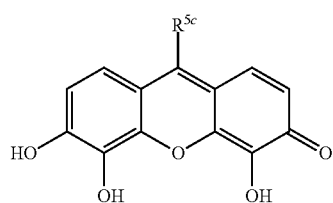

(b)

wherein $R^{5c}$ is a unit selected from the group consisting of phenyl, 2-carboxyphenyl, 3-carboxyphenyl, 4-carboxyphenyl, 2,3-dicarboxyphenyl, 2,4-dicarboxyphenyl, 2,5-dicarboxyphenyl, 2,6-dicarboxyphenyl, 3,4-dicarboxyphenyl, 3,5-dicarboxyphenyl, 2,3,4-tricarboxyphenyl, 2,3,5-tricarboxyphenyl, 2,3,6-tricarboxyphenyl, 2,4,6-tricarboxyphenyl, 2,3,4,5-tetracarboxyphenyl, 2,3,4,6-tetracarboxyphenyl, 2,3,4,5,6-pentacarboxyphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,3,6-trifluorophenyl, 2,4,6-trifluorophenyl, 2,3,4,5-tetrafluorophenyl, 2,3,4,6-tetrafluorophenyl, 2,3,4,5,6-pentafluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,4-trichlorophenyl, 2,3,5-trichlorophenyl, 2,3,6-trichlorophenyl, 2,4,6-trichlorophenyl, 2,3,4,5-tetrachlorophenyl, 2,3,4,6-tetrachlorophenyl, 2,3,4,5,6-pentachlorophenyl, 2-bromophenyl, 3-bromophenyl, 4-bromophenyl, 2,3-dibromophenyl, 2,4-dibromophenyl, 2,5-dibromophenyl, 2,6-dibromophenyl, 3,4-dibromophenyl, 3,5-dibromophenyl, 2,3,4-tribromophenyl, 2,3,5-tribromophenyl, 2,3,6-tribromophenyl, 2,4,6-tribromophenyl, 2,3,4,5-tetrabromophenyl, 2,3,4,6-tetrabromophenyl, 2,3,4,5,6-pentabromophenyl, 2-iodophenyl, 3-iodophenyl, 4-iodophenyl, 2,3-diiodophenyl, 2,4-diiodophenyl, 2,5-diiodophenyl, 2,6-diiodophenyl, 3,4-diiodophenyl, 3,5-diiodophenyl, 2,3,4-triiodo-phenyl, 2,3,5-triiodophenyl, 2,3,6-triiodophenyl, 2,4,6-triiodophenyl, 2,3,4,5-tetraiodophenyl, 2,3,4,6-tetraiodophenyl, 2,3,4,5,6-pentaiodophenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxyphenyl, 3,5-dihydroxyphenyl, 2,3,4-trihydroxyphenyl, 2,3,5-trihydroxyphenyl, 2,3,6-trihydroxy-phenyl, 2,4,6-trihydroxyphenyl, 2,3,4,5-tetrahydroxyphenyl, 2,3,4,6-tetrahydroxyphenyl, 2,3,4,5,6-pentahydroxyphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxy-phenyl, 3,5-dimethoxyphenyl, 2,3,4-trimethoxyphenyl, 2,3,5-trimethoxyphenyl, 2,3,6-trimethoxyphenyl, 2,4,6-trimethoxyphenyl, 2,3,4,5-tetramethoxyphenyl, 2,3,4,6-tetra-methoxyphenyl, 2,3,4,5,6-pentamethoxyphenyl, 2-aminophenyl, 3-aminophenyl, 4-aminophenyl, 2,3-diaminophenyl, 2,4-di-aminophenyl, 2,5-diaminophenyl, 2,6-diaminophenyl, 3,4-diaminophenyl, 3,5-diamino-phenyl, 2,3,4-triaminophenyl, 2,3,5-triaminophenyl, 2,3,6-triaminophenyl, 2,4,6-tri-aminophenyl, 2,3,4,5-tetraaminophenyl, 2,3,4,6-tetraaminophenyl, 2,3,4,5,6-penta-aminophenyl, 2-(dimethylamino)phenyl, 3-(dimethylamino)phenyl, 4-(dimethylamino)phenyl, 2,3-di(dimethylamino)phenyl, 2,4-di(dimethylamino)-phenyl, 2,5-di(dimethylamino)-phenyl, 2,6-di(dimethylamino)phenyl, 3,4-di(dimethylamino)phenyl, 3,5-di(dimethyl-amino)phenyl, 2,3,4-tri(dimethyl-amino)phenyl, 2,3,5-tri(dimethylamino)phenyl, 2,3,6-tri(dimethylamino)phenyl, 2,4,6-tri(dimethylamino)phenyl, 2,3,4,5-tetra(dimethylamino)-phenyl, 2,3,4,6-tetra(dimethylamino)phenyl, and 2,3,4,5,6-penta(dimethylamino)phenyl, and a pharmaceutically acceptable salt thereof.

2. The method of claim 1, wherein the inflammatory condition is selected from the group consisting of asthma, rheumatoid arthritis, reactive arthritis, spondylarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, ischemia reperfusion injury, Alzheimer's disease, transplant rejection (allogeneic and xenogeneic), thermal trauma, any immune complex-induced inflammation, glomerulonephritis, myasthenia gravis, cerebral lupus, Guillaine-Barre syndrome, vasculitis, systemic sclerosis, anaphylaxis, catheter reactions, atheroma, infertility, thyroiditis, ARDS, post-bypass syndrome, hemodialysis, juvenile rheumatoid, Behcets syndrome, hemolytic anemia, pemphigus, bulbous pemphigoid, stroke, atherosclerosis, and scleroderma.

3. The method of claim 1, wherein the disease or condition associated with heart malfunction is selected from the group consisting of myocardial infarction, restenosis, hypertension, primary cardiomyopathy and secondary cardiomyopathy, wherein the primary and secondary cardiomyopathy is selected from the group consisting of dilated cardiomyopathy hypertrophic cardiomyopathy, and restrictive cardiomyopathy, further wherein the hypertrophic cardiomyopathy is selected from the group consisting of ischemic, non-ischemic, idiopathic, congestive, diabetic, peripartium, alcoholic, viral, and valvular.

4. The method of claim 1, wherein the disease or condition affecting the vasculature is selected from the group consisting of peripheral vascular disease, atherosclerosis, restenosis, and hypertension.

* * * * *

```
                        SEQUENCE LISTING

<160> NUMBER OF SEQ ID NOS: 13

<210> SEQ ID NO 1
<211> LENGTH: 15
<212> TYPE: PRT
<213> ORGANISM: Artificial sequence
<220> FEATURE:
<223> OTHER INFORMATION: Synthetic peptide

<400> SEQUENCE: 1

Ser Ile Arg Lys Ala Leu Asn Ile Leu Gly Tyr Pro Asp Tyr Asp
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Synthetic peptide

<400> SEQUENCE: 2

Ser Ile Gly Lys Ala Phe Lys Ile Leu Gly Tyr Pro Asp Tyr Asp
1               5                   10                  15

<210> SEQ ID NO 3
<211> LENGTH: 340
<212> TYPE: PRT
<213> ORGANISM: Rat

<400> SEQUENCE: 3

Met Gly Glu Met Glu Gln Leu Lys Gln Glu Ala Glu Gln Leu Lys Lys
1               5                   10                  15

Gln Ile Ala Asp Ala Arg Lys Ala Cys Ala Asp Ile Thr Leu Ala Glu
                20                  25                  30

Leu Val Ser Gly Leu Glu Val Val Gly Arg Val Gln Met Arg Thr Arg
            35                  40                  45

Arg Thr Leu Arg Gly His Leu Ala Lys Ile Tyr Ala Met His Trp Ala
        50                  55                  60

Thr Asp Ser Lys Leu Leu Val Ser Ala Ser Gln Asp Gly Lys Leu Ile
65                  70                  75                  80

Val Trp Asp Thr Tyr Thr Thr Asn Lys Val His Ala Ile Pro Leu Arg
                85                  90                  95

Ser Ser Trp Val Met Thr Cys Ala Tyr Ala Pro Ser Gly Asn Phe Val
                100                 105                 110

Ala Cys Gly Gly Leu Asp Asn Met Cys Ser Ile Tyr Ser Leu Lys Ser
```

```
            115                 120                 125

Arg Glu Gly Asn Val Lys Val Ser Arg Glu Leu Ser Ala His Thr Gly
    130                 135                 140

Tyr Leu Ser Cys Cys Arg Phe Leu Asp Asp Asn Asn Ile Val Thr Ser
145                 150                 155                 160

Ser Gly Asp Thr Thr Cys Ala Leu Trp Asp Ile Glu Thr Gly Gln Gln
                165                 170                 175

Lys Thr Val Phe Val Gly His Thr Gly Asp Cys Met Ser Leu Ala Val
                180                 185                 190

Ser Pro Asp Tyr Lys Leu Phe Ile Ser Gly Ala Cys Asp Ala Ser Ala
                195                 200                 205

Lys Leu Trp Asp Val Arg Glu Gly Thr Cys Arg Gln Thr Phe Thr Gly
    210                 215                 220

His Glu Ser Asp Ile Asn Ala Ile Cys Phe Phe Pro Asn Gly Glu Ala
225                 230                 235                 240

Ile Cys Thr Gly Ser Asp Asp Ala Ser Cys Arg Leu Phe Asp Leu Arg
                245                 250                 255

Ala Asp Gln Glu Leu Thr Ala Tyr Ser His Glu Ser Ile Ile Cys Gly
                260                 265                 270

Ile Thr Ser Val Ala Phe Ser Leu Ser Gly Arg Leu Leu Phe Ala Gly
                275                 280                 285

Tyr Asp Asp Phe Asn Cys Asn Val Trp Asp Ser Leu Lys Cys Glu Arg
                290                 295                 300

Val Gly Val Leu Ser Gly His Asp Asn Arg Val Ser Cys Leu Gly Val
305                 310                 315                 320

Thr Ala Asp Gly Met Ala Val Ala Thr Gly Ser Trp Asp Ser Phe Leu
                325                 330                 335

Lys Ile Trp Asn
            340

<210> SEQ ID NO 4
<211> LENGTH: 339
<212> TYPE: PRT
<213> ORGANISM: Human
<220> FEATURE:
<221> NAME/KEY: misc_feature
<222> LOCATION: (107)..(107)
<223> OTHER INFORMATION: Xaa can be any naturally occurring amino acid

<400> SEQUENCE: 4

Met Ser Glu Leu Glu Gln Leu Arg Gln Glu Ala Glu Gln Leu Arg Asn
1               5                   10                  15

Gln Ile Arg Asp Ala Arg Lys Ala Cys Gly Asp Ser Thr Leu Thr Gln
                20                  25                  30

Ile Thr Ala Gly Leu Asp Pro Val Gly Arg Ile Gln Met Arg Thr Arg
                35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Xaa Ser Gly Asn Phe Val
                100                 105                 110

Ala Cys Gly Gly Leu Asp Asn Ile Cys Ser Ile Tyr Ser Leu Lys Thr
                115                 120                 125
```

```
Arg Glu Gly Asn Val Arg Val Ser Arg Glu Leu Pro Gly His Thr Gly
            130                 135                 140

Tyr Leu Ser Cys Cys Arg Phe Leu Asp Asp Asn Gln Ile Ile Thr Ser
145                 150                 155                 160

Ser Gly Asp Thr Thr Cys Ala Leu Trp Asp Ile Glu Thr Gly Gln Gln
                165                 170                 175

Thr Val Gly Phe Ala Gly His Ser Gly Asp Val Met Ser Leu Ser Leu
            180                 185                 190

Ala Pro Asn Gly Arg Thr Phe Val Ser Gly Ala Cys Asp Ala Ser Ile
        195                 200                 205

Lys Leu Trp Asp Val Arg Asp Ser Met Cys Arg Gln Thr Phe Ile Gly
        210                 215                 220

His Glu Ser Asp Ile Asn Ala Val Ala Phe Phe Pro Asn Gly Tyr Ala
225                 230                 235                 240

Phe Thr Thr Gly Ser Asp Asp Ala Thr Cys Arg Leu Phe Asp Leu Arg
                245                 250                 255

Ala Asp Gln Glu Leu Leu Met Tyr Ser His Asp Asn His Cys Gly Ile
            260                 265                 270

Thr Ser Val Ala Phe Ser Arg Ser Gly Arg Leu Leu Ala Gly Tyr
        275                 280                 285

Asp Asp Phe Asn Cys Asn Ile Trp Asp Ala Met Lys Gly Asp Arg Ala
290                 295                 300

Gly Val Leu Ala Gly His Asp Asn Arg Val Ser Cys Leu Gly Val Thr
305                 310                 315                 320

Asp Asp Gly Met Ala Val Ala Thr Gly Ser Trp Asp Ser Phe Leu Lys
                325                 330                 335

Ile Trp Asn

<210> SEQ ID NO 5
<211> LENGTH: 15
<212> TYPE: PRT
<213> ORGANISM: Artificial sequence
<220> FEATURE:
<223> OTHER INFORMATION: Synthetic peptide

<400> SEQUENCE: 5

Ser Ile Gly Lys Ala Leu Phe Ile Leu Gly Tyr Pro Asp Tyr Asp
1               5                   10                  15

<210> SEQ ID NO 6
<211> LENGTH: 13
<212> TYPE: PRT
<213> ORGANISM: Artificial sequence
<220> FEATURE:
<223> OTHER INFORMATION: Synthetic peptide

<400> SEQUENCE: 6

Leu Cys Ser Lys Ala Tyr Leu Leu Leu Gly Gln Thr Cys
1               5                   10

<210> SEQ ID NO 7
<211> LENGTH: 15
<212> TYPE: PRT
<213> ORGANISM: Artificial sequence
<220> FEATURE:
<223> OTHER INFORMATION: Synthetic peptide

<400> SEQUENCE: 7

Ser Cys Lys Arg Thr Lys Ala Gln Ile Leu Leu Ala Pro Cys Thr
```

```
1               5                   10                  15
```

<210> SEQ ID NO 8
<211> LENGTH: 15
<212> TYPE: PRT
<213> ORGANISM: Artificial sequence
<220> FEATURE:
<223> OTHER INFORMATION: Synthetic peptide

<400> SEQUENCE: 8

```
Trp Cys Pro Pro Lys Ala Met Thr Gln Leu Gly Ile Lys Ala Cys
1               5                   10                  15
```

<210> SEQ ID NO 9
<211> LENGTH: 16
<212> TYPE: PRT
<213> ORGANISM: Artificial sequence
<220> FEATURE:
<223> OTHER INFORMATION: Synthetic peptide

<400> SEQUENCE: 9

```
Ser Cys Gly His Gly Leu Lys Val Gln Ser Thr Ile Gly Ala Cys Ala
1               5                   10                  15
```

<210> SEQ ID NO 10
<211> LENGTH: 12
<212> TYPE: PRT
<213> ORGANISM: Artificial sequence
<220> FEATURE:
<223> OTHER INFORMATION: Synthetic peptide

<400> SEQUENCE: 10

```
Ser Cys Glu Lys Arg Tyr Gly Ile Glu Phe Cys Thr
1               5                   10
```

<210> SEQ ID NO 11
<211> LENGTH: 12
<212> TYPE: PRT
<213> ORGANISM: Artificial sequence
<220> FEATURE:
<223> OTHER INFORMATION: Synthetic peptide

<400> SEQUENCE: 11

```
Ser Cys Glu Lys Arg Leu Gly Val Arg Ser Cys Thr
1               5                   10
```

<210> SEQ ID NO 12
<211> LENGTH: 12
<212> TYPE: PRT
<213> ORGANISM: Artificial sequence
<220> FEATURE:
<223> OTHER INFORMATION: Synthetic peptide

<400> SEQUENCE: 12

```
Ser Cys Ala Arg Phe Phe Gly Thr Pro Gly Cys Thr
1               5                   10
```

<210> SEQ ID NO 13
<211> LENGTH: 14
<212> TYPE: PRT
<213> ORGANISM: Artificial sequence
<220> FEATURE:
<223> OTHER INFORMATION: Synthetic peptide

```
<400> SEQUENCE: 13

Trp Cys Pro Pro Lys Leu Glu Gln Trp Tyr Asp Gly Cys Ala
1               5                   10
```